(12) United States Patent
Hruby et al.

(10) Patent No.: US 8,026,218 B2
(45) Date of Patent: Sep. 27, 2011

(54) BIFUNCTIONAL ANALGESIC COMPOUNDS FOR OPIOID RECEPTOR AGONISTS AND NEUROKININ-1 RECEPTOR ANTAGONISTS

(75) Inventors: Victor Hruby, Tucson, AZ (US); Padma Nair, Tucson, AZ (US); Takashi Yamamoto, Tokyo (JP)

(73) Assignee: The University of Arizona, Tucson, AZ (US)

( * ) Notice: Subject to any disclaimer, the term of this patent is extended or adjusted under 35 U.S.C. 154(b) by 737 days.

(21) Appl. No.: 11/760,445

(22) Filed: Jun. 8, 2007

(65) Prior Publication Data

US 2008/0039404 A1     Feb. 14, 2008

Related U.S. Application Data

(60) Provisional application No. 60/925,296, filed on Apr. 19, 2007, provisional application No. 60/851,956, filed on Oct. 16, 2006, provisional application No. 60/851,475, filed on Oct. 13, 2006, provisional application No. 60/842,223, filed on Sep. 5, 2006, provisional application No. 60/812,527, filed on Jun. 9, 2006, provisional application No. 60/794,967, filed on Apr. 26, 2006.

(51) Int. Cl.
*A61K 38/06* (2006.01)
*A61P 23/00* (2006.01)
*A61P 25/04* (2006.01)

(52) U.S. Cl. ............... 514/21.6; 514/18.3; 514/18.4; 530/328

(58) Field of Classification Search .......... None
See application file for complete search history.

(56) References Cited

U.S. PATENT DOCUMENTS

| | | | |
|---|---|---|---|
| 4,649,200 A | 3/1987 | Portoghese et al. | |
| 5,245,046 A * | 9/1993 | Youngdale et al. | 548/495 |
| 5,891,842 A | 4/1999 | Kream | |
| 6,759,520 B1 | 7/2004 | Carr et al. | |
| 6,855,807 B1 | 2/2005 | Devi et al. | |
| 6,875,759 B1 | 4/2005 | Lipkowski et al. | |
| 6,881,829 B2 | 4/2005 | Kream | |
| 6,913,760 B2 | 7/2005 | Carr et al. | |
| 2003/0032599 A1 | 2/2003 | Lipkowski et al. | |
| 2003/0170288 A1 | 9/2003 | Carr et al. | |
| 2006/0030532 A1 | 2/2006 | Lipkowski et al. | |
| 2006/0105947 A1 | 5/2006 | Carr et al. | |
| 2006/0241053 A1 | 10/2006 | Lipkowski et al. | |

FOREIGN PATENT DOCUMENTS

| | | |
|---|---|---|
| WO | WO 87/06935 | 11/1987 |
| WO | WO 01/07029 | 2/2001 |
| WO | WO 01/30371 | 5/2001 |
| WO | WO 02/102835 | 12/2002 |
| WO | WO 03/090697 | 11/2003 |
| WO | WO 2004/014943 | 2/2004 |
| WO | WO 2005/007682 | 1/2005 |

OTHER PUBLICATIONS

Bonney, 2004, European Journal of Pharmacology, 488, 91-99.*
Millet, 2002, Bioorganic and Medicinal Chemistry, 10, 2905-2912.*
Bonney et al, Eur. J. Pharmacol., 2004, 488(1-3), pp. 91-99.
Richards et al, Eur. J. Biochem., 2003, 270, pp. 2287-2294.
Fantin et al, Cancer Res., 2005, 65(15), pp. 6891-6900.
Rashid et al, Endocrinology, 2004, 145(6), pp. 2645-2652.
Schiller, The AAPS Journal, 2005, 7(3), Article 56, pp. E560-E565.
Foran et al, JPET, 2000, 295(3), pp. 1142-1148.
Sakurada et al, Pain, 1995, 60, pp. 175-180.
Misterek et al, Life Sciences, 1994, vol. 54, pp. 939-944.
Rupniak et al, Pain, 1996, 67, pp. 189-195.
Sanchez-Blazquez et al, JPET, 1993, 265(2), pp. 835-843.
Maszczynska et al, Analgesia, 1998, 3, pp. 259-268.
Huber et al, J. of Pharmaceutical Sci., 2003, 92(7), pp. 1377-1385.
Towler et al, Neuroscience Letters, 1998, 257, pp. 5-8.
Weltrowska et al, J. Peptide Res., 2004, 63, pp. 63-68.
Maszczynska et al, Letters in Peptide Science, 1998, 5, pp. 395-398.
Millet et al, Journal of Peptide Sci., 2001, 7, pp. 323-330.
Lee et al, J. Med. Chem., 2006, 49(5), pp. 1773-1780.
Foran et al, PNAS, 2000, 97(13), pp. 7621-7626.
Foran et al, Anesthesiology, Supp., 1999, 91(3A): A944.
Agnes et al, J. Med. Chem., 2006, 49, pp. 2868-2875.
Ananthan, The AAPS Journal, 2006, 8(1) Article 14, pp. E118-E125.
Bouchie, BioCentury, The Bernstein Report on BioBusiness, 2007, 15(34), p. A14 of 26.

* cited by examiner

*Primary Examiner* — Cecilia J Tsang
*Assistant Examiner* — Satyanarayana Gudibande
(74) *Attorney, Agent, or Firm* — Oblon, Spivak, McClelland, Maier & Neustadt, L.L.P.

(57) ABSTRACT

The present invention provides a novel chimeric compound comprising an agonist opioid receptor binding moiety at its N-terminus and an antagonist neurokinin-1 (NK1) receptor binding moiety at its C-terminus for producing analgesia, a pharmaceutical composition comprising the chimeric compound, a method of making the compound, and a method of treating pain using the novel chimeric compounds.

43 Claims, 78 Drawing Sheets
(30 of 78 Drawing Sheet(s) Filed in Color)

FIG. 1C

Introduction of Dmt instead of Tyr[1]

H-Xxx-DAla-Gly-Phe-Met-Pro-Leu-Trp-R

| ID | Xxx | R | MVD | | GPI/LMMP | | |
|---|---|---|---|---|---|---|---|
| | | | Opioid (δ) Agonist (IC$_{50}$; nM) | Opioid(μ) Agonist (IC$_{50}$; nM) | Substance P Agonist (IC$_{50}$; nM) | Substance P Antagonist (Ke; nM) | |
| TY005 | Tyr | O-3,5-Bn(CF$_3$)$_2$ | 22.3 | 358.8 | None | 24.7 | |
| TY027 | Tyr | NH-3,5-Bn(CF$_3$)$_2$ | 14.5 | 487.9 | None | 10.0 | |
| TY025 | Tyr | NH-Bn | 4.8 | 61.1 | None | 9.9 | |
| TY033 | Dmt | O-3,5-Bn(CF$_3$)$_2$ | 1.3 | 100.5 | None | 24.5 | |
| TY032 | Dmt | NH-3,5-Bn(CF$_3$)$_2$ | 1.8 | 18.6 | None | 7.5 | |
| TY034 | Dmt | NH-Bn | 6.9 | 11.4 | None | 36.9 | |

FIG. 1D

Introduction of Dmt instead of Tyr1

H-Dmt-DAla-Gly-Phe-Xxx-Pro-Leu-Trp-R

| ID | Xxx | R | Affinity | | | |
|---|---|---|---|---|---|---|
| | | | hDOR (Ki;nM) | rMOR (Ki;nM) | hNK1 (Ki;nM) | rNK1 (Ki;nM) |
| TY032 | Met | NH-3,5-Bn(CF$_3$)$_2$ | 0.12 | 2.0 | 0.0079 | 2.30 |
| TY050 | Nle | NH-3,5-Bn(CF$_3$)$_2$ | N.T. | N.T. | 0.075 | 13.0 |
| TY052 | Nle | NMe-3,5-Bn(CF$_3$)$_2$ | 0.46 | 1.77 | 0.21 | 11.1 |
| TY053 | Nle | NH-3-Bn(CF$_3$) | N.T. | 0.74 | 1.04 | 138 |
| TY054 | Nle | NH-3,5-Bn(OMe)$_2$ | 0.15 | 0.34 | 0.95 | 318 |

FIG. 1E

Cyclization with disulfide bond using Cys

| ID | Sequence |
|---|---|
| TY035 | H-Tyr-[DCys-Gly-Phe-Nle-Pro-Cys]-Trp-NH-3,5-Bn(CF$_3$)$_2$ |
| TY038 | H-Tyr-[DCys-Gly-Phe-Nle-Pro-DCys]-Trp-NH-3,5-Bn(CF$_3$)$_2$ |
| TY039 | H-Tyr-[DCys-Gly-Phe-Cys]-Pro-Leu-Trp-NH-3,5-Bn(CF$_3$)$_2$ |
| TY037 | H-Tyr-[DCys-Gly-Phe-DCys]-Pro-Leu-Trp-NH-3,5-Bn(CF$_3$)$_2$ |

| ID | Affinity | | | | GTP binding | | | | MVD | GPI/LMMP | |
|---|---|---|---|---|---|---|---|---|---|---|---|
| | hDOR (Ki; nM) | rMOR (Ki; nM) | hNK1 (Ki; nM) | rNK1 (Ki; nM) | hDOR | | rMOR | | Opioid (δ) | Opioid (μ) | SP |
| | | | | | EC$_{50}$ (nM) | Emax (%) | EC$_{50}$ (nM) | Emax (%) | Agonist (IC$_{50}$; nM) | Agonist (IC$_{50}$; nM) | Antagonist (Ke; nM) |
| TY035 | 1.29 | 79.2 | 0.091 | 30 | 0.02 | 11 | 36 | 39 | 84.7 | 1007 | 2.2 |
| TY038 | 55.5 | 156 | 0.24 | 7.1 | 14.0 | 87 | 21.7 | 11 | 18.9 | 3% at 1 uM (no antagonist activity) | 12.0 |
| TY039 | 10.7 | 201 | 3.5 | 556 | 50.9 | 37 | 118 | 20 | N.T. | 10% at 1 uM (no antagonist activity) | 433.6 |
| TY037 | 7.8 | 51.5 | 0.49 | 45 | 98.2 | 26 | 52.9 | 8 | 8.3 | 283.7 | 4.7 |

FIG. 1F

Cyclization with disulfide bond using Pen

| ID | Sequence |
|---|---|
| TY047 | H-Tyr-[DPen-Gly-Phe-Nle-Pro-Pen]-Trp-NH-3,5-Bn(CF$_3$)$_2$ |
| TY048 | H-Tyr-[DPen-Gly-Phe-Nle-Pro-DPen]-Trp-NH-3,5-Bn(CF$_3$)$_2$ |
| TY046 | H-Tyr-[DPen-Gly-Phe-Pen]-Pro-Leu-Trp-NH-3,5-Bn(CF$_3$)$_2$ |
| TY049 | H-Tyr-[DPen-Gly-Phe-DPen]-Pro-Leu-Trp-NH-3,5-Bn(CF$_3$)$_2$ |

| ID | Affinity | | | | GTP binding | | | |
|---|---|---|---|---|---|---|---|---|
| | hDOR (Ki; nM) | rMOR (Ki; nM) | hNK1 (Ki; nM) | rNK1 (Ki; nM) | hDOR EC$_{50}$ (nM) | hDOR Emax (%) | rMOR EC$_{50}$ (nM) | rMOR Emax (%) |
| TY047 | 152 | 1970 | 59 | 162.69 | N.T. | N.T. | 2910 | 15 |
| TY048 | N.T. | N.T. | 1.9 | 25.99 | N.T. | N.T. | N.T. | N.T. |
| TY046 | 1.7 | 2330 | 0.0053 | 10.33 | 17.2 | 15 | 28.8 | 14 |
| TY049 | N.T. | N.T. | 0.18 | 4.54 | N.T. | N.T. | N.T. | N.T. |

FIG. 1G

Glycopeptides

| ID | Sequence |
|---|---|
| TY045 | H-Tyr-DAla-Gly-Phe-Nle-Pro-Leu-Trp-NH-3,5-Bn(CF$_3$)$_2$ |
| TY042 | H-Tyr-DAla-Gly-Phe-Ser(OGlc)-Pro-Leu-Trp-NH-3,5-Bn(CF$_3$)$_2$ |
| TY044 | H-Tyr-DAla-Gly-Phe-Nle-Ser(OGlc)-Leu-Trp-NH-3,5-Bn(CF$_3$)$_2$ |
| TY041 | H-Tyr-DAla-Gly-Phe-Nle-Pro-Ser(OGlc)-Trp-NH-3,5-Bn(CF$_3$)$_2$ |

| ID | Affinity | | | | GTP binding | | | | MVD | GPI/LMMP | |
|---|---|---|---|---|---|---|---|---|---|---|---|
| | hDOR (Ki; nM) | rMOR (Ki; nM) | hNK1 (Ki; nM) | rNK1 (Ki; nM) | hDOR | | rMOR | | Opioid (δ) | Opioid (μ) | SP |
| | | | | | EC$_{50}$ (nM) | Emax (%) | EC$_{50}$ (nM) | Emax (%) | Agonist (IC$_{50}$; nM) | Agonist (IC$_{50}$; nM) | Antagonist (Ke; nM) |
| TY045 | 1.0 | 32.0 | 0.0028 | 6.8 | 5.0 | 125 | 18.4 | 67 | 13.6 | 463 | 40.8 |
| TY042 | 58.5 | 256 | 0.00027 | 1.5 | 51.9 | 47 | 176 | 28 | 109 | 1891 | 2.83 |
| TY044 | 36.3 | 3370 | 1.3 | 23 | 50.9 | 162 | 380 | 85 | 18.0* | 249* | 18.4 |
| TY041 | 3.7 | 8.0 | 0.00077 | 14 | 7.9 | 62 | 18.0 | 42 | 12.7 | 517 | 1.80 |

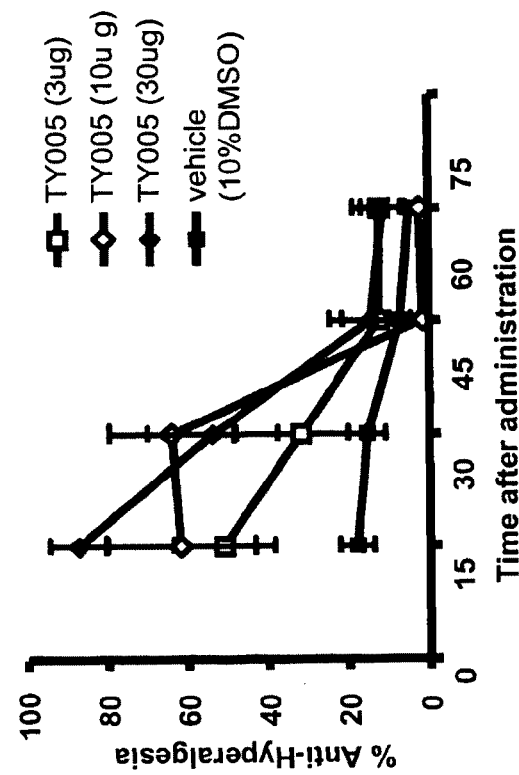
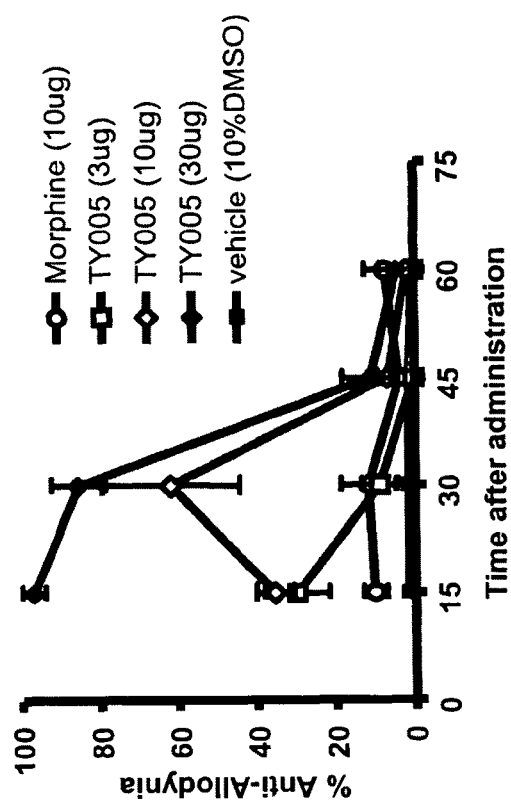
FIG. 9A
FIG. 9B

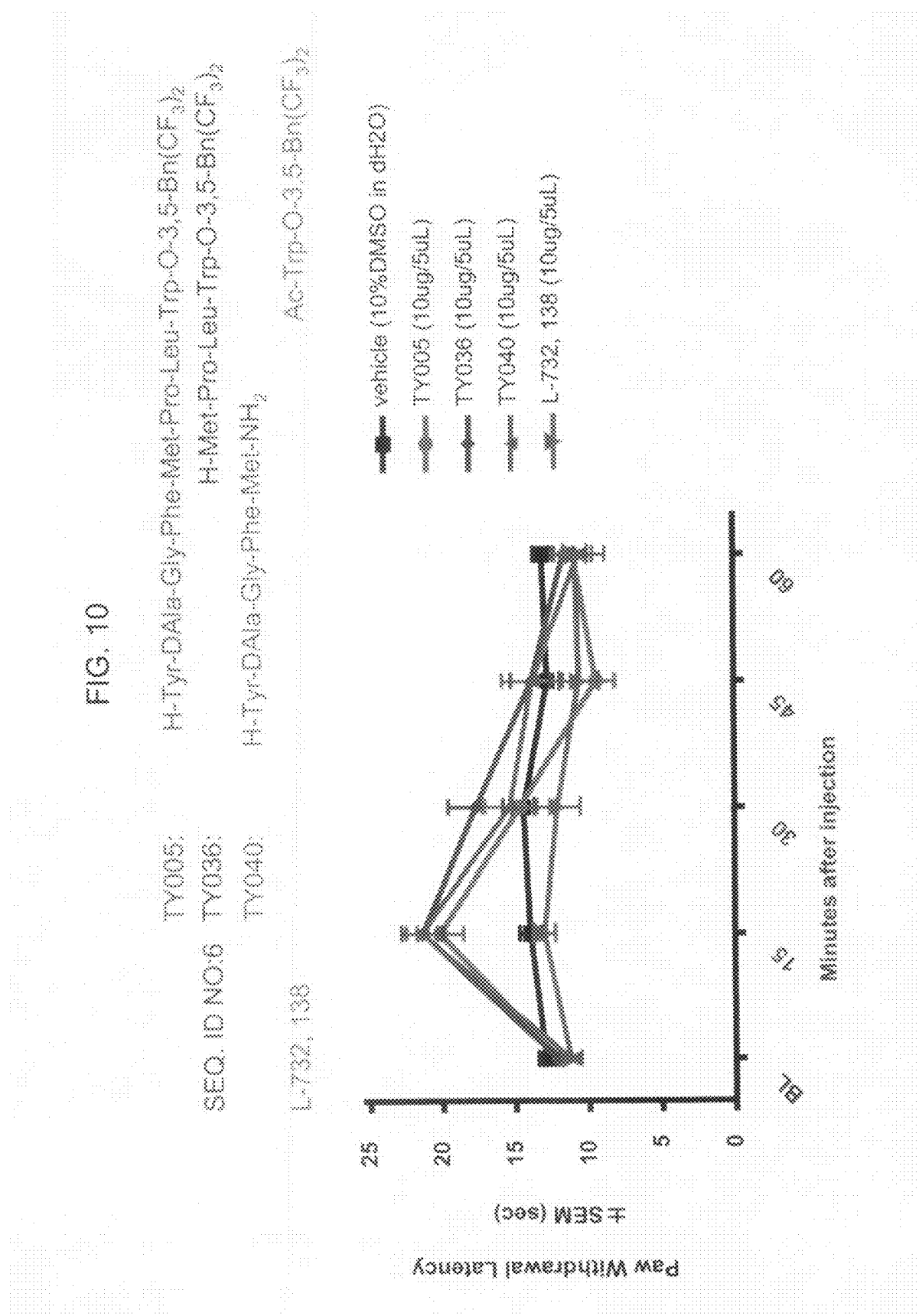

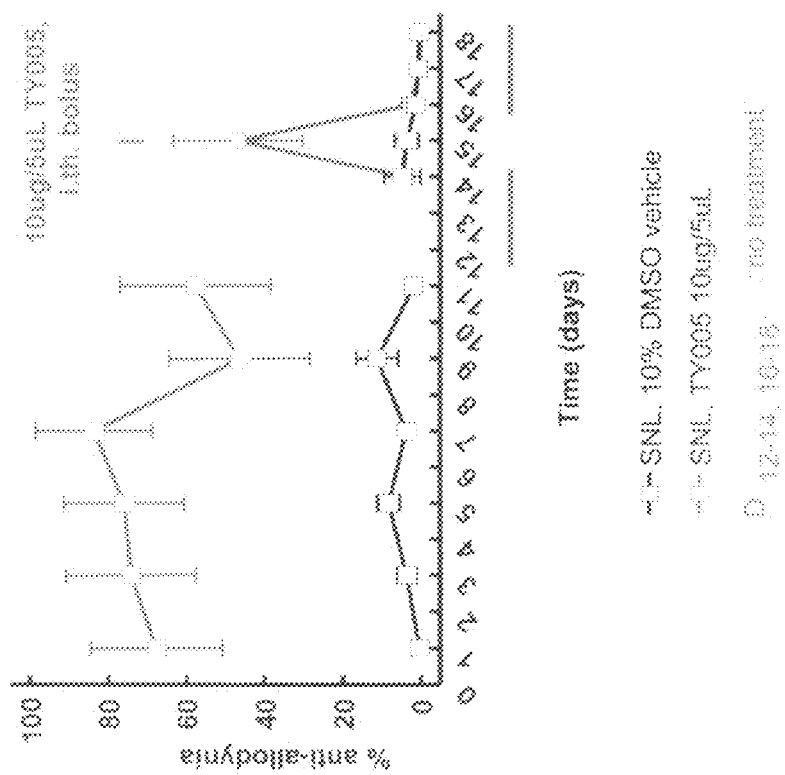
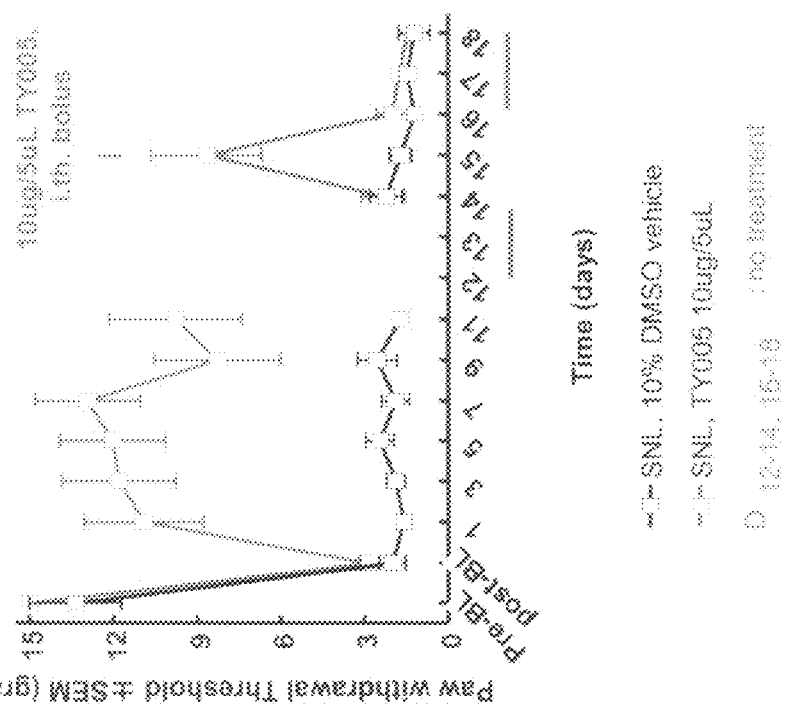

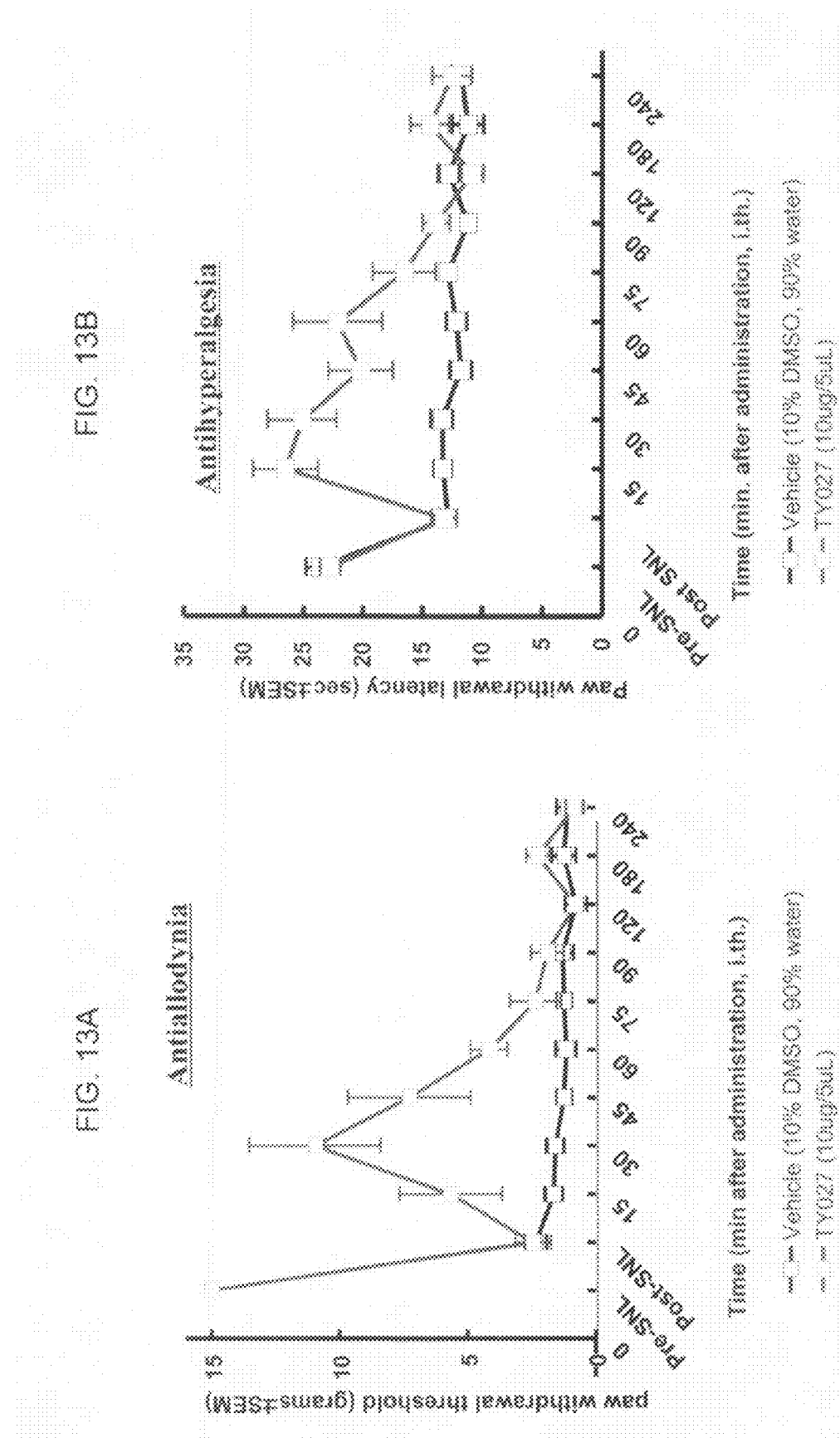

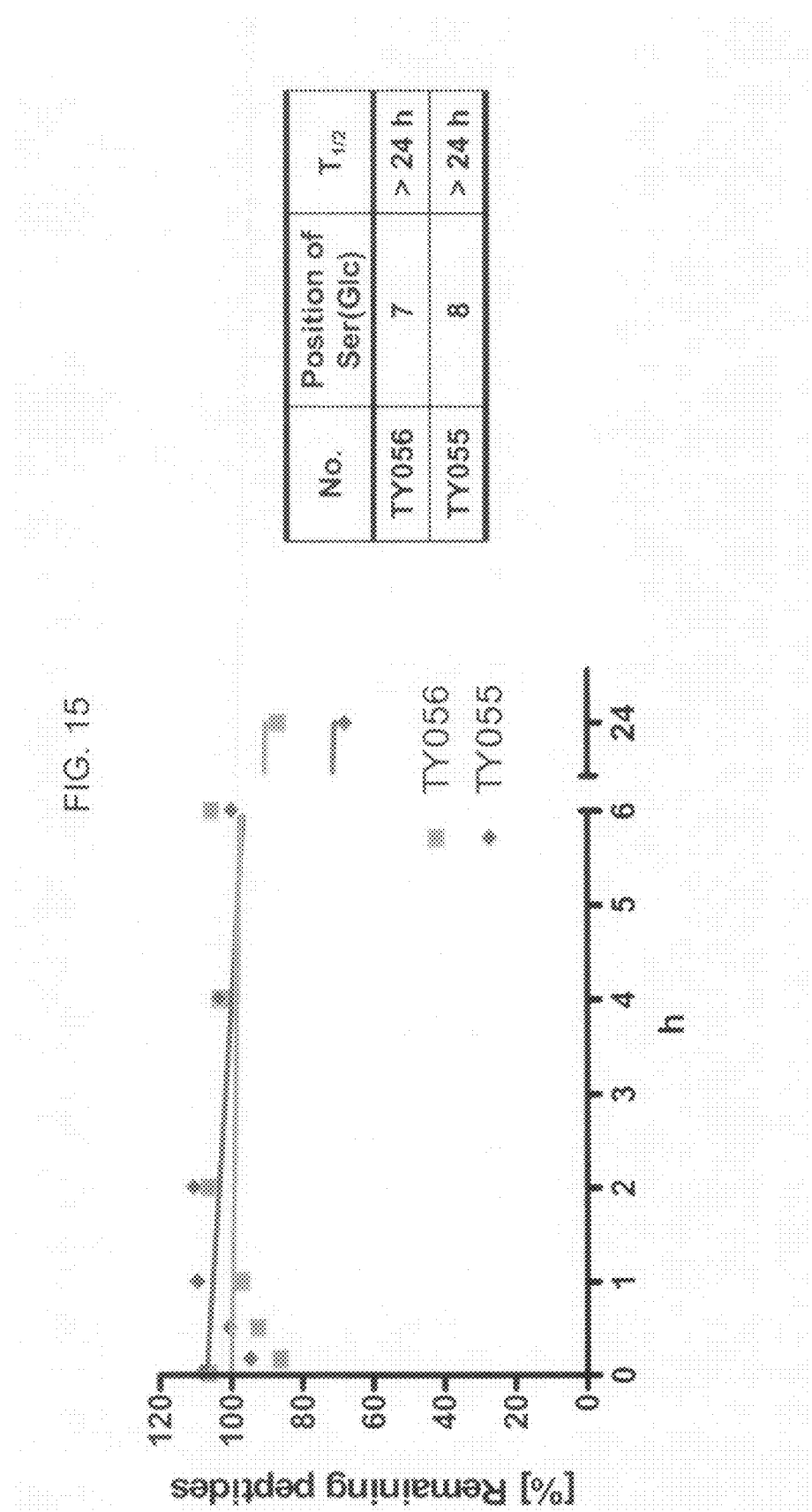

Conc. of TY005 and TY043 in rat plasma after incubation of TY005 at 37°C

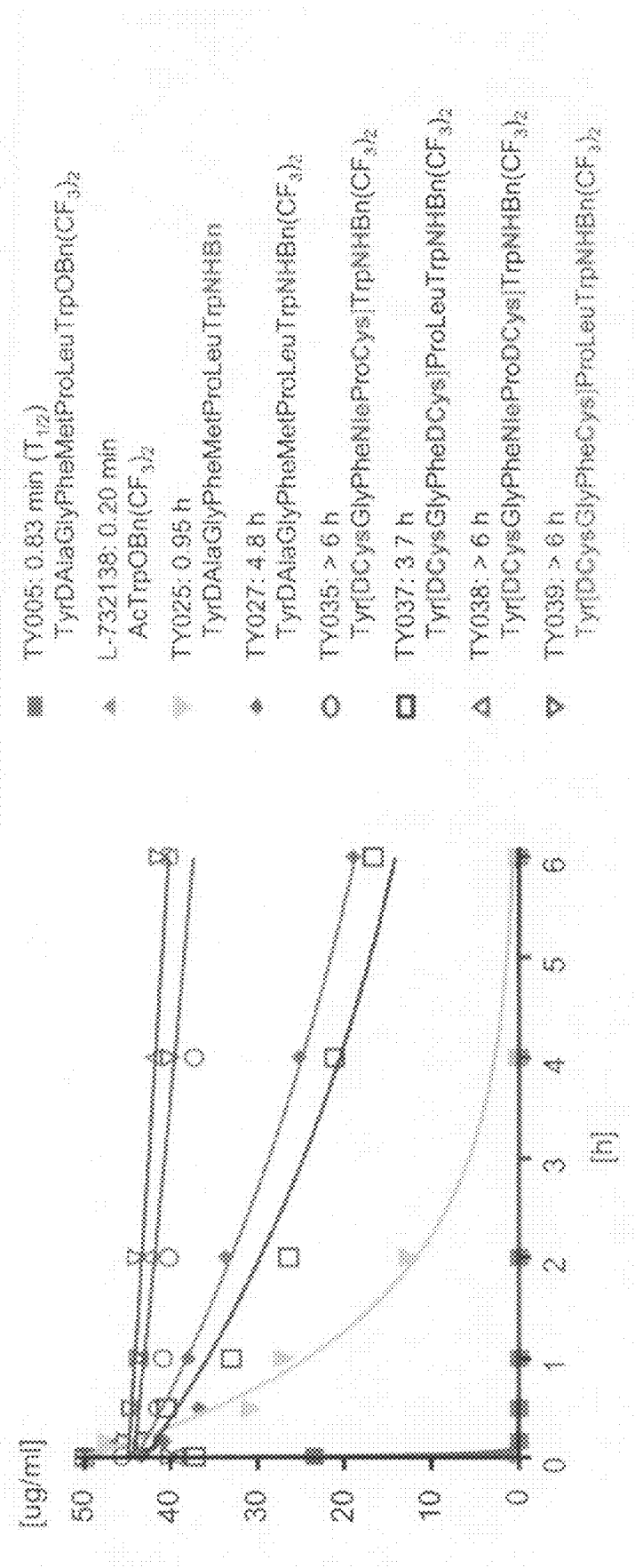

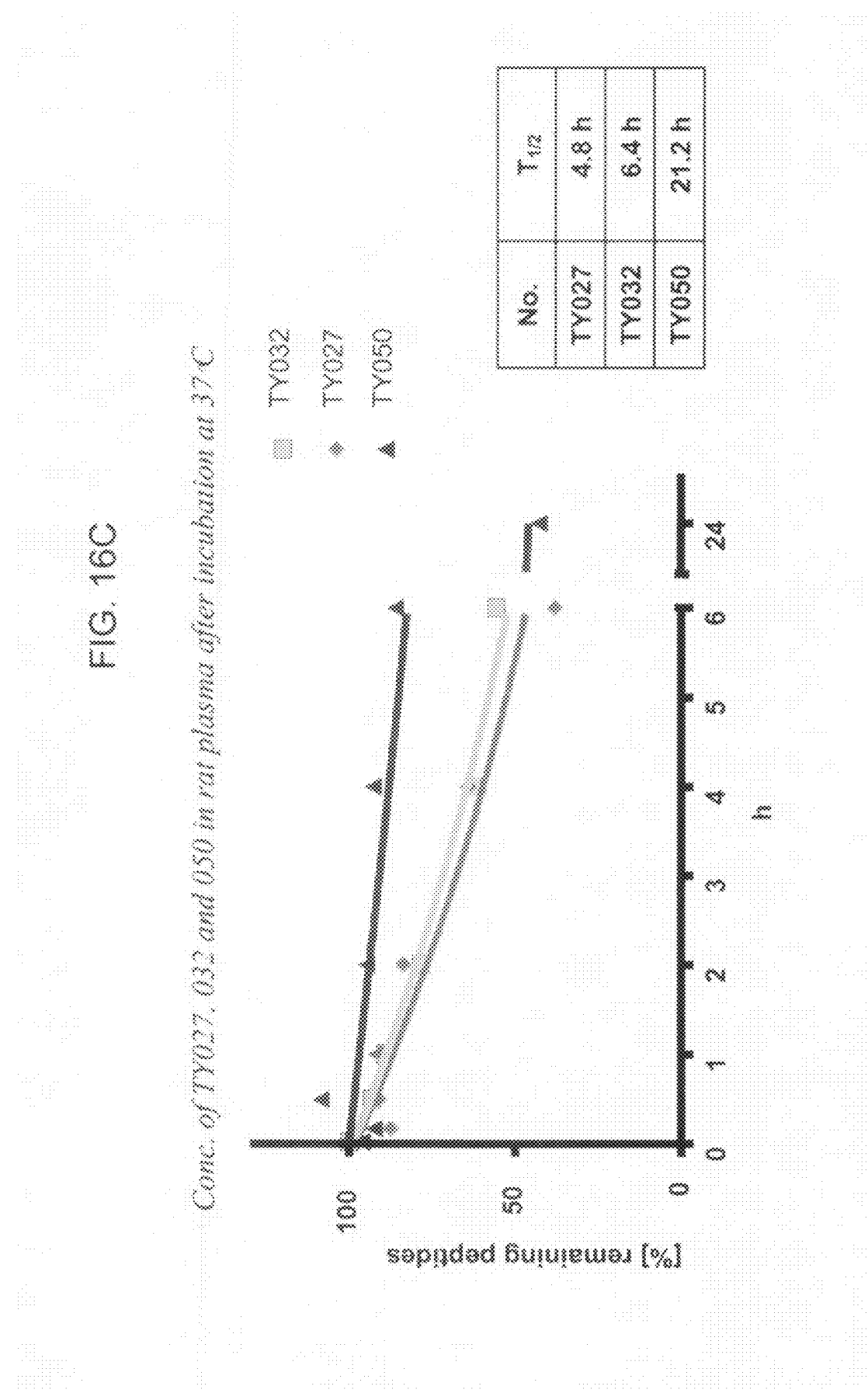

NMR structures of peptides
H-Tyr-DAla-Gly-Phe-Met-Pro-Leu-Trp-R

NMR structures of peptides
H-Tyr-DAla-Gly-Phe-Met-Pro-Leu-Trp-R

NMR structures of peptides
H-Tyr-DAla-Gly-Phe-Met-Pro-Leu-Trp-R

| No. | TY005 | TY027 | TY025 |
|---|---|---|---|
| C-terminal | O-Bn(CF$_3$)$_2$ | NH-Bn(CF$_3$)$_2$ | NH-Bn |
| No of NOE restraints | 136 | 155 | 184 |
| RMSD | 1.82±0.90 | 1.02±0.25 | 0.76±0.42 |
| Found β-turn | res 2-5 (type IV), res 6-9 (Type IV) | res 2-5 (type IV), res 6-9 (Type IV) | Helical |

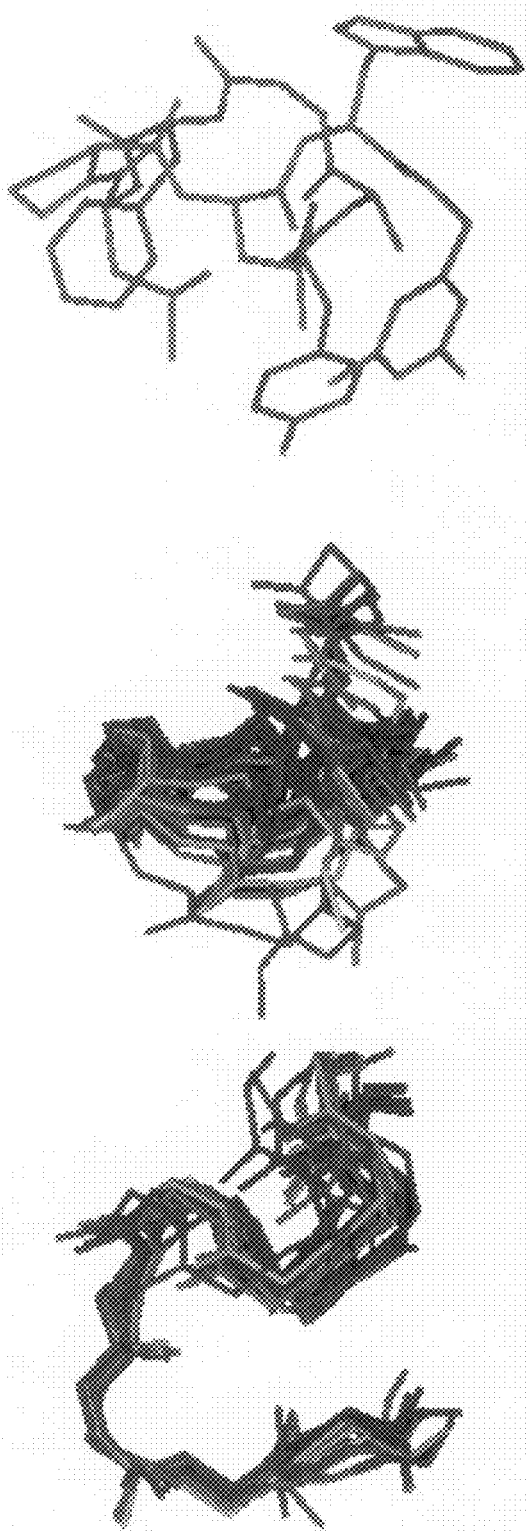

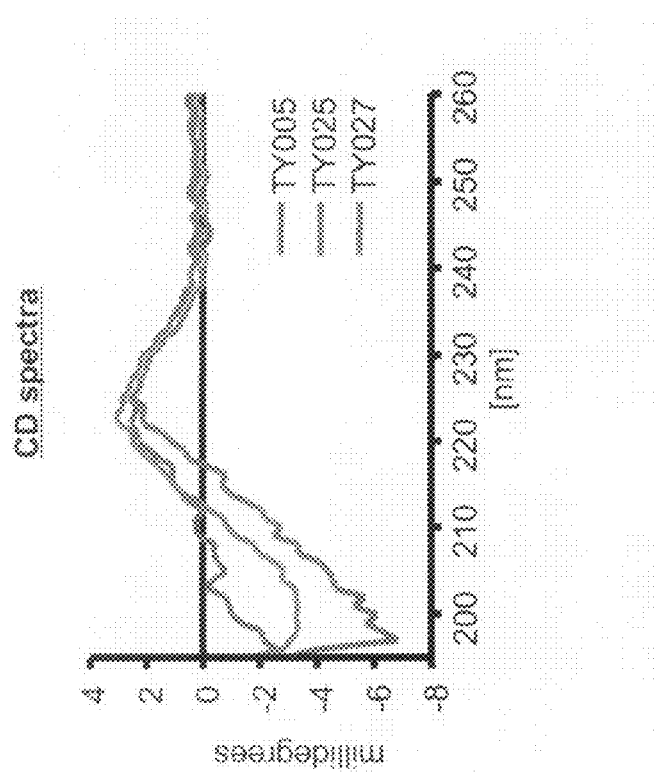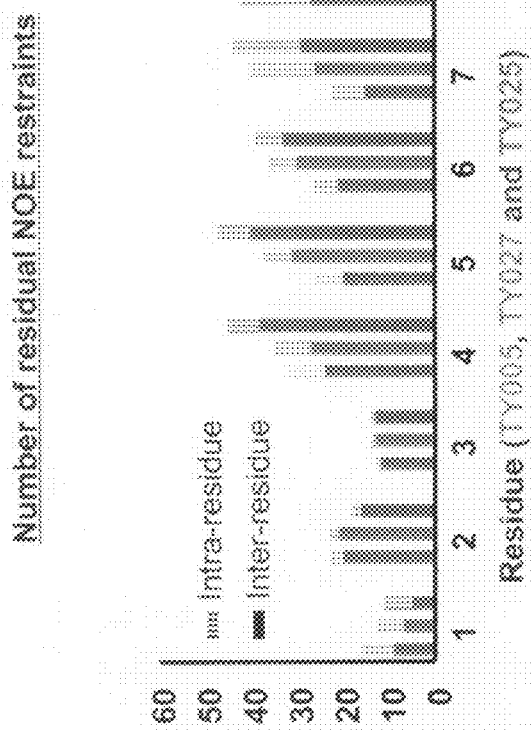
FIG. 18C
FIG. 18D

NMR structure of TY032
Dmt¹-DAla²-Gly³-Phe⁴-Met⁵-Pro⁶-Leu⁷-Trp⁸-NH-3,5-Bn(CF₃)₂

Restriction: NOE: 169
$^3J_{HN-H\alpha}$: 1
RMSD: 1.27±0.41

20 most stable confirmations aligned with backbone atoms of residue 5-8

NMR structure of TY037

H-Tyr-[DCys-Gly-Phe-DCys]-Pro-Leu-Trp-NH-3,5-Bn(CF₃)₂

Restriction: NOE: 224
³J$_{HN,Hα}$: 1
RMSD: 0.70±0.20

20 most stable confirmations aligned with backbone atoms of residue 5~8

NMR structure of TY041 in DPC micelle

| | TY041 |
|---|---|
| No. of NOE | 92 |
| RMSD | 0.52±0.19 |
| Struct. | [Ser(Glc)7] TY027 |
| Found β-turn | res 4-7 (Type I) res 6-9 (Type IV) |

NMR structure of TY044 in DPC micelle

| | TY044 |
|---|---|
| No. of NOE | 110 |
| RMSD | 2.33±0.18 |
| Struct. | [Ser(Glc)6] TY027 |
| Found β-turn | res 4-7 (Type IV), res 5-8 (Type I), res 6-9 (Type I) |

NMR structure of TY042 in DPC micelle

| | TY042 |
|---|---|
| No. of NOE | 101 |
| RMSD | 1.23±0.46 |
| Struct. | [Ser(Glc)5] TY027 |
| Found β-turn | res 2-5 (Type IV), res 5-8 (Type IV), res 6-9 (Type IV) |

NMR and CD data of TY041, 42 and 44

NMR and CD data of TY041, 42 and 44

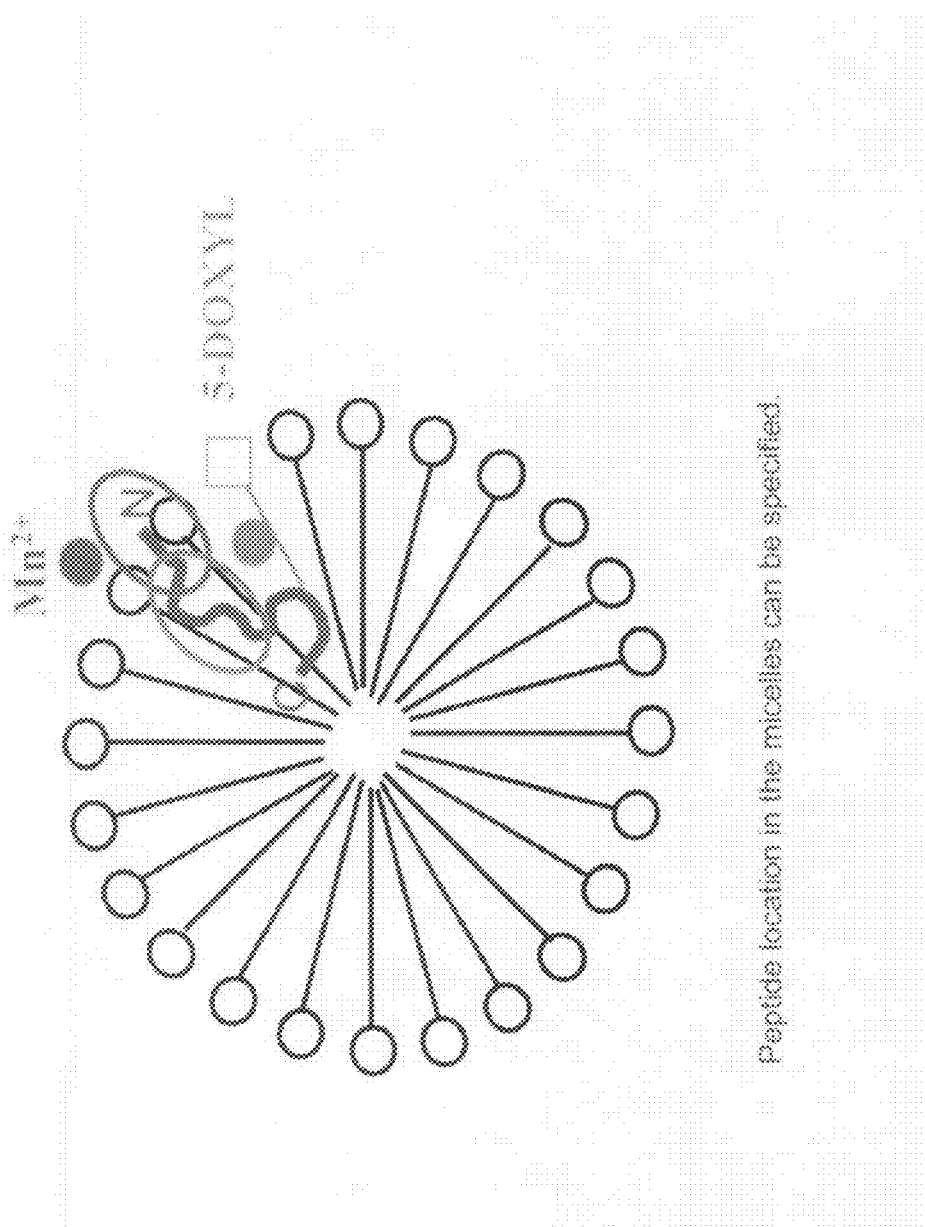

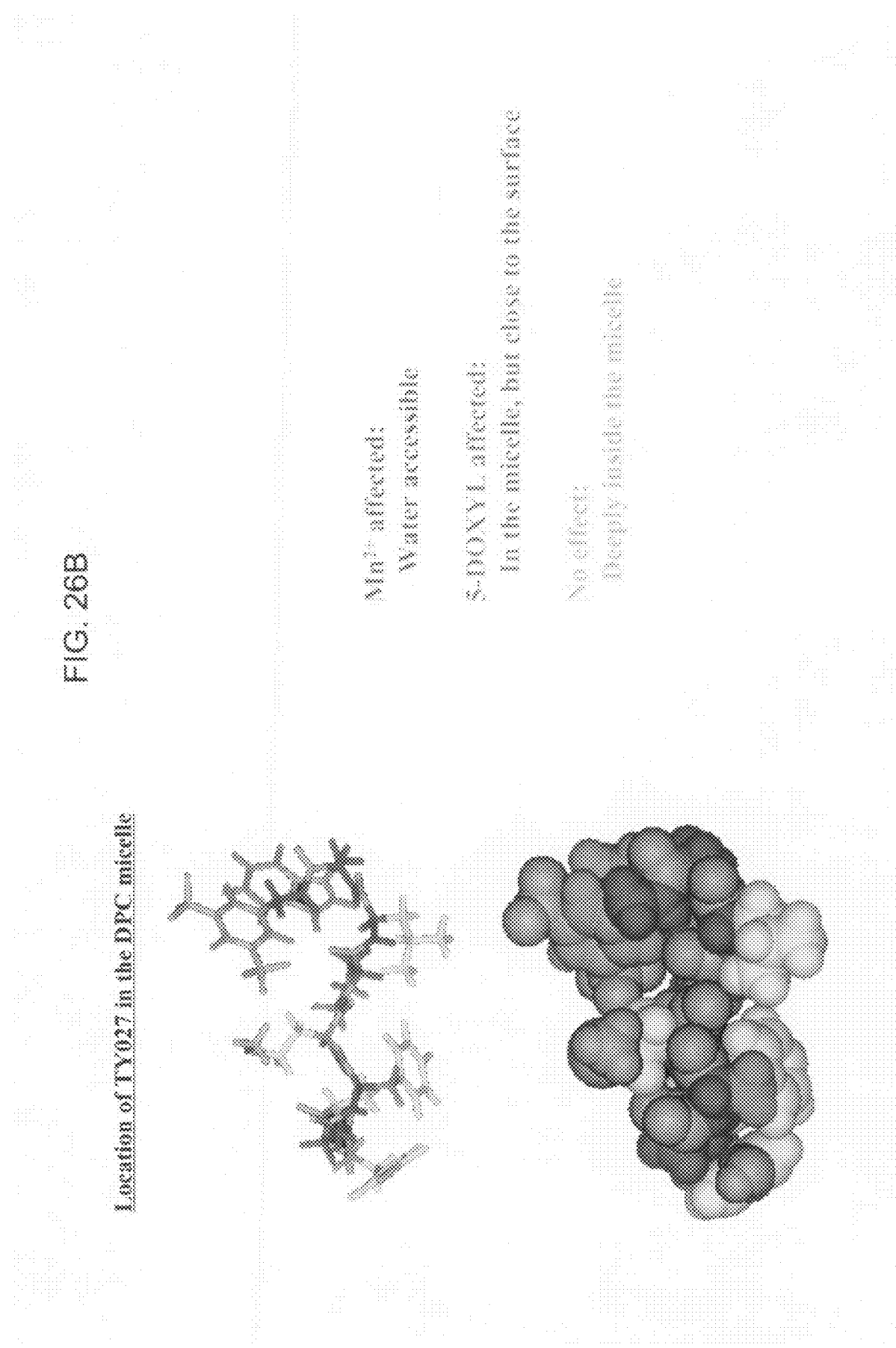

FIG. 27A
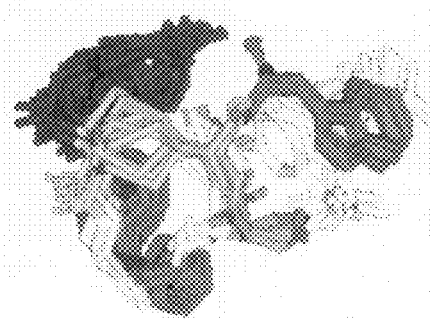
NMR structures of cyclic peptides
| No. | TY037 |
|---|---|
| No of NOE | 224 |
| RMSD | 0.18 ± 0.18 |
| Struct. | [DCys2,DCys5] TY027 |
| Found β-turn | res 2-5 (Type IV), res 5-8 (Type I), res 6-9 (Type I) |
FIG. 27B
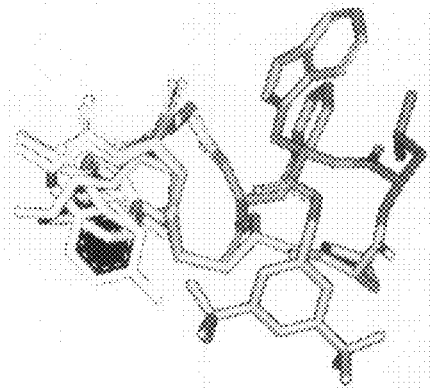
NMR structures of cyclic peptides
| No. | TY035 |
|---|---|
| No of NOE | 141 |
| RMSD | 0.71 ± 0.15 |
| Struct. | [DCys2, Cys7] TY027 |
| Found β-turn | res 1-4 (Type IV), res 2-5 (Type IV), res 3-6 (Type VIII), res 5-8 (Type IV) |
FIG. 27C
NMR structures of cyclic peptides
| No. | TY038 |
|---|---|
| No of NOE | 174 |
| RMSD | 0.92 ± 0.33 |
| Struct. | [DCys2, DCys7] TY027 |
| Found β-turn | res 2-5 (Type IV), res 5-8 (Type IV) |

Location of cyclic peptides in the DPC micelle
TY035

Location of cyclic peptides in the DPC micelle
TY037

Location of cyclic peptides in the DPC micelle
TY038

NMR structures of cyclic peptides

| No. | TY056 |
|---|---|
| No of NOE | 146 |
| RMSD | 0.34 ± 0.23 |
| Struct. | [Dmt1, Ser(Glc)7] TY027 |
| Found β turn | Helical |

NMR structures of cyclic peptides

| No. | TY053 |
|---|---|
| No of NOE | 240 |
| RMSD | 0.45 ± 0.27 |
| Struct. | [Ser(Glc)8, Trp9] TY027 |
| Found β turn | res 2-5 (Type IV), res 7-10 (Type IV) |

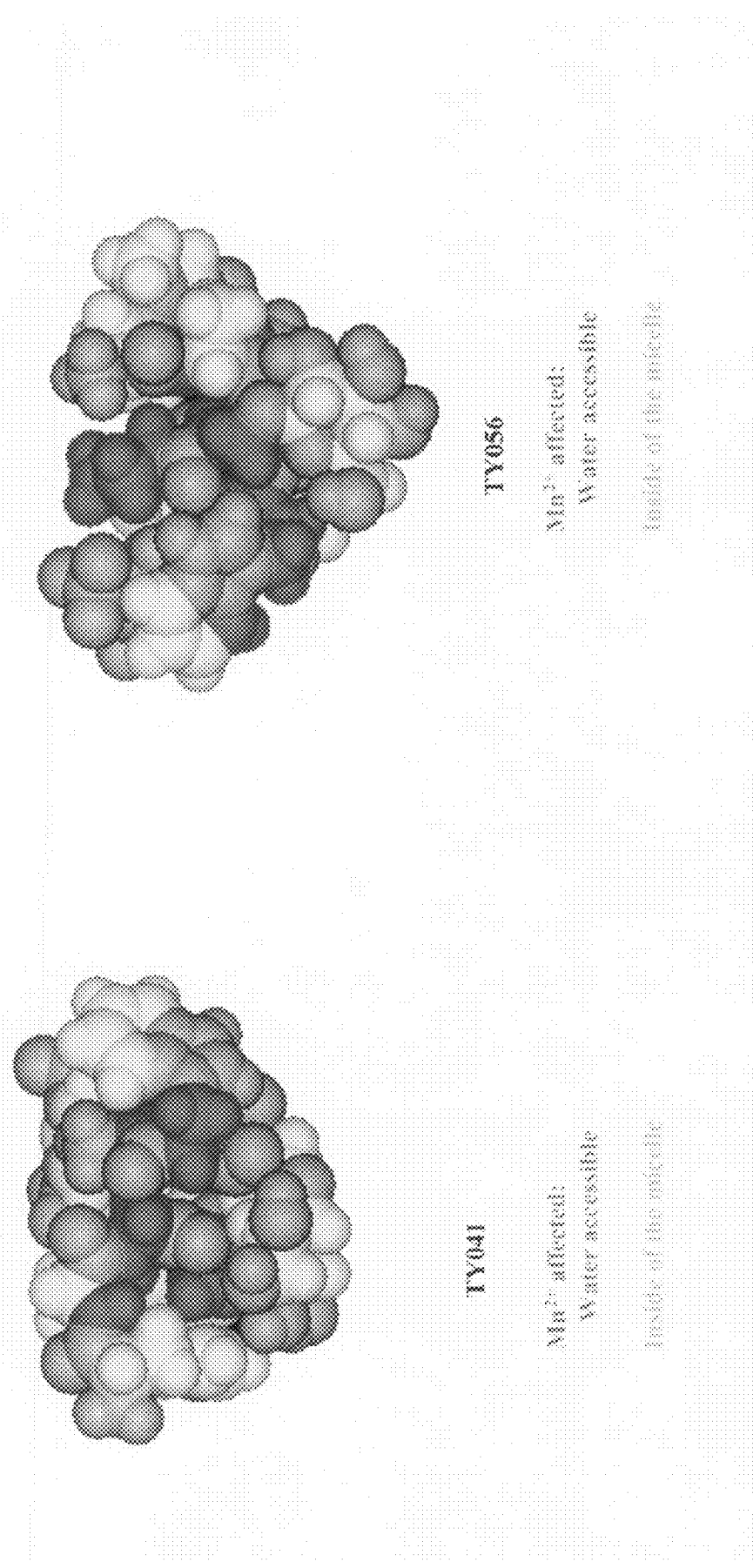

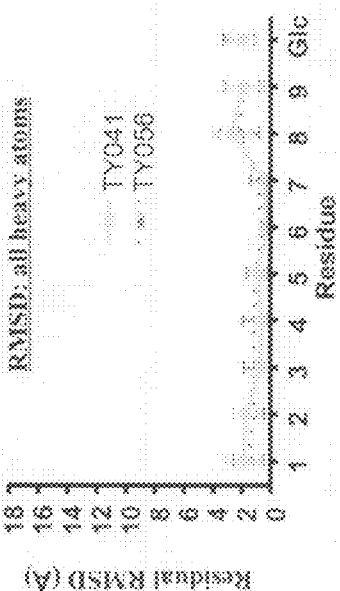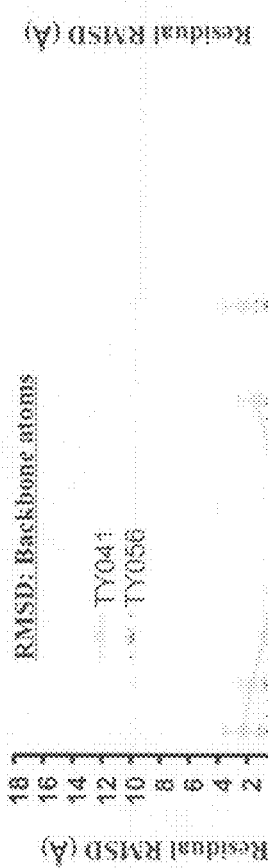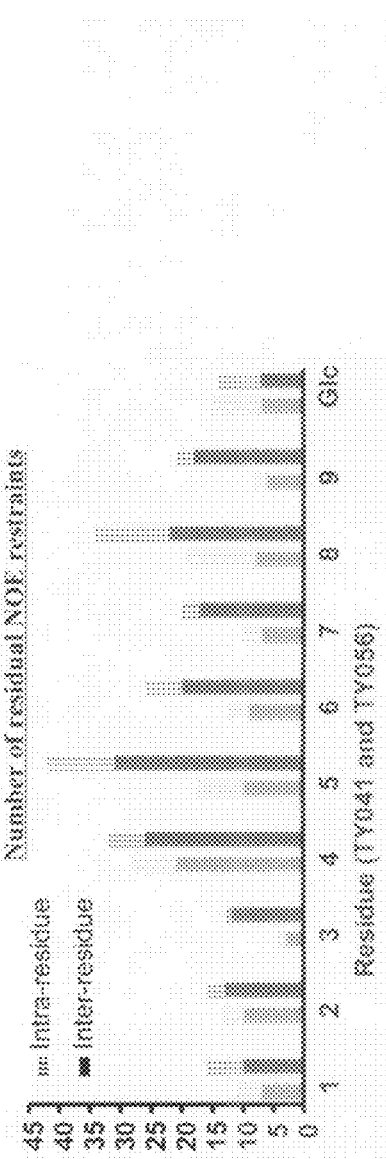
FIG. 29A NMR data of TY041 and 56 RMSD: Backbone atoms
FIG. 29B NMR data of TY041 and 56 RMSD: all heavy atoms
FIG. 29C NMR data of TY041 and 56 Number of residual NOE restraints

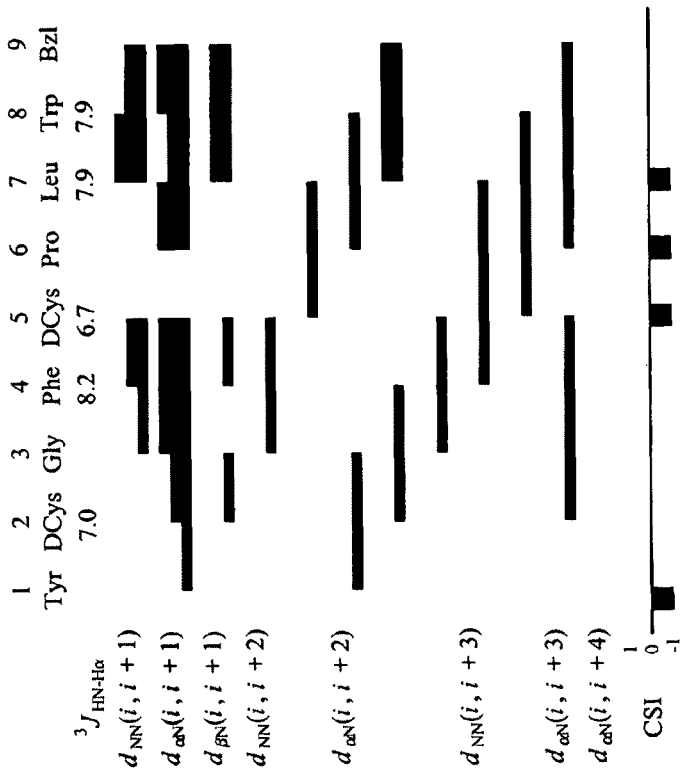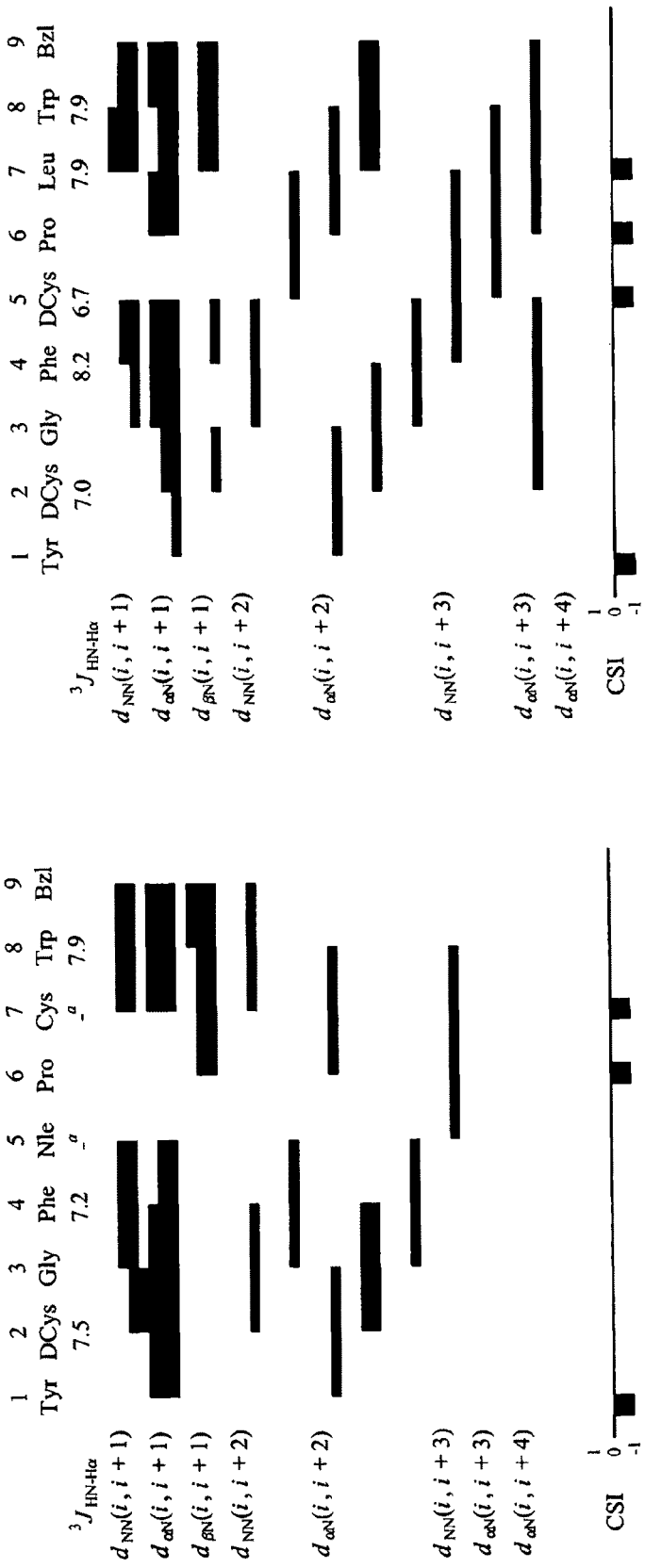
FIG. 32A
FIG. 32B

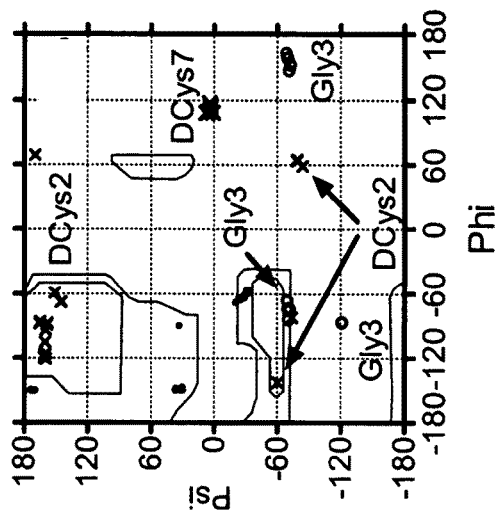
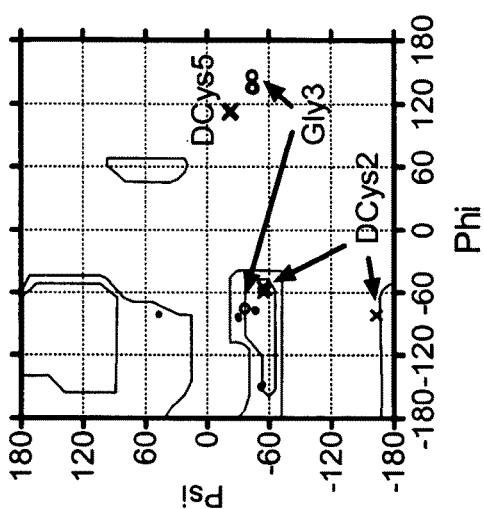
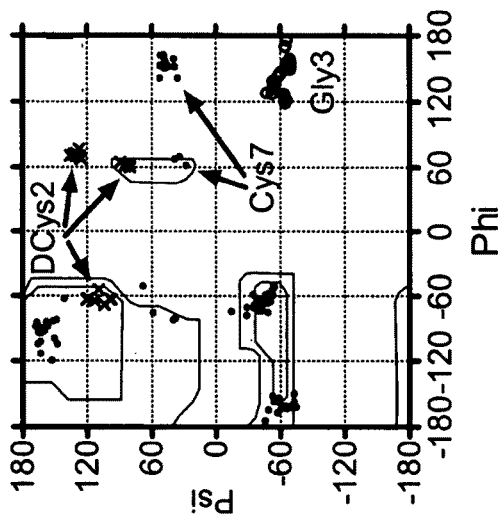

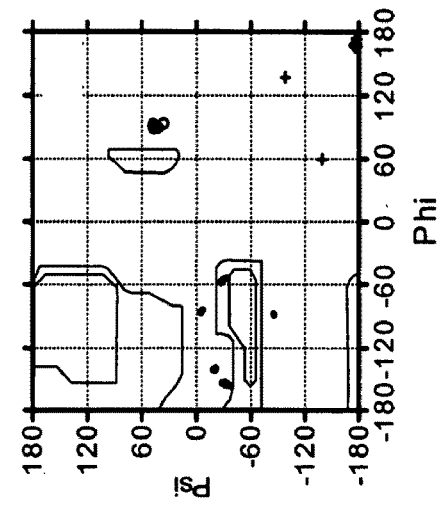
FIG. 40A
FIG. 40B
FIG. 40C
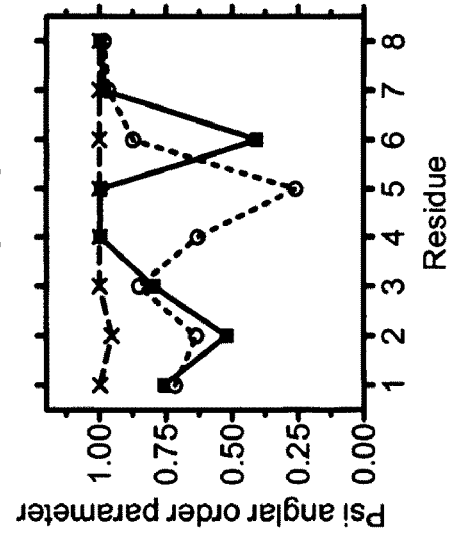
FIG. 40D
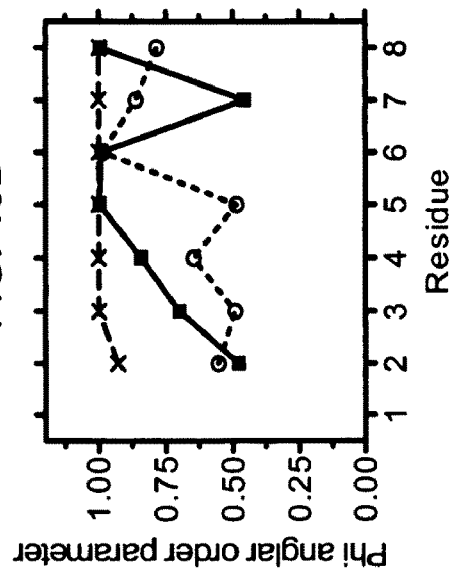
FIG. 40E

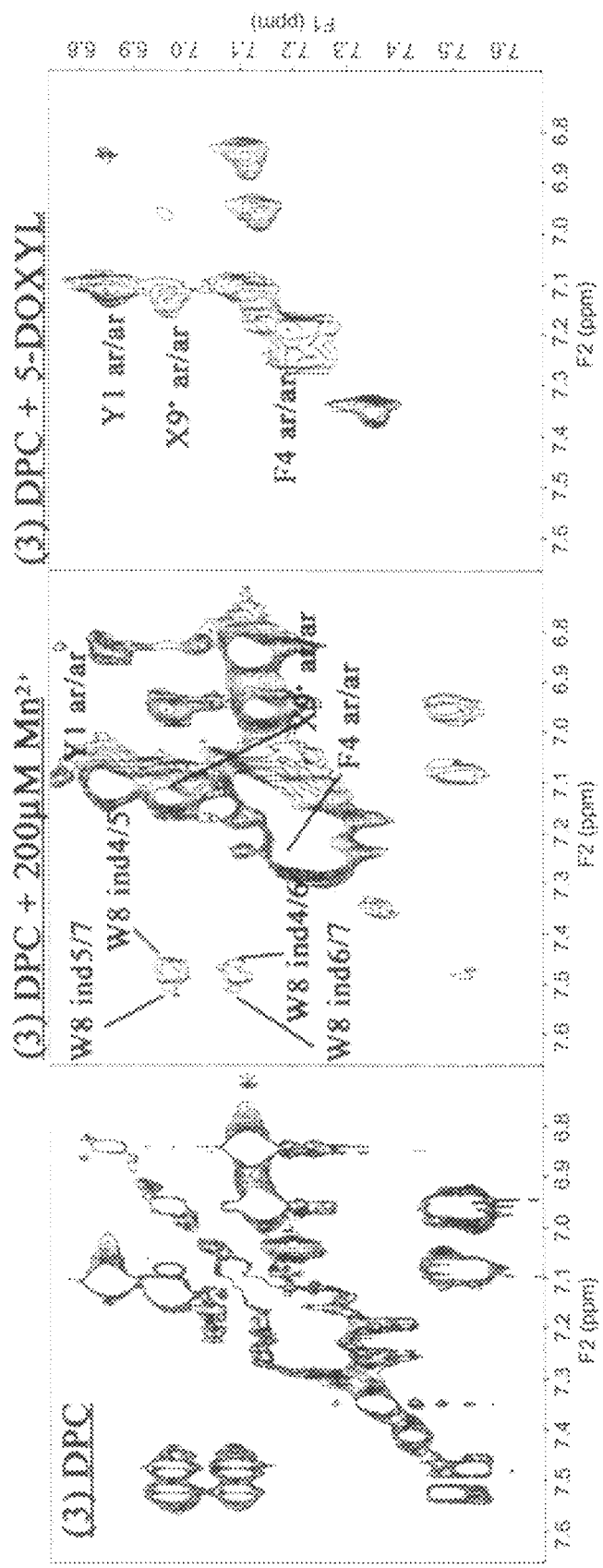

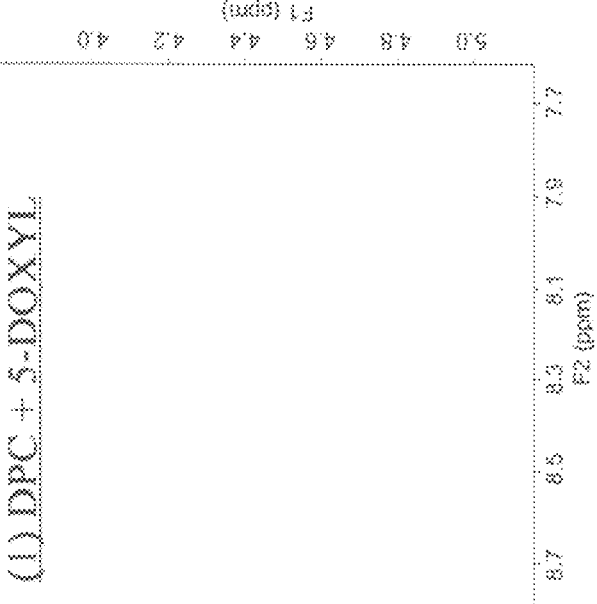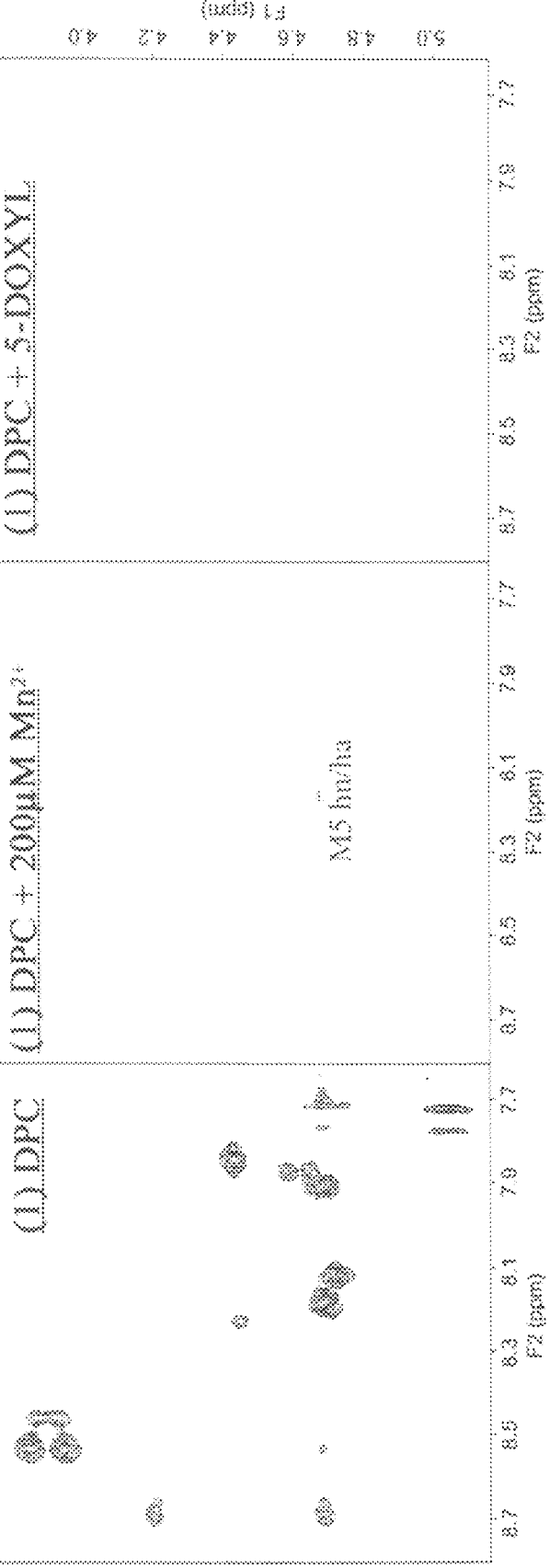

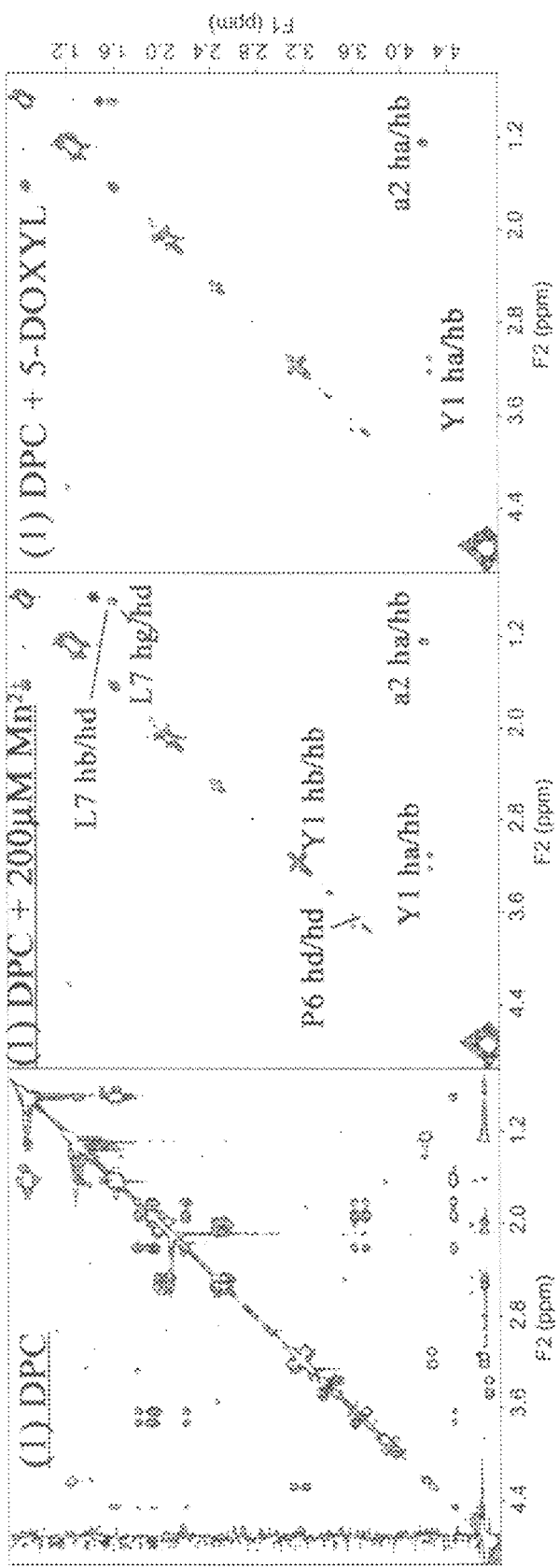

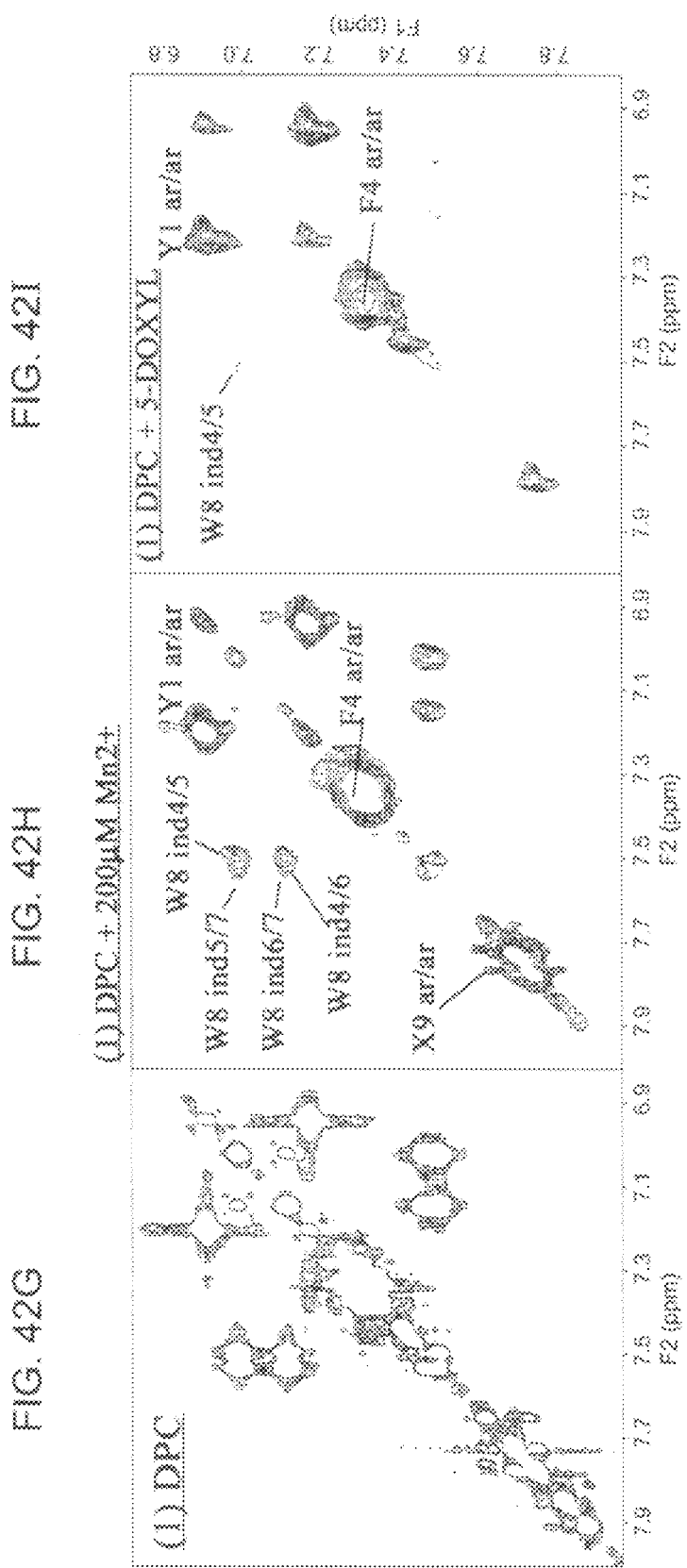

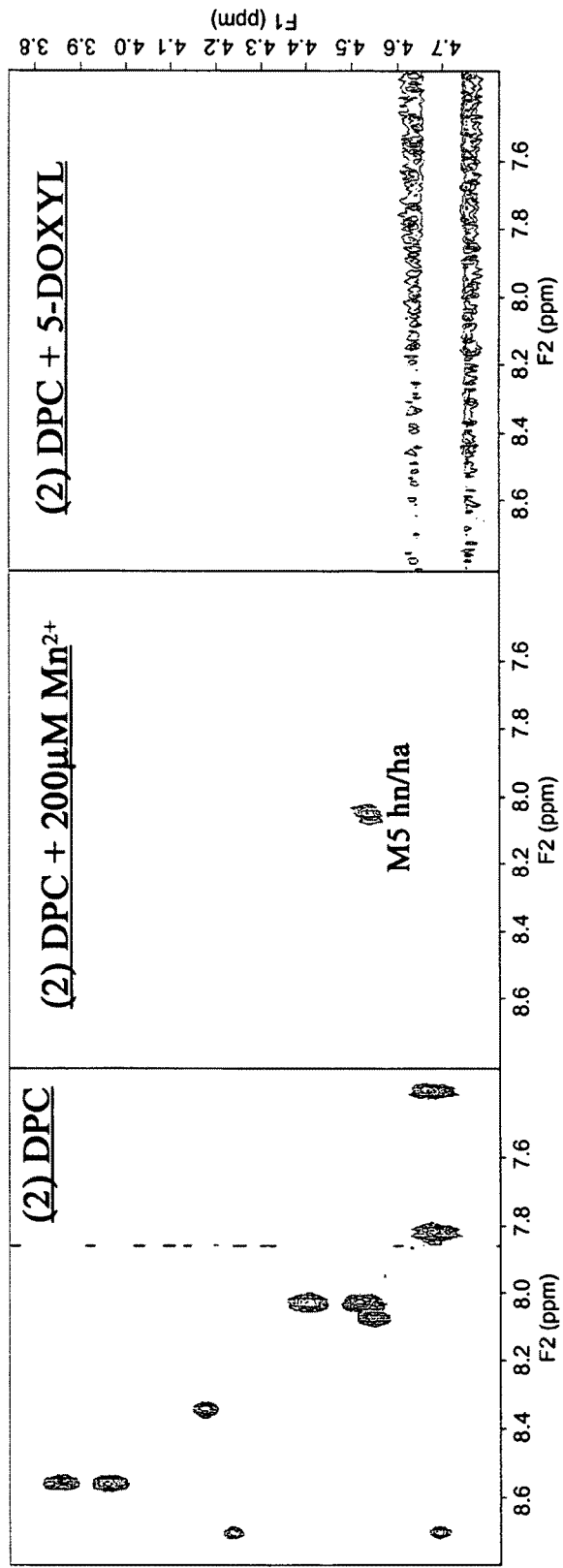

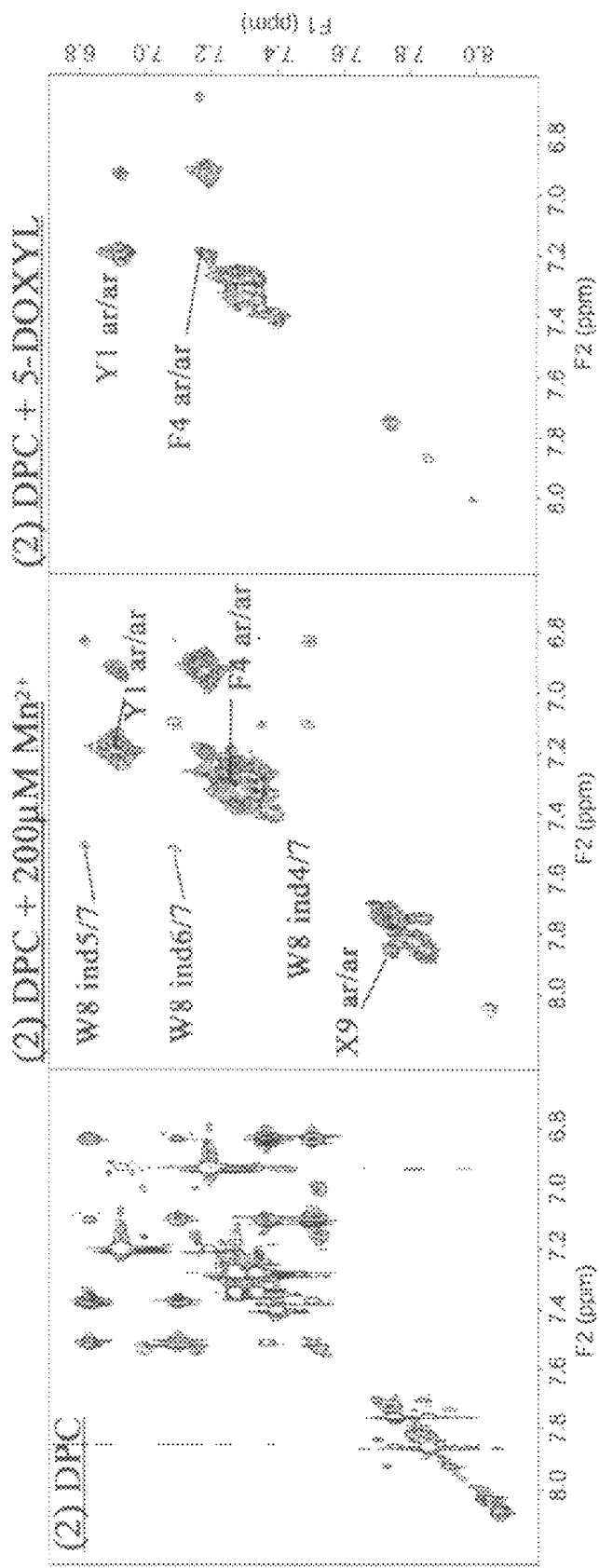

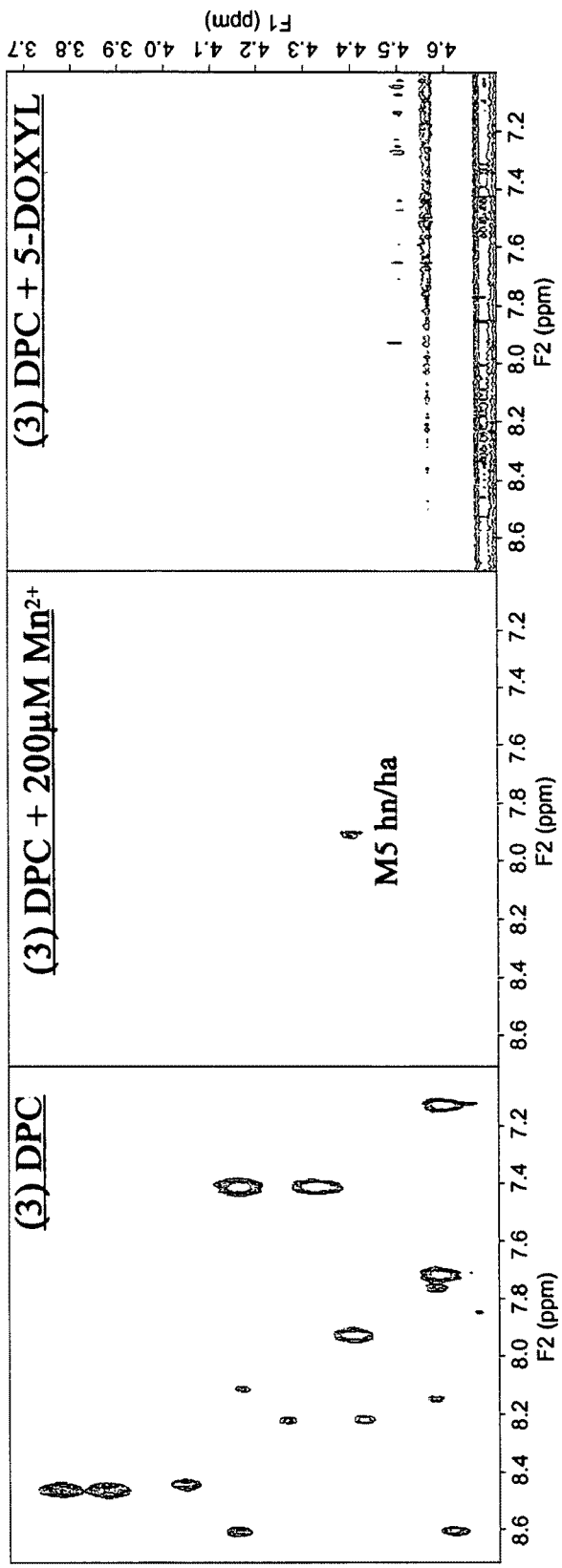

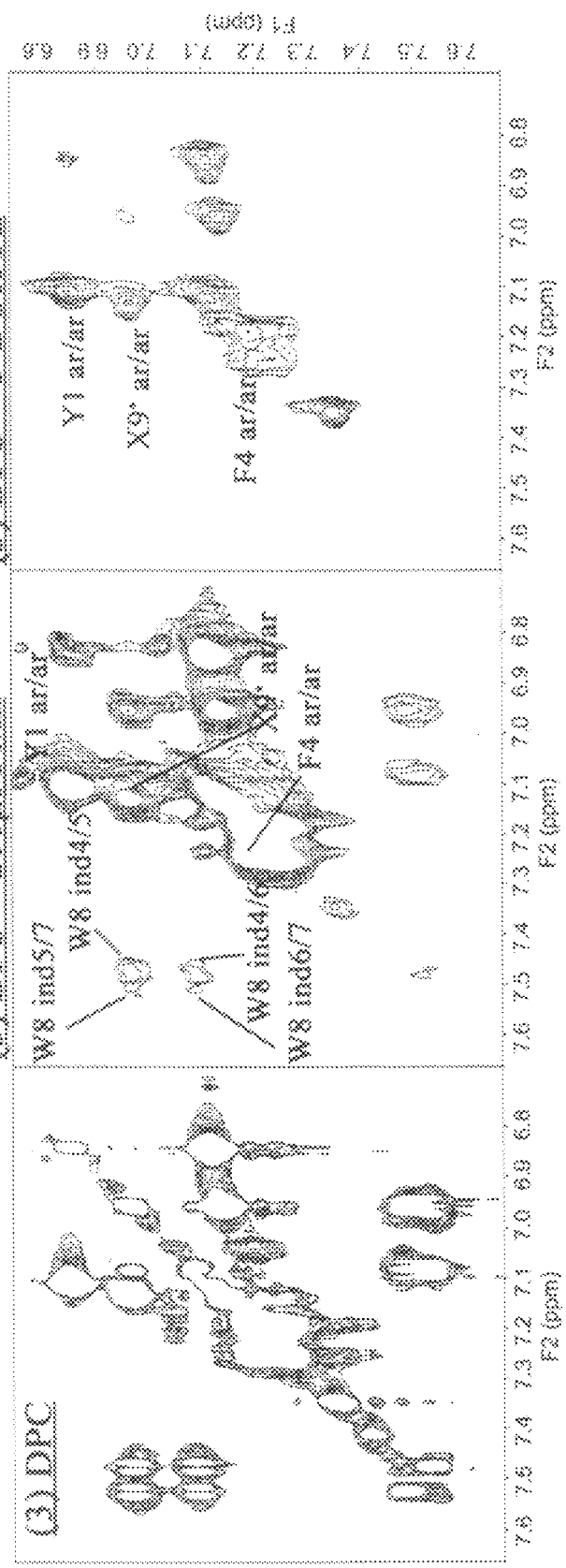

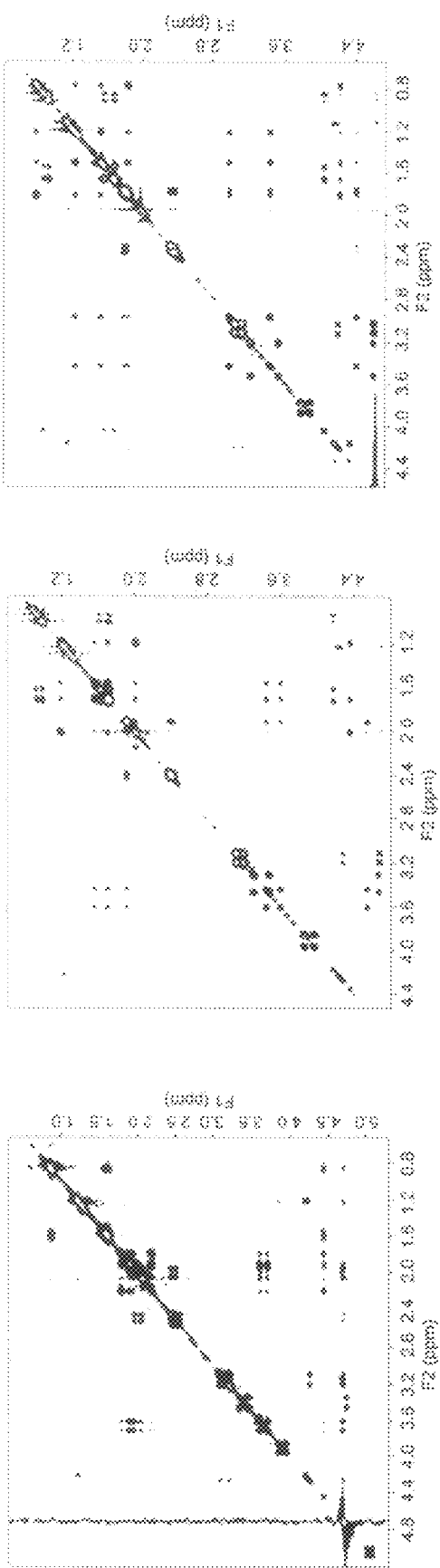

```
                        SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Pro Phe Phe Pro Leu Met
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Pro Phe Phe Gly Leu Met
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Pro Leu Trp
 1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Gly Phe Leu
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Gly Gly Phe Met
 1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Pro Leu Trp
 1

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, substituted Tyr or absent
<220> FEATURE:
<221> NAME/KEY: MOD_RES
<222> LOCATION: (2)..(2)
<223> OTHER INFORMATION: Gly, any D-amino acid or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Phe, substituted Phe or absent
<220> FEATURE:
<221> NAME/KEY: MOD_RES
<222> LOCATION: (5)..(5)
<223> OTHER INFORMATION: Phe, Leu, Met, Gly, DPhe, Nle, Nle(alkyl or a
      substituted alkyl), DCys, Cys, Ser(O-sugar), substituted Cys,
      substituted DCys or absent
<220> FEATURE:
<221> NAME/KEY: MOD_RES
<222> LOCATION: (6)..(6)
<223> OTHER INFORMATION: Pro, Ala, DLeu, DPro, Ser(O-sugar), Aib or
      absent
<220> FEATURE:
<221> NAME/KEY: MOD_RES
<222> LOCATION: (7)..(7)
<223> OTHER INFORMATION: Leu, Cys, DCys, Ser(O-sugar), Pen, DPen, Ala,
      DAla, beta Ala, alpha Abu, gamma Abu, Ava, Aib or absent
<220> FEATURE:
<221> NAME/KEY: MOD_RES
<222> LOCATION: (8)..(8)
<223> OTHER INFORMATION: Ser(O-sugar) or absent
<220> FEATURE:
<223> OTHER INFORMATION: C-terminus may be O, NH, N-alkyl or substituted
      alkyl benzyl or substituted benzyl
<220> FEATURE:
<223> OTHER INFORMATION: see specification as filed for detailed
      description of substitutions and preferred embodiments
```

```
<400> SEQUENCE: 7

Xaa Xaa Xaa Xaa Xaa Xaa Xaa Xaa Trp
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Dmt or absent
<220> FEATURE:
<221> NAME/KEY: MOD_RES
<222> LOCATION: (2)..(2)
<223> OTHER INFORMATION: Gly, DAla, DCyc, DPhe or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Phe, pClPhe, pFPhe, pBrPhe, DPhe or absent
<220> FEATURE:
<221> NAME/KEY: MOD_RES
<222> LOCATION: (5)..(5)
<223> OTHER INFORMATION: Phe, Leu, Met, Gly, DPhe, Nle, Nle(NMe), DCys,
      Cys, Ser(OGlc), Pen, DPen or asbsent
<220> FEATURE:
<221> NAME/KEY: MOD_RES
<222> LOCATION: (6)..(6)
<223> OTHER INFORMATION: Pro, Ala, DLeu, DPro, Ser(OGlc), Aib or absent
<220> FEATURE:
<221> NAME/KEY: MOD_RES
<222> LOCATION: (7)..(7)
<223> OTHER INFORMATION: Leu, Cys, DCys, Ser(OGlc), Pen, DPen, Ala,
      DAla, beta Ala, alpha Abu, gamma Abu, Ava, Aib or absent
<220> FEATURE:
<221> NAME/KEY: MOD_RES
<222> LOCATION: (8)..(8)
<223> OTHER INFORMATION: Ser(OGlc) or absent
<220> FEATURE:
<223> OTHER INFORMATION: C-terminus may be O, NH, NMe, Bzl,
      3',5'-Bzl(CF3)2, Bzl-3'-(CF3), 3',5'-Bzl(OMe)2, Bzl-2',4'-(OMe)2
      or salts thereof
<220> FEATURE:
<223> OTHER INFORMATION: see specification as filed for detailed
      description of substitutions and preferred embodiments

<400> SEQUENCE: 8

Xaa Xaa Xaa Xaa Xaa Xaa Xaa Xaa Trp
 1               5
```

BIFUNCTIONAL ANALGESIC COMPOUNDS FOR OPIOID RECEPTOR AGONISTS AND NEUROKININ-1 RECEPTOR ANTAGONISTS

CROSS-REFERENCE TO RELATED APPLICATION

This application claims benefit of provisional applications 60/794,967, filed Apr. 26, 2006; 60/812,527, filed Jun. 9, 2006; 60/842,223, filed Sep. 5, 2006; 60/851,475, filed Oct. 13, 2006; 60/851,956, filed Oct. 16, 2006; and 60/925,296, filed Apr. 19, 2007.

STATEMENT REGARDING FEDERALLY SPONSORED RESEARCH OR DEVELOPMENT

This invention was made with government support under DA 06284 and RO1 DA013449 awarded by the U.S. Public Health Service, National Institutes of Health, and National Institute of Drug Abuse. The government has certain rights in the invention.

BACKGROUND OF THE INVENTION

1. Field of the Invention

The present invention relates generally to methods and composition for the treatment of pain, more specifically compounds, compositions comprising the compounds, and methods for acute and chronic pain relief and acute and chronic intervention for drug abuse.

2. Description of the Related Art

Opioids are still the main analgesics for both acute and chronic pain states in clinical medication. Pain is caused by a highly complex perception of an aversive or unpleasant sensation, and represents an integrated, complex, perception of noxious stimuli originating from somatic elements such as arms and legs and/or from visceral organs such as heart and liver. The opioid drugs are widely used following major surgery and to control pain of terminal diseases such as cancer, but its use is limited by several undesired side effects including nausea, vomiting, constipation, dizziness, system changes (neuroplasticity) due to prolonged pain or treatment by the opioid drugs and the development of tolerance and physical dependence, which mainly come through the μ opioid receptor (Ananthan, J. Med. Chem., 47:1400-12, 2004; Yaksh, Pain, 11:293-346, 1981; Ossipov, Biopolymers, 80:319-24, 2005). Because of these limitations, the search for the novel type of analgesics which have strong pain controlling effect without development of tolerance and/or physical dependence has been performed for decades (Gentilucci, Curr. Topics in Med. Chem., 4:19-38, 2004).

Opiates work in the brain at specific "opiate receptors." Several types of the opiate receptors are known, but the main receptor is called μ receptor. Administering receptor agonists can cause full or partial stimulation or effect at the receptor, while administering antagonists blocks the effect of the receptor. It is widely accepted that a μ receptor agonist such as morphine has higher antinociceptive activity accompanied with high abuse liability. On the other hand, the activation of the δ opioid receptor has lower analgesic efficacy, but has reduced addictive potential (Kaslo, Eur. J. Pain, 9:131-5, 2005). It is also generally known that the selective agonists at the δ opioid receptor have analgesic activity in numerous animal models with fewer adverse effects, though their efficacy is less potent than that of their widely-used μ counterparts (Ananthan, J. Med. Chem., 47:1400-12, 2004; Yaksh, Pain, 11:293-346, 1981; Ossipov, Biopolymers, 80:319-24, 2005). Thus, selective δ opioid agonists with enhanced analgesic activity are expected as a potent drug candidate for severe pain control.

Substance P is the preferred ligand for the neurokinin 1 (NK1) receptor and is known to contribute to chronic inflammatory pain and participate in central sensitization and associated hyperalgesia. In the pain states, substance P, which is a 11-amino acid polypeptide, is known as a major neurotransmitter of pain signals as well as the signals induced by opioid stimulation (Ananthan, J. Med. Chem., 47:1400-12, 2004; Yaksh, Pain, 11:293-346, 1981; Ossipov, Biopolymers, 80:319-24, 2005). Substance P and NK1 receptor expression increases after sustained opioid administration. Also, repeated morphine exposure results in enhanced levels of substance P both in vitro and in vivo, which could induce increased pain; increased pain could require increased pain-relief and thus be manifested as "antinociceptive tolerance" (King, Neurosignals, 14:194-205, 2005). Interestingly, co-administration of δ/μ opioid agonists and a substance P antagonist showed enhanced antinociceptive effect in acute pain states, and in prevention of opioid-induced tolerance in chronic trials. These results suggest that the signals through opioid receptors and neurokinin 1 (NK1) receptors are not independent, but have strong and critical interaction. Moreover, the mice lacking NK1 receptors, the preferred receptor of substance P, didn't show rewarding properties for opiates (Ananthan, J. Med. Chem., 47:1400-12, 2004).

According to these observations, the use of multimodal combination analgesic therapies or therapies with single molecules possessing multiple analgesic targets has become attractive (Walker, Anesth. Analg., 95:674-715, 2002). Advantages of hybrid compounds system are developing bioactive compounds designed with a broad spectrum of receptor affinities and single administration of a chimeric compound instead of a specific ration of two different compounds. Table A below provides representative listing of opioid analgesics with respect to affinity for the opioid receptors and the NK1 receptor.

TABLE A

Previous Studies of Chimeric compounds

| Compounds | Sequence | Affinity (Ki in nM) | | |
|---|---|---|---|---|
| | | DOR | MOR | rNK1 |
| ESP6 | HTyrProPhePheProLeuMetNH2 (SEQ ID NO: 1) | — | 92 | 305 |
| ESP7 | HTyrProPhePheGlyLeuMetNH2 (SEQ ID NO: 2) | — | 218 | 289 |
| JSOH11 | HTyrDAlaDTrpPheDTrpLeuLeuNH2 | 16.5 | 164 | 7320 |
| JSOH9 | HTyrDAlaDPhePheDTrpLeuMetNH2 | 0.72 | 606 | 2940 |
| AA501 | HTyrDAlaGlyPheNHNHTrpCbz | — | 80 | 5000 |

Many classes of C-terminal modified compounds have attracted the inventors' interest, and a number of approaches to modifying the C-terminal have been reported (Sasubilli, J. Comb. Chem., 6:911-15, 2004; Alsina, Biopol., 71:454-77, 2003; Chan, Fmoc solid phase compound synthesis as practical approach, Oxford Univ. Press: New York, USA, 2000). These approaches can be classified into many categories including nucleophilic cleavage of protected compounds bound from appropriate resins, attachment with a C-terminal functional group, side chain anchoring followed by normal solid phase N-to-C peptide synthesis, backbone amide attachment onto a solid support, inverse C-to-N solid phase biopolymer synthesis, and conventional solution phase synthesis (Alsina, Biopolymers, 71:454-77, 2003). However, it is difficult to synthesize C-terminal esters or tertiary amides by the first two methods, and designed compounds didn't have a suitable side chain moiety to anchor on a resin. Repeated inverse C-to-N coupling leads to severe racemization, and conventional Boc solution phase compound synthesis is very labor intensive for large amounts of longer compounds.

The importance of interactions between biologically active compounds and membrane has become increasingly appreciated recently. The strong influence of these interactions on ligand activity, membrane permeability and toxicity has been increasingly clarified (Seydel, Drug-Membrane interaction; Wiley-VCH: Weinheim, Germany, 2003, pp. 1-31). Among these compounds, peptides function as transmitters of many unique and diverse biological signals which largely depend on their amino acid sequence, and their interactions with membrane localized receptor/acceptors. However, the signal transduction of compounds is made not by the primary sequence but by higher order dynamic three-dimensional conformations. Therefore, the changes in 3D structure and dynamics which are induced by the modification of primary sequence have been a long-term interest, since 3D structure and the dynamics have an influence on the biological properties. In fact, many G-protein coupled receptors (GPCRs), which are the typical membrane-bound proteins, generally have their ligand binding site in the hydrophobic trans-membrane (TM) domains (Berthold, Neurochem. Res., 22(8):1023-31, 1997; Noeskea, QSAR Comb. Sci., 25(2):134-146, 2006; Eguchi, Med. Res. Rev., 24(20): 182-212, 2004; Cascieri, J. Biol. Chem., 269:6587-91, 1994). Compound-membrane interaction also is very important when a compound penetrates membranes, such as the blood brain barrier (Seydel, Drug-Membrane Interaction; Wiley-VCH: Weinheim, Germany, 2003, pp. 1-31; Palian, J. Am. Chem. Soc., 125:5823-31, 2003). Hence, understanding of the membrane-bound structures of compounds and compound-membrane interactions is indispensable to obtain further insight into their diverse biological behaviors.

SUMMARY OF THE INVENTION

Activity of the known analgesics is biased for one of the receptors, and no molecule had sufficient and balanced activities for both of opioid and NK1 receptors. Therefore, the inventors designed and synthesized bifunctional molecules and salts thereof possessing the agonist activities for both δ/µ opioid receptors and NK1 receptor antagonist activities without development of tolerance.

The invention provides pharmaceutical compositions including chimeric compounds and a pharmaceutically acceptable carrier useful for the treatment of pain.

The inventors further combined solid phase and solution phase chemistry to develop a two-step combinatorial approach. In this method, a side chain-protected compound with a free C-terminal carboxylate was synthesized using a $N^\alpha$-Fmoc solid phase compound synthesis on a resin, followed by esterification or amidation in solution phase without any detectable racemization.

The invention also provides a method of treating pain by administering at least one chimeric compound capable of binding to both an opioid receptor and NK1 receptor admixed with a pharmaceutically acceptable carrier. The composition may be administered intrathecally (i.th.), intracerebroverticularlly (i.c.v.) or systemically, for example, intraperitoneally (i.p).

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only.

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIG. 9 A, B. Estimation of analgesic potency of bifunctional compounds: (A) anti-allodynic and (B) anti-hyperalgesic effects of bifunctional compound TY005 in L5/L6 SNL rats. Compound was administered via i.th. route and rats were tested by von Fray filament stimulation (A) and infrared radient heat (B). Each point represents the mean ±SEM with at least five rats.

FIG. 10. Estimation of anti-nociception of bifunctional compounds TY005, TY036, and TY040. Compound was administered via i.th. route and rats were tested by infrared radient heat. Each point represents the mean ± SEM with at least five rats. Figure discloses SEQ ID NO: 6.

FIG. 12 A, B. Chronic TY005 administration reverses mechanical allodynia in SNL-operated animals. (A) Paw withdrawal threshold, (B) % of anti-allodynia.Compound was administered via i.th. route and rats were tested by von Fray filament stimulation. Each point represents the mean ± SEM with at least five rats.

FIG. 13 A, B. Antiallodynic and antihyperalgesic effect of TY027 in SNL-operated rats after acute administration. Compound was administered via i.th. route and rats were tested by von Fray filament stimulation (A) and infrared radient heat (B). Each point represents the mean ±SEM with at least five rats.

FIG. 26 A, B. NMR studies using paramagnetic agents ($Mn^{2+}$ and 5-DOXYL stearic acid). (A) general model. (B) Location of TY027 in the DPC micelle.

FIG. 29 A-C. Structural rigidity of TY041 and TY056. (A) RMSD: backbone atom; (B) RMSD: all heavy atoms; (C) Number of residues NOE restrains.

FIG. 40 A-E. The D-Ala$^2$ (crosses), Gly$^3$ (open circle) and Met$^5$ with positive $\phi$ angles (circled) were indicated in the Ramachandran $\phi,\psi$ plots for (A) TY005, (B) TY027 and (C) TY025 for residues 2-7 of 20 final structures. Angular order parameters for $\phi$ (D) and $\psi$ (E) angles calculated from the 20 final structures for TY005 (open circles), TY027 (filled squares) and TY025 (crosses). For calculating the $\psi$ angles of Trp$^8$, Non-carbonyl oxygen atoms of the C-terminal ester (TY005) and nitrogen atoms of C-terminal amide (TY027 and TY025) were used instead of N (i+3), respectively.

FIG. 41 A, B, C. Typical example of the paramagnetic effects on TOCSY Spectra. The aromatic region of TY025 with DPC micelles (A), with 200 μM Mn$^{2+}$ (B) and 5-DOXYL stearic acid (C). Preserved resonances (labeled) are in a phase not missed by the phase-specific radical probe (Mn$^{2+}$ or DOXYL). Spectra were compared from the same noise level.

FIG. 42 A-I. Effect of Radicals on TOCSY Spectra. TY005 with DPC micelles (A, D, and G), with 200 μM Mn$^{2+}$ (B, E, and H) and 5-DOXYL stearic acid (C, F, and I). Preserved resonances (labeled) are in a phase not missed by the phase-specific radical probe (Mn$^{2+}$ or DOXYL). X9 represents the cross-peaks derived from the corresponding aromatic protons of benzyl moiety. The resonances with asterisk (*) are DPC or 5-DOXYL derived ones. Spectra were compared from the same noise level.

DETAILED DESCRIPTION OF THE PREFERRED EMBODIMENTS

Figure 1A:
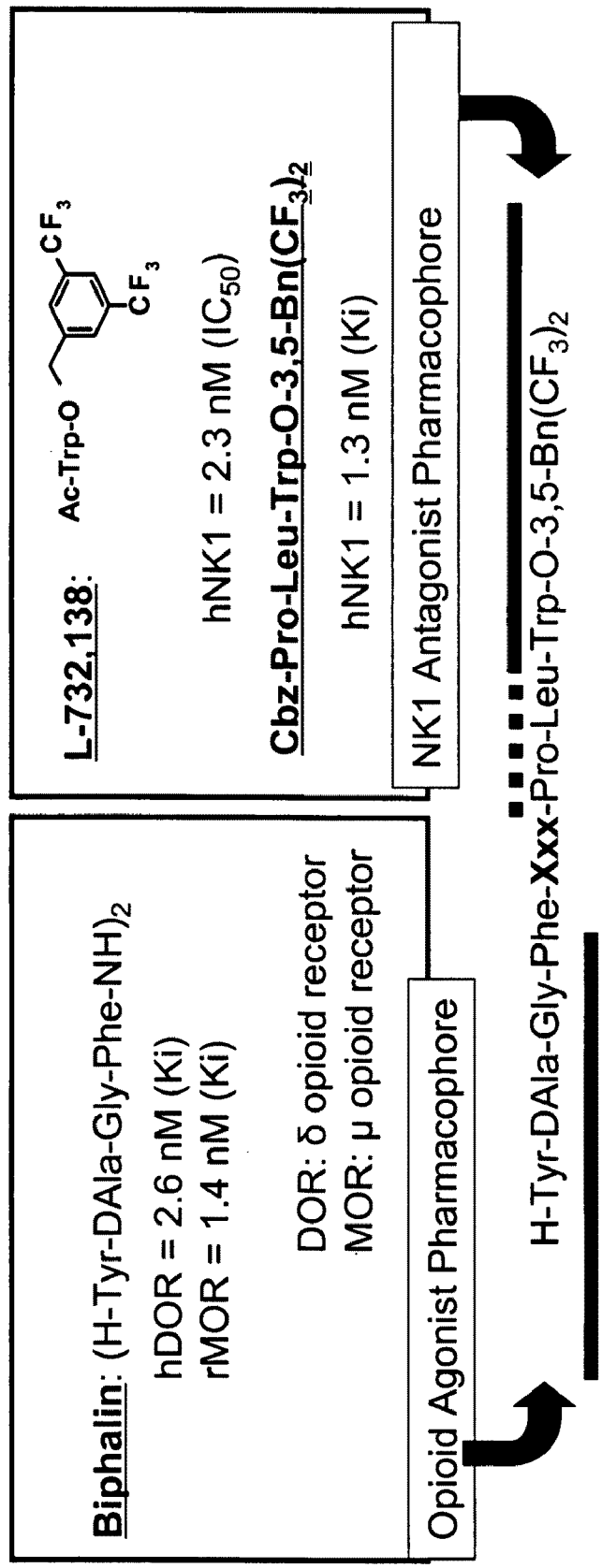
FIG. 1 A-G. Concept of multiple ligand design: (A) combination of two pharmacophores through an amino acid linker, (B) overlapping Phe from two pharmacophores, (C) introducing Dmt instead of Tyr, (D) introducing Dmt instead of Tyr and varying a linker, (E) cyclization with a disulfide bond using Cys or (F) Pen, and (G) glycosylated compounds.

Unless specifically defined, all technical and scientific terms used herein have the same meaning as commonly understood by a skill artisan in chemistry, biochemistry, cellular biology, molecular biology, and medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In this application, the present inventors designed a series of bifunctional compounds with opioid agonist and substance P antagonist bioactivities with the concept of overlapping pharmacophores (FIG. 1), which has been developed by the inventors mainly for bifunctional compounds with opioid agonist and cholecystokinin (CCK) antagonist activities (Lee, J. Med. Chem., 2006, 49(5), 1773-1780; Agnes, J. Med. Chem., 2006, 49(10), 2868-2875; Hruby, Life Sci., 2003, 73(6), 699-704). The bifunctional compounds of the invention have modified C-terminal which acts as agonist for δ/μ opioid receptors and as antagonist for Neurokinin-1 (NK-1) receptors. Some compounds have high δ selectivity. The compounds of the invention show excellent human NK-1 binding affinity up to pico molar level Ki values (e.g., Ki for TY027 is 6.5 pico molar) (see Table 39), which cannot be expected from neither parts of the known bifunctional compounds, for example, biphalin or Trp-based NK-1 antagonist (Bonney, Eur. J. Pharmacol., 2004, 488(1-3), 91-99). These very high affinities come from the combinatorial effect and only can be seen in the compounds of the invention.

"Potency higher at the δ receptor than at the μ receptor" is intended to mean that binding affinity of a derivative compound at the δ receptor is higher than at the μ receptor. Ki(μ)/Ki(δ) ratio may vary from 1.1 to 61 (see Tables 2, 15, and 20). For example, TY005 possesses much more increased δ opioid activity (Ki=2.8 nM) and δ selectivity (Ki(μ)/Ki(δ)= 13-fold) than it was seen over the μ opioid receptor in binding assays (36.3 nM) (Table 2).

"Potency higher at the μ receptor than at the δ receptor" is intended to mean that binding affinity of a derivative compound at the μ receptor is higher than at the δ receptor. Ki(μ)/Ki(δ) ratio may vary from 0.065 to 0.94 (see Tables 2, 15, and 20).

"Substantially no antagonistic activity against substance P" is intended to mean that $A_{50}$ is less than or equal to 2% at concentration of about 1 μM of the compounds. Contraction of isolated tissue treated with a compound is measured (relative to initial contraction with KCL) (Tables 4, 28, 35, and 39).

I. Chemical Structure

The chimeric compounds of the invention comprise an agonist opioid receptor binding moiety at its N-terminus and an antagonist neurokinin-1 (NK1) receptor binding moiety at its C-terminus, and are represented by formula (1) X1-X2-X3-X4-X5-X6-X7-X8-Trp-R1-R2 (SEQ ID NO: 7)

wherein:
X1 is absent or is Tyr or substituted Tyr;
X2 is absent or is Gly or D-amino acid;
X3 is absent or is Gly;
X4 is absent or is Phe or substituted Phe;
X5 is absent or is Phe, Leu, Met, Gly, DPhe, Nle, Nle(R3), DCys, Cys, Ser(O—R4), substituted Cys, or substituted DCys;
X6 is absent or is Pro, Ala, DLeu, DPro, Ser(O—R4) or Aib;
X7 is absent or is Leu, Cys, DCys, Ser(O—R4), Pen, DPen, Ala, DAla, beta Ala, alpha Abu, gamma Abu, Ava, or Aib;
X8 is absent or is Ser(O—R4);
R1 is O, NH, or N—R5;
R2 is benzyl or substituted benzyl;
R3 is alkyl or a substituted alkyl;
R4 is sugar;
R5 is alkyl or substituted alkyl, or salts thereof,
with the proviso that the chimeric compound is not Tyr-DAla-Gly-Phe-Gly-Trp-O-Bzl($CF_3$)$_2$ and Tyr-DAla-Gly-Phe-Ala-Trp-O-Bzl($CF_3$)$_2$, wherein the compound induces analgesia.

In another aspect of the invention, the compounds are represented by formula (2):

X1-X2-X3-X4-X5-X6-X7-X8-Trp-R1-R2 (SEQ ID NO: 8)

wherein:
X1 is absent or is Tyr or Dmt;
X2 is absent or is Gly, DAla, DCyc, or DPhe;
X3 is absent or is Gly;
X4 is absent or is Phe, pClPhe, pFPhe, pBrPhe, or DPhe;
X5 is absent or is Phe, Leu, Met, Gly, DPhe, Nle, Nle(NMe), DCys, Cys, Ser(OGlc), Pen, or DPen;
X6 is absent or is Pro, Ala, DLeu, DPro, Ser(OGlc) or Aib;
X7 is absent or is Leu, Cys, DCys, Ser(OGlc), Pen, DPen, Ala, DAla, beta Ala, alpha Abu, gamma Abu, Ava, or Aib;
X8 is absent or is Ser(OGlc);
R1 is O, NH, or NMe; and
R2 is Bzl; 3',5'-Bzl(CF3)2; Bzl-3'-(CF3); 3',5'-Bzl(OMe)2; Bzl-2',4'-(OMe)2, or salts thereof,
with the proviso that the chimeric compound is not Tyr-DAla-Gly-Phe-Gly-Trp-O-Bzl($CF_3$)$_2$ and Tyr-DAla-Gly-Phe-Ala-Trp-O-Bzl ($CF_3$)$_2$, wherein the compound induces analgesia.

In one aspect of the invention, in formula (1) or (2), the following amino acids are preferred: X1 is Tyr; X2 is DAla; X3 is Gly; X4 is Phe; X5 is Phe, DPhe, Gly, Leu, Met, Met(O), Nle, or N-Me-Nle; X6 is Pro; X7 is Leu, and X8 is absent.

In another aspect of the invention, in formula (1) or (2), the following amino acids are preferred: X1 is Tyr; X2 is DAla; X3 is Gly; X4 is Phe; X5 is absent; X6 is Pro; X7 is Leu; X8 is absent.

In another aspect of the invention, in formula (1) or (2), the following amino acids are preferred: X1 is Tyr; X2 is DCys or DPen; X3 is Gly; X4 is Phe; X5 is Nle, Cys, DCys, Pen, or DPen; X6 is Pro; and X7 is Cys, DCys, Leu, Pen, or DPen, wherein if X2 is DCys, then X5 is Nle, Cys, or DCys, and X7 is Cys, DCys, or Leu; and if X2 is DPen, then X5 is Nle, Pen, or DPen, and X7 is Pen, DPen, or Leu.

In another aspect of the invention, the compound is glycosylated.

In another aspect of the invention, in formula (1) or (2), the following amino acids are preferred: X1 is Tyr or Dmt, X2 is DAla, X3 is Gly, X4 is Phe, X5 is Ser(OGlc) or Nle, X6 is Pro or Ser(OGlc), and X7 is Leu or Ser(OGlc).

In another aspect of the invention, in formula (1) or (2), the following amino acids are preferred: X1 is Tyr or Dmt, X2 is DAla, X3 is Gly, X4 is Phe, X5 is Met or Nle, X6 is Pro, X7 is Leu, and X8 is absent.

In another aspect of the invention, the compound is a cyclic compound comprising a disulfide bond between at least two Cys and/or DCys (FIG. 1E). The cyclic compounds having disulfide bond between [DCys$^2$ and Cys$^7$] (TY035) and [DCys$^2$ and DCys 7] (TY038) have higher binding activity at the hNK1 receptor (Ki=0.10 nM for TY035 and 0.25 nM for TY038) than those with the disulfide ring at residues 2-5, [D-Cys$^2$ and D-Cys$^5$] (TY037) and [D-Cys$^2$ and Cys$^5$] (TY039) ((Ki=0.52 nM for TY037 and 3.7 nM for TY039).

In another aspect of the invention, the compound is a cyclic compound comprising a disulfide bond between at least two Pen and/or DPen. Among cyclic compounds TY046-049, the compounds having disulfide bond between [DPen$^2$ and Pen$^5$] (TY046) and [DPen$^2$ and DPen$^5$] (TY049) have higher binding activity at the hNK1 receptor (Ki=0.0053 nM for TY046 and 0.18 nM for TY049) than those with the disulfide ring at residues 2-7, [DPen$^2$ and DPen$^7$] (TY048) and [DPen$^2$ and Pen$^7$] (TY047) ((Ki=1.9 nM for TY048 and 59 nM for TY047).

To exemplify the present invention and the utility thereof, the present inventors used the enkephalin based tetrapeptide Tyr-DAla-Gly-Phe as an opioid agonist pharmacophore (Horan, *J. Pharmacol. Exp. Ther.*, 1993, 265, 1446-1454; Gentilucci, *Curr. Topics in Med. Chem.*, 2004, 4, 19-38). As for a pharmacophore for a substance P antagonist, the 3',5'-(bistrifluoromethyl)-benzyl ester of the peptide Pro-Leu-Trp was chosen and placed at the C-terminal. The optimization of the C-terminus was performed on the fifth residue, i.e., a linker residue, of the designed compound, which had critical effects on both of activities at δ/μ opioid receptors and NK1 receptors (FIG. 1A). From structure-activity relationships study, the residue at fifth position was found to have critical influence on both of opioid and NK1 activities, since it can act as an "address" element for the NK1 antagonist pharmacophore as well as an "address" region for the opioid receptor (Gentilucci, *Curr. Topics in Med. Chem.* 2004, 4, 19-38; Rapaka, *Pharm. Res.*, 1991, 8(1), 1-8). Eight analogous were tested. Among the synthesized compounds, H-Tyr-D-Ala-Gly-Phe-Met-Pro-Leu-Trp-3,5-Bzl($CF_3$)$_2$ (TY005) had excellent agonist activity for δ opioid receptors with good selectivity over μ opioid receptors, and excellent antagonist activity for substance P.

"Excellent activity" means nanomolar level of affinity in binding assays and about ten nanomolar, more preferably, less than 10 nM, level activity in the functional assays using animal tissues. Because of this excellent profile including distinct δ selectivity over μ opioid receptors, TY005 was selected to be a test compound. TY005 showed very potent anti-nociceptive, anti-hyperalgesic and anti-allodynic effects in several animal models without any sign of toxicity (FIG. 7-12). TY005 showed species difference between rat and guinea pig at NK-1 receptor. Moreover, TY005 showed no sensorimotor impairment in rotarod test to see its side effects (FIG. 7D). These results strongly suggested that these bifunctional compounds at opioid and NK1 receptors were promising analgesic for treatment of various pain states. Thus, the multifunctional ligand approach is useful for treatment of pain, since pain is complicated phenomenon in which a variety of receptors and neurotransmitters are involved.

Figure 1B:
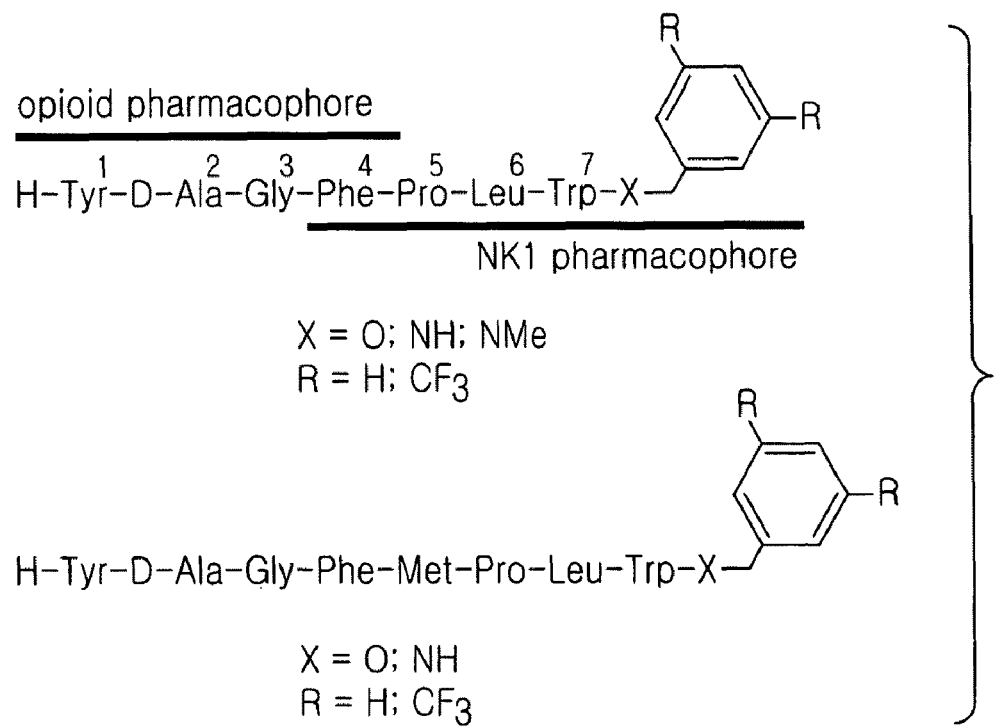

In another aspect of the invention, the enkephalin based tetrapeptide at the N-terminal was combined with the tetrapeptide Phe-Pro-Leu-Trp at the C-terminal (FIG. 1B) (Yamamoto, 2007, *J. Med. Chem.*, in press; Millet, *J. Pept. Sci.* 2001, 7(6), 323-330; Millet, *Lett. Pep. Sci.*, 1999, 6, 255-262). Since the opioid pharmacophore has a Phe in its C-terminal and the substance P pharmacophore has it at the N-terminal, a basic sequence for the bifunctional compound was designed as a 3',5'-(bistrifluoromethyl)-benzyl ester of H-Tyr-D-Ala-Gly-Phe-Pro-Leu-Trp with the Phe overlapped (FIG. 1B). Since the enzymatic hydrolysis of 3',5'-(bistrifluoromethyl)-benzyl ester has been reported, and the highly lipophilic two trifluoromethyl groups might lead to low solubility in aqueous solutions, the inventors" design approach has focused on modifications of the 3',5'-(bistrifluoromethyl)-benzyl ester at the C-terminal to replace its ester by an amide or by complete removal of the trifluoromethyl groups from the C-terminal (FIG. 1B) (Macleod, *J. Med. Chem.*, 1993, 14, 2044-2045; Lewis, *J. Med. Chem.* 1995, 38, 923-933). Also, C-terminal Trp modified by benzyloxycarbonyl previously used in bifunctional compounds (Bonney, Eur. J. Pharmacol., 2004, 488(1-3), 91-99) is not commonly used and the inventors used Trp-benzyl ester or amide that provide for better compounds' characteristics. These modifications at the C-terminus, which is the pharmacophore for substance P antagonist, resulted in different affinities as well as bioactivities not only for the NK1 receptors, but also for the opioid receptors. Among the obtained compounds, the benzyl amide derivative TY008 (H-Tyr-DAla-Gly-Phe-Pro-Leu-Trp-NH-Bzl) exhibited excellent opioid agonist activities and potent substance P antagonist activity in the Guinea Pig Isolated Ileum Assay (GPI) using substance P stimulation in the presence of 1 μM naloxone. The modified compounds showed excellent potency in both opioid agonist and substance P antagonist activities together with the nanomolar affinities at both rNK1 and hNK1 receptors, indicating the importance of trifluoromethyl groups for rNK1 affinity. It should be noted that the C-terminus of compound derivatives acted as not only a critical pharmacophore for the activity of the substance P antagonist, but also as an address region for the opioid agonist pharmacophore.

In another aspect of the invention, 3',5'-(bistrifluoromethyl)-benzyl ester at the C-terminal of TY005 was modified to replace its ester by an amide or by complete removal of the trifluoromethyl groups from the C-terminal (FIG. 1B). Three bifunctional compounds have been studied, TY005, TY027, and TY025 (FIG. 1B). Though their C-terminus was a part of the NK1 antagonist pharmacophore, both the NK1 antagonist and opioid agonist activities were shifted by the modifications in this region. Among them, TY027 was found to be a "potent" and useful analgesic, since it showed picomolar level affinity at the hNK1 receptors together with potent δ opioid receptor selective agonist activities.

Figure 16A:
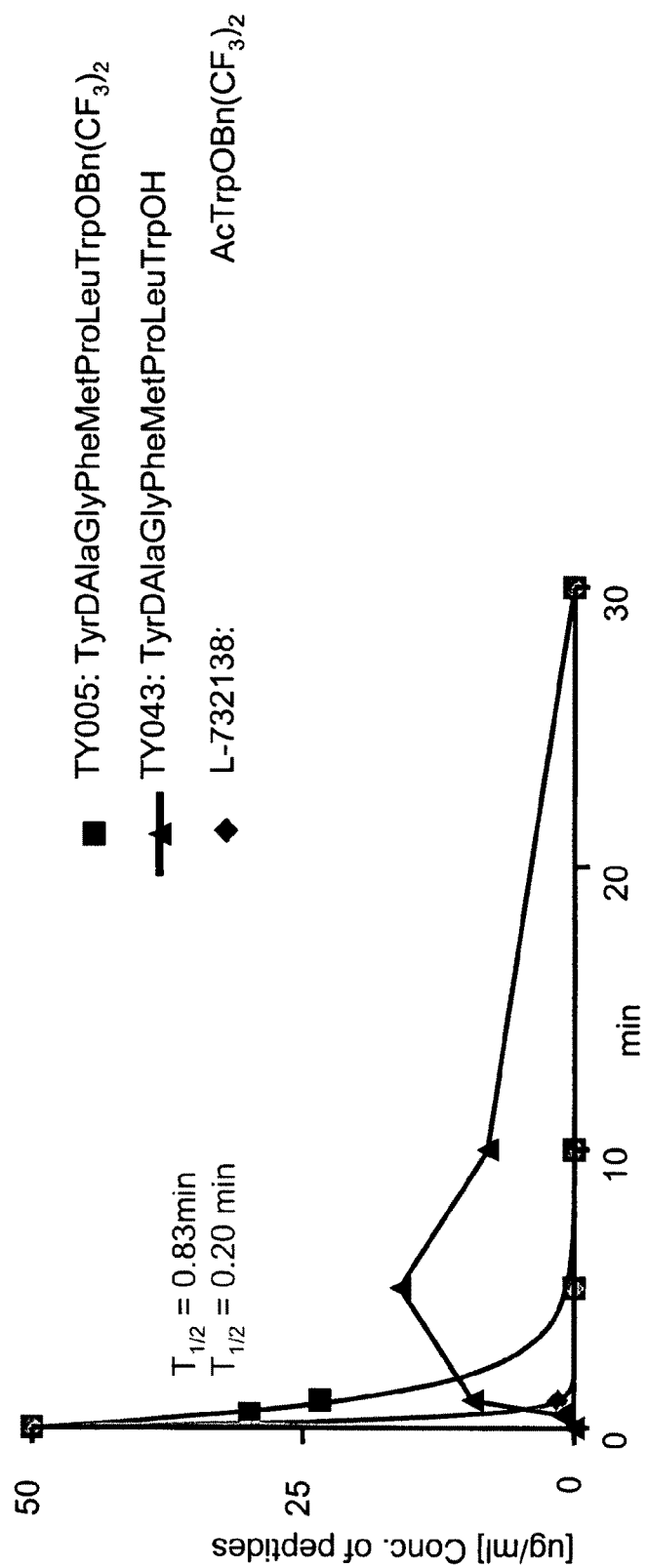
FIG. 16 A-C. Concentration of TY compounds in rat plasma after incubation at 37° C. TY005 and TY043 (A); TY005, TY025, TY027, TY035, TY037, TY038, and TY039 (B); and TY032, TY027, and TY050 (C).

In another aspect of the invention, Tyr of the enkephalin based tetrapeptide Tyr-DAla-Gly-Phe in TY027 was substituted for Dmt (2',6'-dimethyl-L-tyrosine) (FIG. 1C). A significant change was found especially in μ-opioid affinity (FIG. 1C-D). Opioid activity was also increased. Dmt introduction leads to little stability change in rat plasma (FIG. 16C).

In another aspect of the invention, Tyr of the enkephalin based tetrapeptide Tyr-DAla-Gly-Phe was substituted for Dmt and a linker amino acid was either Met or Nle (norleucine) (FIG. 1D). These compounds have high affinities for both opioid (hDOR Ki is 0.12; 0.15; and 0.46 nM; and rMOR Ki is 0.34; 0.74, 1.77, and 2.0 nM) and NK1 receptors (0.0079-318 nM). Substitution of Met for Nle resulted in increased metabolic stability (FIG. 16C).

The conformation of the biological ligand for membrane-bound receptor and its orientation in lipid bilayer have been getting more important, because their clear influence on the activity, selectivity and membrane permeability have been reported (Ossipov, *Biopolymers* 2005, 80, 319-324). For peptide-derived ligands, biological effects came from the spatial location of the pharmacophores which are defined not only by their primary sequence, but by the higher three-dimensional structures like α-helix, β-turn or their combined structures.

In another aspect of the invention, bifunctional compounds were obtained by cyclization (FIG. 1E-F). The inventors report a conformation activity relationship of a series of compounds in which a disulfide bond was incorporated into one of our promising bifunctional compounds TY027 (Tyr-D-Ala-Gly-Phe-Met-Pro-Leu-Trp-NH-3,5-Bzl($CF_3$)$_2$) in which two β-turns were found at D-Ala$^2$-Met$^5$ and Pro$^6$-C-terminal benzyl moiety. (FIG. 1E). Generally, a disulfide bond introduction leads to forming or modifying secondary structure elements which have the important roles in interaction with a receptor as well as changing their selectivity over other receptors (Ossipov, *Biopolymers* 2005, 80, 319-324; Gentilucci, *Curr. Topics in Med. Chem.* 2004, 4, 19-38). The cyclized structure with a disulfide bond could also provide the higher stability against metabolic degradation, which brings longer half life in living body. It is well known that the introduction of several types of D-amino acids in a second position of enkephalin analogues is well accepted, D-Cys was introduced into the second position of TY027 (Ossipov, *Biopolymers* 2005, 80, 319-324; Gentilucci, *Curr. Topics in Med. Chem.* 2004, 4, 19-38; Mantyh, *Proc. Natl. Acad. Sci. USA*, 1995, 92, 2622-2626). Residues 5 and 7 were selected as the other residue to be cyclized, since Tyr$^1$, Gly$^3$, Phe$^4$ and Trp$^8$ were considered as the "message" sequence of each pharmacophores, and Pro$^6$ had some positive effect on the affinity at NK1 receptor. Thus, the cyclization between residues 2 and 5 ([D-Cys$^2$, D-Cys$^5$] (TY037) and [D-Cys$^2$, Cys$^5$] (TY039) was expected to stabilize the corresponding β-turn of TY027, whereas the introduction of a disulfide bond for residues 2 and 7 ([D-Cys$^2$, Cys$^7$] (TY035) and [D-Cys$^2$, D-Cys$^7$] (TY038) might eliminate the turn structure in the Pro$^6$-C-terminal benzyl moiety. The biological activities of cyclized compound derivatives were tested at both δ/μ opioid and NK1 receptors with the corresponding radioligand binding assays as well as the functional assays using guinea pig isolated ileum (GPI) or mouse vas deferens (MVD) to clarify the influence of the structural changes on the activities (FIG. 16B). Their conformations as well as orientations in the membrane-mimicking DPC micelles were also elucidated with 2D $^1$H-NMR technique to discuss about their influence on the activities.

Figure 47:
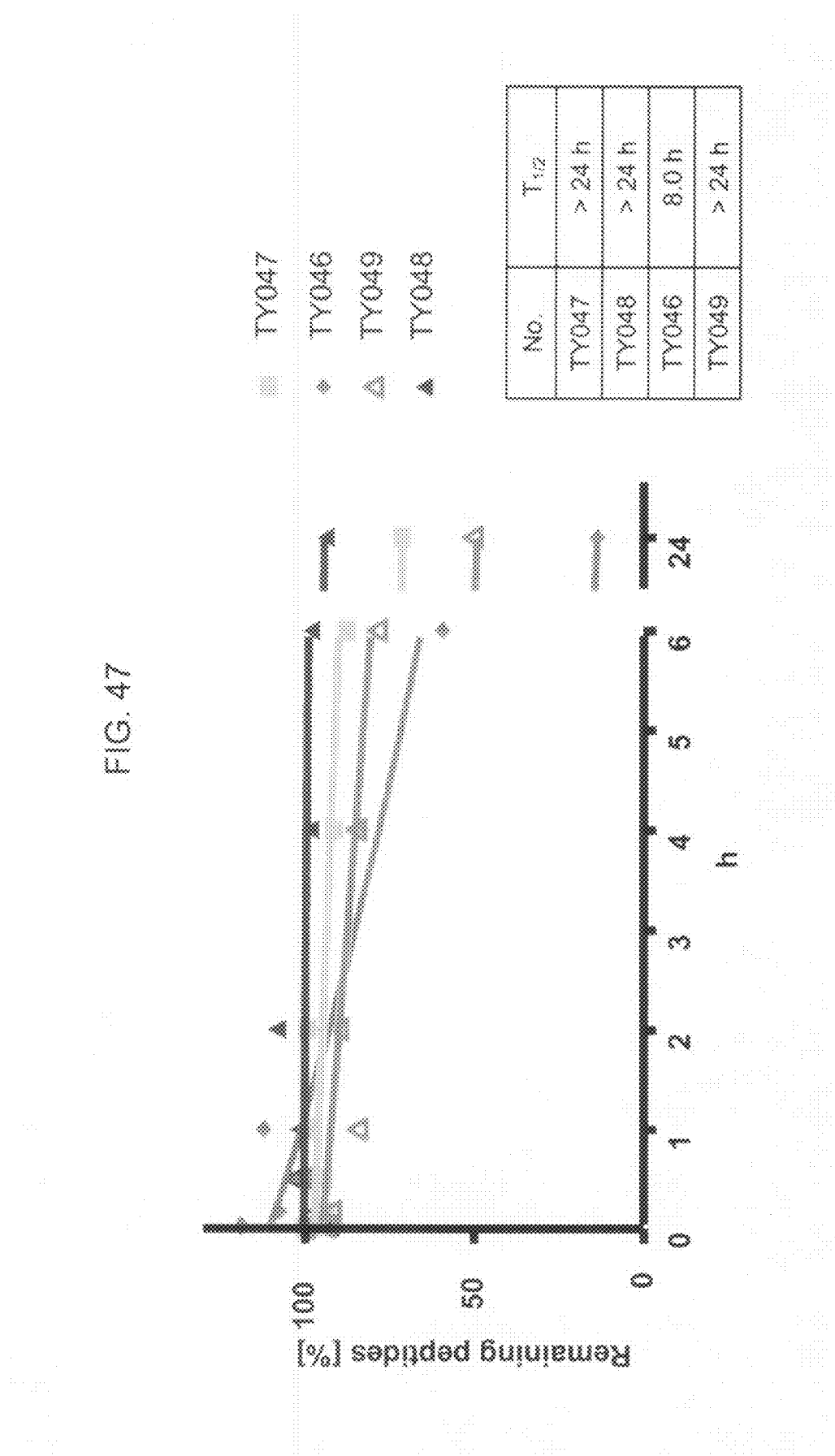
FIG. 47. Concentration of cyclic compounds in rat plasma after incubation at 37° C.

In another aspect of the invention, bifunctional compounds were obtained by cyclization using Pen and D-Pen (L-penicillamine and D-penicillamine, respectively) (FIG. 1F). Compounds TY047, 048, and 049 are extremely stable with $T_{1/2}$ more than 24 hours (FIG. 47). The biological activities of cyclized compound derivatives are shown on FIG. 1E-F and Table 39. In the hNK1 assay, Ki ranges from 0.0053 nM (the best affinity, TY046) to 59 nM. In the rNK1, Ki ranges from 4.54 nM (the best affinity, TY049) to 162.69 nM.

In another aspect of the invention, bifunctional glycosylated compounds were obtained by glycosylation introducing sugar, for example, Ser(OGlc) (O-Glycosylated Serine) or other sugars. TY055 and TY056 have good affinities at both hNK1 and rNK1 and are stable in the rat plasma (FIGS. 15 and 48). Affinities for the hDOR and rMOR vary from 0.00077 nM (the best affinity, TY041 at the hNK1) to 3370 nM (TY044 at the rMOR).

In another aspect of the invention, the inventors explore various small linkers between opioid and NK1 phromacophores, wherein the phromacophors overlap. Various substitution patterns in an opioid pharmacophore at $Phe^4$ position and Dmt substitution at $Tyr^1$ position were explored (Example 20). These NP compounds have a shorter sequence with less lipophilicity than TY compounds except for the glycosylated compounds. These characteristics lead to better absorption property.

II. Chemical Synthesis

Chimeric compounds, and individual moieties or analogs and derivatives thereof, can be chemically synthesized. In the present invention, the inventors have synthesized bifunctional compounds using sequential approach using a solution phase PyBOP/HOBt-chemistry. The synthesis was started from coupling reaction of Boc-Pro-Leu-OH and tryptophan 3,5-(bistrifluoromethyl)benzyl ester hydrochloride followed by deprotection of Boc group using 4M hydrogen chloride in 1,4-dioxane. After subsequent chain elongation, obtained 3,5-(bistrifluoromethyl)benzyl ester of pentapeptide will be coupled with Boc-Tyr-D-Ala-Gly-OH. The final crude compounds were obtained with the treatment of trifluoroacetic acid. Compounds intermediates are isolated by precipitation from cold ether or petroleum ether and obtained final crude compounds were purified by RP-HPLC to give pure (>98%) compounds.

C-terminal modified compounds can be also synthesized by using nucleophilic cleavage of protected compounds bound from appropriate resins, attachment with a C-terminal functional group, side chain anchoring followed by normal solid phase N-to-C peptide synthesis, backbone amide attachment onto a solid support, inverse C-to-N solid phase peptide synthesis, and conventional solution phase synthesis (see Alsina, *Biopolymers,* 2003, 71, 454-477, for a review). However, it is difficult to synthesize C-terminal esters or tertiary amides by the first two methods, and our designed compounds didn't have a suitable side chain moiety to anchor on a resin. Repeated inverse C-to-N coupling leads to severe racemization, and conventional Boc solution phase peptide synthesis is very labor intensive for large amounts of longer peptides.

Figure 2:
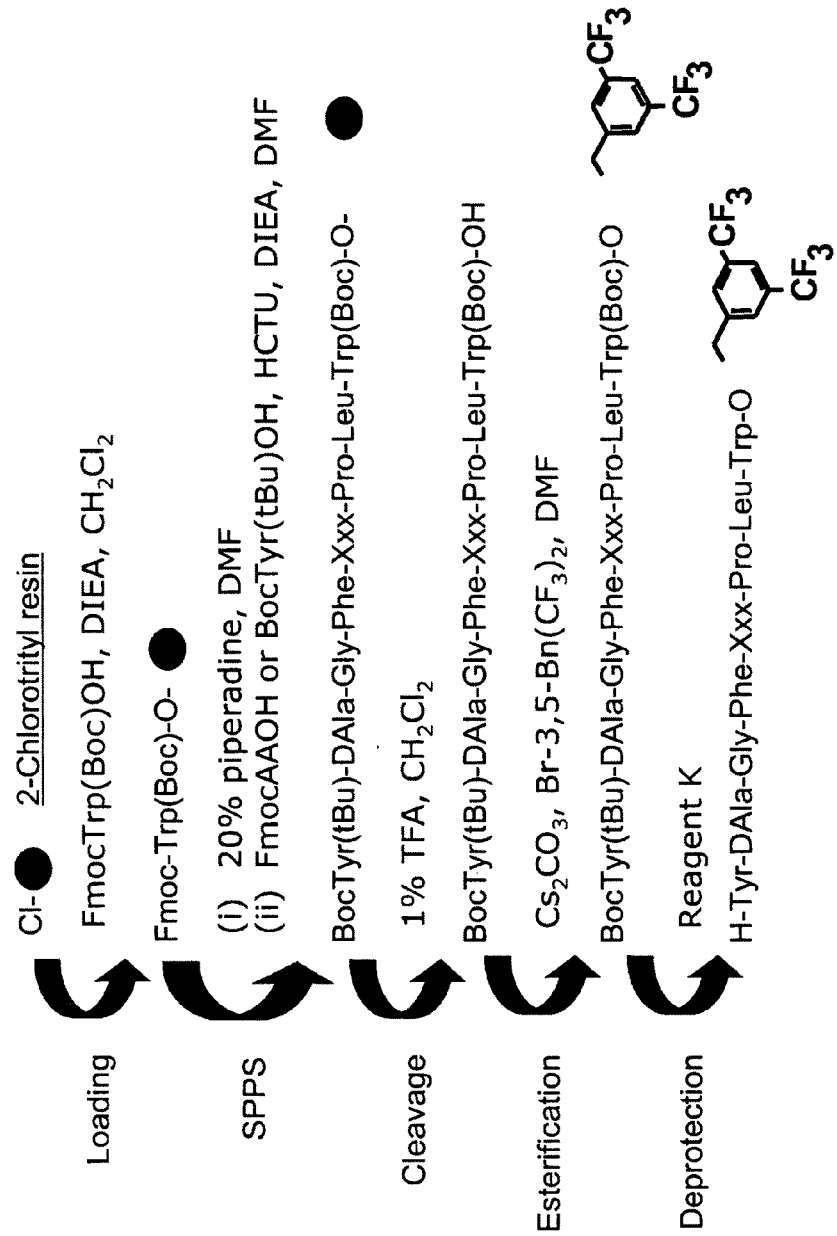
FIG. 2. Compound synthesis strategy for C-terminal esters.
Figure 3:
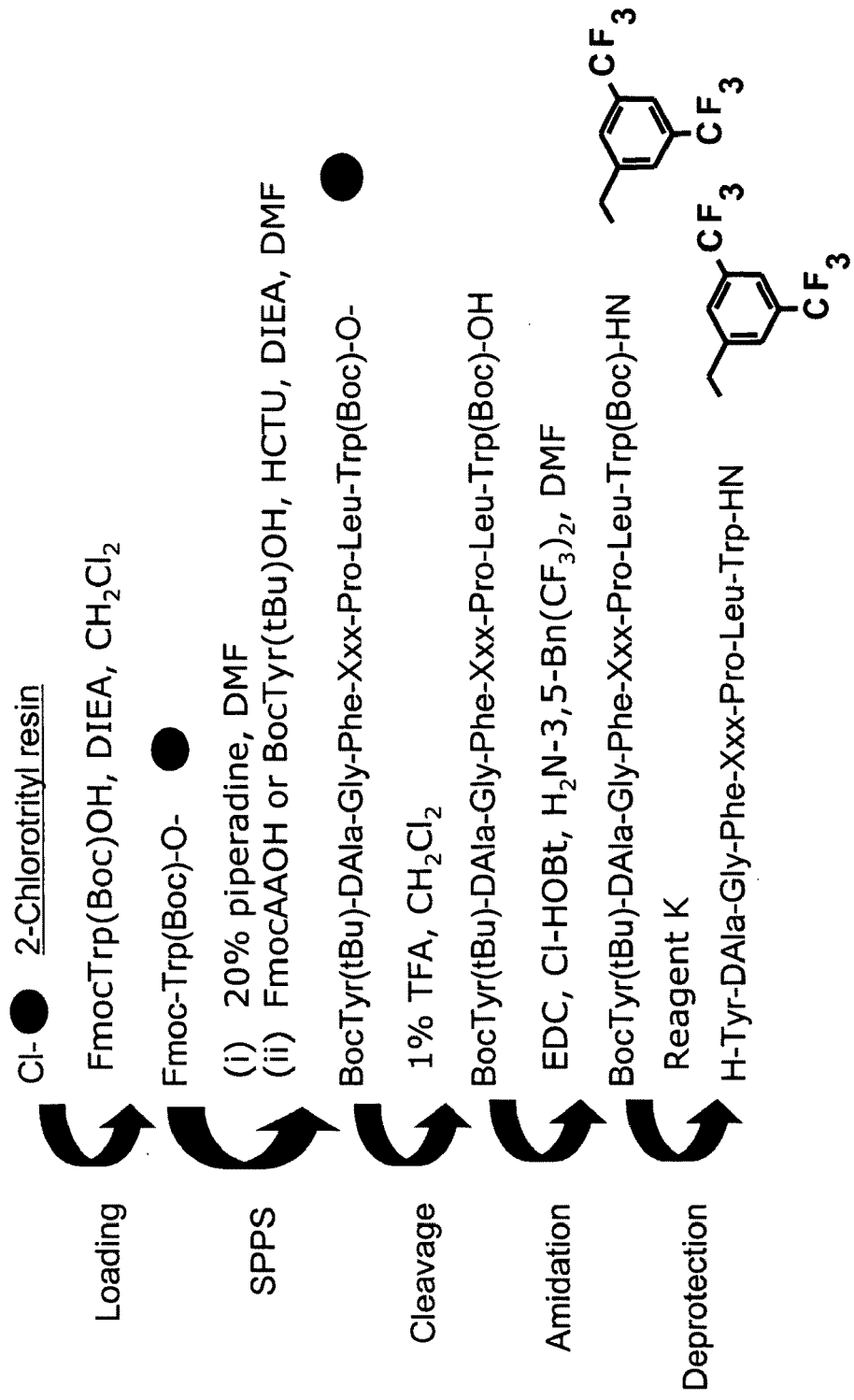
FIG. 3. Compound synthesis strategy for C-terminal amides.

Therefore, in another aspect of the invention, the compounds were synthesized using combination of solid phase and solution phase chemistry to develop a two-step combinatorial approach. In this method, a side chain-protected compound with a free C-terminal carboxylate was synthesized using a $N^\alpha$-Fmoc solid phase peptide synthesis on a resin, followed by esterification or amidation in solution phase without any detectable racemization (FIG. 2-3).

A method of making the chimeric compound comprises the steps:

a. introducing Fmoc-Trp(Boc)-OH on a resin;

b. removing an N-Fmoc protecting group;

c. conducting a step-wise chain elongation, wherein the following amino acids are coupled using in situ activating reagents to obtain a protected intermediate having Boc-Tyr (tBu) or Boc-Dmt on its N-terminus and -Trp(Boc)-O— attached to the resin on its C-terminus;

d. treating the protected intermediate with a cleavage reagent to free the protected intermediate from the resin;

e. conducting esterification or amidation of the protected intermediate compound; and f. conducting a cleavage of the protected intermediate and removing the protecting group(s), thereby obtaining the chimeric compound.

A resin can be represented by 2-chlorotrityl resin, 4,4'-Dimethoxytrityl chloride resin, 4-Methoxytrityl alcohol resin, and 4-Methyltrityl chloride resin. Preferably, the resin is 2-chlorotrityl resin. Cleavage reagents may be trifluoroacetic acid, HCL in dioxane, boron-tris-(trifluoroacetate) and cyanogen bromide.

Esterification is performed using cesium carbonate to form a cesium salt of the protected intermediate, wherein the cesium salt is further reacted with benzyl bromide or 3', 5'-bis(trifluoromethyl)-benzyl bromide. Amidation is performed using EDC/Cl-HOBt coupling chemistry and benzyl amine, 3',5'-bis(trifluoromethyl)-benzyl amine or N-methyl-3', 5'-bis-(trifluoromethyl-benzyl) amine.

Figure 4:
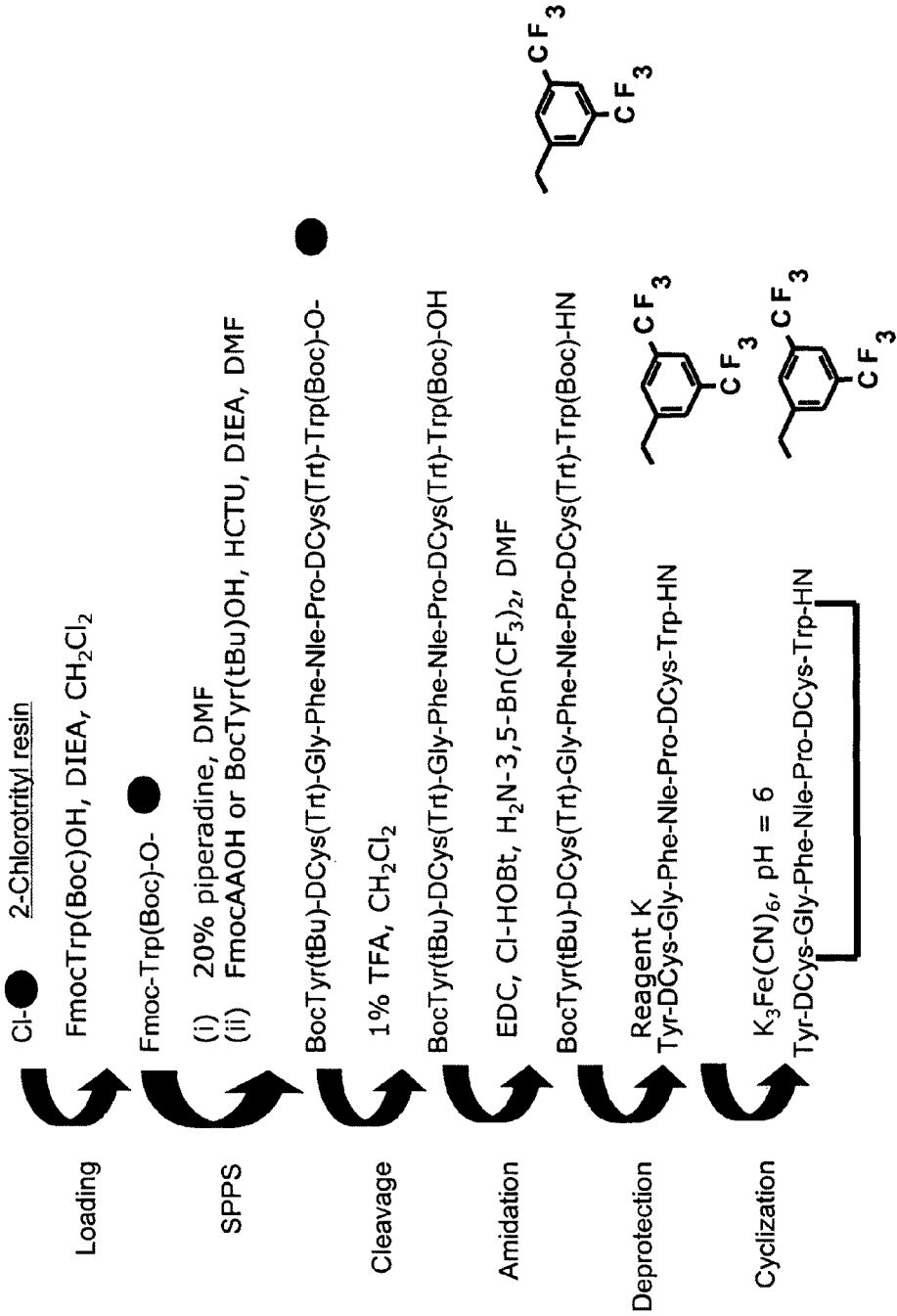
FIG. 4. Compound synthesis strategy for cyclic compounds with Cys/DCys.
Figure 5:
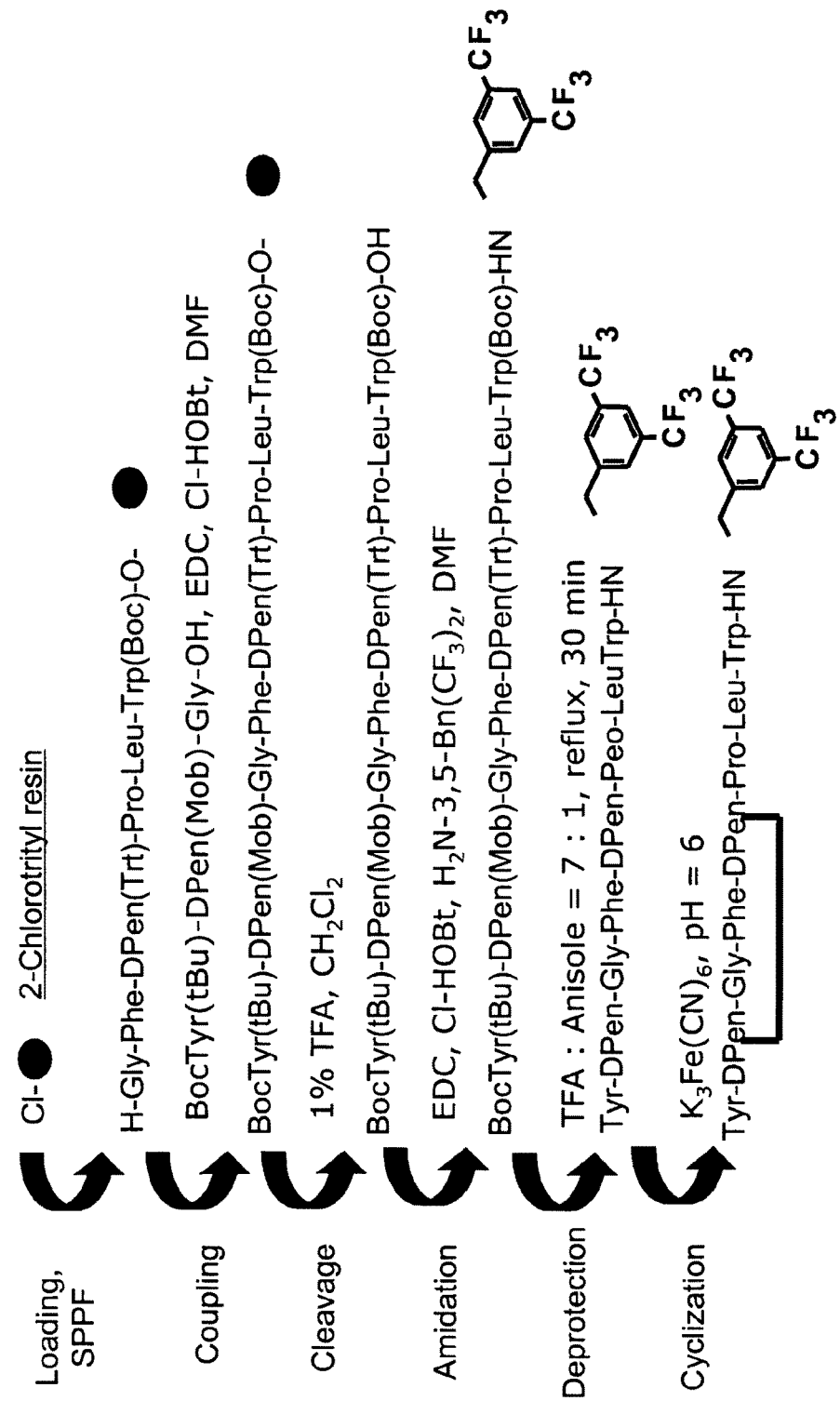
FIG. 5. Compound synthesis strategy for cyclic compounds with Pen/DPen.

In another aspect of the invention, cyclic compounds are synthesized using a $N^\alpha$-Fmoc solid phase peptide synthesis on a resin, followed by amidation in solution phase and cyclization using disulfide bonds of Cys, DCys, Pen, and/or DPen (FIG. 4-5).

Figure 6:
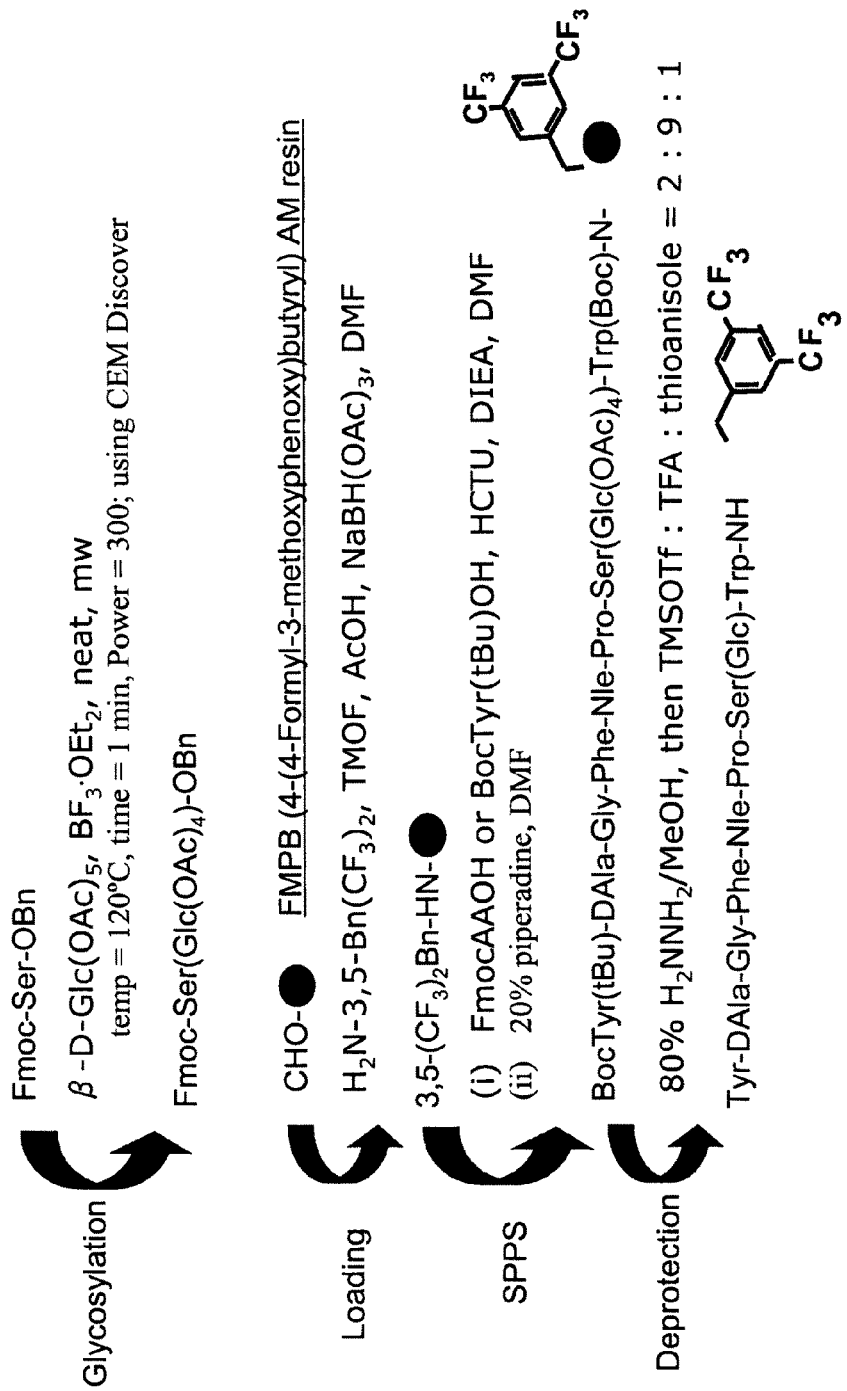
FIG. 6. Compound synthesis strategy for glycosylated compounds.

In another aspect of the invention, glycosylated compounds were synthesized by using glycosylation of Fmoc-Ser-OBzl group with sugar to obtain Fmoc-Ser(Glc(OAc)4)-O-Bzl followed by deprotection of Bzl group using H2/Pd/C to afford Fmoc-Ser(Glc(OAc(4)-OH (FIG. 6).

A method of making a glycosylated compound comprises the steps:

a. conducting glycosylation of Fmoc-Ser-OBzl to obtain Fmoc-Ser(Glc(OAc)$_4$)—OBzl;

b. deprotecting benzyl group to afford Fmoc-Ser(Glc (OAc)$_4$)—OH;

c. introducing 3',5'-bis(trifluoromethyl)-benzyl amine on FMPB (4-(4-Formyl-3-methoxyphenoxy)butyryl) AM resin;

d. conducting a step-wise chain elongation, wherein the following amino acids are coupled using in situ activating reagents to obtain a protected intermediate having Boc-Tyr (tBu) or Boc-Dmt on its N-terminus and -Trp(Boc)-N-3',5'-bis(trifluoromethyl)-benzyl attached to the resin on its C-terminus;

e. treating the protected intermediate to deprotect the protective groups on a sugar; and f. treating the protected intermediate to free the chimeric compound.

Cleavage and deprotection of the protected intermediate in step (f) can be conducted simultaneously. Typically, resins are functionalized with aldehyde. Examples of cleavage reagents comprise trifluoroacetic acid, HCL in dioxane, boron-tris-(trifluoroacetate), cyanogen bromide, trimethylsilyl trifluoromethanesulfonate, and triisopropylsilyl trifluoromethanesulfonate.

Figure 30:
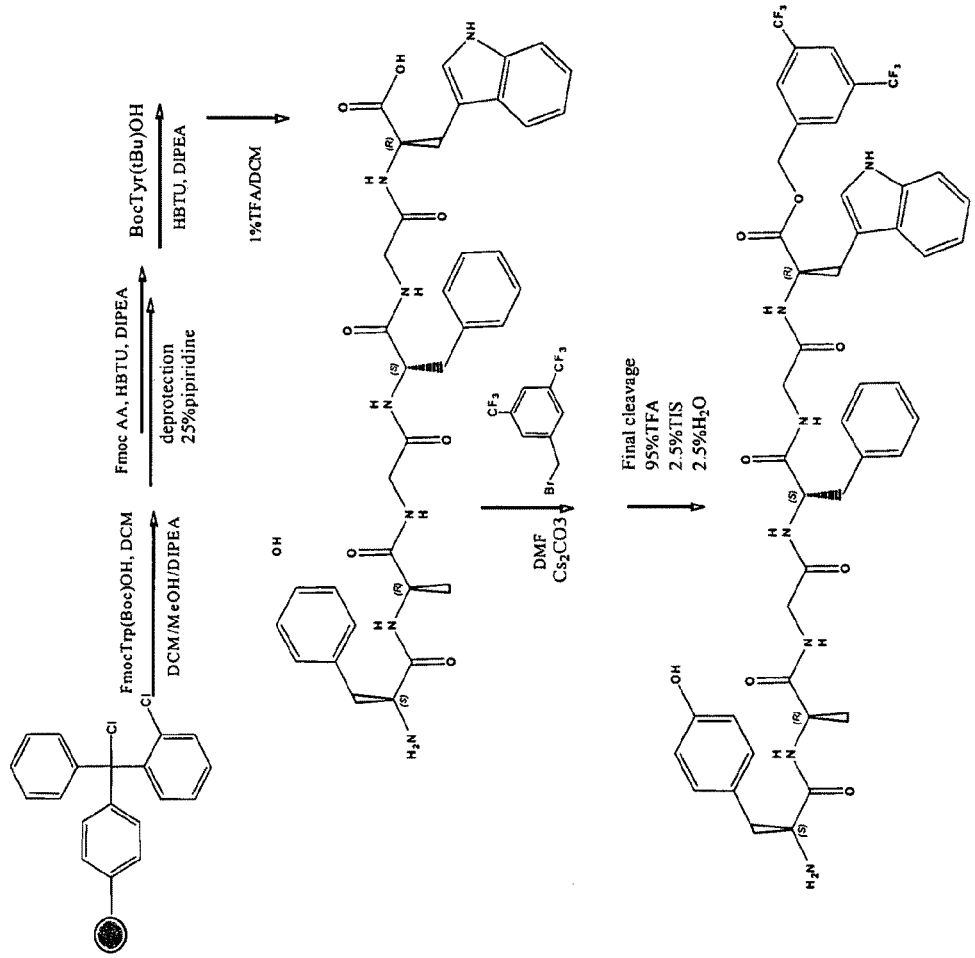
FIG. 30. A method of synthesis of NP compounds.

Derivate compounds NP 32-49, 51-52, and 62 were synthesized using a similar method (FIG. 30).

III. Biological Activity

The opioid binding affinities of synthetic chimeric compounds were evaluated using human δ opioid receptors (hDOR) and rat (rMOR) μ opioid receptors with cells that stably express these receptors as previously described (Lee, *J. Med. Chem.,* 2006, 49(5), 1773-80; Khasabov, *J. Neurosci.,* 2002, 22, 9086-98). [$^3$H]DPDPE and [$^3$H]DAMGO were used as their radioligands, respectively. The human μ opioid receptor (hMOR) can also be used for detecting the opioid binding affinities. Their agonistic efficacies were determined at the level of receptor G-protein interaction measuring agonist simulated binding of the GTP analogue guanosine-5'-O-

(3-[$^{35}$S]thio)triphosphate ([$^{35}$S]GTP-γ) on the same transfected cells for binding affinities assays. (Lee, *J. Med. Chem.*, 2006, 49(5), 1773-80; Misicka, *Life Sci.* 1992, 51(13), 1025-32). The tissue bioassays (MVD and GPI) were also performed for characterizing their agonistic function through δ and μ opioid receptors as described previously. (Lee, *J. Med. Chem.*, 2006, 49(5), 1773-80; Misicka, *Life Sci.* 1992, 51(13), 1025-32). As for their affinity for rat NK1 (rNK1) receptor, receptor binding assay were also used on transfected cells that stably express rNK1 receptors using [$^3$H]substance P as the standard radioligand. To estimate their antagonistic activities against substance P stimulation, tissue bioassay using guinea pig ileum (GPI) was performed. All the synthesized compounds were confirmed to have no or negligible agonistic activities against substance P stimulation (see e.g., Table 4).

The hNK1 receptor is known to have similar sequence and biological properties as the guinea pig (gpNK1) receptor, not with the rat (rNK1) receptor (Datar, *Curr. Top Med. Chem.* 2004, 4, 75-103). Some of the compounds of the invention have an activity difference between rat and human NK1 receptors (Table 7). For example, TY008 is expected to work as a potent compound with opioid agonist and substance P antagonist activities in human, but not in rats (Table 7). TY025 showed a 220 times better Ki value at the hNK1 receptor (3.20 nM) compared to the value at the rNK1 receptor. TY027 shows the largest difference between the affinities at the rNK1 and at the hNK1 (1100-fold), and Ki value for the hNK1 receptor was 6.5 μM.

Figure 14:
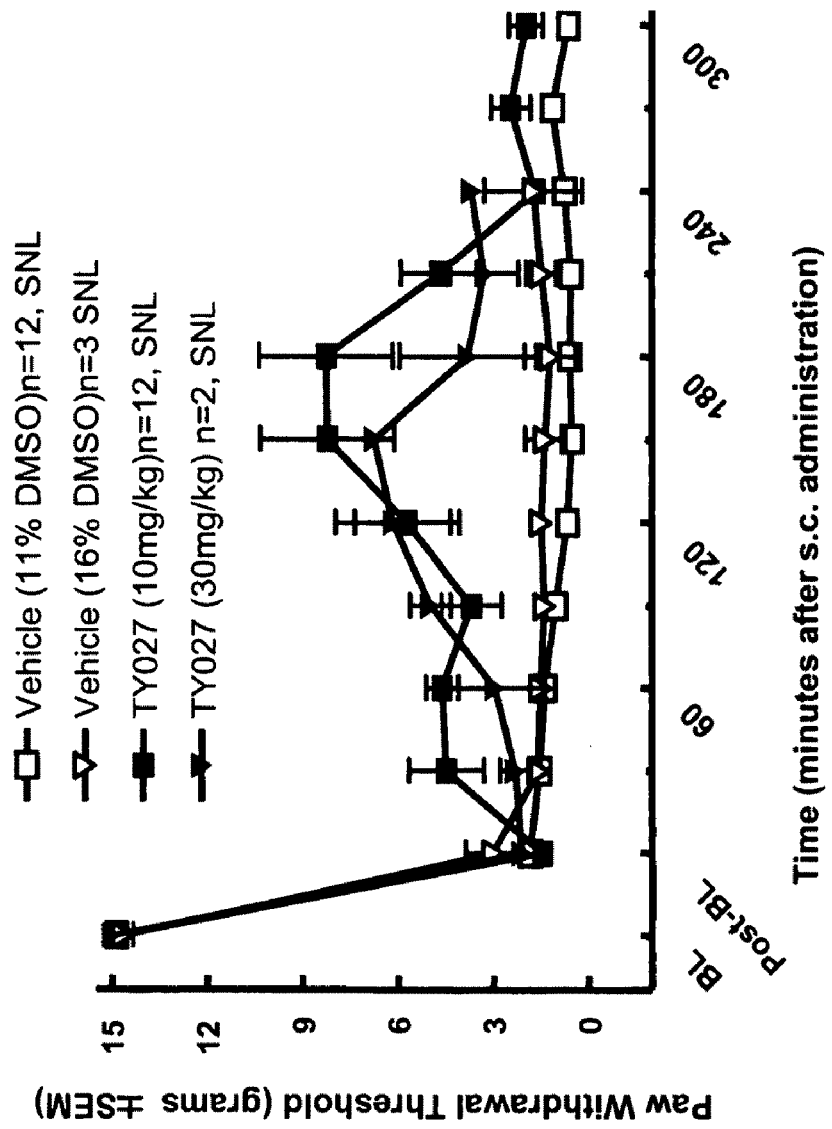
FIG. 14. Antiallodynic effect in L5/L6 SNL-operated male SD rats after systemic administration of TY027. Compound was administered via s.c. route and rats were tested by von Fray filament stimulation FIG. 15. Concentration of glycosylated compounds TY055 and TY056 in rat plasma after incubation at 37° C.
Figure 17A:
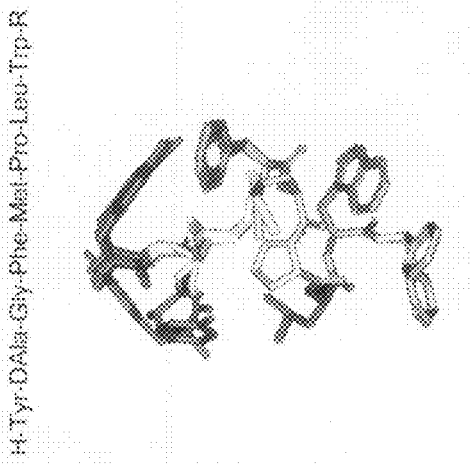
FIG. 17 A-D. NMR structure of TY005 (A), TY025 (B), TY027 (C), and TY004 (D).
Figure 17B:
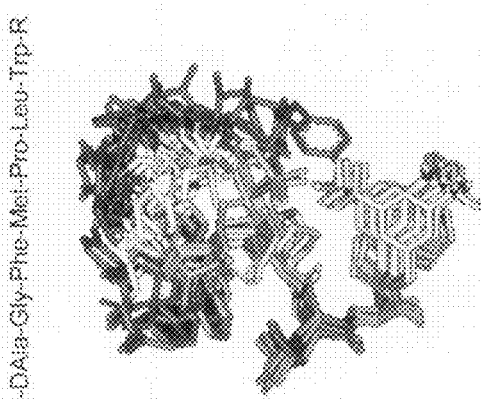
Figure 17C:
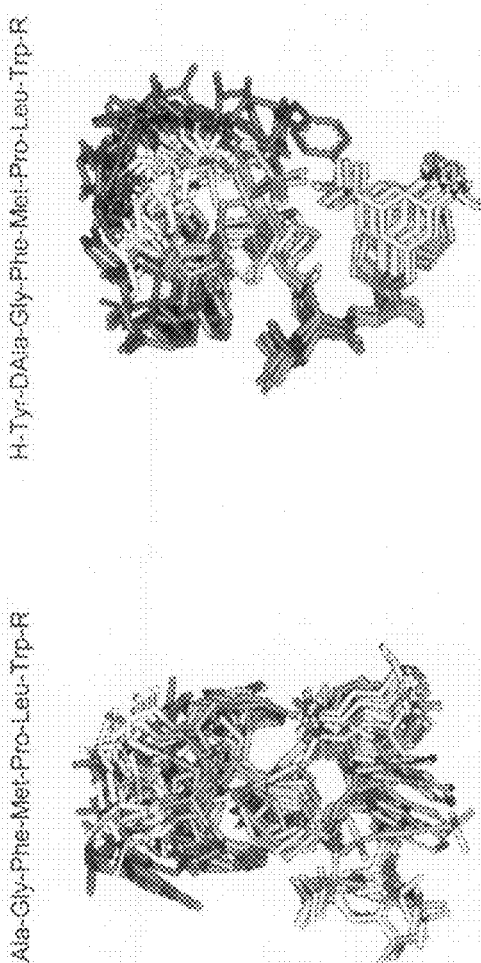

To estimate the analgesic potency of the chimeric compounds, anti-nociceptive, anti-hyperalgecia and anti-allodynic efficacies is tested via intrathecal (i.th.) or systemic (s.c.) administration of the compounds in L5/L6 spinal nerve ligated (SNL) male Sprague Dawley rats. Anti-nociception and anti-hyperalgecia were determined by using the infrared thermal testing, wherein paw withdrawal latencies were measured in response to a mobile radiant heat (FIG. 7-14). Anti-allodynic effect was measured in von Frey filamental testing (FIG. 7-14). Both chronic and acute animal models were tested (FIG. 17-14).

To evaluate whether the analgesic dose of the synthesized derivatives is associated with any toxic effects, motor function before and after administration was assessed in normal, uninjured rats using the rotarod test in which morphine was reported to induce impaired performance. For example, as can be seen in FIG. 7D, no sensorimotor impairment was observed at the highest analgesic dose of TY005 (30 μg).

The derivative compounds were tested for their metabolite stability. The compounds were incubated in rat plasma at 37° C., and aliquots were withdrawn at various time points and analyzed by HPLC to determine the concentration of remaining compound derivatives (FIGS. 15-16, 36, and 47-48).

IV. Structural Studies

The purified compounds were characterized by HRMS, TLC, analytical HPLC and $^1$H-1D-NMR. Sequential assignment of proton resonances was achieved by 2D-TOCSY NMR experiments. High-resolution MS were taken in the positive ion mode using FAB methods. All NMR structures were recorded on a Bruker DRX600 600 MHz spectrometer. Two-dimensional double quantum filtered correlation (DQF-COSY), nuclear Overhauser effect (NOESY), and total correlation spectra (TOCSY) were acquired using standard pulse sequences and processed using XwinNmr and Felix 2000 (Accelrys Inc, San Diego, Calif.). Coupling constants ($^3J_{HN-H\alpha}$) were measured from 2D DQF-COSY spectra by analysis of the fingerprint region. Further experimental details are provided in Examples.

Figure 31A:
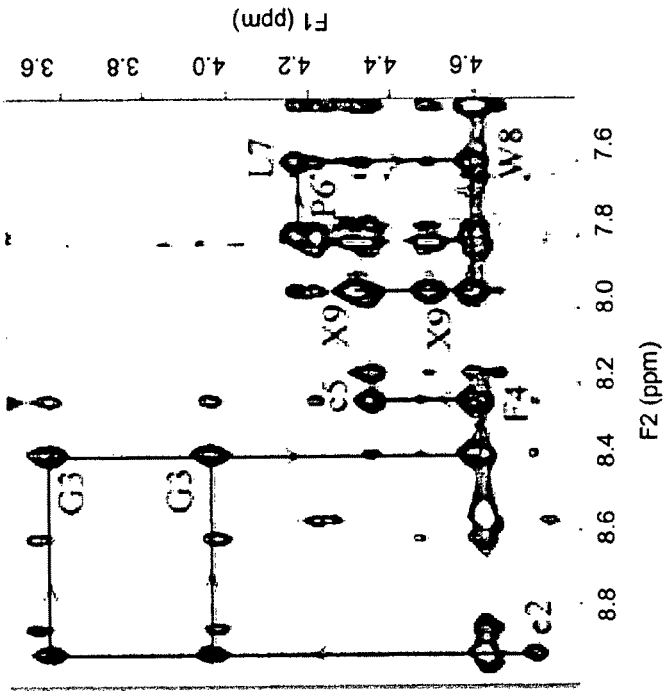
FIG. 31 A-C. Fingerprint ($H^N$-$H^α$) region of the NOESY spectrum of (A) TY035, (B) TY037 and (C) TY038 in DPC micelles. Intraresidue $H^N$-$H^α$ NOE cross-peaks are labeled with residue number, and arrows indicate the connectivity path from N-terminal to C-terminal. X9 represents the cross-peaks derived from the corresponding C-terminal $H^N$ and benzyl protons.
Figure 31B:
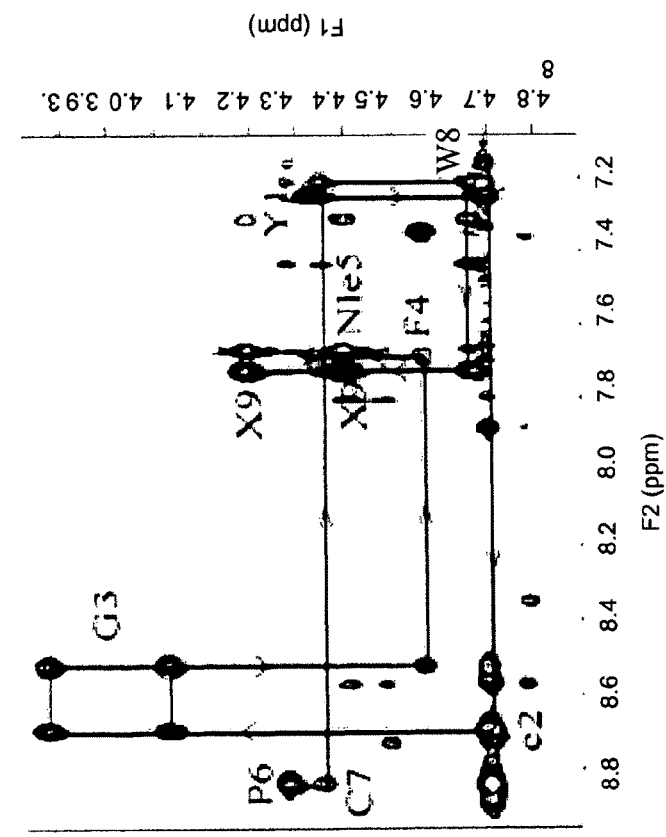
Figure 31C:
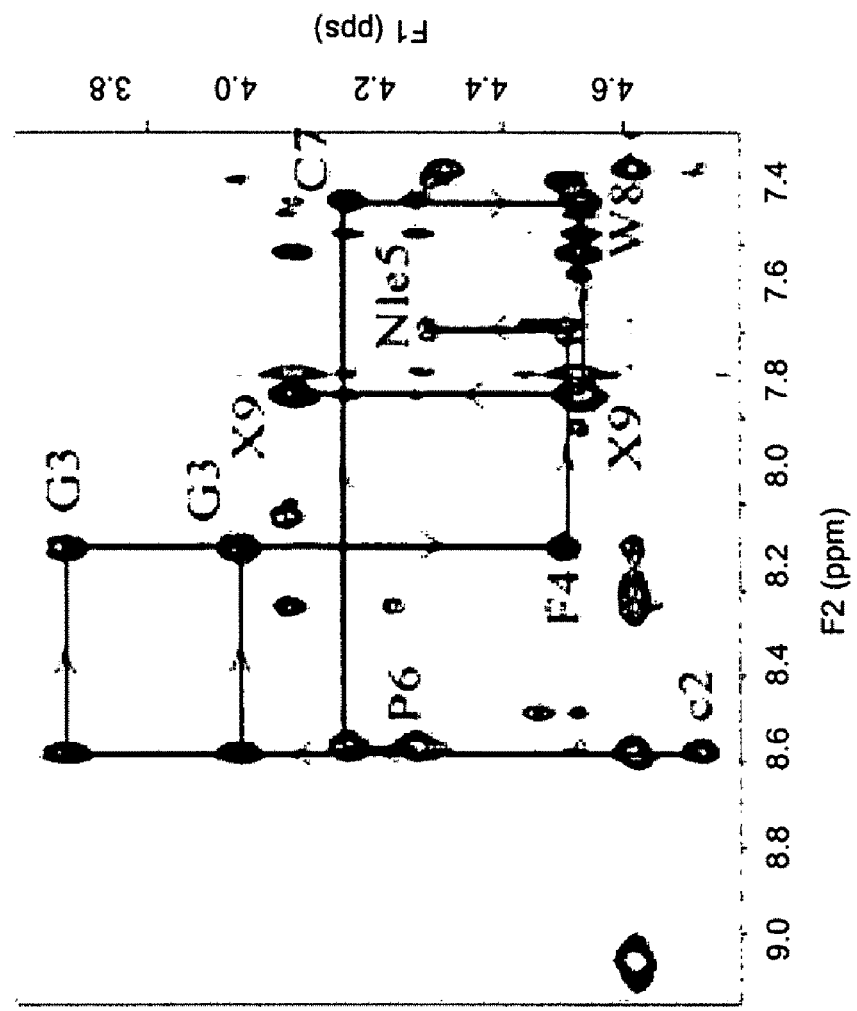
Figure 32C:
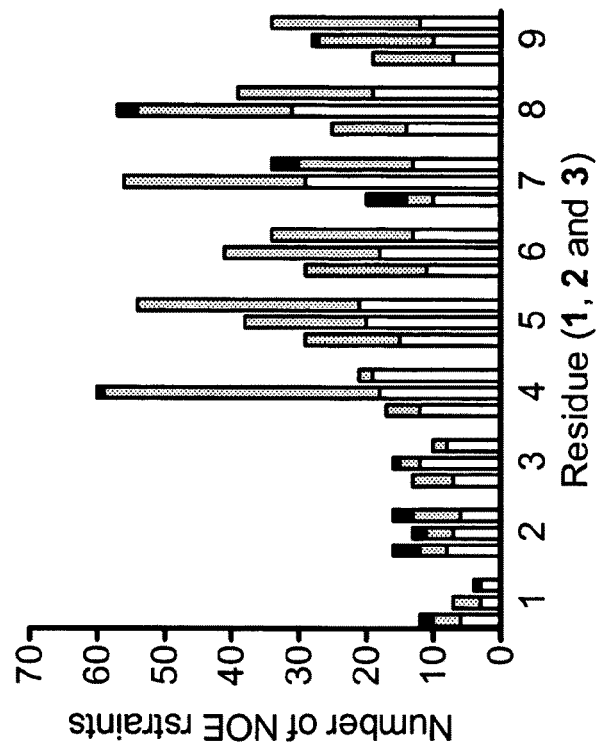
FIG. 32 A-D. Diagram of $H^N$-$H^α$ coupling constants, NOE connectivities, and $H^α$ chemical shift index (CSI) for the (A) TY035, (B) TY037 and (C) TY038. The $H^α$ CSI was calculated using the random-coil values reported by Andersen et al. The residual interresidue NOE distance restraints of TY035 (left), TY037 (middle) and TY038 (right) (D). Each column shows the sequential (i, i+1; open), medium-range (i, i+2-4; hatched) and long-range restraints (i, i+>4; filled), respectively. The residue Bzl or 9 stands for the respective C-terminal moieties. $^α$ the corresponding peak can't be found FIG. 33 A-C. Ensembles of the best 20 calculated structures in 40-fold DPC micelle/pH 4.5 buffer for (A) TY035, (B) TY037 and (C) TY038 with the lowest restraint energy, aligned on backbone atoms of residues (1) 1-8, (2) 1-4 and (3) 5-8. Only backbone atoms in the aligned structures are illustrated with C-terminal benzyl moiety (purple) and disulfide bond (orange). The most stable conformers (4) are shown with all heavy atoms (C, N, O and S).
Figure 32D:
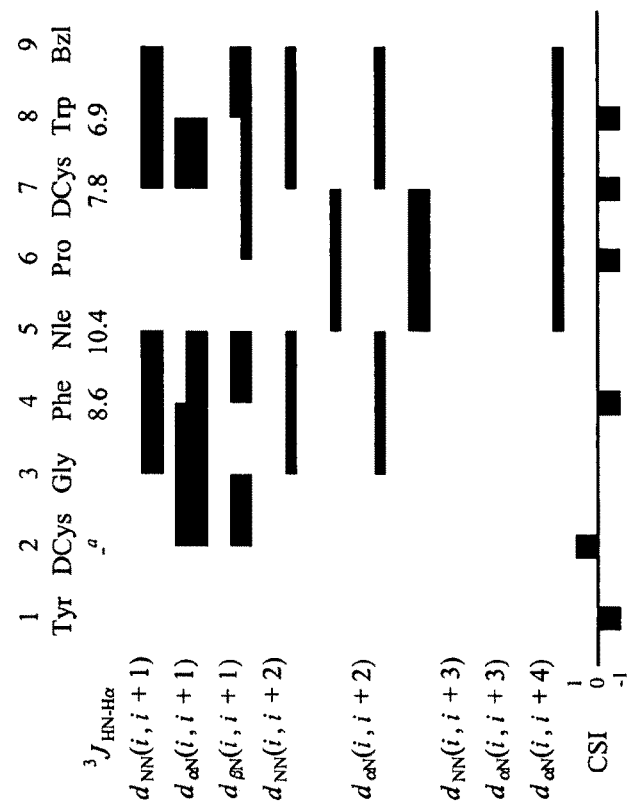
Figure 37C:
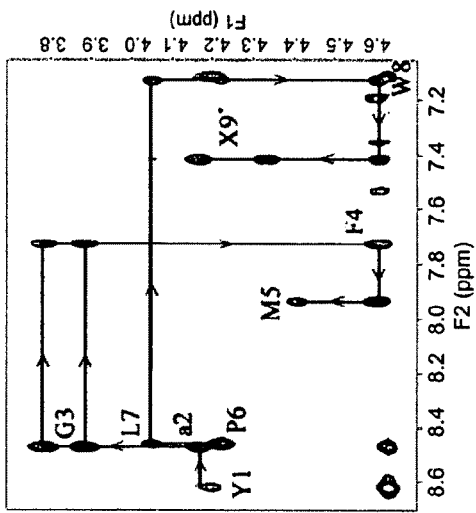
FIG. 37 A-C. Fingerprint ($H^N$-$H^α$) region of the NOESY spectrum of (A) TY005, (B) TY027 and (C) TY025 in DPC micelles. Intraresidue $H^N$-$H^α$ NOE cross-peaks are labeled with residue number, and arrows indicate the connectivity path from N-terminal to C-terminal. X9 represents the cross-peaks derived from the corresponding C-terminal $H^N$ and benzyl protons.
Figure 37B:
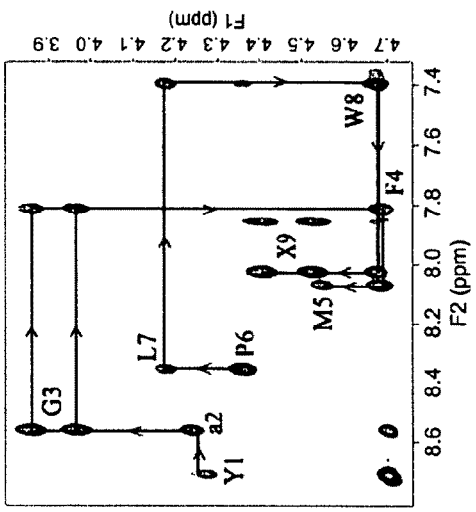
Figure 37A:
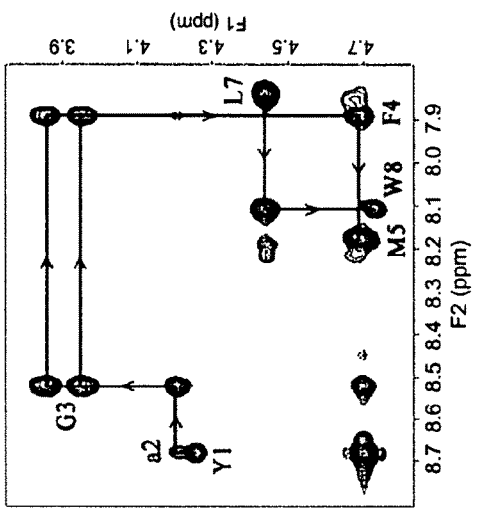
Figure 46C:
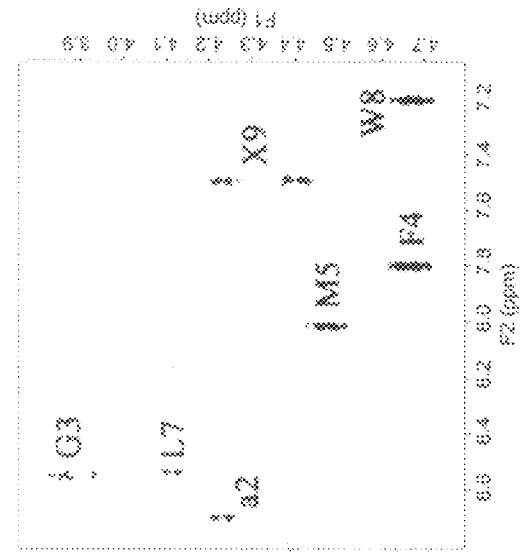
FIG. 46 A-C. Fingerprint ($H^N$-$H^\alpha$) region of the DQF-COSY spectrum of (A) TY005, (B) TY027 and (C) TY025 in DPC micelles. Intraresidue $H^N$-$H^\alpha$ cross-peaks are labeled with residue number. X9 represents the cross-peaks derived from the corresponding C-terminal $H^N$ and benzyl protons.
Figure 46B:
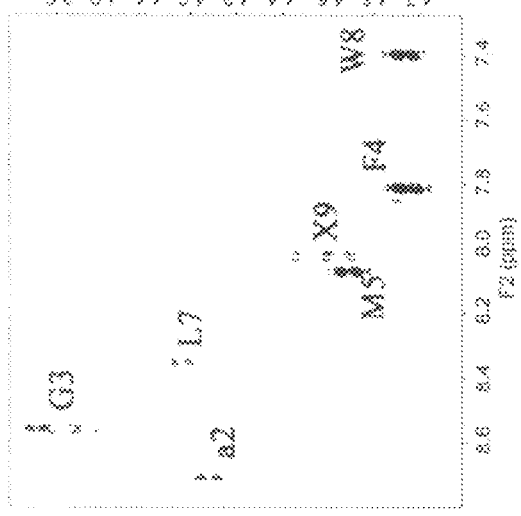
Figure 46A:
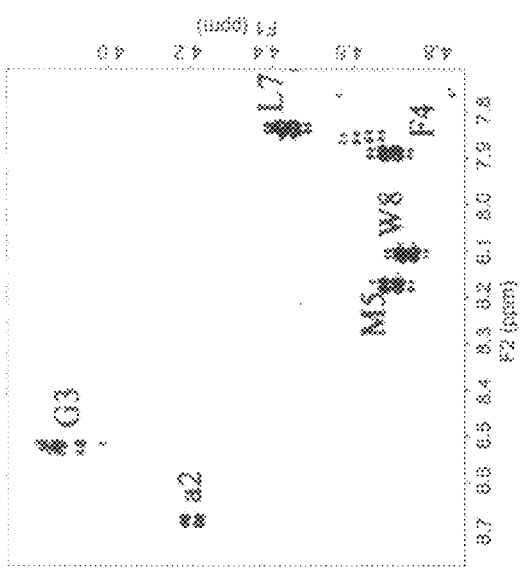

The NMR structures of the compounds in lipid-mimicking DCP micelles were solved to elucidate their conformational activity relationships as well as the interaction between compounds and micelles. Two-dimensional NMR studies including TOCSY, DQF-COSY and NOESY in pH 4.5 buffer (45 mM CD$_3$CO$_2$Na/HCl, 1 mM NaN$_3$, 90% H$_2$O/10% D$_2$O) with 40-fold perdeuterated DPC micelles were performed on the bifunctional compounds. At concentrations above the critical micelle point, DPC forms micelles with an aggregate number of 50 to 90, corresponding to one or two compound molecules per micelle (Lazaridis, *J. Phys. Chem. B* 2005, 109, 15098-15106). All $^1$H chemical shift assignments of the compounds are found in Tables 1.2-1.9, 5.2-5.8, and 9.2-9.7. The interresidual NOE connectivities and the $^3J_{HN-H\alpha}$ coupling constants of the compound derivatives are illustrated in FIGS. 31, 37, and 46. The observed NOE patterns, including $d_{NN}(i, i+1)$, $d_{\alpha N}(i, i+1)$ and some medium-range (i, i+2 or 3) connectivities, suggest the possibility of β-turn structures, while longer-range $d_{\alpha N}(i, i+3)$ and $d_{\alpha N}(i, i+4)$ connectivities indicate the existence of a helical structure in the molecules (FIGS. 32 and 38).

The structural calculations were performed based on NOE cross-peak volumes and $^3J_{HN-H\alpha}$ values. The well-defined β-turn rich conformations were found, for example, for all the tested cyclic compounds, but numbers of turn elements were varied by the cyclic derivatives. The highly-defined structures induced by, for example, a disulfide bond lead to these β-turn-rich structures which might play a key role for the affinities and activities. The particular orientations of the cyclic compound derivatives in DPC micelles were observed using the paramagnetic ion Mn$^{2+}$. Generally, their lipophilic side chains were embedded inside of the micelles but have different orientations due to the chirality of the induced cystein. The backbone atoms were found at the surface of the micelles except for Phe$^4$ and Leu$^7$ in TY037, only which has the ring at residues 2-5.

Figure 39A:
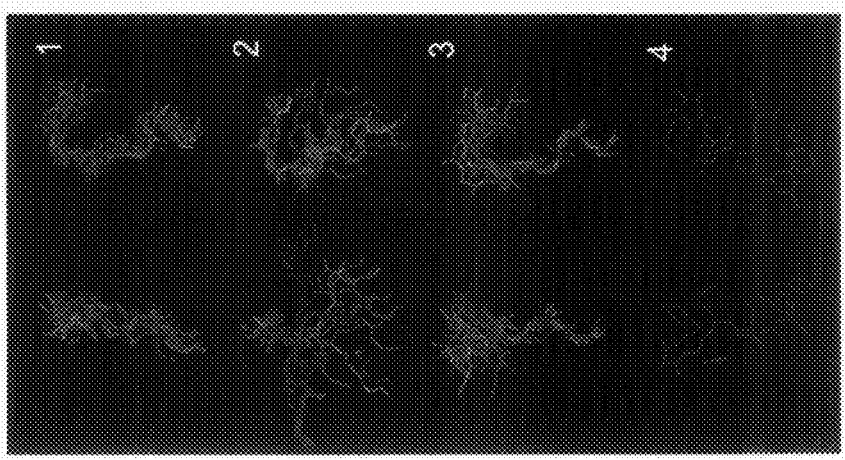
FIG. 39 A-C. Ensembles of the best 20 calculated structures in 40-fold DPC micelle/pH 4.5 buffer for (A) TY005, (B) TY027 and (C) TY025 with the lowest restraint energy, aligned on backbone atoms of residues (1) 1-8, (2) 1-4 and (3) 5-8, from N-terminal (up in the left image) to C-terminal (down). Only backbone atoms were illustrated in (1) and (2) for easier comparison, and the most stable conformers (4) are shown with all non-hydrogen atoms.
Figure 39B:
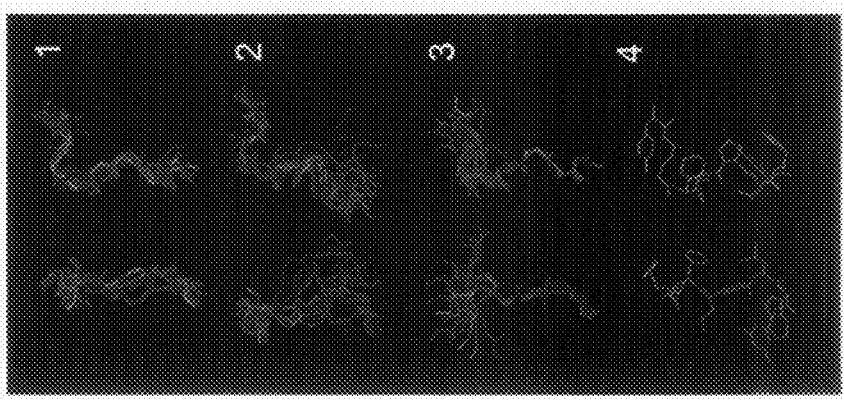

The analysis and statistics of the compound derivatives were performed on the structures with the lowest total energies after restrained molecular dynamics (rMD) refinement (Table 10 and 17). The superimposed images of the best structures are illustrated on FIGS. 33 and 39. The corresponding Ramachandran plots are depicted in FIGS. 34 and 40. These structured conformations of the compound derivatives were also confirmed from the angular order parameters regarding to the backbone dihedral angles φ and ψ (FIGS. 34 and 40). NMR structures and structural parameters are further exemplified on FIGS. 17-18, 21-24, 26B, and 27-29.

Mn$^{2+}$ was used as a paramagnetic ion to determine their location and orientation in the micelles (FIGS. 35 and 41-45). Mn$^{2+}$ ions cause a reduction in the resonance intensities of the solvent-exposed protons, and the effects of the compounds were observed as an ensemble of cross-peaks belonging to the same residue spin system in TOCSY spectra.

Figure 19A:
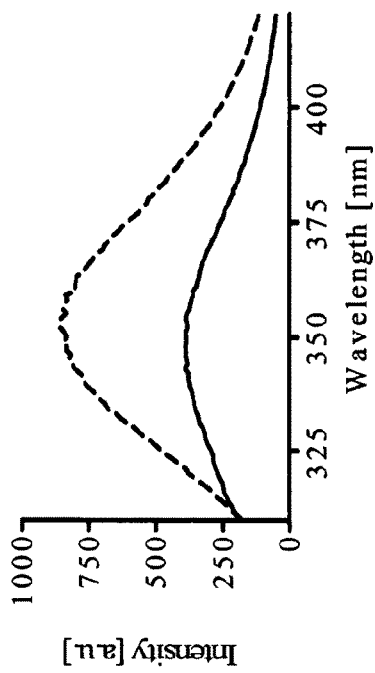
FIG. 19 A-C. Fluorescence blue shift of compounds in DPC micelle, TY005 (A), TY025 (C), and TY027 (B).
Figure 19B:
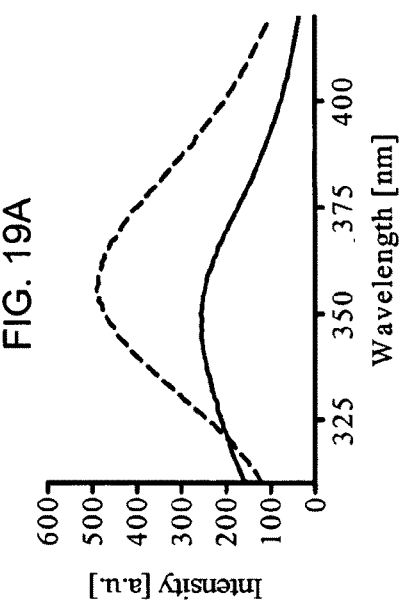
Figure 19C:
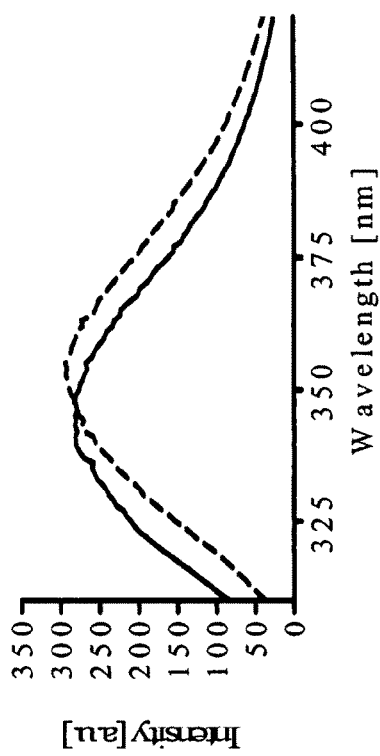
Figure 25:
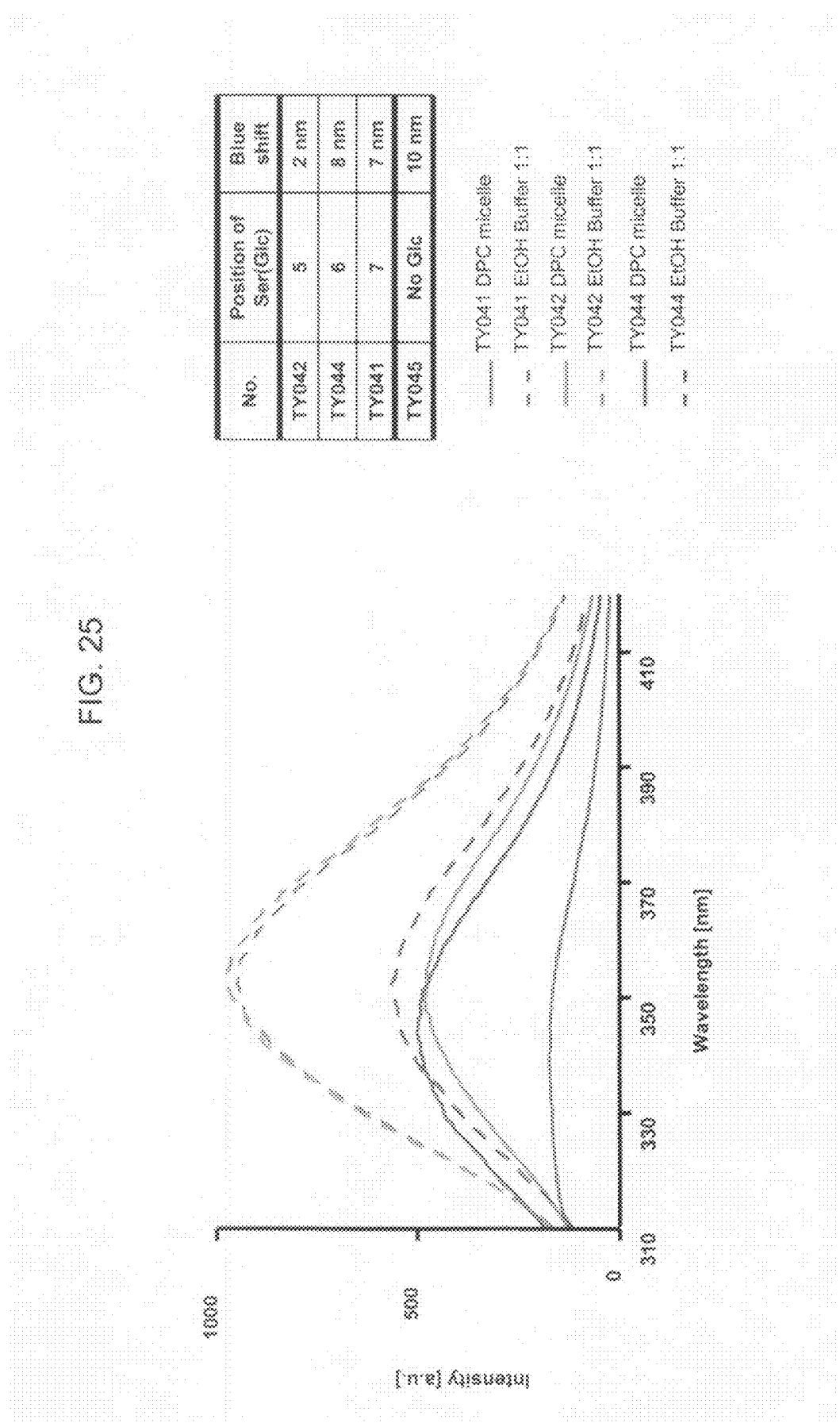
FIG. 25. Fluorescence blue shift study of glycosylated compounds in DPC micelle, TY041, TY042, TY044, and TY045.
Figure 27D:
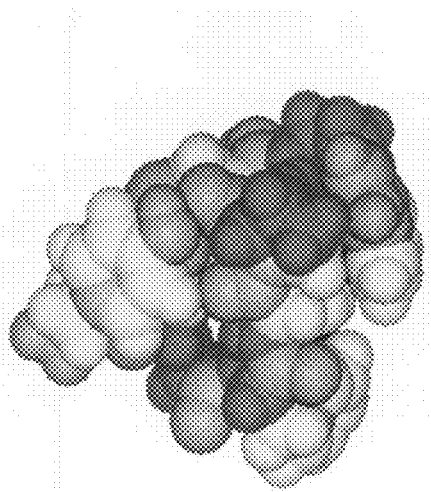
FIG. 27 A-F. NMR structure of cyclic compounds TY037 (A), TY035 (B), and TY038 (C). Location of cyclic compounds in the DPC micelle (NMR studies using paramagnetic agent $Mn^{2+}$) TY037 (D), TY035 (E), and TY038 (F).
Figure 27E:
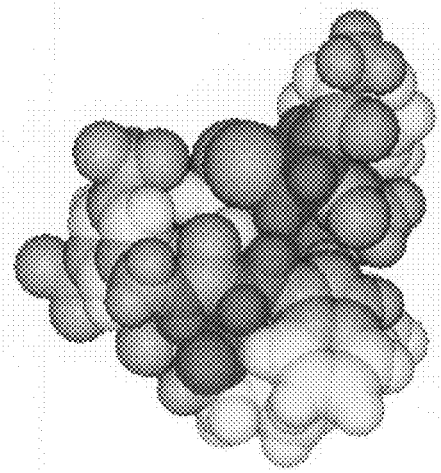
Figure 27F:
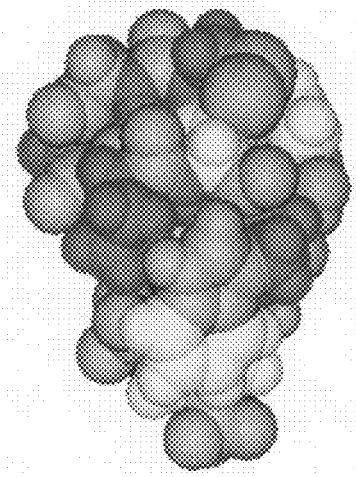
Figure 28B:
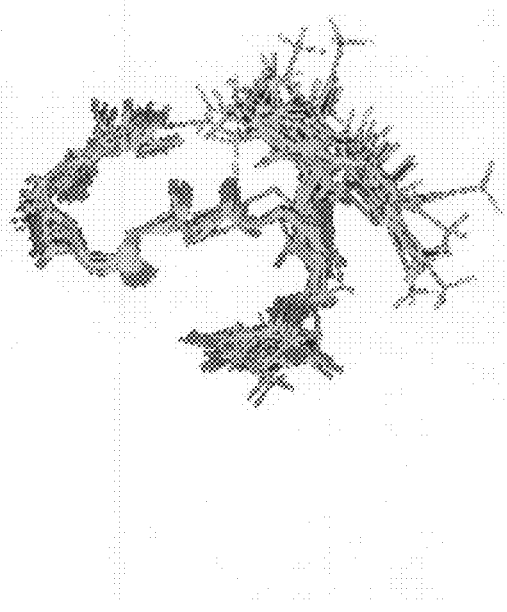
FIG. 28 A-D. NMR structure of cyclic compounds TY055 (A) and TY056 (B). Location of cyclic compounds in the DPC micelle (NMR studies using paramagnetic agent $Mn^{2+}$) TY041 (C) and TY056 (D).
Figure 28A:
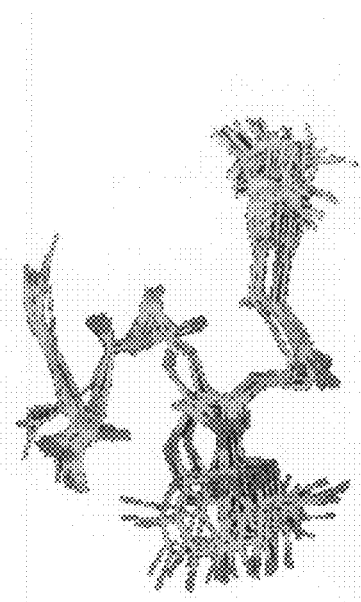

It is well known that the intrinsic fluorescence spectrum of tryptophan shifts to shorter wavelength ("blue shifted") as the polarity of the solvent surrounding the tryptophan residue decreases, and this blue shift is a good index to monitor the lipophilicity of the environment close to the tryptophan (Beechem, *Annu. Rev. Biochem.* 1985, 54, 43-71; Vivian, *Biophys. J.* 2001, 80, 2093-2109). The fluorescence of Trp in the compounds was measured with and without DPC micelles, in order to estimate the interaction between the compounds and membrane-like micelles. The fluorescence spectra in DPC micelles were compared to the spectra in the EtOH-buffer solution (EtOH:pH 7.4 HEPES buffer=1:1) (FIGS. 19 and 25).

Figure 18B:
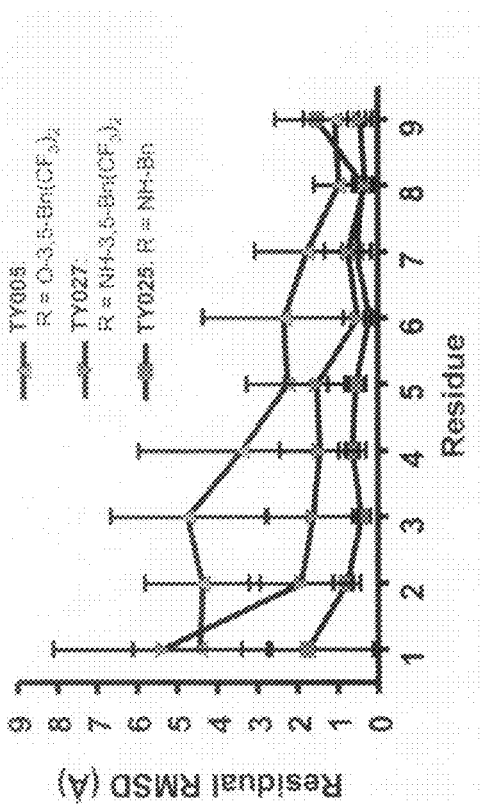
FIG. 18 A-E. Structural rigidity of TY005, TY025, TY027, and TY004. (A) RMSD: backbone atom. (B) RMSD: all heavy atoms; (C) Number of residues NOE restrains; for TY005, TY025, TY027; (D) CD spectra in dodecylphosphocholine (DPC) micelle; (E) Number of interresidue NOE distance restrains for TY005, TY025, TY027, and TY004.
Figure 18A:
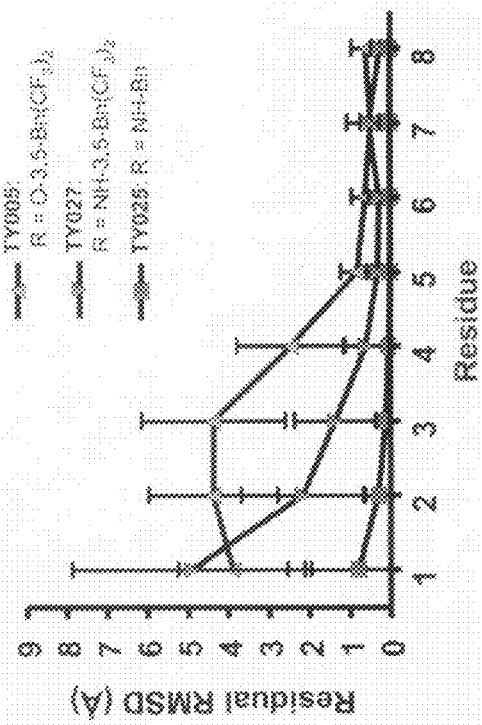
Figure 18E:
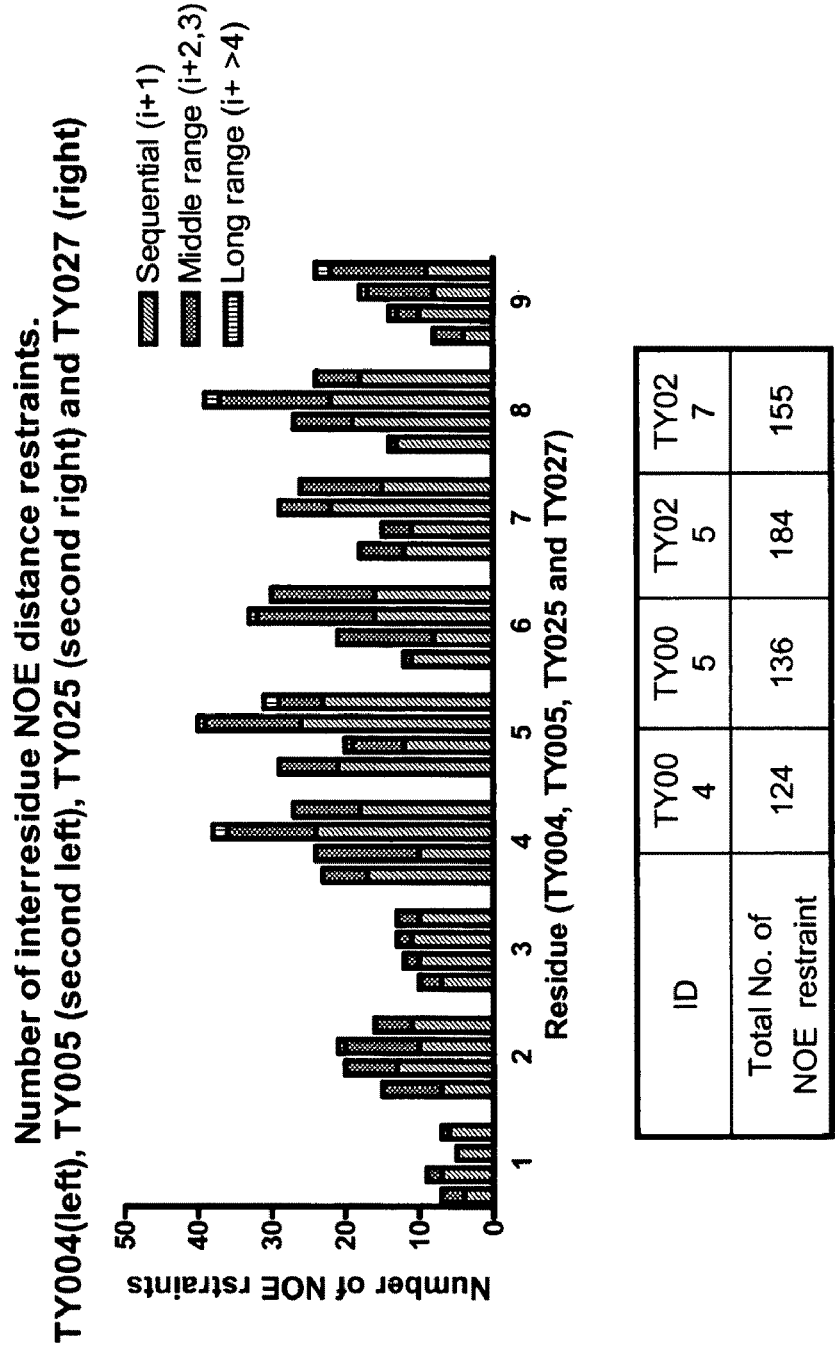

Circular dichroism (CD) spectra were also obtained for the compounds for further structural studies of how C-terminal modifications change structural rigidity of the compounds (FIGS. 18, 22, and 24).

These structural findings provide the significant information about the relationships of the primary sequence, secondary structure, bioactivities and molecule-compound interactions for the candidates of novel analgesics. In addition, our approach, in which the activity, three-dimensional structure and the orientation in micelles were simultaneously taken into consideration, gives the important information related to the compound interaction with membrane as well as with membrane-bound proteins, like GPCRs and ion channels.

V. Pharmaceutical Compositions

The chimeric compounds of the invention, salts, and derivatives thereof can be incorporated into pharmaceutical compositions suitable for administration. Such compositions typically comprise the compound and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the chimeric compounds can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric compounds) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding the chimeric compounds of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

VI. Treatment of Pain

The invention further provides methods of treating pain in animals in need of such treatment by administering an effective amount of one or more bifunctional analgesic component in order to produce analgesia in animals. Animals are preferably mammals, and more preferably, human.

Most acute pain serves a clear purpose: some problem needs to be addressed. Acute pain is characterized by help-seeking behavior. In most cases people cry out and move about in a very obvious manner. Physiologic responses to acute pain include tachycardia, tachypnea, and sweating due to discharge in the sympathetic nervous system. It is easy to recognize and empathize with acute pain. It is practically automatic. We wince if we see severe, acute pain and respond with our own "sympathetic" discharge. The treatment of acute pain can be difficult in that the intensity of pain may change dramatically over a short period of time. Physicians may have trouble adjusting pain medications rapidly enough to match the level of pain being experienced because pain intensity tends to escalate and decrease swiftly. Both under- and overtreatment can easily occur. Undertreatment risks excessive suffering. Overtreatment poses real medical risks. Thus, as acute pain changes rapidly, treatment of such pain requires frequent reassessment of the patient's status in order to avoid extremes of under- and overtreatment.

Chronic pain is very different from acute pain. It serves no biological purpose. While the suffering engendered may be as great as is that in acute pain, it is subjectively experienced and objectively displayed in a very different way. For reasons not well understood, chronic pain is characterized by physical and mental withdrawal. Vegetative signs very similar to those found in depression, such as anorexia, anhedonia, lethargy, and sleep disturbance are often present. Chronic pain frequently coexists with depression, making it difficult at times to distinguish between the two. Obvious displays of distress, as are found in acute pain, are usually absent. Chronic pain is very difficult to recognize. Even when recognized we tend not to experience the same intense, visceral empathy that arises so easily in the presence of acute pain.

Certain structural spine conditions (for example, degenerative disc disease, spinal stenosis and spondylolisthesis) can cause ongoing pain until successfully treated. These conditions are due to a diagnosable anatomical problem.

The analgesic components of the invention are potent for treating moderate to severe acute and chronic pain, and for acute and chronic intervention for drug abuse. The analgesic compound of the invention have potential therapeutic value for the treatment pain such as cancer pain, non-cancer pain, and chronic pain due to malignancy, particularly where opioid tolerancy is to be averted. Pain may be nerve associated pain and neuropathic pain. Neuropathic pain is an abnormal pain that can result from injuries to nerves and is difficult to treat. The use of opioids for the treatment of this chronic pain state remains problematic due to the side-effects associated with the doses necessary to achieve sufficient pain relief in patients. In addition, the use of opioids for the treatment of chronic pain, including cancer pain, is sometime limited by the development of time-dependent reduction in pain relief (analgesic tolerance). The effective treatment of chronic pain such as neuropathic pain and improved antinociceptive actions are associated with the compounds of the invention.

The compounds of this invention are also effective in treatment of neurogenic inflammation (e.g., neurogenic oedema), movement-related pain (e.g., chronic low lumbar back pain or other chronic spine conditions), and non-cancer pain (e.g., in a bedridden patient with multiple sclerosis).

One method to assess the analgesic properties of the chimeric compounds in an animal mode is the tail flick test, wherein the compound is administered to rats following intrathecal, intracerebroventricular, and intraperitoneal administration. The effects of opioid agonists and antagonists and NK1 antagonists and agonists on the activity of the compounds can be assessed according to methods common in the art.

The phrase "an effective amount" for treating a condition is used herein to mean an amount sufficient to reduce by at least 15%, preferably by at least 50%, more preferably by at least 90%, and more preferably prevent, a clinically significant deficit in the activity, function and response of the host. Alternatively, an effective amount is sufficient to cause an improvement in a clinically significant condition in the host. These parameters will depend on the severity of the condition being treated, other actions, such as diet modification, that are implemented, the weight, age, and sex of the subject, and other criteria, which can be readily determined according to standard good medical practice by those skill in the art. For example, doses of the administered components range from 0.03 to 100 mg/kg of body weight daily via peripheral administration or 1 to 100 microgram per body daily via intrathecal administration.

In order that this invention may be better understood, the following examples are set forth. These examples are for the

EXAMPLES

Example 1

Preparation of H-Pro-Leu-Trp-O-3,5-Bzl(CF$_3$)$_2$.HCl.

Boc-Pro-Leu-OH (2.05 g, 6.41 mmol), H-Trp-O-3,5-Bzl(CF$_3$)$_2$.HCl (2.76 g, 6.41 mmol) are dissolved in DMF (20 mL). HOBt (865 mg, 7.69 mmol), PyBOP (3.33 g, 7.69 mmol) and NMM (1.42 g, 14.1 mmol) were added to the solution at 0° C. After stirring for overnight, saturated aqueous sodium bicarbonate was added to the solution and most of the organic solvent was removed under reduced pressure. The residue was extracted with ethyl acetate three times followed by washing with saturated aqueous sodium chloride. The solution was dried over sodium sulfate. The solvent was evaporated and the crude compound was precipitated in cold petroleum ether, centrifuged and dried under reduced pressure.

The obtained solid was dissolved in 4M HCl in 1,4-dioxane (5 mL) at 0° C. After stirring for 1 h at r.t., the solution was concentrated under vacuum. Saturated aqueous sodium bicarbonate was added to the residue and extracted with ethyl acetate three times followed by washing with saturated aqueous sodium chloride. The solution was dried over sodium sulfate and concentrated under reduced pressure. The obtained residue was purified over silica gel chromatography (dichloromethane:methanol=100:2 to 100:10). The residue was dissolved in dichloromethane (10 mL) and 4M HCl in 1,4-dioxane (3 mL) was added at 0° C. The precipitate was centrifuged, dried under reduced pressure to obtain the title compound (2.40 g, 55.4%).

$^1$H-NMR (DMSO-d$_6$) δ: 0.78 (3H, d, J=5.5 Hz), 0.81 (3H, d, J=5.5 Hz), 1.33-1.42 (2H, m), 1.50-1.60 (1H, m), 1.65-1.73 (1H, m), 1.74-1.89 (2H, m), 2.16-2.27 (1H, m), 3.10-3.26 (4H, m), 4.10-4.20 (1H, m), 4.40 (1H, dd, J=7.5, 15.5 Hz), 4.58 (1H, dd, J=7.0, 14.5 Hz), 5.16 (1H, d, J=13.5 Hz), 5.24 (1H, d, J=13.5 Hz), 6.96 (1H, dd, J=7.5, 7.5 Hz), 7.05 (1H, dd, J=7.5, 7.5 Hz), 7.20 (1H, s), 7.33 (1H, d, J=8.5 Hz), 7.47 (1H, d, J=8.0 Hz), 7.96 (2H, s), 8.07 (1H, s), 8.46 (1H, bs), 8.60-8.68 (2H, m), 9.98 (1H, bs), 10.93 (1H, s).: MS (ESI) 641 (MH)$^+$

Example 2

General Procedure for the preparation of compounds H-Tyr-D-Ala-Gly-Phe-Xxx-Pro-Leu-Trp-O-3,5-Bzl(CF$_3$)$_2$.TFA (TY003, TY007, TY006, TY004, TY005, TY023, TY018, TY019). H-Pro-Leu-Trp-O-3,5-Bzl(CF$_3$)$_2$.HCl was coupled stepwise with 1.1 eq of Boc-Xxx-OH, Boc-Phe-OH, and Boc-Tyr-D-Ala-Gly-OH using the standard PyBOP/HOBt procedure to afford crude H-Tyr-D-Ala-Gly-Phe-Xxx-Pro-Leu-Trp-O-3,5-Bzl(CF$_3$)$_2$ .TFA (TY003, TY007, TY006, TY004, TY005, TY023, TY018, TY019). In every coupling, PyBOP (1.2 eq), HOBt (1.2 eq) and NMM (2.2 eq) were used in DMF. After the coupling was completed, saturated aqueous sodium bicarbonate was added to the solution and most of the organic solvent was removed under reduced pressure. The residue was extracted with ethyl acetate three times followed by washing with saturated aqueous sodium chloride. The solution was dried over sodium sulfate. The solvent was evaporated and the crude compound was precipitated in cold ether or cold petroleum ether, centrifuged and dried under reduced pressure. The obtained Boc-protected compound was treated with 4M HCl in 1,4-dioxane (for Boc-Xxx-OH and Boc-Phe-OH) or TFA (for Boc-Tyr-D-Ala-Gly-OH). After the deprotection was completed, the solution was concentrated and the crude compound was precipitated in cold ether, centrifuged and dried under reduced pressure. The yield and purity of obtained crude compounds through this three couplings were as follows: H-Tyr-D-Ala-Gly-Phe-Phe-Pro-Leu-Trp-O-3,5-Bzl(CF$_3$)$_2$.TFA (TY003), 96% yield, 77% purity; H-Tyr-D-Ala-Gly-Phe-D-Phe-Pro-Leu-Trp-O-3,5-Bzl(CF$_3$)$_2$.TFA (TY007), 60% yield, 60% purity; H-Tyr-D-Ala-Gly-Phe-Gly-Pro-Leu-Trp-O-3,5-Bzl(CF$_3$)$_2$.TFA (TY006), 66% yield, 81% purity; H-Tyr-D-Ala-Gly-Phe-Leu-Pro-Leu-Trp-O-3,5-Bzl(CF$_3$)$_2$.TFA (TY004), 63% yield, 83% purity; H-Tyr-D-Ala-Gly-Phe-Met-Pro-Leu-Trp-O-3,5-Bzl(CF$_3$)$_2$.TFA (TY005), 61% yield, 84% purity; H-Tyr-D-Ala-Gly-Phe-Met(O)-Pro-Leu-Trp-O-3,5-Bzl(CF$_3$)$_2$.TFA (TY023), 67% yield, 38% purity; H-Tyr-D-Ala-Gly-Phe-Nle-Pro-Leu-Trp-O-3,5-Bzl(CF$_3$)$_2$.TFA (TY018), 55% yield, 55% purity; H-Tyr-D-Ala-Gly-Phe-N-Me-Nle-Pro-Leu-Trp-O-3,5-Bzl(CF$_3$)$_2$.TFA (TY019), 49% yield, 30% purity. Pure compounds were obtained by following RP-HLC purification.

Example 3

Characterization of Compounds

Coupling and deprotection reactions were monitored by TLC. Preparative RP-HPLC was performed on Waters Delta Prep 4000 with Vydac 218TP C-18 column (22×250 mm, 10-15 μm, 42-57% of acetonitrile) or Waters XTerra C-18 column (19×250 mm, 10 μm, 40-60% of acetonitrile). The purified compounds were characterized by HRMS, TLC, analytical HPLC and $^1$H-1D-NMR (Table 1). $^1$H-NMR studies showed that cis/trans isomerization at Pro$^6$ residue was found in some of synthesized compounds. The ratio of two amide rotamers and their assignments are available in Tables 1.2-1.9.

TABLE 1.1

Sequence and analytical data of bifunctional compound ligands.

| | | m/z (M + H)$^+$ | | HPLC$^a$ log/k' | | TLC$^b$ (R$_f$) | | |
|---|---|---|---|---|---|---|---|---|
| no | Sequence | Obs. (ESI) | Calc. | (A) | (B) | (I) | (II) | (III) |
| 1 | H-Tyr-D-Ala-Gly-Phe-Phe-Pro-Leu-Trp-O-3,5-Bzl(CF$_3$)$_2$ (TY003) | 1226.5139 | 1226.5151 | 20.12 | 11.75 | 0.16 | 0.77 | 0.82 |
| 2 | H-Tyr-D-Ala-Gly-Phe-D-Phe-Pro-Leu-Trp-O-3,5-Bzl(CF$_3$)$_2$ (TY007) | 1226.5127 | 1226.5151 | 20.95 | 13.26 | 0.19 | 0.72 | 0.88 |
| 3 | H-Tyr-D-Ala-Gly-Phe-Gly-Pro-Leu-Trp-O-3,5-Bzl(CF$_3$)$_2$ (TY006) | 1136.4745 | 1136.4681 | 18.46 | 10.16 | 0.04 | 0.45 | 0.72 |

TABLE 1.1-continued

Sequence and analytical data of bifunctional compound ligands.

| no | Sequence | m/z (M + H)+ Obs. (ESI) | m/z (M + H)+ Calc. | HPLC[a] log k' (A) | HPLC[a] log k' (B) | TLC[b] (R_f) (I) | TLC[b] (R_f) (II) | TLC[b] (R_f) (III) |
|---|---|---|---|---|---|---|---|---|
| 4 | H-Tyr-D-Ala-Gly-Phe-Leu-Pro-Leu-Trp-O-3,5-Bzl(CF$_3$)$_2$ (TY004) | 1192.5286 | 1192.5307 | 19.51 | 11.42 | 0.23 | 0.81 | 0.79 |
| 5 | H-Tyr-D-Ala-Gly-Phe-Met-Pro-Leu-Trp-O-3,5-Bzl(CF$_3$)$_2$ (TY005) | 1210.4810 | 1210.4871 | 19.21 | 11.14 | 0.14 | 0.73 | 0.79 |
| 6 | H-Tyr-D-Ala-Gly-Phe-Met(O)-Pro-Leu-Trp-O-3,5-Bzl(CF$_3$)$_2$ (TY023) | 1226.4786 | 1226.4820 | 16.91 | 9.49 | 0.06 | 0.44 | 0.62 |
| 7 | H-Tyr-D-Ala-Gly-Phe-Nle-Pro-Leu-Trp-O-3,5-Bzl(CF$_3$)$_2$ (TY018) | 1192.5291 | 1192.5307 | 19.70 | 11.64 | 0.21 | 0.79 | 0.82 |
| 8 | H-Tyr-D-Ala-Gly-Phe-N-Me-Nle-Pro-Leu-Trp-O-3,5-Bzl(CF$_3$)$_2$ (TY019) | 1206.5489 | 1206.5464 | 19.94 | 11.94 | 0.20 | 0.79 | 0.85 |

[a] HPLC log k' = log [(compound retention time − solvent retention time)/solvent retention time]. (A) 10-90% of acetonitrile containing 0.1% TFA within 40 min and up to 95% within additional 5 min, 1 mL/min, (B) 30-70% of acetonitrile containing 0.1% TFA within 20 min and up to 95% within additional 5 min, 1 mL/min.
[b] (I) CHCl$_3$:MeOH:AcOH = 90:10:3, (II) EtOAc:n-BuOH:water:AcOH = 5:3:1:1, (III) n-BuOH:water:AcOH = 4:1:1.

TABLE 1.2

1H-NMR data.
H-Tyr-D-Ala-Gly-Phe-Phe-Pro-Leu-Trp-O-3,5-Bzl(CF$_3$)$_2$•TFA (TY005);
$^1$H-NMR (DMSO-d$_6$) δ:

| AA | NH | α | β | misc. |
|---|---|---|---|---|
| Tyr[1] | 8.05(3H, bs) | 3.93-4.20(1H, m) | 2.78(1H, dd, J = 8.5, 14.0 Hz), 2.89(1H, dd, J = 8.5, 14.0 Hz) | 6.70(2H, d, J = 8.5 Hz: PhH), 7.02(2H, d, J = 8.0 Hz: PhH), 9.33(1H, bs: PhOH) |
| D-Ala[2] | 8.53(1H, d, J = 7.5 Hz) | 4.31-4.40(1H, m) | 1.06(3H, d, J = 7.0 Hz) | — |
| Gly[3] | 8.17(1H, t, J = 6.0 Hz) | 3.59(1H, dd, J = 5.5, 16.5 Hz), 3.69(1H, dd, J = 5.5, 17.0 Hz) | — | — |
| Phe[4] | 7.89(1H, d, J = 9.0 Hz) | 4.50-4.59(1H, m) | 2.69(1H, dd, J = 9.5, 14.0 Hz), 2.89-2.96(1H, m) | 7.12-7.29(5H, m: PhH) |
| Phe[5] | 8.45(1H, d, J = 8.0 Hz) | 4.65(1H, dd, J = 6.5, 12.5 Hz) | 2.90-2.95(1H, m), 2.96-3.06(1H, m) | 7.12-7.29(5H, m: PhH) |
| Pro[6] | — | 4.28-4.39(1H, m) | 1.80-1.88(1H, m), 1.89-1.97(1H, m) | 1.69-1.80(2H, m: γCH$_2$), 3.40-3.51(2H, m: δCH$_2$) |
| Leu[7] | 7.87(1H, d, J = 8.5 Hz) | 4.31-4.40(1H, m) | 1.34-1.42(2H, m) | 1.53-1.64(1H, m: γCH$_2$), 0.74(3H, d, J = 6.5 Hz: δCH$_2$), 0.79(3H, d, J = 6.0 Hz: δCH$_2$) |
| Trp[8] | 8.40(1H, d, J = 7.0 Hz) | 4.51-4.60(1H, m) | 3.15(1H, dd, J = 6.5, 15.0 Hz), 3.21(1H, dd, J = 6.5, 14.0 Hz) | 6.95(1H, dd, J = 7.5, 7.5 Hz: Ind5), 7.05(1H, dd, J = 7.5, 7.5 Hz: Ind6), 7.17(1H, s: Ind2), 7.32(1H, d, J = 8.0 Hz: Ind4), 7.46(1H, d, J = 8.0 Hz: Ind7), 10.88(1H, bs, IndNH) |
| 3,5-Bn(CF$_3$)$_2$ | — | — | — | 5.12(1H, d, J = 13.5 Hz: CH$_2$Ph), 5.21(1H, d, J = 13.0 Hz: CH$_2$Ph), 7.90(2H, s: PhH), 8.05(1H, s: PhH) |

TABLE 1.3

1H-NMR data.
H-Tyr-D-Ala-Gly-Phe-D-Phe-Pro-Leu-Trp-O-3,5-Bzl(CF$_3$)$_2$•TFA (TY007),
2 amide bond rotamers at the Pro[6] N, ca. 1:1 ratio; $^1$H-NMR (DMSO-d$_6$) δ:

| AA | NH | α | β | misc. |
|---|---|---|---|---|
| Tyr[1] | 8.03/8.07(3H, bs) | 3.93-4.03(1H, m) | 2.78-2.92(2H, m) | 6.70(2H, d, J = 8.5 Hz: PhH), 7.02(2H, d, J = 8.0 Hz: PhH), 9.33(1H, bs: PhOH) |
| D-Ala[2] | 8.50/8.56(1H, d, J = 7.5 Hz) | 4.31(1H, qua, J = 6.5 Hz) | 1.03/1.05(3H, d, J = 7.0 Hz) | — |
| Gly[3] | 8.13-8.21(1H, m) | 3.50-3.71(2H, m) | — | — |
| Phe[4] | 7.79/7.88(1H, d, J = 7.5 Hz) | 4.44-4.50/4.58-4.64(1H, m) | 2.26-2.34/2.50-2.58(1H, m), 2.48-2.53/2.72-2.80(1H, m) | 7.07-7.30(5H, m: PhH) |
| D-Phe[5] | 8.66/8.68(1H, d, J = 8.0 Hz) | 4.36-4.44/4.71(1H, m/dd, J = 6.5, 13.0 Hz) | 2.71-2.76/2.75-2.81(1H, m), 2.90-2.89(1H, m) | 6.88-6.92, 7.07-7.30(5H, m: PhH) |
| Pro[6] | — | 4.22-4.28/4.84-4.88(1H, m) | 1.65-1.70/1.94-1.99(1H, m), 1.77-1.82/2.12-2.18(1H, m) | 1.62-1.65/1.63-1.69(1H, m: γCH$_2$), 1.70-1.77/1.70-1.75(1H, m: |

TABLE 1.3-continued

1H-NMR data.
H-Tyr-D-Ala-Gly-Phe-D-Phe-Pro-Leu-Trp-O-3,5-Bzl(CF$_3$)$_2$•TFA (TY007),
2 amide bond rotamers at the Pro$^6$ N, ca. 1:1 ratio; $^1$H-NMR (DMSO-d$_6$) δ:

| AA | NH | α | β | misc. |
|---|---|---|---|---|
| | | | | γCH$_2$), 3.48-3.55/3.45-3.49(1H, m: δCH$_2$), 3.12-3.15/3.35-3.40(1H, m: δCH$_2$) |
| Leu$^7$ | 7.82/8.27(1H, d, J = 7.5 Hz) | 4.20-4.27/ 4.42-4.48(1H, m) | 1.35-1.46(2H, m) | 1.52-1.62(1H, m: γCH$_2$), 0.75/0.77(3H, d, J = 6.5 Hz: δCH$_2$), 0.80/0.81(3H, d, J = 6.5 Hz: δCH$_2$) |
| Trp$^8$ | 8.29/8.63(1H, d, J = 9.0 Hz) | 4.50-4.58(1H, m) | 3.09-3.22(2H, m) | 6.94(1H, dd, J = 7.5, 7.5 Hz: Ind5), 7.05(1H, dd, J = 8.0, 8.0 Hz: Ind6), 7.17(1H, s: Ind2), 7.31(1H, d, J = 7.5 Hz: Ind4), 7.41/7.46(1H, d, J = 7.5 Hz: Ind7), 10.86/10.88(1H, bs, IndNH) |
| 3,5-Bn(CF$_3$)$_2$ | — | — | — | 5.08/5.10(1H, d, J = 13.0 Hz: CH$_2$Ph), 5.17/5.19(1H, d, J = 13.0 Hz: CH$_2$Ph), 7.90/7.91(2H, s: PhH), 8.05(1H, s: PhH) |

TABLE 1.4

1H-NMR data.
H-Tyr-D-Ala-Gly-Phe-Gly-Pro-Leu-Trp-O-3,5-Bzl(CF$_3$)$_2$•TFA (TY006),
2 amide bond rotamers at the Pro$^6$ N, ca. 2:1 ratio; $^1$H-NMR (DMSO-d$_6$) δ:

| AA | NH | α | β | misc. |
|---|---|---|---|---|
| Tyr$^1$ | 8.05(3H, bs) | 3.92-4.03(1H, m) | 2.84(1H, dd, J = 7.0, 13.5 Hz), 2.90(1H, dd, J = 6.5, 13.5 Hz) | 6.70(2H, d, J = 8.0 Hz: PhH), 7.02(2H, d, J = 8.5 Hz: PhH), 9.33(1H, bs: PhOH) |
| D-Ala$^2$ | 8.52(1H, d, J = 7.0 Hz) | 4.28-4.33(1H, m) | 1.06(3H, d, J = 7.0 Hz) | — |
| Gly$^3$ | 8.13-8.20(1H, m) | 3.57-3.65(1H, m), 3.67-3.75(1H, m) | — | — |
| Phe$^4$ | 8.01-8.06(1H, m) | 4.53-4.65 (1H, m) | 2.25(1H, dd, J = 10.0, 13.5 Hz), 2.97-3.07(1H, m) | 7.12-7.24(5H, m: PhH) |
| Gly$^5$ | 8.27/8.11(1H, t, J = 5.5 Hz) | 3.83-3.94/3.29-3.38(1H, m), 3.90-4.00(1H, m) | — | — |
| Pro$^6$ | — | 4.30-4.35/4.43-4.45(1H, m) | 1.78-1.87/1.69-1.75(2H, m) | 1.67-1.73/1.76-1.84(1H, m: γCH$_2$), 1.91-1.99/2.10-2.18(1H, m: γCH$_2$), 3.40-3.53/3.35-3.44(2H, m: δCH$_2$) |
| Leu$^7$ | 7.91/8.25(1H, d, J = 8.5 Hz) | 4.28-4.33/4.37-4.44(1H, m) | 1.32-1.43(2H, m) | 0.75/0.76(3H, d, J = 6.0/5.0 Hz: δCH$_2$), 0.79(3H, d, J = 6.5 Hz: δCH$_2$), 1.50-1.60(1H, m: γCH$_2$) |
| Trp$^8$ | 8.29/8.51(1H, d, J = 7.0 Hz) | 4.52-4.60(1H, m) | 3.14(1H, dd, J = 6.5, 14.0 Hz), 3.21(1H, dd, J = 6.5, 14.0 Hz) | 6.96(1H, dd, J = 7.5, 7.5 Hz: Ind5), 7.05(1H, dd, J = 7.0, 7.0 Hz: Ind6), 7.17(1H, s: Ind2), 7.32(1H, d, J = 8.0 Hz: Ind4), 7.45/7.47(1H, d, J = 7.5/5.5 Hz: Ind7), 10.86/10.88(1H, bs, IndNH) |
| 3,5-Bn(CF$_3$)$_2$ | — | — | — | 5.11/5.14(1H, d, J = 13.5 Hz: CH$_2$Ph), 5.20/5.22(1H, d, J = 13.0 Hz: CH$_2$Ph), 7.92/7.94(2H, s: PhH), 8.05(1H, s: PhH) |

TABLE 1.5

1H-NMR data.
H-Tyr-D-Ala-Gly-Phe-Leu-Pro-Leu-Trp-O-3,5-Bzl(CF$_3$)$_2$•TFA (TY004);
$^1$H-NMR (DMSO-d$_6$) δ:

| AA | NH | α | β | misc. |
|---|---|---|---|---|
| Tyr$^1$ | 8.12(3H, bs) | 4.00(1H, bs) | 2.84-2.93(2H, m) | 6.71(2H, d, J = 7.5 Hz: PhH), 7.03(2H, d, J = 8.0 Hz: PhH), 9.49(1H, bs: PhOH) |
| D-Ala$^2$ | 8.57(1H, d, J = 7.0 Hz) | 4.28-4.38(1H, m) | 1.06(3H, d, J = 6.5 Hz) | — |
| Gly$^3$ | 8.20(1H, m) | 3.61(1H, dd, J = 5.0 16.5 Hz), 3.72(1H, dd, J = 5.0, 17.0 Hz) | — | — |

TABLE 1.5-continued

1H-NMR data.
H-Tyr-D-Ala-Gly-Phe-Leu-Pro-Leu-Trp-O-3,5-Bzl(CF$_3$)$_2$•TFA (TY004);
$^1$H-NMR (DMSO-d$_6$) δ:

| AA | NH | α | β | misc. |
|---|---|---|---|---|
| Phe$^4$ | 7.91(1H, m) | 4.48-4.59(1H, m) | 2.68-2.78(1H, m), 2.90-3.00(1H, m) | 7.12-7.27(5H, m: PhH) |
| Leu$^5$ | 8.39(1H, d, J = 6.5 Hz) | 4.50-4.61(1H, m) | 1.41-1.49(2H, m) | 0.86(3H, d, J = 7.5 Hz: δCH$_2$), 0.88(3H, d, J = 7.0 Hz: δCH$_2$), 1.57-1.67(1H, m: γCH$_2$) |
| Pro$^6$ | — | 4.27-4.40(1H, m) | 1.71-1.85(2H, m) | 1.81-1.96(1H, m: γCH$_2$), 3.10-3.25(2H, m: δCH$_2$) |
| Leu$^7$ | 7.85(1H, d, J = 7.5 Hz) | 4.30-4.44(1H, m) | 1.30-1.38(2H, m) | 0.76(3H, d, J = 6.0 Hz: δCH$_2$), 0.79(3H, d, J = 6.0 Hz: δCH$_2$), 1.51-1.60(1H, m: γCH$_2$) |
| Trp$^8$ | 8.33(1H, d, J = 7.5 Hz) | 4.50-4.59(1H, m) | 3.18(2H, s) | 6.96(1H, dd, J = 7.0, 7.0 Hz: Ind5), 7.05(1H, dd, J = 7.5, 7.5 Hz: Ind6), 7.17(1H, s: Ind2), 7.33(1H, d, J = 8.0 Hz: Ind4), 7.46(1H, d, J = 8.0 Hz: Ind7), 10.87(1H, bs, IndNH) |
| 3,5-Bn(CF$_3$)$_2$ | — | — | — | 5.12(1H, d, J = 13.0 Hz: CH$_2$Ph), 5.21(1H, d, J = 13.5 Hz: CH$_2$Ph), 7.93(2H, s: PhH), 8.04(1H, s: PhH) |

TABLE 1.6

1H-NMR data.
H-Tyr-D-Ala-Gly-Phe-Met-Pro-Leu-Trp-O-3,5-Bzl(CF$_3$)$_2$•TFA (TY005);
$^1$H-NMR (DMSO-d$_6$) δ:

| AA | NH | α | β | misc. |
|---|---|---|---|---|
| Tyr$^1$ | 8.05(3H, bs) | 3.93-4.13(1H, m) | 2.86(1H, dd, J = 6.5, 9.5 Hz), 2.89(1H, dd, J = 6.5, 9.5 Hz) | 6.69(2H, d, J = 8.0 Hz: PhH), 7.03(2H, d, J = 8.0 Hz: PhH), 9.33(1H, bs: PhOH) |
| D-Ala$^2$ | 8.55(1H, d, J = 8.0 Hz) | 4.28-4.39(1H, m) | 1.06(3H, d, J = 7.0 Hz) | — |
| Gly$^3$ | 8.19(1H, t, J = 5.0 Hz) | 3.63(1H, dd, J = 6.5 16.0 Hz), 3.71(1H, dd, J = 6.5, 16.0 Hz) | — | — |
| Phe$^4$ | 7.97(1H, d, J = 8.0 Hz) | 4.50-4.59(1H, m) | 2.74(1H, dd, J = 9.5, 13.0 Hz), 2.90-2.99(1H, m) | 7.17-7.25(5H, m: PhH) |
| Met$^5$ | 8.41(1H, d, J = 9.5 Hz) | 4.59-4.66(1H, m) | 1.75-1.81(1H, m), 1.89-1.95(1H, m) | 2.45-2.51(2H, m: γCH$_2$), 2.03(3H, s: SCH$_3$) |
| Pro$^6$ | — | 4.28-4.39(1H, m) | 1.68-1.74(1H, m), 1.92-1.98(1H, m) | 1.75-1.81(1H, m: γCH$_2$), 1.85-1.92(1H, m: γCH$_2$), 3.52-3.61(2H, m: δCH$_2$) |
| Leu$^7$ | 7.88(1H, d, J = 8.0 Hz) | 4.27-4.38(1H, m) | 1.31-1.37(2H, m) | 1.52-1.61(1H, m: γCH$_2$), 0.76(3H, d, J = 6.5 Hz: δCH$_2$), 0.79(3H, d, J = 6.5 Hz: δCH$_2$) |
| Trp$^8$ | 8.39(1H, d, J = 7.5 Hz) | 4.50-4.59(1H, m) | 3.14(1H, dd, J = 6.5, 9.5 Hz), 3.20(1H, dd, J = 6.5, 9.5 Hz) | 6.96(1H, dd, J = 7.5, 7.5 Hz: Ind5), 7.07(1H, dd, J = 7.0, 7.0 Hz: Ind6), 7.17(1H, s: Ind2), 7.32(1H, d, J = 8.0 Hz: Ind4), 7.47(1H, d, J = 7.5 Hz: Ind7), 10.86(1H, bs, IndNH) |
| 3,5-Bn(CF$_3$)$_2$ | — | — | — | 5.11(1H, d, J = 13.0 Hz: CH$_2$Ph), 5.21(1H, d, J = 13.5 Hz: CH$_2$Ph), 7.92(2H, s: PhH), 8.05(1H, s: PhH) |

TABLE 1.7

1 H-NMR data.
H-Tyr-D-Ala-Gly-Phe-Met(O)-Pro-Leu-Trp-O-3,5-Bzl(CF$_3$)$_2$•TFA (TY023),
2 amide bond rotamers at the Pro$^6$ N, ca. 10:1 ratio; $^1$H-NMR (DMSO-d$_6$) δ:

| AA | NH | α | β | misc. |
|---|---|---|---|---|
| Tyr$^1$ | 8.08/8.11(3H, bs) | 3.98(1H, bs) | 2.83-2.94(2H, m) | 6.70(2H, d, J = 8.0 Hz: PhH), 7.02(2H, d, J = 8.5 Hz: PhH), 9.38(1H, bs: PhOH) |
| D-Ala$^2$ | 8.54(1H, d, J = 7.0 Hz) | 4.29-4.36(1H, m) | 1.07(3H, d, J = 7.0 Hz) | — |
| Gly$^3$ | 8.26-8.35(1H, m) | 3.57-3.65(1H, m), 3.65-3.78(1H, m) | — | — |
| Phe$^4$ | 8.01(1H, d, J = 8.0 Hz) | 4.52-4.57(1H, m) | 2.74-2.80(1H, m), 2.93-3.00(1H, m) | 7.13-7.28(5H, m: PhH) |

TABLE 1.7-continued

1 H-NMR data.
H-Tyr-D-Ala-Gly-Phe-Met(O)-Pro-Leu-Trp-O-3,5-Bzl(CF$_3$)$_2$•TFA (TY023),
2 amide bond rotamers at the Pro$^6$ N, ca. 10:1 ratio; $^1$H-NMR (DMSO-d$_6$) δ:

| AA | NH | α | β | misc. |
|---|---|---|---|---|
| Met(O)$^5$ | 8.44-8.49/8.48-8.51(1H, m) | 4.61-4.73(1H, m) | 1.85-1.93(1H, m), 2.02-2.10(1H, m) | 2.66-2.74(1H, m: γCH$_2$), 2.77-2.84(1H, m: γCH$_2$), 2.50(3H, s: SCH$_3$) |
| Pro$^6$ | — | 4.29-4.33(1H, m) | 1.65-1.72(1H, m), 1.93-2.01(1H, m) | 1.71-1.79(1H, m: γCH$_2$), 1.78-1.87(1H, m: γCH$_2$), 3.51-3.57/3.46-3.51(H, m: δCH$_2$), 3.51-3.57/3.55-3.60(H, m: δCH$_2$) |
| Leu$^7$ | 7.91/8.25(1H, d, J = 8.5 Hz) | 4.29-4.36(1H, m) | 1.30-1.40(2H, m) | 0.76(3H, d, J = 5.0 Hz: δCH$_2$), 0.79(3H, d, J = 6.5 Hz: δCH$_2$), 1.50-1.62(1H, m: γCH$_2$) |
| Trp$^8$ | 8.38/8.21(1H, d, J = 6.5 Hz) | 4.51-4.57/4.47-4.52(1H, m) | 3.15(1H, dd, J = 7.5, 14.5 Hz), 3.21 (1H, dd, J = 6.5, 15.0 Hz) | 6.96(1H, dd, J = 7.5, 7.5 Hz: Ind5), 7.05(1H, dd, J = 7.5, 7.5 Hz: Ind6), 7.17(1H, s: Ind2), 7.32(1H, d, J = 8.0 Hz: Ind4), 7.46(1H, d, J = 8.0 Hz: Ind7), 10.88(1H, bs, IndNH) |
| 3,5-Bn(CF$_3$)$_2$ | — | — | — | 5.12/5.21(1H, d, J = 13.5 Hz: CH$_2$Ph), 5.21/5.29(1H, d, J = 13.5 Hz: CH$_2$Ph), 7.92/7.99(2H, s: PhH), 8.05(1H, s: PhH) |

TABLE 1.8

1H-NMR data.
H-Tyr-D-Ala-Gly-Phe-Nle-Pro-Leu-Trp-O-3,5-Bzl(CF$_3$)$_2$•TFA (TY018);
$^1$H-NMR (DMSO-d$_6$) δ:

| AA | NH | α | β | misc. |
|---|---|---|---|---|
| Tyr$^1$ | 8.05(3H, bs) | 3.98(1H, bs) | 2.84(1H, dd, J = 7.5, 13.5 Hz), 2.91(1H, dd, J = 7.0, 13.5 Hz)) | 6.71(2H, d, J = 7.5 Hz: PhH), 7.03(2H, d, J = 8.5 Hz: PhH), 9.33(1H, bs: PhOH) |
| D-Ala$^2$ | 8.53(1H, d, J = 7.0 Hz) | 4.29-4.36(1H, m) | 1.07(3H, d, J = 7.0 Hz) | — |
| Gly$^3$ | 8.19(1H, t, J = 6.0 Hz) | 3.62(1H, dd, J = 5.5, 15.0 Hz), 3.71(1H, dd, J = 5.5, 15.0 Hz) | — | — |
| Phe$^4$ | 7.92(1H, d, J = 8.0 Hz) | 4.53-4.59(1H, m) | 2.73(1H, dd, J = 10.5, 15.0 Hz), 2.90-3.00(1H, m) | 7.13-7.28(5H, m: PhH) |
| Nle$^5$ | 8.32(1H, d, J = 7.5 Hz) | 4.45(1H, dd, J = 7.0, 13.0 Hz) | 1.46-1.52(1H, m), 1.60-1.68(1H, m) | 0.80-0.88(3H, m: εCH$_3$), 1.16-1.30(4H, m: γCH$_2$, δCH$_2$) |
| Pro$^6$ | — | 4.33-4.38(1H, m) | 1.80-1.93(2H, m) | 1.69-1.80(2H, m: γCH$_2$), 3.42-3.51(1H, m: δCH$_2$), 3.51-3.60(1H, m: δCH$_2$) |
| Leu$^7$ | 7.83(1H, d, J = 8.5 Hz) | 4.26-4.39(1H, m) | 1.31-1.38(2H, m) | 0.76(3H, d, J = 6.5 Hz: δCH$_2$), 0.79(3H, d, J = 5.5 Hz: δCH$_2$), 1.52-1.60(1H, m: γCH$_2$) |
| Trp$^8$ | 8.38(1H, d, J = 7.0 Hz) | 4.52-4.55(1H, m) | 3.14(1H, dd, J = 7.0, 14.0 Hz), 3.20(1H, dd, J = 7.0, 15.0 Hz) | 6.96(1H, dd, J = 7.5, 7.5 Hz: Ind5), 7.05(1H, dd, J = 7.5, 7.5 Hz: Ind6), 7.17(1H, s: Ind2), 7.32(1H, d, J = 8.0 Hz: Ind4), 7.46(1H, d, J = 8.5 Hz: Ind7), 10.86(1H, bs, IndNH) |
| 3,5-Bn(CF$_3$)$_2$ | — | — | — | 5.11(1H, d, J = 13.5 Hz: CH$_2$Ph), 5.21(1H, d, J = 13.5 Hz: CH$_2$Ph), 7.93(2H, s: PhH), 8.04(1H, s: PhH) |

TABLE 1.9

1H-NMR data.
H-Tyr-D-Ala-Gly-Phe-N-Me-Nle-Pro-Leu-Trp-O-3,5-Bzl(CF$_3$)$_2$•TFA (TY019),
2 amide bond rotamers at the Pro$^6$ N, ca. 10:1 ratio; $^1$H-NMR (DMSO-d$_6$) δ:

| AA | NH | α | β | misc. |
|---|---|---|---|---|
| Tyr$^1$ | 8.05/8.09(3H, bs) | 3.97(1H, bs) | 2.81-2.93(2H, m) | 6.71(2H, d, J = 8.5 Hz: PhH), 7.03(2H, d, J = 8.5 Hz: PhH), 9.32(1H, bs: PhOH) |

TABLE 1.9-continued

1H-NMR data.
H-Tyr-D-Ala-Gly-Phe-N-Me-Nle-Pro-Leu-Trp-O-3,5-Bzl(CF$_3$)$_2$•TFA (TY019),
2 amide bond rotamers at the Pro$^6$ N, ca. 10:1 ratio; $^1$H-NMR (DMSO-d$_6$) δ:

| AA | NH | α | β | misc. |
|---|---|---|---|---|
| D-Ala$^2$ | 8.54/8.60(1H, d, J = 7.0 Hz) | 4.30-4.38(1H, m) | 1.03-1.10(3H, m) | — |
| Gly$^3$ | 8.23/8.24-27(1H, t/m, J = 5.5 Hz) | 3.69(2H, d, J = 5.5 Hz) | — | — |
| Phe$^4$ | 8.35(1H, d, J = 8.5 Hz) | 4.95/4.97-5.01(1H, dd/m, J = 8.0, 16.0 Hz) | 2.74-2.81(1H, m), 2.96-3.03(1H, m) | 7.13-7.28(5H, m: PhH) |
| Nle$^5$ | — | 5.09-5.13(1H, m) | 1.40-1.48(1H, m), 1.60-1.68(1H, m) | 0.80-0.88(3H, m: εCH$_3$), 1.13-1.35(4H, m: γCH$_2$, δCH$_2$) |
| Pro$^6$ | — | 4.17-4.22/4.24-4.28(1H, dd/m, J = 2.5, 8.0 Hz) | 1.66-1.72/1.67-1.82(1H, m), 1.83-1.92/1.85-1.93(1H, m) | 1.60-1.68/1.75-1.80(1H, m: γCH$_2$), 1.72-1.78/1.79-1.85(1H, m: γCH$_2$), 2.86-2.97/3.23-3.28(1H, m: δCH$_2$), 3.31-3.39/3.43-3.48(1H, m: δCH$_2$) |
| Leu$^7$ | 7.82(1H, d, J = 8.0 Hz) | 4.26-4.32(1H, m) | 1.32-1.42(2H, m) | 0.73-0.76(3H, m), 0.77-0.81(3H, m), 1.52-1.56(1H, m: γCH$_2$) |
| Trp$^8$ | 8.22/8.31-8.33(1H, d/m J = 6.5 Hz) | 4.52(1H, dd, J = 7.0, 14 Hz) | 3.14(1H, dd, J = 7.5, 15.0 Hz), 3.21(1H, dd, J = 6.5, 15.0 Hz) | 6.96(1H, dd, J = 7.5, 7.5 Hz: Ind5), 7.06(1H, dd, J = 7.0, 7.0 Hz: Ind6), 7.15(1H, s: Ind2), 7.32(1H, d, J = 8.0 Hz: Ind4), 7.45(1H, d, J = 7.5 Hz: Ind7), 10.87(1H, bs, IndNH) |
| 3,5-Bn(CF$_3$)$_2$ | — | — | — | 5.11(1H, d, J = 13.0 Hz: CH$_2$Ph), 5.20(1H, d, J = 13.5 Hz: CH$_2$Ph), 7.90(2H, s: PhH), 8.03(1H, s: PhH) |

Sequential assignment of proton resonances was achieved by 2D-TOCSY NMR (Davis, *J. Am. Chem. Soc.* 1985, 107, 2820-2821) experimental. Mass spectra were taken in the positive ion mode under ESI methods at the University of Arizona Mass Spectrometry Facility. TLC was performed on aluminum sheets coated with a 0.2 mm layer of silica gel 60 F$_{254}$ Merck using the following solvent systems: (1) CHCl$_3$:MeOH:AcOH=90:10:3; (2) EtOAc:n-BuOH:water:AcOH=5:3:1:1; and (3) n-BuOH:water:AcOH=4:1:1. TLC chromatograms were visualized by UV light and by ninhydrin spray followed by heating (hot plate). Analytical HPLC was performed on a Hewlett Packard 1100 with Waters NOVA-Pak C-18 column (3.9×150 mm, 5 μm). $^1$H-1D-NMR spectra were recorded on a Bruker DRX-500 spectrometer. 2D-TOCSY NMR spectra were performed on a Bruker DRX-600 spectrometer equipped with 5 mm Nalorac triple-resonance single-axis gradient probe. Both of NMR experiments were conducted in DMSO-d$_6$ at 298K. Spectra were referenced to residual solvent protons as 2.49 ppm. The processing of NMR data was performed with XwinNmr software (Bruker BioSpin, Fremont, Calif.) and the Felix2000 package (Accelrys Inc., San Diego, Calif.). In TOCSY experiment, TPPI mode (Marion, *Biochem. Biophys. Res. Commun.* 1983, 113, 967-974) with MLEV-17 Mixing Sequence (Braunschweiler, *J. Magn. Reson.* 1983, 53, 521-528) were used with a mixing time of 62.2 ms, at a spin-lock field of 8.33 kHz. TOCSY spectra were acquired with 1024 complex pairs in t$_1$ and 750 or 1024 FIDs using a 90'-shifted sine-squared window function in both dimensions and zero-filtering was performed before Fourier transformation.

Example 4

Structure Activity Relationships

Example 4.1

Cell Lines. For opioid receptors, the cDNA for the human DOR was a gift from Dr. Brigitte Kieffer (IGBMC, Illkirch, France). The cDNA for the rat MOR was a gift from Dr. Huda Akil (University of Michigan, Mich.). Stable expression of the rat MOR (pCDNA3) and the human DOR (pCDNA3) in the neuroblastoma cell line, HN9.10 were achieved the cells with the respective cDNA by calcium phosphate precipitation followed by clonal selection in neomycin. Expression of the respective receptors was initially verified and the level of expression periodically monitored by radioligand saturation analysis (see below). All cells were maintained at a 37° C., 95% air/5% CO$_2$, humidified atmosphere in a Form a Scientific incubator in DMEM with 10% BSA and 100 U mL penicillin/100 μg mL streptomycin. For NK-1 receptor, the rNK-1/CHO cell line was obtained from Dr. James Krause (University of Washington Medical School, St. Louis, Mich.). Expression of the receptor was verified as previously described by Krause. All cells were maintained at a 37° C., 95% air and 5% CO$_2$, humidified atmosphere, in a Form a Scientific incubator in Ham'S F12 with 2.5 mM HEPES, 10% fetal bovine serum and 100 U mL penicillin/100 μg mL streptomycin/500 μg mL Geneticin.

Example 4.2

Radioligand Labeled Binding Assays. For opioid receptors, crude membranes were prepared as previously described (Lorenzen, *Mol. Pharmacol.* 1993, 44(1), 115-123) from the transfected cells that express the MOR or the DOR. The protein concentration of the membrane preparations was determined by the Lowry method and the membranes were stored at −80° C. until use. Membranes were resuspended in assay buffer (50 mM Tris, pH 7.4, containing 50 μg/mL bacitracin, 30 μM bestatin, 10 μM captopril, 100 μM phenylmethylsulfonylfluoride (PMSF), 1 mg/mL BSA). For saturation analysis, six concentrations of [$^3$H]DAMGO (0.02-6 nM, 47.2 Ci/mmol), or six concentrations of [$^3$H]DPDPE (0.1 nM-10 nM, 44 Ci/mmol) were each mixed with 200 μg of membranes from MOR or DOR expressing cells, respectively, in a final volume of 1 mL. For competition analysis, ten concentrations of a test compound were each incubated with 50 µg of membranes from MOR or DOR expressing cells and the Kd concentration of [$^3$H]DAMGO (1.0 nM, 50 Ci/mmol), or of [$^3$H]DPDPE (1.0 nM, 44 Ci/mmol), respectively. Naloxone at 10 µM was used to define the non-specific binding of the radioligands in all assays. All samples were carried out in duplicates. The samples were incubated in a shaking water bath at 25° C. for 3 hours, followed by rapid filtration through Whatman Grade GF/B filter paper (Gaithersburg, Md.) pre-soaked in 1% polyethyleneimine, washed 4 times each with 2 mL of cold saline, and the radioactivity determined by liquid scintillation counting (Beckman LS5000 TD). For NK-1 receptor, crude membranes were prepared from the transfected cells expressing the rat NK-1 receptor. The protein concentration of the membrane preparations was determined by the Bradford method, performed on the assay day. Membranes were suspended in assay buffer (50 mM Tris, pH 7.4, containing 5 mM $MgCl_2$, 50 µg/mL bacitracin, 30 µM bestatin, 10 µM captopril, 100 µM phenylmethylsulfonylfluoride (PMSF), 1 mg/mL BSA). For competition analysis, five concentrations of a test compound were each incubated with 100 µL of membrane homogenate from rNK-1 expressing cells and the Kd concentration of [$^3$H] Sub P (~0.5 nM, 135 Ci/mmol). Substance P at 10 µM was used to define the non-specific binding of the radioligands in all assays. All samples were carried out in duplicates. The samples were incubated in a shaking water bath at 30° C. for 90 minutes, followed by rapid filtration through a Brandell-Harvester apparatus using a GF/B glass filter (Brandell Inc.) pre-soaked in 0.5% polyethyleneimine, washed 4 times each with 2 mL of cold saline, and the radioactivity determined by liquid scintillation counting (Beckman LS 6000SC). The $logIC_{50}$±SEM of a compound for each receptor type was determined by non-linear regression analysis of data pooled from at least two independent experiments using GraphPad Prism4 (Graph Pad, San Diego, Calif.). The $K_i$ values were calculated as the anti-logarithmic value of the $IC_{50}$. For competition analysis using [$^3$H]DAMGO or [$^3$H]DPDPE, the $K_i$ values were calculated from the $IC_{50}$ by the Cheng and Prusoff equation.

Example 4.3

[$^{35}$S]GTP-γ-S Binding Assay. The method was carried out according to that previously described (Lorenzen, *Mol. Pharmacol.* 1993, 44(1), 115-123). Membrane preparation (10 µg) to a final volume of 1 mL incubation mix (50 mM Hepes, pH 7.4, 1 mM EDTA, 5 mM $MgCl_2$, 30 µM GDP, 1 mM dithiothreitol, 100 mM NaCl, 0.1 mM PMSF, 0.1% BSA, 0.1 nM [$^{35}$S]GTP-γ-S) was added along with various concentrations, in duplicates or triplicates, of the test drug and incubated for 90 min at 30° C. in a shaking water bath. Reactions were terminated by rapid filtration through Whatman GF/B filters (pre-soaked in water), followed by 4 washes with 4 mL of ice-cold wash buffer (50 mM Tris, 5 mM $MgCl_2$, 100 mM NaCl, pH 7.4). The radioactivity was determined by liquid scintillation counting as above. Basal level of [$^{35}$S]GTPγS binding was defined as the amount bound in the absence of any test drug. Non-specific binding was determined in the presence of 10 µM unlabeled GTP-γ-S. Total binding was defined as the amount of radioactivity bound in the presence of test drug. The effect of the drug at each concentration on [$^{35}$S]GTP-γ-S binding was calculated as a percentage by the following equation: [Total bounD−Basal]/[Basal−Non-specific]×100. Data were expressed as $logEC_{50}$±SEM from at least two independent experiments analyzed by non-linear regression analysis using GraphPad Prism4.

Example 4.4

Guinea Pig Isolated Ileum Assay. The in vitro tissue bioassay was performed as described previously (Yamamoto, 2007, *J. Med. Chem.*, in press; Yamamoto, 2007, *J. Med. Chem.*, submitted). Male Hartley guinea pigs under ether anesthesia were killed by decapitation and a non-terminal portion of the ileum removed and the longitudinal muscle with myenteric plexus (LMMP) was carefully separated from the circular muscle as described previously (Porreca, *J. Pharmacol Exp. Ther.* 1983, 225(3), 688-693). These tissues were tied to gold chains with suture silk and mounted between platinum wire electrodes in 20 mL organ baths at a tension of 1 g and bathed in oxygenated (95:5 $O_2$:$CO_2$) Kreb's bicarbonate buffer at 37° C. and stimulated electrically (0.1 Hz, 0.4 msec duration) at supramaximal voltage. Following an equilibration period, compounds were added cumulatively to the bath in volumes of 14-60 µL until maximum inhibition was reached. A baseline PL-017 was constructed to determine tissue integrity and allow calculation of antagonist activity before opioid analog testing began. If no agonist activity was observed at 1 uM, a repeat PL-017 dose-response curve was constructed to test for antagonist qualities.

All substance P parent compound and analog testing was performed in the presence of 1 µM naloxone to block opioid effects on the tissue. Two minutes after naloxone was added to the bath, the substance P analog was added. Four minutes after naloxone was added, the test dose of substance P was added to the bath, the peak height noted and the tissues washed. Agonist activity of the analog was also observed during this period. Testing stopped at 1 mM concentrations of the test compound.

Example 4.5

Mouse Isolated Vas Deferens (MVD) Assay. The in vitro tissue bioassay was performed as described previously (Yamamoto, 2007, *J. Med. Chem.*, in press; Yamamoto, 2007, *J. Med. Chem.*, submitted). Male ICR mice under ether anesthesia were killed by cervical dislocation and the vasa deferentia removed. Tissues were tied to gold chains with suture silk and mounted between platinum wire electrodes in 20 mL organ baths at a tension of 0.5 g and bathed in oxygenated (95:5 $O_2$:$CO_2$) magnesium free Kreb's buffer at 37° C. and stimulated electrically (0.1 Hz, single pulses, 2.0 msec duration) at supramaximal voltage as previously described. Following an equilibration period, compounds were added to the bath cumulatively in volumes of 14-60 µL until maximum inhibition was reached. Response to an $IC_{50}$ dose of DPDPE (10 nM) was measured to determine tissue integrity before test compound testing.

Example 4.6

Analysis of GPI and MVD assays. For opioid data analysis, percentage inhibition was calculated using the average tissue contraction height for 1 min preceding the addition of the agonist divided by the contraction height 3 min after exposure to the dose of agonist. $IC_{50}$ values represent the mean of not less than 4 tissues. $IC_{50}$ and $E_{max}$ estimates were determined by computerized nonlinear least-squares analysis (the pharmacological statistics package FlashCalc: Dr. Michael Ossipov, University of Arizona, Tucson, Ariz.). For substance P data analysis, the height of the maximum peak produced during the control substance P dose-response curve was used as a 100% response and other values calculated as a percentage. $A_{50}$ values represent the mean of not less than 4 tissues. $A_{50}$ and $E_{max}$ estimates were determined by computerized nonlinear least-squares analysis (FlashCalc).

Discussion.

The opioid receptor binding affinities of synthesized bifunctional compounds were evaluated using human δ opioid receptors (hDOR) and rat μ opioid receptors (rMOR) with cells that stably express these receptors as previously described (Table 2).

TABLE 2

Binding affinities of bifunctional compounds at δ/μ opioid receptors and NK-1 receptors.

| no | hDOR[a], [³H]DPDPE[b] | | rMOR[a], [³H]DAMGO[c] | | Ki(μ)/Ki(δ) | rNK1[d], [³I]Substance P | |
|---|---|---|---|---|---|---|---|
| | LogIC$_{50}$[e,f] | (Ki, nM)[g] | LogIC$_{50}$[e,f] | (Ki, nM)[g] | | LogIC$_{50}$[e,f] | (IC$_{50}$, nM) |
| TY003 | −7.50 ± 0.14 | 14.6 | −7.22 ± 0.10 | 28.3 | 1.9 | −7.72 ± 0.09 | 19.3 |
| TY007 | −6.70 ± 0.13 | 93.0 | −6.09 ± 0.15 | 381 | 4.1 | −7.22 ± 0.19 | 66.7 |
| TY006 | −7.11 ± 0.06 | 36.1 | −7.24 ± 0.15 | 27.0 | 0.75 | −7.83 ± 0.15 | 15.6 |
| TY004 | −7.97 ± 0.07 | 5.0 | −7.30 ± 0.07 | 23.3 | 4.7 | −7.70 ± 0.14 | 20.9 |
| TY005 | −8.22 ± 0.06 | 2.8 | −7.11 ± 0.11 | 36.3 | 13 | −8.22 ± 0.15 | 6.4 |
| TY023 | −7.92 ± 0.04 | 4.8 | −7.89 ± 0.07 | 5.5 | 1.1 | −7.27 ± 0.09 | 54.5 |
| TY018 | −8.42 ± 0.15 | 1.8 | −7.69 ± 0.05 | 9.7 | 5.4 | −7.87 ± 0.18 | 14.8 |
| TY019 | −6.79 ± 0.13 | 77.1 | −6.54 ± 0.09 | 137 | 1.8 | −6.95 ± 0.27 | 135 |

[a]Competition analyses were carried out using membrane preparations from transfected HN9.10 cells that constitutively expressed the respectively receptor types.
[b]$K_d$ = 0.45 ± 0.1 nM.
[c]$K_d$ = 0.50 ± 0.1 nM.
[d]Competition analyses were carried out using membrane preparations from transfected CHO cells that constitutively expressed rat NK1 receptors.
[e]Competition analyses were carried out using whole cell lysate preparations from transfected HEK293 cells that constitutively expressed the respective receptor types.
[f]Logarithmic values determined from the non-linear regression analysis of data collected from at least 2 independent experiments.
[g]Competition against radio labeled ligand.
[g]Anti-logarithmic value of the respective IC$_{50}$.

[³H]DPDPE and [³H]DAMGO were used as their radioligands, respectively. Their agonistic efficacies were determined at the level of receptor G-protein interaction measuring agonist simulated binding of the GTP analogue guanosine-5′-O-(3-[³⁵S]thio)triphosphate ([³⁵S]GTP-γ) on the same transfected cells for binding affinities assays (Table 3).

TABLE 3

Opioid agonist functional activities in [³⁵S]GTP-γ-S binding assays.

| No | hDOR[a] | | | rMOR[a] | | | Ki(μ)/Ki(δ) |
|---|---|---|---|---|---|---|---|
| | LogEC$_{50}$[b] | EC$_{50}$ (nM)[c] | Emax (%)[d] | LogEC$_{50}$[b] | EC$_{50}$ (nM)[c] | Emax (%)[d] | |
| TY003 | −7.68 ± 0.20 | 20.8 | 39 | −7.23 ± 0.18 | 58.7 | 41 | 2.8 |
| TY007 | −7.78 ± 0.36 | 16.8 | 26 | −6.46 ± 0.38 | 345 | 22 | 20.5 |
| TY006 | −7.30 ± 0.24 | 50.2 | 35 | −7.38 ± 0.20 | 41.7 | 39 | 0.8 |
| TY004 | −8.09 ± 0.18 | 9.6 | 44 | −7.48 ± 0.16 | 33.0 | 46 | 3.4 |
| TY005 | −8.54 ± 0.21 | 2.9 | 51 | −7.50 ± 0.09 | 32.0 | 45 | 11 |
| TY023 | −8.73 ± 0.20 | 1.8 | 53 | −7.47 ± 0.12 | 33.8 | 52 | 19 |
| TY018 | −8.40 ± 0.11 | 4.0 | 129 | −7.56 ± 0.06 | 27.6 | 121 | 6.9 |
| TY019 | −6.44 ± 0.27 | 364 | 316 | −6.82 ± 0.08 | 150 | 118 | 0.4 |
| Biphali | −8.95 ± 0.17 | 1.1 | 83 | — | — | — | — |
| DPDP | −8.80 ± 0.25 | 1.6 | 69 | — | — | — | — |
| DAMG | — | — | — | −7.44 ± 0.19 | 37.0 | 150 | — |

[a]Expressed from CHO cell.
[b]Logarithmic values determined from the non-linear regression analysis of data collected from at least 2 dependent experiments.
[c]Anti-logarithmic value of the respective EC$_{50}$.
[d]Net total bound/basal binding × 100

The tissue bioassays (MVD and GPI) were also performed for characterizing their agonistic function through δ and μ opioid receptors as described previously (Table 4). As for their affinity for rat NK1 (rNK1) receptor, receptor binding assay were also used on transfected cells that stably express rNK1 receptors using [$^3$H]substance P as the standard radioligand (Table 2). To estimate their antagonistic activities against substance P stimulation, tissue bioassay using guinea pig ileum (GPI) was performed. All the synthesized compounds were confirmed to have no or negligible agonistic activities against substance P stimulation (Table 4).

TABLE 4

Functional assay result for bifunctional compound ligands at opioid and Substance P receptors.

| no | Opioid agonist | | | Substance P GPI | |
|---|---|---|---|---|---|
| | MVD (δ), IC$_{50}$ (nM)$^a$ | GPI (μ), IC$_{50}$ (nM)$^a$ | IC$_{50}$(MVD)/ IC$_{50}$(GPI) | agonist (A$_{50}$)$^b$ | antagonist, Ke (nM)$^c$ |
| TY003 | 905 ± 186 | 7% at 1 μM$^b$ | — | 0% at 1 μM | 14.4 ± 4.9 |
| TY007 | 412 ± 106 | 9% at 1 μM$^b$ | — | 0% at 1 μM | 69.6 ± 7.1 |
| TY006 | 172 ± 26 | 384 ± 28 | 2.2 | 0% at 1 μM | 5.4 ± 1.4 |
| TY004 | 101 ± 25 | 341 ± 71 | 3.4 | 0% at 1 μM | 19.4 ± 5.0 |
| TY005 | 22.3 ± 1.2 | 359 ± 127 | 16 | 0% at 1 μM | 24.7 ± 8.8 |
| TY023 | 33.0 ± 7.0 | 154 ± 51 | 4.7 | — | 7.8 ± 4.0 |
| TY018 | 16.8 ± 2.4 | 372 ± 65 | 22 | 0% at 1 μM | 7.9 ± 1.9 |
| TY019 | 188 ± 21 | 12% at 1 μM$^b$ | — | 2% at 1 μM | 4.6 ± 1.2 |
| Biphalin | 2.7 ± 1.5 | 8.8 ± 0.3 | — | — | — |
| L-732, 138 | — | — | — | — | 247 ± 87 |

$^a$Concentration at 50% inhibition of muscle concentration at electrically stimulated isolated tissues.
$^b$Contraction of isolated tissue relative to initial muscle contraction with KCl.
$^c$Inhibitory activity against the Substance P induced muscle contraction, Ke: concentration of antagonist needed to inhibit Substance P to half its activity.

According to the rational design as described above, we first tested two compounds, H-Tyr-D-Ala-Gly-Phe-Phe-Pro-Leu-Trp-3,5-Bzl(CF$_3$)$_2$ (TY003) and H-Tyr-D-Ala-Gly-Phe-D-Phe-Pro-Leu-Trp-3,5-Bzl(CF$_3$)$_2$ (TY007), in which both of opioid agonist pharmacophore (H-Tyr-D-Ala-Gly-Phe) and substance P antagonist pharmacophore (Phe-Pro-Leu-Trp-3,5-Bzl(CF$_3$)$_2$ (SEQ ID NO: 3) or D-Phe-Pro-Leu-Trp-3,5-Bzl(CF$_3$)$_2$) were fused into one molecule with simple amide bond. Interestingly, all the affinities of TY003 at both δ/μ opioid and rNK1 receptors were within 10~30 nM range (Ki=14.6 nM, δ opioid and 28.3 nM, μ opioid; IC$_{50}$=19.3 nM, rNK1). Compound TY003 showed consistent opioid agonist efficacies in the [$^{35}$S]GTP-γ-S binding assays with the EC$_{50}$ values of 20.8 and 58.7 nM, respectively. Moreover, GPI assay elucidated that TY003 acted as an antagonist against substance P stimulation (Ke=14.4 nM). It should be noted that TY003 had good affinity at rat NK1 receptors as well as good functional activity using guinea pig tissue, which means TY003could show its substance P antagonist activities in animal models with both of the species. Moreover, these affinity and activity of TY003 were greatly improved from those of L-732,138whose IC$_{50}$ value for rNK1 was reported to be around 460 nM in radioligand binding assay and Ke value in GPI tissue was 247 nM (25-fold and 12-fold, respectively). Even though compound TY003 showed not so high δ opioid selectivity over μ receptors, these results clearly proved the success and rationality of our design. However, compound possessing D-amino acid at fifth position (TY007) was found to have drastically lower affinities than TY003 had (Ki=93.0 nM, δ opioid and 381 nM, μ opioid; IC$_{50}$=66.7 nM, rNK1), which suggested that an amino acid residue at fifth position preferred L-form to D-form. It is reasonable that the fifth position of compounds played an important role not only at NK1receptors, but also at δ/μ opioid receptors, since it acted as the part of NK1 antagonist pharmacophore as well as the "address" region of opioid pharmacophore. Considering these results, we focused our work on optimizing the fifth position of TY003 to find the bifunctional compounds possessing potent substance P antagonist activity and effective δ/μ opioid agonist activities with high δ selectivity. First, Gly which is the simplest amino acid was introduced at fifth position of TY003 in order to estimate the importance of aromatic side chain of Phe$^5$ (H-Tyr-D-Ala-Gly-Phe-Gly-Pro-Leu-Trp-3,5-Bzl(CF$_3$)$_2$; TY006). Although the binding assays of TY006 showed lesser affinity at δ opioid receptors (Ki =36.1 nM) than that of TY003, the affinities at both μ opioid and rNK1 receptors were maintained (Ki=27.0, μ opioid; IC$_{50}$=15.6 nM, rNK1). The opioid agonist activities of ligand TY006 in MVD and GPI assays were much higher than expected from binding assay results which was not greatly improved from the results of TY003 (IC$_{50}$=171 and 384 nM, respectively). The antagonist activity of TY006 against substance P stimulation in GPI tissue assay was also higher than that of TY003 (IC$_{50}$=5.4 nM). These improvements in tissue assays might indicate that the aromatic side chain at fifth position led to low activity or metabolical unstability, and we chose Leu and Met for next substituents (H-Tyr-D-Ala-Gly-Phe-Leu-Pro-Leu-Trp-3,5-Bzl(CF$_3$)$_2$; TY004 and H-Tyr-D-Ala-Gly-Phe-Met-Pro-Leu-Trp-3,5-Bzl (CF$_3$)$_2$; TY005). In these modification, the 1-5 residues of two compounds (H-Tyr$^1$-D-Ala$^2$-Gly$^3$-Phe$^4$-Leu$^5$ of TY004 and H-Tyr$^1$-D-Ala$^2$-Gly$^3$-Phe$^4$-Met$^5$ of TY005) were very similar to endogenetic opioid compounds Leu-enkephalin (H-Tyr-Gly-Gly-Phe-Leu-OH) (SEQ ID NO: 4) and Met-enkephalin (H-Tyr-Gly-Gly-Phe-Met-OH) (SEQ ID NO: 5), both of which have potent opioid activities as well as higher δ selectivity. As can be seen in Table 2, binding affinities at δ opioid receptors of TY004 was improved from that of TY006 (Ki=5.0 nM) and its Ki value at δ opioid receptors was 23.3 nM with 4.7-fold δ selectivity over μ receptors. The agonist activities of ligand TY004 in the [$^{35}$S]GTP-γ-S binding assays showed similar tendency of EC$_{50}$ values of 9.6 and 33.0 nM, respectively (3.4-fold δ selectivity). This δ selectivity was maintained in its. MVD and GPI assays (3.4-fold). The affinity at rNK1receptors of TY004 was retained from that of TY006 (IC$_{50}$=20.9 nM) with slightly decreased antagonist activity in GPI assay (IC$_{50}$=19.4 nM). In the case of compound TY005, much more increased δ opioid activity (Ki=2.8 nM) and δ selectivity (13-fold) was seen over μ opioid receptors in binding assays. The agonist activities for both δ and μ opioid receptors in [$^{35}$S]GTP-γ-S binding assays were consistent with the results of binding assays ($EC_{50}$=2.9 and 32.0 nM, respectively). Moreover, ligand TY5 showed "excellent" functional opioid agonist activity in MVD assay ($IC_{50}$=22.3 nM) with better selectivity over that of GPI assay (16-fold). Although the substance P antagonist activity of TY005 in GPI assay was lesser than that of TY006, it still retained good activity (Ke=24.7 nM) with excellent affinity at rNK1 receptors ($IC_{50}$=6.4 nM). Moreover, the Ke value of TY005 in GPI assay against substance P stimulation was almost equivalent to its $IC_{50}$ value in MVD assay against opioid stimulation. Therefore, we could say that compound TY005 is highly active, highly balanced and high δ selective bifunctional compound at δ/μ opioid and NK1 receptors in which opioid agonist activities and substance P antagonist activity are almost equipotent. Next, we made further modifications of fifth position based on TY005 for much more improved efficacies and δ selectivity. The oxidized form of ligand TY5 at Met$^5$, H-Tyr-D-Ala-Gly-Phe-Met(O)-Pro-Leu-Trp-3,5-Bzl($CF_3$)$_2$ (TY023), was synthesized and tested since some articles reported that methionine oxidation enhances opioid activities as well as δ selectivity for enkephalin analogues (*Lord, Nature*, 1977, 207, 495-9; *Kiritsy-Roy, Life Sci.* 1983, 32(8),889-93). In fact, this modification showed better affinity at μ opioid receptors than that of TY005 (Ki=5.5 nM), but decreased Ki value at δ opioid receptors was observed which led to almost equivalent affinities at both δ and μ opioid receptors (1.1-fold). As for the $EC_{50}$ values in [$^{35}$S]GTP-γ-S binding assays, ligand TY023 showed the highest agonist activity at δ opioid receptors with the best δ selectivity (19-fold). However, this good δ selectivity was decreased to 4.7-fold in MVD and GPI assays ($IC_{50}$=33.0 and 154 nM, respectively). The affinity of ligand TY023 at rNK1 receptors was decreased from that of TY005 (Ki=54.5 nM), but its substance P antagonist activity in GPI assay was improved (Ke=7.8 nM). The introduction of Nle which is general bioisoster of Met was also performed at the fifth position of the sequence (H-Tyr-D-Ala-Gly-Phe-Nle-Pro-Leu-Trp-3,5-Bzl($CF_3$)$_2$; TY018). In receptor binding assays, ligand TY018 showed the best affinity at δ opioid receptors (Ki=1.8 nM) and its Ki value at μ opioid receptors was less than 10 nM (9.8 nM; 5.4-fold δ selectivity). The δ selectivity showed distinct increase in tissue assays (22-fold), in which $IC_{50}$ value in MVD assay was still the best among all the tested ligands (16.8 nM). However, in [$^{35}$S]GTP-δ-S binding assays, the δ selectivity of TY018 was moderate (6.9-fold) just as in the case of receptor binding assays. The rNK1 affinity and substance P antagonist activity of TY018were increased from that of TY005 (Ki=14.8 nM and Ke=7.9 nM, respectively). Finally, we tested N-methylation of Nle$^5$ of 7 (H-Tyr-D-Ala-Gly-Phe-N-Me-Nle-Pro-Leu-Trp-3,5-Bzl ($CF_3$)$_2$; TY019) since highly δ selective and potent enkephalin analogue was reported with N-methylation at fifth position (*Glavin, Life Sci.* 1990, 46(15), 1075-9; *Burkhardt, Peptides.* 1982, 3(5), 869-71). However, although this modification led to the best substance P antagonist activity in functional assay ($IC_{50}$=4.6 nM), ligand TY019 showed significant decrease of binding affinities at both δ and μ opioid receptors as well as agonist activities in [$^{35}$S]GTP-δ-S binding assays, with low δ selectivity (1.8 and 0.4-fold, respectively). These results elucidated that the introduction of N-methyl amino acid at fifth position decreases the activities not only at opioid receptors but at rNK1 receptors.

Example 5

In vivo Biological Activity. 200-225 g male Sprague Dawley rats were obtained and cared for under the University of Arizona IACUC standards. Food and water was available ad libitum. All preparations and testing were performed in accordance with the policies and recommendations of the International Association for the Study of Pain, National Institute of Health and Animal Care at the University of Arizona. Intrathecal catheter implantation: Rats were anesthetized using ketamine/xylazine 100 mg/kg i.p. and placed in a steriotaxic head holder. The cisternum magnum was exposed and an 8 mm catheter was implanted, as described, terminating in the lumbar region of the spinal chord. Animals were allowed to recover for 5 days. Spinal Nerve Ligation (SNL): The L5 and L6 spinal nerves were tightly ligated with 4-0 silk to induce nerve injury without limiting the use of the left hind paw of the animals. Some animals underwent Sham surgeries, in which the nerve areas were exposed but not ligated. Animals were allowed 7 days to recover before any compound administration commenced. I.th. Compound administration: 5 L of each treatment was given followed 1 μL air bubble/9 μL saline push. Von Frey filament testing (VF, behavioral): Rats were allowed to acclimate within suspended wire mesh cages for 20 minutes prior to baseline testing (pre- and post-nerve ligation/exposure). Test days included treatment administration and measured responses to calibrated von Frey filaments (g) probed perpendicularly on the left hind paw for 7 seconds, every 15 minutes after the compound administration. Paw withdrawal thresholds were calculated in grams using the Dixon non-parametric test and expressed as the Mean Withdrawal Threshold ±SEM in Prism (by Graph Pad Prism4). Infrared thermal testing (IR, behavioral): Rats were allowed to acclimate within Plexiglas holders for baseline testing (pre- and post-nerve ligation/exposure) for 20 minutes. A mobile radiant heat source was used to direct heat to the left hind paw. Paw withdrawal latencies were measured in seconds, with an automatic shutoff of the heat source at 33.8 seconds. Pre-nerve injury baselines were calibrated to be between 20-25 seconds. On test days, animals were administered a treatment and tested with radiant heat, ever 15 minutes after said administration. Paw withdrawal latencies were calculated and expressed as the Mean Withdrawal Latency ±SEM in Prism (by Graph Pad Prism4). Rotarod Motor Skills: Animals were trained on the day of testing. Training included placement on the rotarod machinery while turned off, while on, and then while on and moving. Each training session lasted three minutes. Baseline abilities were measured, with a cut off of 180 seconds. Depending on route of administration, testing was either performed in 15 or 30 minute increments (i.th). Discussion.

Among the synthesized bifunctional compounds, TY005 was chosen as the test compound for in vivo study because of its excellent δ selectivity for all the in vitro and tissue assays as well as the high affinity and activity at δ opioid receptors. Although the antagonist activity of TY005 against substance P stimulation in GPI assay was moderate among the synthesized compounds, this activity could be enough since its activity was 10-fold more potent than that of L-732,138, whose biological activities in vivo were reported in several animal models. As for its binding at rat NK1 receptor, TY005 showed the best affinity.

Figure 7B:
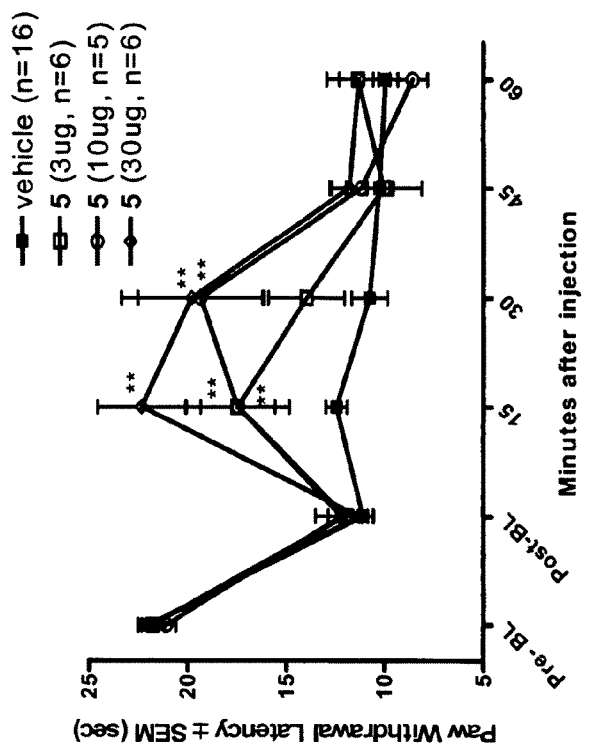
FIG. 7 A-F. Estimation of analgesic potency of bifunctional compounds: (A) Anti-nociceptive effect of bifunctional compound TY005 in male Sprague Dawley rats. (B) Anti-hyperalgesic and (C) anti-allodynic effects of bifunctional compound TY005 in L5/L6 SNL rats. (D) Rotarod motor skill behavioral test for TY005 in male Sprague Dawley rat. (E) Dose response curve at 15 min after administration (anti-hyperalgesia). (F) Dose response curve at 30 min after administration (anti-allodynic effect). Compound was administered via i.th. route and rats were tested by (A and B) infrared radient heat and (C) von Fray filament stimulation. Sensorimotor performance was determined by monitoring the ability of rats to balance on a rotarod moving at a speed of 4 revolutions per min (D). Each point represents the mean ±SEM with at least five rats.
Figure 7A:
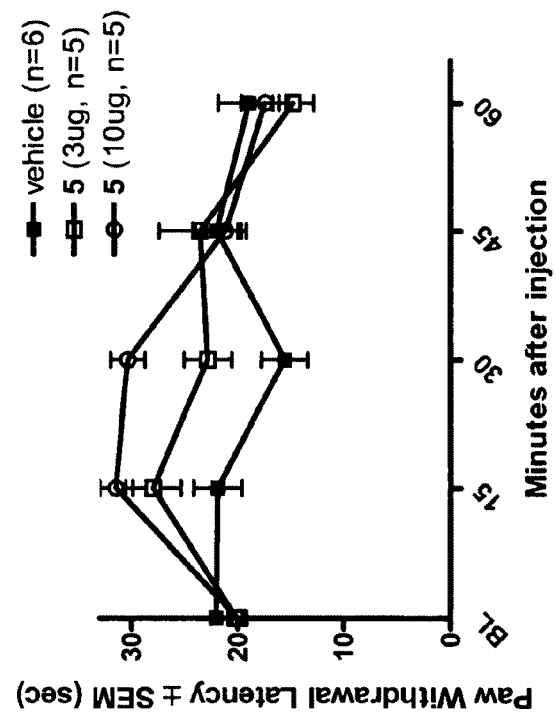
Figure 7D:
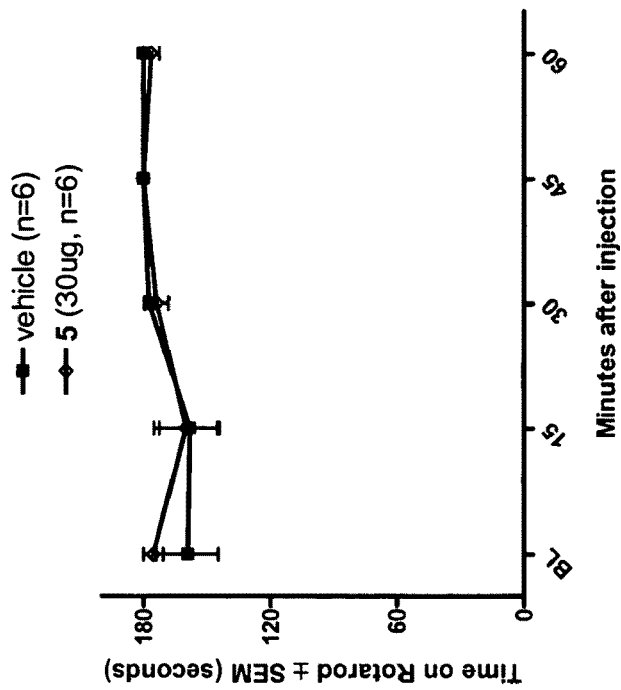
Figure 7C:
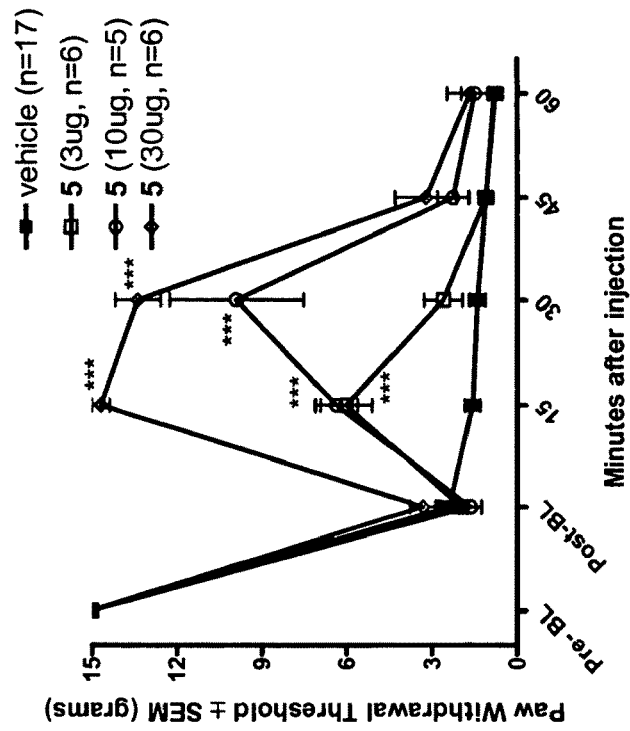
Figure 7F:
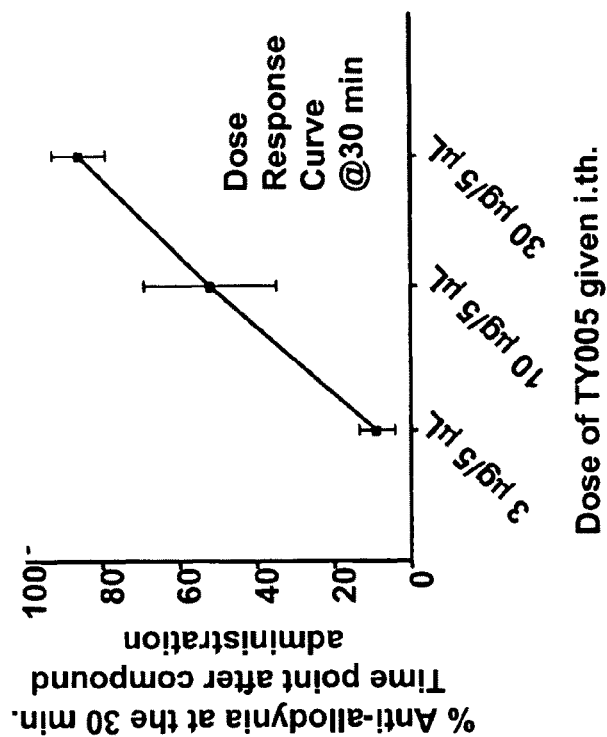
Figure 7E:
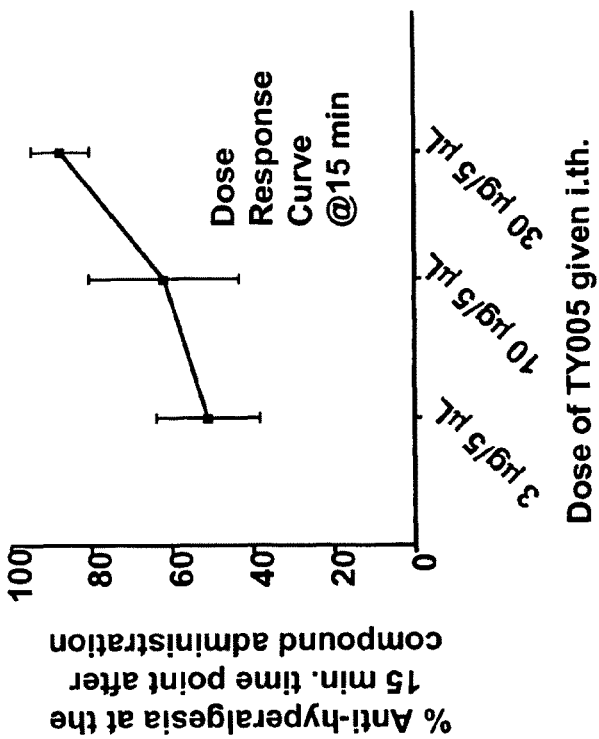
Figure 8B:
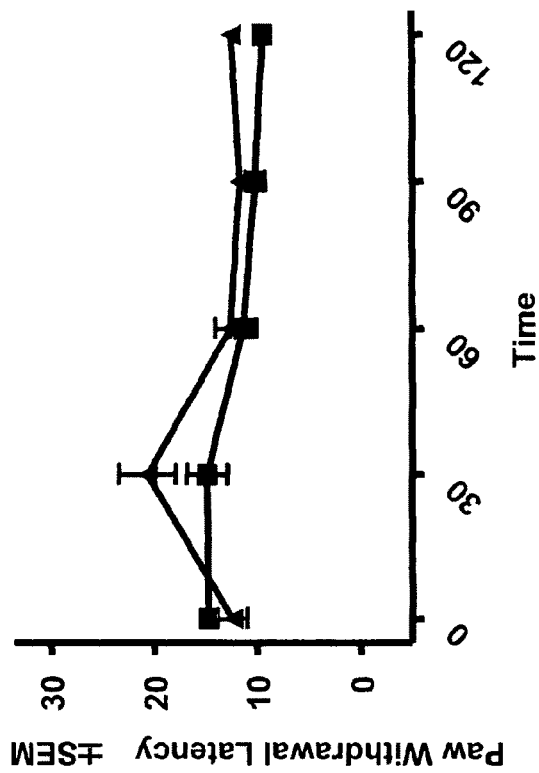
FIG. 8 A, B. Estimation of analgesic potency of bifunctional compounds: (A) anti-allodynic and (B) anti-hyperalgesic effects of bifunctional compound TY005 in L5/L6 SNL rats. Compound was administered via intravenous route and rats were tested by von Fray filament stimulation (A) and infrared radient heat (B). Each point represents the mean ±SEM with at least five rats.
Figure 8A:
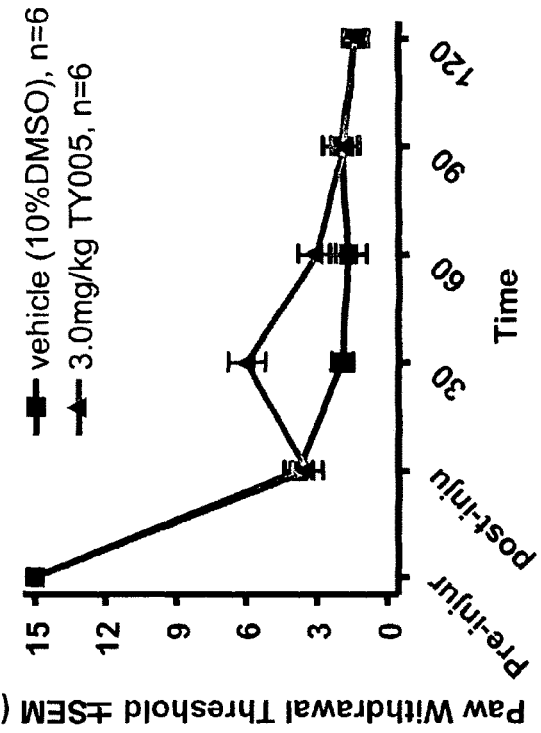
Figure 11B:
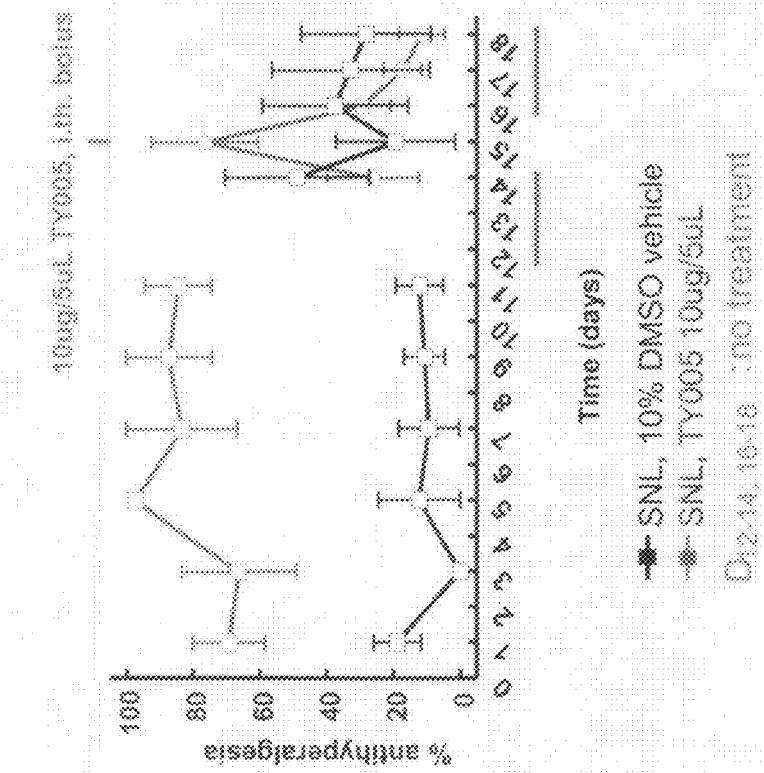
FIG. 11 A, B. Chronic TY005 administration attenuates thermal hyperalgesia in SNL-operated animals. (A) Paw withdrawal latency, (B) % of antihyperalgesia. Compound was administered via i.th. route and rats were tested by infrared radient heat. Each point represents the mean ± SEM with at least five rats.
Figure 11A:
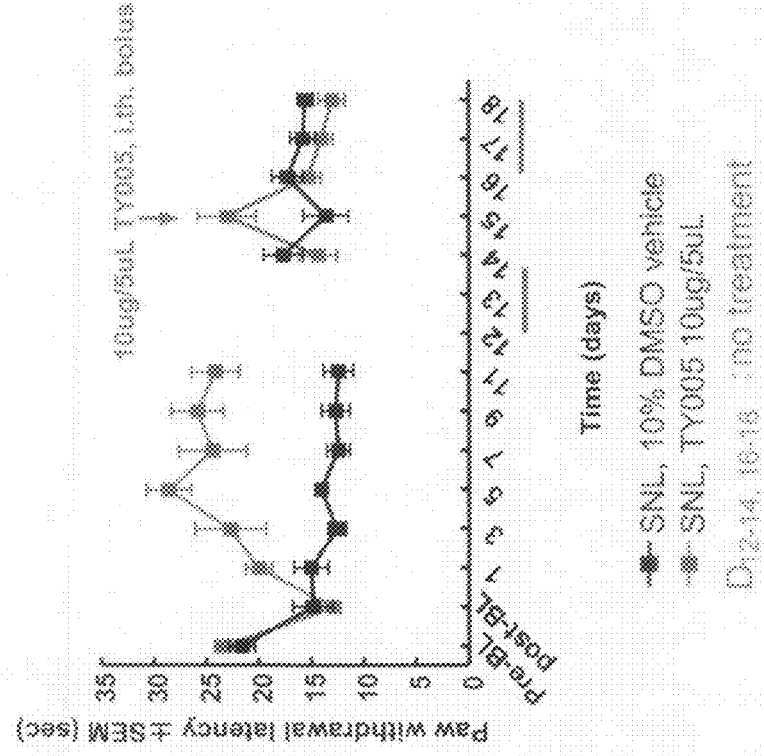

To estimate the analgesic potency of bifunctional compound TY005, anti-nociceptive, anti-hyperalgesia and anti-allodynic efficacies were tested via intrathecal administration (FIG. 7A-F). These assays gave the inventors very encouraging results. Compound TY005 showed distinct anti-nociceptive effect in male Sprague Dawley rats with excellent dose-dependency (FIG. 7A). It should be noted that the efficacy of TY005 was disappeared 45 min after administration, presumably because of metabolic degradation. Dose dependent antihyperalgesic efficacy was also observed in neuropathic pain model using L5/L6 spinal nerve ligation (SNL) rats with almost 100% recovery at 30 µg i.th. administration (FIG. 7B). Moreover, compound TY005 showed very potent anti-allodynic effect against mechanical stimulation in SNL rats. Since morphine had negligible anti-allodynic efficacy in this model, this analgesic effect seemed to mainly come from substance P antagonist activity or combinational effect of substance P antagonist and opioid agonist activities. Finally, to evaluate whether the analgesic dose of compound TY005 was associated with any toxic side effects, motor function before and after drug administration was assessed in normal, uninjured rats using the rotarod test in which morphine was reported to induce impaired performance. As can be seen in FIG. 7D, no sensorimotor impairment was observed at the highest analgesic dose of TY005 (30 µg). In fact, throughout these in vivo studies, compound TY005 showed no sign of toxicity. In vivo activity of TY005 is further illustrated in FIGS. 8-12 and TY027 in FIGS. 13-14.

Example 6

Compound Synthesis

A series of compounds was obtained through a two-step synthetic approach (FIG. 3). The first step was the synthesis of Boc-Tyr(tBu)-DAla-Gly-Phe-Pro-Leu-Trp(Boc)-OH as a shared intermediate using $N^\alpha$-Fmoc chemistry on a 2-chlorotrityl resin, which is a common support for batch SPPS of protected compounds with a free C-terminal. First, Fmoc-Trp (Boc)-OH was introduced on a resin in the presence of DIEA in DMF. Resin-bound Fmoc-Trp(Boc) was treated with 20% piperidine to remove a N-Fmoc protecting group. Couplings of the following amino acids were carried out with standard in situ activating reagents used in routine Fmoc SPPS with HCTU, in the presence of DIEA, to generate Cl-HOBt esters. The obtained resin-bound Boc-Tyr(tBu)-DAla-Gly-Phe-Pro-Leu-Trp(Boc) was cleaved off the resin with 1% TFA in DCM in 30 min. The protected compound was obtained after evaporation followed by precipitation with chilled petroleum ether. The resulting white solid was washed twice with chilled petroleum ether, then dried under vacuum to give the protected compound with good purity (98.8%) and moderate yield (57.0%: based on the substitution of the resin).

The second step was esterification or amidation of the protected intermediate followed by side-chain deprotection in the solution phase. The esterification was performed employing cesium carbonate to form the cesium salt of the protected compound to react with benzyl bromide or 3',5'-bis (trifluoromethyl)-benzyl bromide (Hruby, *Life Sci.* 2003, 73(6), 699-704; Horan, *J. Pharmacol. Exp. Ther.* 1993, 265, 1446-1454). The crude esters, H-Tyr-DAla-Gly-Phe-Pro-Leu-Trp-O-3,5-Bzl(CF$_3$)$_2$ (TY001) and H-Tyr-DAla-Gly-Phe-Pro-Leu-Trp-O-3,5-Bzl (TY011), were obtained quantitatively by one hour treatment with the cleavage cocktail (82.5% v/v TFA, 5% water, 5% thioanisole, 2.5% 1,2-ethanedithiol and 5% phenol) to quench the highly stabilized carbocations released from permanent protecting groups. Some acid mediated hydrolysis of C-terminal benzyl ester occurred during the final cleavage, but the purities of the final crude compounds were still moderate to good (84% for TY001 and 67% for TY011). For the amidation, standard EDC/Cl-HOBt coupling chemistry with two equivalents of reactant amine was used. The crude amides TY008, 010, 012, and 013 were obtained with 98% to quantitative yield and good purity (75~93%).

Example 6.1

Boc-Tyr(tBu)-DAla-Gly-Phe-Pro-Leu-Trp(Boc)-OH. The compound was synthesized manually by the $N^\alpha$-Fmoc solid-phase methodology using HCTU as the coupling reagents. 2-Chlorotrityl resin (2.0 g, 1.56 mmol/g) was placed into a 50 mL polypropylene syringe with the frit on the bottom and swollen in DMF (20 mL) for 1 h. The resin was washed with DMF (3×15 mL) and then with DCM (3×15 mL). Fmoc-Trp (Boc)-OH (1.2 equiv) was dissolved in 30 mL of DCM, and then DIEA (5 equiv) was added. The reaction mixture was transferred into the syringe with the resin then shaken for 2 h. The resin was washed three times with DMF (15 mL) and three times with DCM (15 mL), and then with DMF (3×15 mL). The Fmoc protecting group was removed by 20% piperidine in DMF (1×2 min and 1×20 min). The deprotected resin was washed with DMF (3×15 mL), DCM (3×15 mL) and then with DMF (3×15 mL). Fmoc-Leu-OH (3 equiv) and HCTU (2.9 equiv) were dissolved in 30 mL of DMF, then DIEA (6 equiv) was added. The coupling mixture was transferred into the syringe with the resin, and then shaken for 2 h. All the other amino acids, Pro, Phe, Gly, DAla and Tyr were consecutively coupled using the procedure described above, using the TNBS test (all the amino acids except for Phe) or chloranil test (only for Phe) to check the extent of coupling. In case of a positive test result, the coupling was repeated until a negative test result was obtained. The resulting batch of the resin-bound protected Boc-Tyr(tBu)-DAla-Gly-Phe-Pro-Leu-Trp(Boc) was carefully washed with DMF (3×15 mL), DCM (3×15 mL), DMF (3×15 mL), and DCM (3×15 mL), and dried under reduced pressure. The dry resin was placed in 10 mL fritted polypropylene syringes and swollen with DCM for 1 h. The compound was cleaved off the solid support with 1% v/v TFA in DCM (30 mL) for 30 min, and most of the organic solvent was removed under reduced pressure. The obtained crude compound was precipitated out by the addition of chilled petroleum ether (45 mL) to give a white precipitate. The suspension was centrifuged for 20 min at 7000 rpm, and then the liquid was decanted off. The crude compound was washed with petroleum ether (2×50 mL), and after the final centrifugation, the intermediate compound was dried under vacuum (2 h) to obtain the title compound (1.99 g, 57.0%). The purity of the final products (99.8%) was checked by analytical RP-HPLC using a Hewlett Packard 1090m system (230 nm) on a reverse phase column (Vydac 218TP104 C-18 4.6×75 mm, 5 µm). The compound was eluted with a linear gradient of aqueous CH$_3$CN/0.1% CF$_3$CO$_2$H (30-100% in 40 minutes) at a flow rate of 1.0 mL/min. The crude compound was used for next reactions without further purification. MS (ESI) 1109 (MH)$^+$.

Example 6.2

H-Tyr-DAla-Gly-Phe-Pro-Leu-Trp-O-3,5-Bzl(CF$_3$)$_2$ TFA (TY001). Boc-Tyr(tBu)-DAla-Gly-Phe-Pro-Leu-Trp(Boc)-OH (150 mg, 0.135 mmol) and 3,5-bis(trifluoromethyl)benzyl bromide (104 mg, 0.338 mmol) were dissolved in DMF (2 mL). Cesium carbonate (220 mg, 0.676 mmol) was added to the solution at 0° C. After stirring for 2 h at r.t., saturated aqueous sodium bicarbonate (50 mL) was added to the solution, and extracted with ethyl acetate (30 mL) three times. The combined organic phases were washed with 5% aqueous citrate and saturated aqueous sodium chloride (50 mL each), and dried over sodium sulfate. The solvent was evaporated off and the crude compound was precipitated in cold petroleum ether (45 mL) and centrifuged two times, and dried under reduced pressure. The obtained protected compound was treated with 82.5% v/v TFA, 5% water, 5% thioanisole, 2.5% 1,2-ethanedithiol and 5% phenol (1.5 mL, 1 h). The crude compound was precipitated out by the addition of chilled diethyl ether (45 mL) to give white precipitates. The suspension was centrifuged for 20 min at 7000 rpm, and then the liquid was decanted. The crude compounds were washed with diethyl ether (2×45 mL), and after the final centrifugation, the compounds were dried under vacuum (2 h). The resulting white residues (116 mg, quantitative) were dissolved in 3:1 mixture of acetonitrile and distilled water (5 mL), and the insoluble impurities were removed by passing the solutions through syringe filters (Gelman Laboratory, Ann Arbor, Mich., Acrodisc 13 mm syringe filter with 0.45 μM PTFE membrane). Final purification was accomplished by preparative RP-HPLC, and then lyophilized.

Example 6.3

H-Tyr-DAla-Gly-Phe-Pro-Leu-Trp-O-Bzl TFA (TY011). The title compound was prepared using same method as described for H-Tyr-DAla-Gly-Phe-Pro-Leu-Trp-O-3,5-Bzl $(CF_3)_2$.TFA (TY001). The yield of obtained crude compound was 98.3%.

Example 6.4

H-Tyr-DAla-Gly-Phe-Pro-Leu-Trp-NH-Bzl TFA (TY008). Boc-Tyr(tBu)-DAla-Gly-Phe-Pro-Leu-Trp(Boc)-OH (50 mg, 0.045 mmol) and Cl-HOBt (8.7 mg, 0.054 mmol) were dissolved in DMF (1 mL). Benzyl amine (5.8 mg, 0.090 mmol) and EDC (10.4 mg, 0.054 mmol) were added to the solution at r.t and stirred until the starting material wasn't detected in TLC; then saturated aqueous sodium bicarbonate (50 mL) was added. The reaction mixture was extracted with ethyl acetate (30 mL) three times. The combined organic phases were washed with 5% aqueous citrate and saturated aqueous sodium chloride (50 mL each), then dried over sodium sulfate. The solvent was evaporated and the crude compound was precipitated in cold petroleum ether (45 mL). The product was twice dispersed in cold petroleum ether, centrifuged and decanted, then dried under reduced pressure. The obtained protected compound was treated with 82.5% v/v TFA, 5% water, 5% thioanisole, 2.5% 1,2-ethanedithiol, and 5% phenol (1.5 mL, 1 h). The crude compound was precipitated out by the addition of chilled diethyl ether (45 mL) to give a white precipitate. The resulting compound suspensions were centrifuged for 20 min at 7000 rpm, and the liquid was decanted. The crude compounds were washed with diethyl ether (2×45 mL), and after a final centrifugation, the compounds were dried under vacuum (2 h). The resulting white residues (53 mg, quantitative) were dissolved in a 3:1 mixture of acetonitrile and distilled water (1 mL), and the insoluble impurities were removed by passing the solutions through syringe filters (Gelman Laboratory, Acrodisc 13 mm syringe filter with 0.45 μM PTFE membrane). Final purification was accomplished by preparative RP-HPLC. The pure title compound was obtained after lyophilization.

Example 6.5

H-Tyr-D-Ala-Gly-Phe-Pro-Leu-Trp-NMe-Bzl-TFA (TY010). The title compound was prepared using same method as described for H-Tyr-D-Ala-Gly-Phe-Pro-Leu-Trp-NH-3,5-Bzl-TFA (TY008). The crude compound was obtained quantitatively.

Example 6.6

H-Tyr-D-Ala-Gly-Phe-Pro-Leu-Trp-NH-3,5-Bzl$(CF_3)_2$ TFA (TY012). The title compound was prepared using same method as described for H-Tyr-D-Ala-Gly-Phe-Pro-Leu-Trp-NH-3,5-Bzl-TFA (TY008). The yield of obtained crude compounds was 98.1%.

Example 6.7

H-Tyr-D-Ala-Gly-Phe-Pro-Leu-Trp-NMe-3,5-Bzl$(CF_3)_2$ TFA (TY013). The title compound was prepared using same method as described for H-Tyr-D-Ala-Gly-Phe-Pro-Leu-Trp-NH-3,5-Bzl-TFA (TY008). The crude compound was obtained quantitatively.

Example 7

Characterization of the Compounds

Example 7.1

Preparative RP-HPLC was performed on Waters Delta Prep 4000 with Waters XTerra C-18 column (19×250 mm, 10 μm, a linear gradient of 33-53% or 40-60% acedtonitrile/0.1% TFA at a flow rate of 15.0 mL/min). The purified compounds were characterized by HRMS, TLC, analytical HPLC and $^1$H-1D-NMR (Table 5).

TABLE 5.1

Sequence and analytical data of bifunctional compound ligands.

| no | Sequence | m/z$^a$ (M + H)$^+$ | | HPLC$^b$ log/k' | | TLC$^c$ (R$_f$) | | | Purity (%)$^{d,f}$ | Yield (%)$^f$ | logD$_{7.4}$$^g$ |
|---|---|---|---|---|---|---|---|---|---|---|---|
| | | Obs. (ESI) | Calc. | (A)$^c$ | (B)$^d$ | (I) | (II) | (III) | | | |
| 1 | H-Tyr-D-Ala-Gly-Phe-Pro-Leu-Trp-O-3,5-Bzl(CF$_3$)$_2$ (TY001) | 1079.4466 | 1079.4495 | 19.03 | 7.36 | 0.13 | 0.71 | 0.77 | 85.3 | 57.0 | >4 |
| 2 | H-Tyr-D-Ala-Gly-Phe-Pro-Leu-Trp-O-Bzl (TY011) | 943.4719 | 943.4764 | 15.82 | 3.42 | 0.18 | 0.71 | 0.77 | 84.2 | 57.0 | 3.8 |
| 3 | H-Tyr-D-Ala-Gly-Phe-Pro-Leu-Trp-NH-Bzl (TY008) | 942.4879 | 942.4942 | 13.80 | 4.28 | 0.07 | 0.57 | 0.78 | 93.3 | 57.0 | 3.3 |
| 4 | H-Tyr-D-Ala-Gly-Phe-Pro-Leu-Trp-NMe-Bzl (TY010) | 956.5035 | 956.5188 | 14.97 | 4.97 | 0.11 | 0.58 | 0.81 | 66.9 | 56.0 | 3.5 |
| 5 | H-Tyr-D-Ala-Gly-Phe-Pro-Leu-Trp-NH-3,5-Bzl(CF$_3$)$_2$ (TY012) | 1078.4626 | 1078.4616 | 16.83 | 6.27 | 0.11 | 0.67 | 0.81 | 80.3 | 55.9 | >4 |

TABLE 5.1-continued

Sequence and analytical data of bifunctional compound ligands.

| no | Sequence | m/z[a] (M + H)+ | | HPLC[b] log k' | | TLC[e] (R_f) | | | Purity | Yield | |
|---|---|---|---|---|---|---|---|---|---|---|---|
| | | Obs. (ESI) | Calc. | (A)[c] | (B)[d] | (I) | (II) | (III) | (%)[d,f] | (%)[f] | logD$_{7.4}$[g] |
| 6 | H-Tyr-D-Ala-Gly-Phe-Pro-Leu-Trp-NMe-3,5-Bzl(CF$_3$)$_2$ (TY013) | 1092.4783 | 1092.4806 | 17.98 | 6.76 | 0.13 | 0.68 | 0.81 | 74.6 | 57.0 | >4 |

[a]High-resolution mass spectroscopy using electrospray ionization method.
[b]HPLC log k' = log [(compound retention time – solvent retention time)/solvent retention time]. All the obtained final compounds showed >99% prrity.
[c]10-90% of acetonitrile containing 0.1% TFA within 40 min and up to 95% within additional 5 min, 1 mL/min, 230 nm, Waters NOVA-Pak C-18 column (3.9 × 150 mm, 5 μm, 60 Å).
[d]30-70% of acetonitrile containing 0.1% TFA within 40 min and up to 95% within an additional 5 min, 1 mL/min, 230 nm, Vydac 218TP104 C-18 column (4.6 × 250 mm, 10 μm, 300 Å).
[e](I) CHCl$_3$:MeOH:AcOH = 90:10:3, (II) EtOAc:n-BuOH:water:AcOH = 5:3:1:1, (III) n-BuOH:water:AcOH = 4:1:1.
[f]Determined of the crude product.
[g]Logarithm of octanol/saline distribution coefficient in 0.05 N HEPES buffer in 0.1 N NaCl solution.

TABLE 5.2

1H-NMR data.
H-Tyr-D-Ala-Gly-Phe-Pro-Leu-Trp-O-3,5-Bzl(CF$_3$)$_2$•TFA (TY001);
2 amide bond rotamers at the Pro[6] N, ca. 7:1 ratio; $^1$H-NMR (DMSO-d$_6$) δ:

| AA | NH | α | β | misc. |
|---|---|---|---|---|
| Tyr[1] | 8.06/8.10(3H, bs) | 3.93-4.05(1H, m) | 2.84(1H, dd, J = 7.0, 11.5 Hz), 2.90(1H, dd, J = 6.5, 11.5 Hz) | 6.70(2H, d, J = 8.0 Hz: PhH), 7.02(2H, d, J = 8.5 Hz: PhH), 9.33(1H, bs: PhOH) |
| D-Ala[2] | 8.50/8.60(1H, d, J = 6.5 Hz) | 4.28-4.33(1H, m) | 1.05/1.10(3H, d, J = 7.0 Hz) | — |
| Gly[3] | 8.14/8.25(1H, t, J = 5.5 Hz) | 3.59/3.55(1H, dd, J = 6.0, 17.0 Hz), 3.70/3.73(1H, dd, J = 5.5, 16.5 Hz) | — | — |
| Phe[4] | 8.23(1H, d, J = 8.0 Hz) | 4.63-4.70(1H, m) | 2.73(1H, dd, J = 9.5, 14.0 Hz), 2.98(1H, dd, J = 3.5, 14.0 Hz) | 7.12-7.30(5H, m: PhH) |
| Pro[5] | — | 4.31-4.35/4.14-4.17(1H, m) | 1.69-1.77/1.69-1.73(1H, m), 1.89-1.96/1.69-1.73(1H, m) | 1.77-1.91/1.57-1.62(2H, m: γCH$_2$), 3.45-3.52/3.33-3.38(1H, m: δCH$_2$), 3.56-3.64/3.22-3.26(1H, m: δCH$_2$) |
| Leu[6] | 7.84(1H, d, J = 8.5 Hz) | 4.30-4.38/4.25-4.28(1H, m) | 1.37(2H, dd, J = 7.5, 7.5 Hz) | 1.53-1.65(1H, m: γCH$_2$), 0.78/0.72(3H, d, J = 6.5 Hz: δCH$_2$), 0.80(3H, d, J = 6.5 Hz: δCH$_2$) |
| Trp[7] | 8.41(1H, d, J = 6.5 H\z) | 4.56(1H, dd, J = 7.0, 14.0 Hz) | 3.15(1H, dd, J = 6.5, 15.0 Hz), 3.21(1H, dd, J = 6.5, 15.0 Hz) | 6.95(1H, dd, J = 7.5, 7.5 Hz: Ind5), 7.05(1H, dd, J = 7.0, 7.0 Hz: Ind6), 7.15(1H, s: Ind2), 7.32(1H, d, J = 8.0 Hz: Ind4), 7.46(1H, d, J = 7.5 Hz: Ind7), 10.88(1H, bs, IndNH) |
| 3,5-Bn(CF$_3$)$_2$ | — | — | — | 5.12(1H, d, J = 13.0 Hz: CH$_2$Ph), 5.22(1H, d, J = 13.5 Hz: CH$_2$Ph), 7.93(2H, s: PhH), 8.06(1H, s: PhH) |

TABLE 5.3

1H-NMR data.
H-Tyr-D-Ala-Gly-Phe-Pro-Leu-Trp-O-Bzl•TFA (TY011);
2 amide bond rotamers at the Pro[6] N, ca. 7:1 ratio; $^1$H-NMR (DMSO-d$_6$) δ:

| AA | NH | α | β | misc. |
|---|---|---|---|---|
| Tyr[1] | 8.06 (3H, bs) | 3.93-4.03(1H, m) | 2.84(1H, dd, J = 7.0, 13.5 Hz), 2.90(1H, dd, J = 6.5, 13.5Hz) | 6.70(2H, d, J = 8.5 Hz: PhH), 7.02(2H, d, J = 8.5 Hz: PhH), 9.33(1H, bs: PhOH) |
| D-Ala[2] | 8.51/8.60(1H, d, J = 6.5 Hz) | 4.27-4.32(1H, m) | 1.05/1.10(3H, d, J = 7.0 Hz) | — |
| Gly[3] | 8.16/8.23(1H, t, J = 5.5 Hz) | 3.59(1H, dd, J = 6.0, 16.5 Hz), 3.70/3.74(1H, dd, J = 6.0, 17.0 Hz) | — | — |
| Phe[4] | 8.23/8.25(1H, d, J = 7.5 Hz) | 4.61-4.71(1H, m) | 2.74(1H, dd, J = 9.0, 13.5 Hz), 2.99(1H, dd, J = 4.5, 14.0 Hz) | 7.10-7.33(5H, m: PhH) |
| Pro[5] | — | 4.31-4.36/4.13-4.16(1H, m) | 1.71-1.77/1.70-1.76(1H, m), 1.91-1.96/1.70-1.76(1H, m) | 1.78-1.90/1.59-1.61(2H, m: γCH$_2$), 3.47-3.52(1H, m: δCH$_2$), 3.56-3.63(1H, m: δCH$_2$) |

TABLE 5.3-continued

1H-NMR data.
H-Tyr-D-Ala-Gly-Phe-Pro-Leu-Trp-O-Bzl•TFA (TY011);
2 amide bond rotamers at the Pro$^6$ N, ca. 7:1 ratio; $^1$H-NMR (DMSO-d$_6$) δ:

| AA | NH | α | β | misc. |
|---|---|---|---|---|
| Leu$^6$ | 7.86/8.21(1H, d, J = 8.0 Hz) | 4.33-4.40/4.25-4.29(1H, m) | 1.36-1.48(2H, m) | 1.55-1.68(1H, m: γCH$_2$), 0.83/0.76(3H, d, J = 6.5 Hz: δCH$_2$), 0.86(3H, d, J = 6.5 Hz) |
| Trp$^7$ | 8.33(1H, d, J = 7.0 Hz) | 4.56(1H, dd, J = 6.5, 14.0 Hz) | 3.12(1H, dd, J = 7.5, 14.5 Hz), 3.19(1H, dd, J = 6.5, 14.5 Hz) | 6.99(1H, dd, J = 7.5, 7.5 Hz: Ind5), 7.08(1H, dd, J = 7.5, 7.5 Hz: Ind6), 7.16(1H, s: Ind2), 7.34(1H, d, J = 8.5 Hz: Ind4), 7.48(1H, d, J = 7.5 Hz: Ind7), 10.86(1H, bs, IndNH) |
| Bzl | — | 4.97(1H, d, J = 13.0 Hz), 5.02(1H, d, J = 12.5 Hz) | — | 7.10-7.33(5H, m: PhH) |

TABLE 5.4

1H-NMR data.
H-Tyr-D-Ala-Gly-Phe-Pro-Leu-Trp-NH-Bzl•TFA (TY008);
2 amide bond rotamers at the Pro$^6$ N, ca. 5:1 ratio; $^1$H-NMR (DMSO-d$_6$) δ:

| AA | NH | α | β | misc. |
|---|---|---|---|---|
| Tyr$^1$ | 8.05/8.09(3H, bs) | 3.94-4.04(1H, m) | 2.84(1H, dd, J = 7.5, 14.0 Hz), 2.90(1H, dd, J = 7.0, 13.5 Hz) | 6.70(2H, d, J = 8.0 Hz: PhH), 7.02(2H, d, J = 8.0 Hz: PhH), 9.33(1H, bs: PhOH) |
| D-Ala$^2$ | 8.52/8.60(1H, d, J = 6.5 Hz) | 4.28-4.33(1H, m) | 1.05/1.10(3H, d, J = 7.0 Hz) | — |
| Gly$^3$ | 8.16/8.23(1H, t, J = 5.5 Hz) | 3.59 (1H, dd, J = 6.0, 16.0 Hz), 3.70/3.73(1H, dd, J = 5.5, 16.5 Hz) | — | — |
| Phe$^4$ | 8.23/8.25(1H, d, J = 8.0 Hz) | 4.63-4.70/4.48-4.53(1H, m) | 2.74/2.95(1H, dd, J = 9.5, 14.0 Hz), 2.98/3.27(1H, dd, J = 4.0, 14.0 Hz) | 7.05-7.30(5H, m: PhH) |
| Pro$^5$ | — | 4.29-4.34/4.10-4.14(1H, m) | 1.69-1.76/1.67-1.75(1H, m), 1.90-1.98/1.67-1.75 (1H, m) | 1.76-1.90/1.55-1.58(2H, m: γCH$_2$), 3.45-3.51/3.17-3.25(1H, m: δCH$_2$), 3.56-3.63/3.32-3.35(1H, m: δCH$_2$) |
| Leu$^6$ | 7.96/8.27(1H, d, J = 6.5 Hz) | 4.23-4.33/4.15-4.18(1H, m) | 1.40(2H, dd, J = 7.5, 7.5 Hz) | 1.55-1.65(1H, m: γCH$_2$), 0.83/0.77(3H, d, J = 6.5 Hz: δCH$_2$), 0.88/0.86(3 H, d, J = 6.5 Hz: δCH$_2$) |
| Trp$^7$ | 7.84/7.82(1H, d, J = 8.0 Hz) | 4.57(1H, dd, J = 7.5, 14.0 Hz) | 3.03/3.01(1H, dd, J = 7.5, 14.5 Hz), 3.15/3.10(1H, dd, J = 6.0, 14.5 Hz) | 6.96(1H, dd, J = 7.5, 7.5 Hz: Ind5), 7.06(1H, dd, J = 8.0, 8.0 Hz: Ind6), 7.09(1H, s: Ind2), 7.33(1H, d, J = 8.0 Hz: Ind4), 7.56(1H, d, J = 7.5 Hz: Ind7), 10.88(1H, bs, IndNH) |
| Bzl | 8.36/8.43(1H, t, J = 5.5 Hz) | — | — | 4.15-4.25/4.25-4.32(2H, m), 7.05-7.30(5H, m: PhH) |

TABLE 5.5

1H-NMR data.
H-Tyr-D-Ala-Gly-Phe-Pro-Leu-Trp-NMe-Bzl•TFA (TY010);
2 amide bond rotamers at the Pro$^6$ N, ca. 7:1 ratio (read from NH-DAla),
2 amide bond rotamers at the BzlN, ca. 2:1 ratio (read from IndNH-Trp);
$^1$H-NMR (DMSO-d$_6$) δ:

| AA | NH | α | β | misc. |
|---|---|---|---|---|
| Tyr$^1$ | 8.06(3H, bs) | 3.96(1H, m) | 2.83(1H, dd, J = 7.8, 13.8 Hz), 2.88(1H, dd, J = 6.6, 13.8 Hz) | 6.69/6.70(2H, d, J = 7.8 Hz: PhH), 7.00(2H, d, J = 8.4 Hz: PhH), 9.33(1H, bs: PhOH) |
| D-Ala$^2$ | 8.50/8.59(1H, d, J = 7.2 Hz) | 4.26-4.33(1H, m) | 1.03/1.09(3H, d, J = 6.6 Hz) | — |
| Gly$^3$ | 8.15/8.24(1H, t, J = 5.4 Hz) | 3.56-3.63 (1H, m), 3.69/3.74(1H, dd, J = 6.0, 16.8 Hz) | — | — |
| Phe$^4$ | 8.22/8.20/7.68 (1H, d, J = 7.8 Hz) | 4.63-4.70/4.22-4.25/4.50-4.56(1H, m) | 2.75/2.90/2.83(1H, dd, J = 9.6, 13.8 Hz), 2.92-3.08/3.12-3.16/2.78-2.90(1H, m) | 6.90-7.30(5H, m: PhH) |

TABLE 5.5-continued

1H-NMR data.
H-Tyr-D-Ala-Gly-Phe-Pro-Leu-Trp-NMe-Bzl•TFA (TY010);
2 amide bond rotamers at the Pro⁶ N, ca. 7:1 ratio (read from NH-DAla),
2 amide bond rotamers at the BzlN, ca. 2:1 ratio (read from IndNH-Trp);
$^1$H-NMR (DMSO-$d_6$) δ:

| AA | NH | α | β | misc. |
|---|---|---|---|---|
| Pro$^5$ | — | 4.34-4.39/4.13-4.17(1H, m) | 1.77-1.88/1.62-1.65(1H, m), 1.95-2.03/1.73-1.78 (1H, m) | 1.88-1.95/1.80-1.86(2H, m: γCH$_2$), 3.50-3.57(1H, m: δCH$_2$), 3.58-3.67(1H, m: δCH$_2$) |
| Leu$^6$ | 7.91/7.87/8.25 (1H, d, J = 8.4 Hz) | 4.32-4.41/4.31-4.37/4.25-4.28(1H, m) | 1.44/1.41/1.45(2H, dd, J = 7.2, 7.2 Hz) | 1.60-1.65/1.60-1.62/1.42-1.45(1H, m: γCH$_2$), 0.81-0.90/0.76-0.79(6H, m: δCH$_2$) |
| Trp$^7$ | 8.22/8.20/8.18/8.16(1H, d, J = 7.8 Hz) | 5.07/4.98(1H, dd, J = 7.8, 14.4 Hz) | 2.90-3.05(1H, m), 3.11-3.25 (1H, m) | 6.96/6.88(1H, dd, J = 7.2, 7.2 Hz: Ind5), 7.05/7.03(1H, dd, J = 7.2, 7.2 Hz: Ind6), 7.12/7.12/7.07/7.07(1H, s: Ind2), 7.33/7.32(1H, d, J = 8.4 Hz: Ind4), 7.55/7.35/7.54(1H, d, J = 8.4 Hz: Ind7), 10.86/10/82(1H, bs, IndNH) |
| Bzl | — | — | — | 2.68/2.66(3H, s, NCH$_3$), 6.90-7.30(5H, m: PhH) |

TABLE 5.6

1H-NMR data.
H-Tyr-D-Ala-Gly-Phe-Pro-Leu-Trp-NH-3,5-Bzl(CF$_3$)$_2$•TFA (TY012);
2 amide bond rotamers at the Pro⁶N, ca. 6:1 ratio (read from H$_β$-DAla);
$^1$H-NMR (DMSO-$d_6$) δ:

| AA | NH | α | β | misc. |
|---|---|---|---|---|
| Tyr$^1$ | 8.05/8.10(3H, bs) | 3.92-4.00(1H, m) | 2.83(1H, dd, J = 7.2, 13.8 Hz), 2.88(1H, dd, J = 6.6, 13.8 Hz) | 6.69(2H, d, J = 8.4 Hz: PhH), 7.00(2H, d, J = 8.4 Hz: PhH), 9.32(1H, bs: PhOH) |
| D-Ala$^2$ | 8.49/8.58(1H, d, J = 7.8 Hz) | 4.28-4.33(1H, m) | 1.03/1.08(3H, d, J = 6.6 Hz) | — |
| Gly$^3$ | 8.14/8.24(1H, t, J = 5.4 Hz) | 3.52-3.63(1H, m), 3.68/3.70(1H, dd, J = 5.4, 16.8 Hz) | | |
| Phe$^4$ | 8.22(1H, d, J = 7.8 Hz) | 4.62-4.67(1H, m) | 2.71(1H, dd, J = 9.0, 13.8 Hz), 2.95(1H, dd, J = 3.6, 13.8 Hz) | 7.12-7.28(5H, m: PhH) |
| Pro$^5$ | — | 4.30-4.34/4.14-4.17(1H, m) | 1.65-1.74/1.68-1.74(1H, m), 1.87-1.96/1.68-1.74 (1H, m) | 1.75-1.86/1.53-1.58(2H, m: γCH$_2$), 3.44-3.52/3.21-3.25(1H, m: δCH$_2$), 3.56-3.64/3.31-3.36(1H, m: δCH$_2$) |
| Leu$^6$ | 7.91/8.20(1H, m) | 4.24-4.28/4.18-4.22(1H, m) | 1.40/1.43(2H, dd, J = 7.2, 7.2 Hz) | 1.51-1.64/1.38-1.41(1H, m: γCH$_2$), 0.79/0.73(3H, d, J = 6.6 Hz: δCH$_2$), 0.83(3H, d, J = 6.6 Hz: δCH$_2$) |
| Trp$^7$ | 7.95(1H, m) | 4.52(1H, dd, J = 7.2, 13.8 Hz) | 3.02(1H, dd, J = 7.2, 14.4 Hz), 3.14(1H, dd, J = 5.4, 14.4 Hz) | 6.93(1H, dd, J = 7.2, 7.2 Hz: Ind5), 7.03(1H, dd, J = 7.2, 7.2 Hz: Ind6), 7.09(1H, s: Ind2), 7.30(1H, d, J = 7.8 Hz: Ind4), 7.52(1H, d, J = 7.8 Hz: Ind7), 10.80(1H, bs, IndNH) |
| 3,5-Bn(CF$_3$)$_2$ | 8.59(1H, t, J = 6.0 Hz) | — | — | 4.35(1H, dd, J = 5.4, 9.6 Hz: CH$_2$Ph), 4.45(1H, dd, J = 5.4, 10.2 Hz: CH$_2$Ph), 7.89(2H, s: PhH), 7.94(1H, s: PhH) |

TABLE 5.7

1H-NMR data.
H-Tyr-D-Ala-Gly-Phe-Pro-Leu-Trp-NMe-3,5-Bzl(CF$_3$)$_2$•TFA (TY013);
2 amide bond rotamers at the Pro⁶ N, ca. 9:1 ratio (read from NH-DAla),
2 amide bond rotamers at the BzlN, ca. 3:1 ratio (read from IndNH-Trp);
$^1$H-NMR (DMSO-$d_6$) δ:

| AA | NH | α | β | misc. |
|---|---|---|---|---|
| Tyr$^1$ | 8.06(3H, bs) | 3.98(1H, m) | 2.84(1H, dd, J = 8.5, 14.5 Hz), 2.90(1H, dd, J = 7.0, 14.5 Hz) | 6.70(2H, d, J = 8.5 Hz: PhH), 7.02(2H, d, J = 8.5 Hz: PhH), 9.32(1H, bs: PhOH) |
| D-Ala$^2$ | 8.49/8.58(1H, d, J = 7.5 Hz) | 4.27-4.33(1H, m) | 1.05/1.10(3H, d, J = 6.5 Hz) | — |

TABLE 5.7-continued

1H-NMR data.
H-Tyr-D-Ala-Gly-Phe-Pro-Leu-Trp-NMe-3,5-Bzl(CF$_3$)$_2$•TFA (TY013);
2 amide bond rotamers at the Pro$^6$ N, ca. 9:1 ratio (read from NH-DAla),
2 amide bond rotamers at the BzlN, ca. 3:1 ratio (read from IndNH-Trp);
$^1$H-NMR (DMSO-d$_6$) δ:

| AA | NH | α | β | misc. |
|---|---|---|---|---|
| Gly$^3$ | 8.16/8.25(1H, t, J = 5.0 Hz) | 3.55-3.62(1H, m), 3.70/3.75(1H, dd, J = 6.0, 16.5 Hz) | — | — |
| Phe$^4$ | 8.25/8.23/7.66 (1H, d, J = 7.5 Hz) | 4.63-4.70/4.48-4.52(1H, m) | 2.68-2.75/2.78-2.85(1H, m), 2.94-3.04/2.78-2.85/3.04-3.08(1H, m) | 7.15-7.30(5H, m: PhH) |
| Pro$^5$ | — | 4.33-4.37/4.16-4.19(1H, m) | 1.75-1.83/1.74-1.79(2H, m) | 1.86-1.92/1.60-1.64(1H, m: γCH$_2$), 1.94-2.00/1.60-1.64(1H, m: γCH$_2$), 3.49-3.57(1H, m: δCH$_2$), 3.60-3.67(1H, m: δCH$_2$) |
| Leu$^6$ | 7.83/7.85/8.16 (1H, d, J = 7.5 Hz) | 4.32-4.40/4.25-4.30(1H, m) | 1.38-1.44/1.40-1.45/1.33-1.38(2H, m) | 1.56-1.67/1.40-1.45(1H, m: γCH$_2$), 0.84/0.77(3H, d, J = 7.5 Hz: δCH$_2$), 0.87/0.82(3H, d, J = 7.5 Hz: δCH$_2$) |
| Trp$^7$ | 8.35/8.32/8.30/8.17(1H, d, J = 8.0 Hz) | 4.90-5.00 (1H, m) | 2.95-3.03(1H, m), 3.11-3.23 (1H, m) | 6.97/6.88(1H, dd, J = 7.5, 7.5 Hz: Ind5), 7.07/7.02(1H, dd, J = 7.5, 7.5 Hz: Ind6), 7.13/7.12(1H, s: Ind2), 7.34/7.30(1H, d, J = 8.0 Hz: Ind4), 7.54/7.53(1H, d, J = 8.0 Hz: Ind7), 10.83/10/80(1H, bs, IndNH) |
| 3,5-Bn(CF$_3$)$_2$ | — | — | — | 2.77/2.79(3H, s, NCH, ), 7.85(2H, s: PhH), 7.98(1H, s: PhH) |

TABLE 5.8

1H-NMR data.
Boc-Tyr(t-Bu)-D-Ala-Gly-Phe-Pro-Leu-Trp(Boc)-OH;
2 amide bond rotamers at the Pro$^6$ N, ca. 7:1 ratio (read from NH-Phe),
2 amide bond rotamers at the —CO-IndN, ca. 5:1 ratio (read from Ind2 Trp);
$^1$H-NMR (DMSO-d$_6$) δ:

| AA | NH | α | β | misc. |
|---|---|---|---|---|
| Tyr$^1$ | 6.93/6.91(1H, d, J = 8.4 Hz) | 4.08-4.15(1H, m) | 2.60-2.72(1H, m), 2.85(1H, dd, J = 5.4, 13.8 Hz) | 6.82(2H, d, J = 7.8 Hz: PhH), 7.11(2H, d, J = 7.8 Hz: PhH), 1.60(9H, s: (CH3)$_3$COPh), 1.23(9H, s: (CH3)$_3$CO(CO)N) |
| D-Ala$^2$ | 7.98-8.02/7.96-7.98/8.01-8.04(1H, m) | 4.22-4.30(1H, m) | 1.05-1.12(3H, m) | — |
| Gly$^3$ | 7.96-8.02/8.04-8.07/8.10-8.14(1H, m) | 3.50-3.60/3.59-3.63(1H, m), 3.67/3.70(1H, dd, J = 6.0, 17.4 Hz) | — | — |
| Phe$^4$ | 8.17/7.71 (1H, d, J = 7.8 Hz) | 4.60-4.68/4.48-4.50(1H, m) | 2.63-2.74/2.80-2.83(1H, m), 2.93/2.84(1H, dd, J = 4.2, 13.2 Hz) | 7.12-7.25(5H, m: PhH) |
| Pro$^5$ | — | 4.32-4.36/4.03-4.07(1H, m) | 1.70-1.86/1.53-1.60(2H, m) | 1.89-1.96/1.69-1.72(2H, m: γCH$_2$), 3.40-3.47/3.21-3.25(1H, m: δCH$_2$), 3.55-3.63/3.32-3.36(1H, m: δCH$_2$) |
| Leu$^6$ | 7.85/8.14(1H, d, J = 7.8 Hz) | 4.25-4.33/4.19-4.22(1H, m) | 1.41/1.45 (2H, dd, J = 7.2, 7.2 Hz) | 1.60-1.64/1.39-1.42(1H, m: γCH$_2$), 0.81/0.74(3H, d, J = 6.6 Hz: δCH$_2$), 0.85/0.83(3H, d, J = 6.6 Hz: δCH$_2$) |
| Trp$^7$ | 8.01-8.07(1H, m) | 4.50-4.60 (1H, m) | 3.05(1H, dd, J = 8.4, 15.0 Hz), 3.15(1H, dd, J = 4.8, 15.0 Hz) | 7.20-7.25(1H, m: Ind5), 7.30(1H, dd, J = 7.2, 7.2 Hz: Ind6), 7.48/7.47(1H, s: Ind2), 7.59(1H, d, J = 7.8 Hz: Ind4), 7.98-8.03(1H, m: Ind7), 1.26/1.27(9 H, s: (CH3)$_3$CO(CO)N) |

Sequential assignment of proton resonances was achieved by 2D-TOCSY NMR experiments. (Braunschweiler, *J. Magn. Reson.* 1983, 53, 521-528; Davis, *J. Am. Chem. Soc.* 1985, 107, 2820-2821; Subramanian, *J. Magn. Reson.* 1987, 71, 325-330; Rance, *J. Magn. Reson.* 1987, 74, 557-564; Bax, *J. Magn. Reson.* 1985, 65, 355-360). High-resolution MS were taken in the positive ion mode using ESI methods at the University of Arizona Mass Spectrometry Facility. TLC was performed on aluminum sheets coated with a 0.2 mm layer of silica gel 60 F$_{254}$ Merck using the following solvent systems: (1) CHCl$_3$:MeOH:AcOH=90:10:3; (2) EtOAc:n-BuOH:water:AcOH=5:3:1:1; and (3) n-BuOH:water:AcOH=4:1:1. TLC chromatograms were visualized by UV light and by ninhydrin spray followed by heating (hot plate). Analytical HPLC was performed on a Hewlett Packard 1100 or Hewlett Packard 1090m with Waters NOVA-Pak C-18 column (3.9×

150 mm, 5 μm, 60 Å) or Vydac 218TP104 C-18 column (4.6×250 mm, 10 μm, 300 Å). $^1$H-1D-NMR spectra were recorded on Bruker DRX-500 or DRX-600 spectrometer. 2D-TOCSY NMR spectra were performed on a Bruker DRX-600 spectrometer equipped with 5 mm Nalorac triple-resonance single-axis gradient probe. The NMR experiments were conducted in DMSO-$d_6$ solution at 298K. Spectra were referenced to residual solvent protons as 2.49 ppm. The processing of NMR data was performed with the XwinNmr software (Bruker BioSpin, Fremont, Calif.) and the Felix2000 package (Accelrys Inc., San Diego, Calif.). In TOCSY experiment, the TPPI mode with MLEV-17 Mixing Sequence were used with a mixing time of 62.2 ms, at a spin-lock field of 8.33 kHz. TOCSY spectra were acquired with 2 k complex pairs in $t_2$ and 750 FIDs using a 90°-shifted sine-squared window function in both dimensions.

Example 7.2

Octanol/Saline Distribution ($logD_{7.4}$)

HEPES buffer (0.05 M HEPES buffer in 0.1 M NaCl, pH 7.4, 500 μL) was added to 2 mg of compound and mixed with 500 μL of 1-octanol. The sample was shaken at r.t. for 12 h to allow equilibrating. The sample was centrifuged at 6500 rpm in a VanGuard V6500 (GlaxoSmithKline, Research Triangle Park, N.C.) for 15 min. The layers were separated and each layer was centrifuged once again. The compound concentrations of obtained layers were analyzed by HPLC (30-70% of acetonitrile containing 0.1% TFA within 20 min and up to 95% within additional 5 min, 1 mL/min, 230 nm, Vydac 218TP104 C-18 column). The logarithm of 1-octanol/saline distribution ($logD_{7.4}$) was calculated as the ratio of compound concentration in the 1-octanol and saline phases.

Example 8

Structure Activity Relationship

Example 8.1

Cell Lines. Cell Line experiments were performed as in Example 4.1.

Example 8.2

Radioligand Labeled Binding Assays were carried out as in Example 4.2.

Example 8.3

[$^{35}$S]GTPγS Binding Assay were performed as in Example 4.3.

Example 8.4

Guinea Pig Isolated Ileum Assay were carried out as in Example 4.4.

Example 8.5

Mouse Isolated Vas Deferens (MVD) Assay were performed as in Example 4.5.

Example 8.6

Analysis of the GPI and MVD assays were performed as in Example 4.6.

Discussion.

The opioid receptor binding affinities of compounds TY001, 011, 008, 010, 012, and 013 were evaluated using human δ-opioid receptors (hDOR) and rat μ-opioid receptors (rMOR) with cells that stably express these receptors as previously described (Agnes, *J. Med. Chem.* 2006, 49(10), 2868-2875) (Table 6).

TABLE 6

Binding affinities of bifunctional compounds at δ/μ opioid receptors and NK1 receptors.

| no | hDOR[a], [$^3$H]DPDPE[b] LogIC$_{50}$[g] | $K_i$ (nM) | rMOR[a], [$^3$H]DAMGO[c] LogIC$_{50}$[g] | $K_i$ (nM) | $K_i(\mu)/K_i(\delta)$ | hNK1[d], [$^3$H]Substance P[e] LogIC$_{50}$[g] | $K_i$ (nM) | rNK1[d], [$^3$H]Substance P[f] LogIC$_{50}$[g] | $K_i$ (nM) | $K_i$(rNK1)/$K_i$(hNK1) |
|---|---|---|---|---|---|---|---|---|---|---|
| TY001 | −7.0 ± 0.10 | 50 | −6.4 ± 0.20 | 180 | 3.6 | −11.3 ± 0.07 | 0.0023 | −8.3 ± 0.06 | 1.6 | 700 |
| TY011 | −7.2 ± 0.14 | 31 | −7.2 ± 0.17 | 29 | 0.94 | −6.7 ± 0.07 | 100 | −6.1 ± 0.04 | 270 | 2.7 |
| TY008 | −7.7 ± 0.09 | 10 | −8.9 ± 0.09 | 0.65 | 0.065 | −7.5 ± 0.03 | 14 | 30 ± 9.9%[h] | — | — |
| TY010 | −6.8 ± 0.24 | 77 | −7.0 ± 0.33 | 46 | 0.60 | −8.5 ± 0.04 | 1.6 | 33 ± 7.6%[h] | — | — |
| TY012 | −6.8 ± 0.08 | 72 | −7.7 ± 0.21 | 9.5 | 0.13 | −8.9 ± 0.06 | 0.61 | −7.0 ± 0.06 | 33 | 54 |
| TY013 | −6.5 ± 0.09 | 31 | −7.8 ± 0.13 | 6.8 | 0.22 | −8.5 ± 0.06 | 1.4 | −7.7 ± 0.03 | 6.1 | 4.4 |
| Biphalin[h] | | 2.6 | | 1.4 | 0.54 | | | | | |
| L-732, 138 | | | | | | −8.8 +/− | 0.73 | −6.4 ± 0.12 | 130 | 180 |

[a]Competition analyses were carried out using membrane preparations from transfected HN9.10 cells that constitutively expressed the δ and μ opioid receptors, respectively.
[b]$K_d$ = 0.45 ± 0.1 nM.
[c]$K_d$ = 0.50 ± 0.1 nM.
[d]Competition analyses were carried out using membrane preparations from transfected CHO cells that constitutively expressed rat NK1 receptors.
[e]$K_d$ = 0.16 ± 0.03 nM.
[f]$K_d$ = 0.40 ± 0.17 nM.
[g]Logarithmic values of IC$_{50}$ determined from the non-linear regression analysis of data collected from at least two independent experiments performed in duplicate.
[h]Inhibition % at 1 μM.
[i]reference (Lipkowski, Bioorg. Med. Chem. Lett. 1999, 9(18), 2763-6)

[³H]DPDPE and [³H]DAMGO were used as δ and μ radioligands, respectively. The agonist efficacies were determined by examining receptor-G-protein interactions measuring agonist simulated binding of the GTP analogue guanosine-5'-O-(3-[³⁵S]thio)triphosphate ([³⁵S]GTPγ) using the same transfected cells as used for the binding affinity assays (Table 3).

TABLE 7

Opioid agonist functional activities in [³⁵S]GTP-γ-S binding assays.

| No | hDOR[a] | | | rMOR[a] | | |
|---|---|---|---|---|---|---|
| | LogEC$_{50}$[b] | EC$_{50}$ (nM)[c] | Emax (%)[d] | LogEC$_{50}$[b] | EC$_{50}$ (nM)[c] | Emax (%)[d] |
| TY001 | −7.5 ± 0.28 | 35 | 18 | −6.8 ± 0.24 | 140 | 26 |
| TY011 | −7.1 ± 0.14 | 85 | 130 | −7.4 ± 0.21 | 36 | 68 |
| TY008 | −7.8 ± 0.28 | 17 | 56 | −8.2 ± 0.44 | 0.71 | 100 |
| TY010 | −6.8 ± 0.16 | 150 | 70 | −7.5 ± 0.36 | 29 | 130 |
| TY012 | −7.1 ± 0.13 | 80 | 160 | −7.2 ± 0.26 | 57 | 60 |
| TY013 | −6.9 ± 0.21 | 120 | 140 | −7.1 ± 0.17 | 72 | 69 |
| Biphalin | −9.0 ± 0.17 | 1.1 | 83 | — | — | — |
| DPDPE | −8.8 ± 0.25 | 1.6 | 69 | — | — | — |
| DAMGO | — | — | — | −7.4 ± 0.19 | 37 | 150 |

[a]Expressed from HN9.10 cell.
[b]Logarithmic values determined from the non-linear regression analysis of data collected from at least three dependent experiments.
[c]Anti-logarithmic value of the respective EC$_{50}$.
[d]Net total bound/basal binding × 100

Tissue bioassays (MVD and GPI) also were performed to characterize agonist function through δ and μ opioid receptors, respectively (Table 8) (Yamamoto, 2007, *J. Med. Chem.*, in press).

TABLE 8

Functional assay result for bifunctional compound ligands at opioid and Substance P receptors.

| | Opioid agonist | | Substance P antagonist |
|---|---|---|---|
| No | MVD (δ), IC$_{50}$ (nM)[a] | GPI (μ), IC$_{50}$ (nM)[a] | GPI, Ke (nM)[b] |
| TY001 | 400 ± 23 | 520 ± 40 | 3.6 ± 1.1 |
| TY011 | 40 ± 4.4 | 74 ± 25 | 150 ± 17 |
| TY008 | 50 ± 10 | 13 ± 3.3 | 26 ± 3.9 |
| TY010 | 41 ± 8.6 | 9.0 ± 0.5 | 59 ± 18 |
| TY012 | 45 ± 6.3 | 350 ± 91 | 8.5 ± 2.1 |
| TY013 | 150 ± 26 | 52 ± 9.4 | 6.9 ± 1.1 |
| Biphalin | 2.7 ± 1.5 | 8.8 ± 0.3 | — |
| L-732, 138 | — | — | 250 ± 87 |

[a]Concentration at 50% inhibition of muscle concentration at electrically stimulated isolated tissues.
[b]Inhibitory activity against the Substance P induced muscle contraction in the presence of 1 μM naloxone, Ke: concentration of antagonist needed to inhibit Substance P to half its activity.

As for their affinity for rat NK1 (rNK1) receptors, receptor binding assays also were used on transfected cells that stably express rNK1 receptors using [³H]substance P as the standard radioligand (Table 6). To estimate antagonistic activities against substance P stimulation, tissue bioassays using guinea pig ileum (GPI) in the presence of naloxone were performed. All the synthesized compounds were confirmed to have no or negligible agonist activities against substance P stimulation (Table 8) (Yamamoto, 2007, *J. Med. Chem.*, in press). For evaluating lipophilicity of compounds the logarithm of distribution coefficient between 1-octanol and saline (logD$_{7.4}$) was measured (Table 5) (Egleton, *Brain Res.* 2000, 881, 37-46).

As shown in Table 6, compound TY001, with a 3',5'-(bis-trifluoromethyl)-benzyl ester at the C-terminal had moderate binding affinity at the DOR and MOR (Ki=50 and 180 nM, respectively). In the MVD, GPI and [³⁵S]GTPγS binding assay, the opioid agonist activity of TY001 showed results consistent with the binding assays. As expected, TY001 showed a very lipophilic character with its logD$_{7.4}$ value being above the detectable limit (greater than 4.0). Interestingly, the removal of the two trifluoromethyl groups of TY001 (TY011) resulted in increasing opioid affinity especially at the MOR (Ki=31 nM, DOR; 29 nM, MOR) (Table 6). Moreover, in the functional tissue assays, the activity in the MVD assay also was increased (IC$_{50}$=40 nM, MVD; 74 nM, GPI). A much more critical role for the trifluoromethyl groups was observed for the substance P antagonist pharmacophore. As seen in Table 6, compound TY001 with a 3',5'-(bistrifluoromethyl)-benzyl ester had a good binding affinity for the rNK1 receptor (Ki=1.6 nM) and good functional activity against substance P stimulation (Ke=3.6 nM, GPI). It should be noted that some of the reported NK1 antagonists had a large activity difference between rat NK1 and human NK1 (hNK1) receptors because of the species difference. The hNK1 receptor is known to have similar sequence and biological properties as the guinea pig NK1 (gpNK1) receptor, not with rNK1 (Datar, *Curr. Top Med. Chem.* 2004, 4, 75-103). L-732,138 (Ac-Trp-3,5-O-Bzl(CF$_3$)$_2$), which was part of substance P antagonist pharmacophore of TY001, was earlier found to have high affinity at human NK1 (hNK1) receptor, but had 200-fold less affinity for rNK1 receptor (Cascieri, *J. Biol. Chem.* 1994, 269(9), 6587-6591). Surprisingly, in the case of TY001 with longer compound sequence than L-732,138, the species difference was 700-fold, and the K$_i$ value at hNK1 was 2.3 μM. It should be noted that TY001 showed the differences between affinities in the binding assays and activities in the GPI or MVD assays, implying the decreased potency of TY001 in the tissues. As for the affinity of TY011 at the rNK1, only 270 nM of K$_i$ value was observed, whereas the K$_i$ values for hNK1 showed more potency (100 nM). The Ke value of TY011 in the GPI assay (150 nM) was 42 times less active than TY001. However, the Ke value of the benzyl amide derivative without trifluoromethyl groups (TY008) was 26 nM, which was 10 times more active than that of L-732,138. Since TY008 had only few affinity for the rNK1 receptor (30% inhibition at 1.0 μM), the species difference between the guinea pig and the rat should be large (more than 40-fold), while the difference between human and guinea pig was only two-fold (Ki=14 nM). Surprisingly, the opioid activities of TY008 showed large increases. Its affinity at the DOR was 10 nM and subnanomolar-level affinity was found at the MOR ($K_i$=0.65 nM), which were consistent with the results in the [$^{35}$S]GTPγS binding, MVD and GPI assays. These results indicated that TY008 is expected to work as a highly potent bifunctional compound with opioid agonist and substance P antagonist activities in humans, but not in rats. Interestingly, though the C-terminal is structurally apart from the opioid pharmacophore, it may act as an address region for opioids. It is possible to suggest that the trifluoromethyl groups had a critical influence on rNK1 binding, but its effect on hNK1 or gpNK1 receptor is limited. The introduction of a benzyl amide at C-terminal efficiently improved opioid binding and agonist activities, and retained antagonist activity against the rNK1. However, a simple N-methylation of the amide (TY010) decreased affinities at both opioid receptors, and the affinity at the MOR was more than 70-fold less ($K_i$=77 nM, DOR; 46 nM, MOR). This biological trend was maintained in the [$^{35}$S]GTPγS binding assay, but TY010 showed excellent potency in the MVD and GPI assays ($IC_{50}$=41 nM, MVD; 9.0 nM, GPI). The functional activity of TY010 as a substance P antagonist was more than two times less potent than TY008 (Ke=59 nM, GPI), though its $K_i$ value at hNK1 was improved (1.6 nM). Here, the $logD_{7.4}$ values of the compounds without trifluoromethyl groups (TY011, 008, and 010) showed moderately lipophilic values (3.8, TY011; 3.3, TY008; 3.5, TY010) which were decreased from that of TY001 (Table 5). Because the introduction of amide at the C-terminal was successful in the benzyl amide derivative TY008, we prepared the 3',5'-(bistrifluoromethyl)-benzyl amide derivative TY012. It showed a nanomolar-level affinity at the MOR and a moderate affinity at the DOR ($K_i$=72 nM, DOR; 9.5 nM, MOR). However, although TY012 displayed high affinity at the MOR, the [$^{35}$]GTPγS binding assay exhibited only a moderate $EC_{50}$ value at the MOR (57 nM), with Ke value of 350 nM in the GPI assay. Therefore, TY012 could strongly bind at the t opioid receptor, but its functional activity to regulate an opioid signal was apparently decreased. As for its substance P antagonist activity, ligand TY012 had decreased affinities at both the hNK1 and rNK1 receptors from those of the C-terminal ester TY001 ($K_i$=0.61 and 33 nM, respectively). The Ke value with substance P stimulation was also decreased from that of TY001, but still within the nanomolar range (8.5 nM). Considering the increased antagonist activity of the benzyl amide TY008 compared to benzyl ester TY011 in GPI with substance P stimulation (Ke=26 nM and 150 nM, respectively), the substitution of a benzyl ester to the amide with trifluoromethyl groups at the C-terminus showed a different SAR and it had less influence on substance P antagonist activity (Ke=3.6 nM for TY001, 8.5 nM for TY012). Finally, the introduction of a methyl group on the nitrogen atom of benzyl amide TY013 had a small effect on binding affinities compared to TY012, but its influence on the tissue-based assay were significant. For opioids, TY013 showed moderate binding at the DOR and high affinity for the MOR ($K_i$=31 nM, DOR; 6.8 nM, MOR), and this trend was maintained in the $IC_{50}$ values in MVD and GPI assays (150 and 52 nM, respectively), although its functional activities are relatively low in the [$^{35}$S]GTPγS binding ($EC_{50}$=120 nM, DOR; 72 nM, MOR). The binding affinity of TY013 at the hNK1 receptor was two times les TY012 ($K_i$=6.1 nM), and its Ke value in the GPI assay with substance P stimulation was 6.9 nM, which was almost equipotent to TY012. Consequently, TY013 was also found as a potent bifunctional compound derivative with opioid agonist and substance P antagonist activities which is expected to work in both human and rat.

Example 9

Compound Synthesis: TY005, TY027, and TY025

Example 9.1

Boc-Tyr(tBu)-D-Ala-Gly-Phe-Met-Pro-Leu-Trp(Boc)-OH. The compound was synthesized manually by the $N^\alpha$-Fmoc solid-phase methodology using HBTU as the coupling reagents as previously reported (Yamamoto, 2007, *J. Med. Chem.*, in press; Yamamoto, 2007, *J. Med. Chem.*, submitted). 2-Chlorotrityl resin (2.0 g, 1.56 mmol/g) was placed into a 50 mL polypropylene syringe with the frit on the bottom and swollen in DMF (20 mL) for 1 h. The resin was washed with DMF (3×15 mL) and then with DCM (3×15 mL). Fmoc-Trp(Boc)-OH (1.2 equiv) was dissolved in 30 mL of DCM, and then DIEA (5 equiv) was added. The reaction mixture was transferred into the syringe with the resin then shaken for 2 h. The resin was washed three times with DMF (15 mL) and three times with DCM (15 mL), and then with DMF (3×15 mL). The Fmoc protecting group was removed by 20% piperidine in DMF (1×2 min and 1×20 min). The deprotected resin was washed with DMF (3×15 mL), DCM (3×15 mL) and then with DMF (3×15 mL). Fmoc-Leu-OH (3 equiv) and HBTU (2.9 equiv) were dissolved in 30 mL of DMF, then DIEA (6 equiv) was added. The coupling mixture was transferred into the syringe with the resin, then shaken for 2 h. All other amino acids, Pro, Met, Phe, Gly, D-Ala and Tyr were consecutively coupled using the procedures described above, using the TNBS test (all the amino acids except for Met) or chloranil test (only for Met) to check the extent of coupling. In case of a positive test result, the coupling was repeated until a negative test result was obtained. The resulting batch of the resin-bound protected Boc-Tyr(tBu)-D-Ala-Gly-Phe-Met-Pro-Leu-Trp(Boc) was carefully washed with DMF (3×15 mL), DCM (3×15 mL), DMF (3×15 mL), and DCM (3×15 mL), and dried under reduced pressure. The compound was cleaved off the solid support with 1% v/v TFA in DCM (30 mL) for 30 min, and most of the organic solvent was removed under reduced pressure. The obtained crude compounds were precipitated out by the addition of chilled petroleum ether (45 mL) to give a white precipitate. The suspensions were centrifuged for 20 min at 7000 rpm, then the liquid was decanted off. The crude compounds were washed with petroleum ether (2×50 mL), and after the final centrifugation, the compounds were dried under vacuum (2 h) to obtain the title compound (2.89 g, 74.8%). The purity of the final products (93.6%) was checked by analytical RP-HPLC using a Hewlett Packard 1100 system (230 nm) on a reverse phase column (Waters NOVA-Pak C-18 column, 3.9×150 mm, 5 μm, 60 Å). The compound was eluted with a linear gradient of aqueous $CH_3CN$/0.1% $CF_3CO_2H$ (10-90% in 40 minutes) at a flow rate of 1.0 mL/min. The crude compound was used for next reactions without further purification. $^1$H-NMR (DMSO-$d_6$): 0.79 (3H, d, J=6.6 Hz), 0.84 (3H, d, J=6.6 Hz), 1.10 (3H, d, J=6.6 Hz), 1.24 (9H, s), 1.26 (9H, s), 1.38-1.41 (2H, m), 1.61 (10H, s), 1.70-1.77 (3H, m), 1.80-1.94 (3H, m), 2.01 (3H, s), 2.42-2.47 (2H, m), 2.67 (1H, d-d, J=3.6, 13.2 Hz), 2.75 (1H, d-d, J=9.6, 13.8 Hz), 2.87 (1H, d-d, J=4.2, 13.2 Hz), 2.94 (1H, d-d, 2.4, 13.2 Hz), 3.04 (1H, d-d, 8.4, 15.0 Hz), 3.14 (1H, d-d, 4.8, 15.0 Hz), 3.48-3.53 (1H, m), 3.54-3.63 (2H, m), 3.68 (1H, d-d, J=5.4, 16.8 Hz), 4.15 (1H, d-d, J=6.0, 12.0 Hz), 4.20-4.30 (2H, m), 4.32 (1H, d-d, 3.6, 7.8 Hz), 4.48-4.55 (2H, m), 4.58 (1H, J=7.2, 14.4 Hz), 6.83 (2H, d, J=7.8 Hz), 6.92 (1H, d, J=8.4 Hz), 7.12 (2H, d, J=7.8 Hz), 7.14-7.24 (7H, m), 7.30 (1H, t, J=7.8 Hz), 7.47 (1H, s), 7.87-7.92 (2H, m), 7.98-8.08 (4H, m), 8.30 (1H, d, J=7.2 Hz). MS (ESI): 1262 (M+Na)$^+$.

Example 9.2

H-Tyr-D-Ala-Gly-Phe-Met-Pro-Leu-Trp-O-3,5-Bzl (CF$_3$)$_2$ TFA (TY005). Boc-Tyr(tBu)-D-Ala-Gly-Phe-Met-Pro-Leu-Trp(Boc)-OH (2.0 g, 1.61 mmol) and 3,5-bis(trifluoromethyl)benzyl bromide (1.24 g, 4.02 mmol) were dissolved in DMF (8 mL). Cesium carbonate (1.05 g, 3.22 mmol) was added to the solution at r.t. After stirring for 2 h, saturated aqueous sodium bicarbonate (200 mL) was added to the solution, and extracted with ethyl acetate (200 mL) three times. The combined organic phases were washed with 5% aqueous citrate and saturated aqueous sodium chloride (200 mL each), and dried over sodium sulfate. The solvent was evaporated off and the crude compound was precipitated in cold petroleum ether (45 mL) and centrifuged two times, and dried under reduced pressure. The obtained protected compound was treated with 82.5% v/v TFA, 5% water, 5% thioanisole, 2.5% 1,2-ethanedithiol, and 5% phenol (10 mL, 1 h). The crude compound was precipitated out by the addition of chilled diethyl ether (45 mL) to give white precipitates. The suspension was centrifuged for 20 min at 7000 rpm, then the liquid was decanted. The crude compounds were washed with diethyl ether (2×45 mL), and after the final centrifugation, the compounds were dried under vacuum (2 h). The resulting white residues (2.48 g, quantitative) were dissolved in 3:1 mixture of acetonitrile and distilled water (5 mL), and the insoluble impurities were removed by passing the solutions through syringe filters (Gelman Laboratory, Ann Arbor, Mich., Acrodisc 13 mm syringe filter with 0.45 µM PTFE membrane). Final purification was accomplished by preparative RP-HPLC, then lyophilized.

Example 9.3

H-Tyr-D-Ala-Gly-Phe-Met-Pro-Leu-Trp-NH-3,5-Bzl (CF$_3$)$_2$ TFA (TY027). Boc-Tyr(tBu)-D-Ala-Gly-Phe-Met-Pro-Leu-Trp(Boc)-OH (3.0 g, 2.42 mmol) and Cl-HOBt (428 mg, 2.66 mmol) were dissolved in DMF (10 mL). 3,5-bistrifluoromethylbenzyl amine (1.17 g, 4.84 mmol) and EDC (508 mg, 2.66 mmol) were added to the solution at r.t and stirred until the starting material wasn't detected in TLC; then saturated aqueous sodium bicarbonate (250 mL) was added. The reaction mixture was extracted with ethyl acetate (250 mL) three times. The combined organic phases were washed with 5% aqueous citrate and saturated aqueous sodium chloride (250 mL each), then dried over sodium sulfate. The solvent was evaporated and the crude compound was precipitated in cold petroleum ether (45 mL). The product was twice dispersed in cold petroleum ether, centrifuged and decanted, then dried under reduced pressure. The obtained protected compound was treated with 82.5% v/v TFA, 5% water, 5% thioanisol, 2.5% 1,2-ethanedithiol, and 5% phenol (1.5 mL, 1 h). The crude compound was precipitated out by the addition of chilled diethyl ether (45 mL) to give a white precipitate. The resulting compound suspensions were centrifuged for 20 min at 7000 rpm, and the liquid was decanted. The crude compounds were washed with diethyl ether (2×45 mL), and after a final centrifugation, the compounds were dried under vacuum (2 h). The resulting white residues (3.42 g, quantitative) were dissolved in a 3:1 mixture of acetonitrile and distilled water (5 mL), and the insoluble impurities were removed by passing the solutions through syringe filters (Gelman Laboratory, Acrodisc 13 mm syringe filter with 0.45 µM PTFE membrane). Final purification was accomplished by preparative RP-HPLC. The pure title compound was obtained after lyophilization.

Example 9.4

H-Tyr-D-Ala-Gly-Phe-Met-Pro-Leu-Trp-NH-Bzl TFA (TY025). The title compound was prepared using same method as described for H-Tyr-D-Ala-Gly-Phe-Met-Pro-Leu-Trp-NH-3,5-Bzl(CF$_3$)$_2$.TFA (TY027). The crude compound was obtained quantitatively.

Example 10

Characterization of the Compounds

Example 10.1

Preparative RP-HPLC was performed on Waters Delta Prep 4000 with Waters XTerra C-18 column (19×250 mm, 10 µm, a linear gradient of 33-53% or 40-60% acedtonitrile/ 0.1% TFA at a flow rate of 15.0 mL/min). The purified compounds were characterized by HRMS, TLC, analytical HPLC and $^1$H-1D-NMR (Tables 9.1-9.7).

TABLE 9.1

Sequence and analytical data of bifunctional compound ligands

| no | Sequence | m/z$^a$ (M + H)$^+$ Obs. (ESI) | Calc. | HPLC$^b$ log/k' (A)$^c$ | (B)$^d$ | TLC$^e$ (R$_f$) (I) | (II) | (III) |
|---|---|---|---|---|---|---|---|---|
| 1 | H-Tyr-D-Ala-Gly-Phe-Met-Pro-Leu-Trp-O-3,5-Bzl(CF$_3$)$_2$ (TY005) | 1210.4810 | 1210.4871 | 19.21 | 11.14 | 0.14 | 0.73 | 0.79 |
| 2 | H-Tyr-D-Ala-Gly-Phe-Met-Pro-Leu-Trp-NH-3,5-Bzl(CF$_3$)$_2$ (TY027) | 1209.3055 | 1209.5031 | 17.29 | 7.94 | 0.09 | 0.67 | 0.58 |
| 3 | H-Tyr-D-Ala-Gly-Phe-Met-Pro-Leu-Trp-NH-3,5-Bzl (TY025) | 1073.3096 | 1073.5283 | 14.14 | 4.19 | 0.14 | 0.67 | 0.55 |

$^a$High-resolution mass spectroscopy using electrospray ionization method.
$^b$HPLC log k' = log [(compound retention time - solvent retention time)/solvent retention time]. All the obtained final compounds showed >99% purity.
$^c$10-90% of acetonitrile containing 0.1% TFA within 40 min and up to 95% within an additional 5 min, 1 mL/min, 230 nm, Waters NOVA-Pak C-18 column (3.9 × 150 mm, 5 µm, 60 Å).
$^d$30-70% acetonitrile containing 0.1% TFA within 40 min and up to 95% within an additional 5 min, 1 mL/min, 230 nm, Vydac 218TP104 C-18 column (4.6 × 250 mm, 10 µm, 300 Å).
$^e$(I) CHCl$_3$:MeOH:AcOH = 90:10:3, (II) EtOAc:n-BuOH:water:AcOH = 5:3:1:1, (III) n-BuOH:water:AcOH = 4:1:1.

Tables 9.2-9.4. $^1$H Resonance Assignments for Micelle-Bound Bifunctional Compounds with 40-fold DPC in 90% H$_2$O/10% D$_2$O, 45 mM CD$_3$CO$_2$Na, 1 mM NaN$_3$ at 310 K.

TABLE 9.2

Tyr-D-Ala-Gly-Phe-Met-Pro-Leu-Trp-O-3,5-Bzl(CF$_3$)$_2$•TFA (TY005), 3.8 mM, only for the major isomer, δ:

| AA | NH | α | β | misc. |
|---|---|---|---|---|
| Tyr[1] |  | 4.26 | 3.09, 3.20 | 2,6H: 7.18, 3,5H: 6.93 |
| D-Ala[2] | 8.69 | 4.20 | 1.22 |  |
| Gly[3] | 8.52 | 3.86, 3.96 |  |  |
| Phe[4] | 7.89 | 4.70 | 3.15, 3.20 | 2,6H: 7.32, 3,5H: 7.35, 4H$^a$ |
| Met[5] | 8.17 | 4.69 | 1.96, 2.05 | γ: 2.45, 2.51, CH$_3$: 2.08 |
| Pro[6] |  | 4.45 | 1.59, 2.20 | γ: 1.78, 1.90, δ: 3.61, 3.71 |
| Leu[7] | 7.84 | 4.44 | 1.59 | γ: 1.59, δ: 0.86 |
| Trp[8] | 8.11 | 4.73 | 3.34, 3.47 | Ind2: 7.42, Ind4: 7.52, Ind5: 7.13, Ind6: 7.00, Ind7: 7.48 |
| 3,5-Bn(CF$_3$)$_2$ |  | 5.02, 5.08 |  | 2.6H: 7.70, 4H: 7.76 |

TABLE 9.3

-Tyr-D-Ala-Gly-Phe-Met-Pro-Leu-Trp-NH-3,5-Bzl(CF$_3$)$_2$•TFA (TY027), 3.5 mM, only for the major isomer, δ:

| AA | NH | α | β | misc. |
|---|---|---|---|---|
| Tyr[1] |  | 4.28 | 3.11, 3.22 | 2,6H: 7.20, 3,5H: 6.93 |
| D-Ala[2] | 8.71 | 4.24 | 1.22 |  |
| Gly[3] | 8.56 | 3.86, 3.96 |  |  |
| Phe[4] | 7.82 | 4.68 | 3.13, 3.19 | 2,6H: 7.27, 3,5H: 7.34, 4H$^a$ |
| Met[5] | 8.07 | 4.55 | 1.91 | γ: 2.40, CH$_3$: 2.01 |
| Pro[6] |  | 4.36 | 1.18, 2.01 | γ: 1.56, 1.69, 6: 3.44, 3.60 |
| Leu[7] | 8.35 | 4.18 | 1.71 | γ: 1.61, δ: 0.92, 0.98 |

TABLE 9.3-continued

-Tyr-D-Ala-Gly-Phe-Met-Pro-Leu-Trp-NH-3,5-Bzl(CF$_3$)$_2$•TFA (TY027), 3.5 mM, only for the major isomer, δ:

| AA | NH | α | β | misc. |
|---|---|---|---|---|
| Trp[8] | 7.40 | 4.67 | 3.31, 3.47 | Ind2: 7.40, Ind4: 7.37, Ind5: 6.83, Ind6: 7.10, Ind7: 7.51 |
| 3,5-Bn(CF$_3$)$_2$ | 8.03 | 4.41, 4.52 |  | 2.6H: 7.85, 4H: 7.75 |

TABLE 9.4 yr-D-Ala-Gly-Phe-Met-Pro-Leu-Trp-NH-Bzl•TFA (TY025), 4.0 mM, only for the major isomer, δ:

| AA | NH | α | β | misc. |
|---|---|---|---|---|
| Tyr[1] |  | 4.20 | 3.04, 3.13 | 2,6H: 7.11, 3,5H: 6.85 |
| D-Ala[2] | 8.62 | 4.17 | 1.14 |  |
| Gly[3] | 8.47 | 3.78, 3.88 |  |  |
| Phe[4] | 7.73 | 4.60 | 3.04, 3.11 | 2,6H: 7.19, 3,5H: 7.26, 4H$^a$ |
| Met[5] | 7.94 | 4.41 | 1.79 | γ: 2.31, 2.37, CH$_3$: 2.04 |
| Pro[6] |  | 4.23 | 0.78, 1.83 | γ: 1.23, 1.50, δ: 2.97, 3.43 |
| Leu[7] | 8.46 | 4.05 | 1.67 | γ: 1.55, δ: 0.85, 0.93 |
| Trp[8] | 7.14 | 4.61 | 3.23, 3.54 | Ind2: 7.36, Ind4: 7.53, Ind5: 6.96, Ind6: 7.10, Ind7: 7.48 |
| Bzl | 7.42 | 4.17, 4.33 |  | 2.6H: 7.14, 3,5H: 7.09, 4H$^a$ |

$^a$not observed. Ind# represents the corresponding resonances in indole ring of Trp.

Tables 9.5-9.7. $^1$H Resonance Assignments of bifunctional compounds in DMSO at 298K.

TABLE 9.5

H-Tyr-D-Ala-Gly-Phe-Pro-Met-Leu-Trp-O-3,5-Bzl(CF$_3$)$_2$•TFA (TY005); Only one isomer was found; $^1$H-NMR (DMSO-d$_6$) δ:

| AA | NH | α | β | misc. |
|---|---|---|---|---|
| Tyr[1] | 8.05(3H, bs) | 3.95-4.02(1H, m) | 2.80-2.91(2H, m) | 6.71(2H, d, J = 8.5 Hz: PhH), 7.03(2H, d, J = 9.0 Hz: PhH), 9.33(1H, bs: PhOH) |
| D-Ala[2] | 8.52(1H, d, J = 6.5 Hz) | 4.29-4.35(1H, m) | 1.06(3H, d, J = 7.0 Hz) | — |
| Gly[3] | 8.19(1H, t, J = 5.0 Hz) | 3.62(1H, dd, J = 5.0, 17.0 Hz), 3.68 (1H, dd, J = 5.5, 17.0 Hz) | — | — |
| Phe[4] | 7.47(1H, d, J = 7.5 Hz) | 4.52-4.60(1H, m) | 2.68-2.75(1H, m), 2.88-2.98(1H, m) | 7.13-7.28(5H, m: PhH) |
| Met[5] | 8.41(1H, d, J = 8.0 Hz) | 4.62(1H, d, J = 7.5 Hz) | 1.75-1.82(1H, m), 1.89-1.98(1H, m) | 2.42-2.52(2H, m: γCH$_2$), 2.02(3H, s: δCH$_3$) |
| Pro[5] | — | 4.28-4.38(1H, m) | 1.67-1.75(1H, m), 1.88-1.98(1H, m) | 1.73-1.80(1H, m: γCH$_2$), 1.82-1.90(1H, m: γCH$_2$), 3.50-3.60(2H, m: δCH$_2$) |

TABLE 9.5-continued

H-Tyr-D-Ala-Gly-Phe-Pro-Met-Leu-Trp-O-3,5-Bzl(CF$_3$)$_2$•TFA (TY005); Only one isomer was found; $^1$H-NMR (DMSO-d$_6$) δ:

| AA | NH | α | β | misc. |
|---|---|---|---|---|
| Leu$^6$ | 7.89(1H, d, J = 8.0 Hz) | 4.28-4.33(1H, m) | 1.35(2H, dd, J = 7.0, 7.0 Hz) | 1.53-1.61(1H, m: γCH$_2$), 0.76(3H, d, J = 6.5 Hz: δCH$_2$), 0.79(3H, d, J = 6.5 Hz: δCH$_2$) |
| Trp$^7$ | 8.40(1H, d, J = 7.5 Hz) | 4.52-4.60(1H, m) | 3.13(1H, dd, J = 6.5, 15.0 Hz), 3.20(1H, dd, J = 5.5, 14.5 Hz) | 6.96(1H, dd, J = 7.0, 7.0 Hz: Ind5), 7.05(1H, dd, J = 7.0, 7.0 Hz: Ind6), 7.17(1H, s: Ind2), 7.32(1H, d, J = 8.0 Hz: Ind4), 7.46(1H, d, J = 7.5 Hz: Ind7), 10.88(1H, bs, IndNH) |
| 3,5-Bzl(CF$_3$)$_2$ | — | 5.11(1H, d, J = 13.5 Hz:), 5.21(1H, d, J = 13.5 Hz:) | — | 7.89(2H, s: PhH), 8.04(1H, s: PhH) |

TABLE 9.6

H-Tyr-D-Ala-Gly-Phe-Pro-Met-Leu-Trp-NH-3,5-Bzl(CF$_3$)$_2$•TFA (TY027); Only one isomer was found; $^1$H-NMR (DMSO-d$_6$) δ:

| AA | NH | α | β | misc. |
|---|---|---|---|---|
| Tyr$^1$ | 8.04(3H, bs) | 3.93-4.00(1H, m) | 2.80-2.92(2H, m) | 6.69(2H, d, J = 7.2 Hz: PhH), 7.01(2H, d, J = 7.2 Hz: PhH), 9.31(1H, bs: PhOH) |
| D-Ala$^2$ | 8.50(1H, d, J = 7.8 Hz) | 4.28-4.33(1H, m) | 1.04(3H, d, J = 6.6 Hz) | — |
| Gly$^3$ | 8.17(1H, t, J = 6.0 Hz) | 3.60(1H, dd, J = 5.4, 16.8 Hz), 3.69 (1H, dd, J = 5.4, 16.2 Hz) | — | — |
| Phe$^4$ | 7.93-8.00(1H, m) | 4.50-4.55(1H, m) | 2.72(1H, dd, J = 9.6, 13.8 Hz), 2.89-2.95(1H, m) | 7.13-7.28(5H, m: PhH) |
| Met$^5$ | 8.38(1H, d, J = 7.2 Hz) | 4.59(1H, dd, J = 7.8, 14.4 Hz) | 1.70-1.80(1H, m), 1.86-1.94(1H, m) | 2.42-2.47 (2H, m: γCH$_2$), 2.02(3H, s: δCH$_3$) |
| Pro$^5$ | — | 4.28-4.33(1H, m) | 1.63-1.68(1H, m), 1.85-1.92(1H, m) | 1.66-1.84(2H, m: γCH$_2$), 3.50-3.60(2H, m: δCH$_2$) |
| Leu$^6$ | 7.95-8.02(1H, m) | 4.21(1H, dd, J = 8.0, 15.0 Hz) | 1.38(2H, dd, J = 7.2, 7.2 Hz) | 1.53-1.61(1H, m: γCH$_2$), 0.76(3H, d, J = 6.6 Hz: δCH$_2$), 0.82(3H, d, J = 6.6 Hz: δCH$_2$) |
| Trp$^7$ | 7.92(1H, d, J = 7.8 Hz) | 4.50-4.55(1H, m) | 3.01(1H, dd, J = 7.8, 14.4 Hz), 3.13(1H, dd, J = 5.4, 14.4 Hz) | 6.94(1H, dd, J = 7.8, 7.8 Hz: Ind5), 7.04(1H, dd, J = 8.4, 8.4 Hz: Ind6), 7.08(1H, s: Ind2), 7.30(1H, d, J = 8.4 Hz: Ind4), 7.51(1H, d, J = 7.8 Hz: Ind7), 10.88(1H, bs, IndNH) |
| 3,5-Bzl(CF$_3$)$_2$ | 8.57(1H, t, J = 6.0 Hz) | 4.32(1H, dd, J = 5.4, 16.2 Hz), 4.44(1H, d, J = 6.6, 15.6 Hz) | — | 7.88(2H, s: PhH), 7.94(1H, s: PhH) |

TABLE 9.7

H-Tyr-D-Ala-Gly-Phe-Pro-Met-Leu-Trp-NH-Bzl•TFA (TY025); Only one isomer was found; $^1$H-NMR (DMSO-d$_6$) δ:

| AA | NH | α | β | misc. |
|---|---|---|---|---|
| Tyr$^1$ | 8.03(3H, bs) | 3.93-4.02(1H, m) | 2.85(1H, dd, J = 7.5, 14.0 Hz), 2.89(1H, dd, J = 7.0, 14.0 Hz) | 6.70(2H, d, J = 7.0 Hz: PhH), 7.02(2H, d, J = 8.5 Hz: PhH), 9.31(1H, bs: PhOH) |
| D-Ala$^2$ | 8.55(1H, d, J = 7.5 Hz) | 4.33(1H, dd, J = 6.5, 6.5 Hz) | 1.06(3H, d, J = 6.0 Hz) | — |
| Gly$^3$ | 8.19(1H, t, J = 6.0 Hz) | 3.62(1H, dd, J = 6.0, 17.0 Hz), 3.70(1H, dd, J = 6.0, 16.5 Hz) | — | — |
| Phe$^4$ | 7.97(1H, dd, J = 7.5 Hz) | 4.56(1H, dd, J = 7.0, 14.0 Hz) | 2.74(1H, dd, J = 9.5, 13.5 Hz), 2.95(1H, dd, J = 5.5, 15.0 Hz) | 7.05-7.28(5H, m) |
| Met$^5$ | 8.41(1H, d, J = 7.5 Hz) | 4.61(1H, dd, J = 7.0, 14.5 Hz) | 1.75-1.82(1H, m), 1.89-1.97(1H, m) | 2.45-2.52(2H, m: γCH$_2$), 2.02(3H, s: δCH$_3$) |

TABLE 9.7-continued

H-Tyr-D-Ala-Gly-Phe-Pro-Met-Leu-Trp-NH-Bzl•TFA (TY025);
Only one isomer was found; $^1$H-NMR (DMSO-$d_6$) δ:

| AA | NH | α | β | misc. |
|---|---|---|---|---|
| Pro[5] | — | 4.33(1H, dd, J = 6.5, 6.5 Hz) | 1.70-1.80(2H, m) | 1.82-1.88(1H, m: γCH$_2$), 1.90-1.99(1H, m: γCH$_2$), 3.49-3.55(1H, m: δCH$_2$), 3.55-3.62(1H, m: δCH$_2$) |
| Leu[6] | 8.01(1H, d, J = 7.5 Hz) | 4.19-4.25(1H, m) | 1.41(2H, dd, J = 7.0, 7.0 Hz) | 1.55-1.64(1H, m: γCH$_2$), 0.80(3H, d, J = 6.5 Hz: δCH$_2$), 0.86(3H, d, J = 6.5 Hz: δCH$_2$) |
| Trp[7] | 7.83(1H, dd, J = 8.0 Hz) | 4.56(1H, dd, J = 7.0, 14.0 Hz) | 3.02(1H, dd, J = 7.5, 15.0 Hz), 3.15(1H, dd, J = 6.0, 14.5 Hz) | 6.97(1H, dd, J = 7.5, 7.5 Hz: Ind5), 7.03-7.08(1H, m: Ind6), 7.09(1H, s: Ind2), 7.34(1H, d, J = 8.0 Hz: Ind4), 7.55(1H, d, J = 8.0 Hz: Ind7), 10.88(1H, bs, IndNH) |
| Bzl | 8.33(1H, t, J = 6.0 Hz) | 4.18-4.30(2H, m) | — | 7.05-7.28(5H, m) |

Sequential assignment of proton resonances was achieved by 2D-TOCSY NMR experiments. High-resolution MS were taken in the positive ion mode using ESI methods at the University of Arizona Mass Spectrometry Facility. TLC was performed on aluminum sheets coated with a 0.2 mm layer of silica gel 60 F$_{254}$ Merck using the following solvent systems: (1) CHCl$_3$:MeOH:AcOH=90:10:3; (2) EtOAc:n-BuOH:water:AcOH=5:3:1:1; and (3) n-BuOH:water:AcOH=4:1:1. TLC chromatograms were visualized by UV light and by ninhydrin spray followed by heating (hot plate). Analytical HPLC was performed on a Hewlett Packard 1100 or Hewlett Packard 1090m with Waters NOVA-Pak C-18 column (3.9× 150 mm, 5 μm, 60 Å) or Vydac 218TP104 C-18 column (4.6×250 mm, 10 μm, 300 Å). $^1$H-1D-NMR spectra were obtained on Bruker DRX-500 or DRX-600 spectrometer. 2D-TOCSY NMR spectra were performed on a Bruker DRX-600 spectrometer equipped with a 5 mm Nalorac triple-resonance single-axis gradient probe. The NMR experiments were conducted in DMSO-$d_6$ solution at 298K. Spectra were referenced to residual solvent protons as 2.49 ppm. The processing of NMR data was performed with the XwinNmr software (Bruker BioSpin, Fremont, Calif.). In the TOCSY experiments, the TPPI mode with MLEV-17 Mixing Sequence were used with a mixing time of 62.2 ms, at a spin-lock field of 8.33 kHz. TOCSY spectra were acquired with 2 k complex pairs in t$_2$ and 750 or 1024 FIDs using a 90'-shifted sine-squared window function in both dimensions.

Example 10.2

NMR Spectroscopy in DPC amphipathic media. (Ying, *Biochemistry*, 2003, 42, 2825-2835; Jacobsen, *Biochemistry*, 1996, 35, 3402-3417). All NMR spectra were recorded on a Bruker DRX600 600 MHz spectrometer with 5 mm Nalorac triple-resonance single-axis gradient probe. The compound concentration for the NMR experiments varied from 3 to 4 mM. The samples were prepared by dissolving the compound in 0.5 mL of 45 mM sodium acetate-$d_3$ buffer (pH 4.5) containing 40 equivalents of dodecylphosphocholine-$d_{38}$ and 1 mM sodium azide (90% H$_2$O/10% D$_2$O) followed by sonication for 5 min. Two-dimensional double quantum filtered correlation (DQF-COSY), nuclear Overhauser effect (Kumar, *Biochem. Biophys. Res. Commun.*, 1980, 95(1), 1-6) (NOESY), and total correlation spectra (Davis, *J. Am. Chem. Soc. J. Am. Chem. Soc.* 1985, 107, 2820-2821) (TOCSY) were acquired using standard pulse sequences and processed using XwinNmr and Felix 2000 (Accelrys Inc, San Diego, Calif.). The mixing time for NOESY spectra was 450 ms. All 2D spectra were acquired in the TPPI mode with 2 k or 1 k complex data points in t$_2$ and 750 real data points in t$_1$, and the spectral processing using shifted sine bell window functions in both dimensions. For suppressing the H$_2$O signal, the 3-9-19 WATERGATE pulse sequence was used. Experiments were conducted at 310 K, and referenced to the H$_2$O shift (4.631 ppm). Coupling constants ($^3J_{NH-H\alpha}$) were measured from 2D DQF-COSY spectra by analysis of the fingerprint region. The matrix rows of each of the upper and lower halves of a cross-peak were summed to give an antiphase 1D spectrum, which was fitted using a 5-parameter Levenberg-Marquardt nonlinear least-squares protocol (Press, *Numerical Recipes in C. The Art of Scientific Computing*, Cambridge University Press, New York, 1988) to a general antiphase doublet. The analysis yielded two independent determinations of the J coupling and line width for each cross-peak, one from the upper half and one from the lower half, and the one with better fitted curve was used for structure calculations. Cross-peak volumes for determination of distance restraints were measured using the Felix 2000 software. In the radical experiment using Mn$^{2+}$, a stock solution of 5 mM MnCl$_2$ was prepared and added to the sample to achieve a total concentration of 200 μM in Mn$^{2+}$. The DPC micelles with 5-DOXYL stearic acid were prepared as the same procedure with about 1 mg mL$^{-1}$ of 5-DOXYL stearic acid but sonicating for 30 min.

Example 10.3

Conformational Structure Determination. The methods used for structure calculations have been described previously (Ying, *Biochemistry*, 2003, 42, 2825-2835; Jacobsen, *Biochemistry*, 1996, 35, 3402-3417). The volumes of the assigned cross-peaks in the 2D NOESY spectrum were converted into upper distance bounds of 3.0, 3.8, 4.8, or 5.8 Å. For overlapping cross-peaks, the distance categories was increased by one or two levels, depending on the qualitative estimate of the extent of overlap. Pseudoatoms were created for nonstereospecifically assigned methylene protons with a correction of 1.0 Å applied to their upper bound distances (Wüthrich, *J. Mol. Biol.*, 1983, 169, 949-96). In addition to the distance constraints, φ dihedral angle constraints derived from $^3J_{HN-H\alpha}$ coupling constants were set to between −90 and 40° for $^3J_{HN-H\alpha}$<6 Hz and to between −150 and −90° for $^3J_{HN-H\alpha}$>8 Hz. Dihedral angle constraints of 180°±5° for compound bonds (ω) were also used to maintain the planarity of these bonds.

Simulated annealing molecular dynamics analysis was done for all the compounds to obtain an ensemble of NMR structures using the NOE-derived distance constraints and dihedral angle (φ) constraints using the DGII (Havel, *Prog. Biophys. Mol. Biol.* 1991, 56, 43-78) program within the software package Insight II 2000 (Accelrys Inc., San Diego, Calif.). Solvent was not explicitly included in the calculations. All the embedded structures successfully passed the simulated annealing step and were minimized using the consistent valency force field (CVFF) (Accelrys Inc.). The 50 structures with the lowest penalty function were further refined by two rounds of restrained molecular dynamics (rMD) using the all-atom AMBER force field with additional parameters for fluorine atom, (Weiner, *Am. Chem. Soc.* 1984, 106, 765-784; Weiner, *J. Comput. Chem.* 1986, 7, 230-252; Gough, *J. Comp. Chem.*, 1992, 13(8), 963-970) using the standalone DISCOVER ver. 2.98 program (Accelrys Inc.). A 12.0 Å cutoff for nonbonded interactions and a distance-dependent dielectric constant (4r) were used. All amide bonds were constrained to trans conformation by a 100 kcal mol$^{-1}$ rad$^{-2}$ energy penalty. The distance constraints and dihedral angles (φ) constraints were applied with a force constant of 25 kcal mol$^{-1}$ Å$^{-2}$ and 100 kcal mol$^{-1}$ rad$^{-2}$ were applied, respectively. After 100 steps of steepest descents minimization and 1000 steps of conjugate gradient minimization on the initial structures, an rMD equilibration at 500 K was performed for 1.5 ps, during which a scale factor of 0.1 was applied to the experimental restraint force constants. During the next 2 ps, full values of the experimental restraint force constants were applied. A further 1 ps rMD simulation was run at 500 K, and the system was then cooled to 0 K over 3 ps. After another 1 ps at 0 K, 100 cycles of steepest descents and 2000 steps of conjugate gradient minimization were performed. The final 20 structures with the lowest energies were used for the analysis. All calculations were performed on a Silicon Graphics Octane computer.

Example 10.4

Fluorescence emission spectra. The Fluorescence spectra were recorded on a Cary Eclipse fluorescence spectrometer (Varian, Darmstadt, Germany). Emission spectra were obtained by excitation at 290 nm and recorded in the wavelength range of 310-420 nm with continuous stirring at 25° C. A scan step was 1 nm and scan speed was 120 nm min$^{-1}$. Excitation and emission bandwidths were set at 5 and 10 nm, respectively. The compound concentration was 500 μM in HEPES buffer (10 mM HEPES, 150 mM NaCl, 1 mN NaN$_3$, 0.1 mM EDTA, pH=7.40) with 40-fold DPC or standard solution (EtOH:HEPES buffer=1:1).[31] At least two scans were accumulated and averaged for each spectrum.

Example 10.5

Solubility. HEPES buffer (0.05 M HEPES buffer in 0.1 M NaCl, pH 7.4, 500 μL) was added to 1 mg of compound. The sample was vortexed for 30 sec, sonicated for 5 min, shaken at r.t. for 2 h, and then allowed to be stayed overnight to equilibration. The sample was filtrated with an Acrodisc Syringe Filter (13 mm, 0.45 μm pore, PTFE membrane, Pall Life Sciences, East Hills, N.Y.). The compound concentration of the obtained filtrate was analyzed by HPLC (30-70% of acetonitrile containing 0.1% TFA within 20 min and up to 95% within additional 5 min, 1 mL/min, 230 nm, Vydac 218TP104 C-18 column).

Discussion

1. Secondary Structure Analysis Based on Assigned $^1$H NMR.

Two-dimensional NMR studies including TOCSY, DQF-COSY and NOESY in pH 4.5 buffer (45 mM CD$_3$CO$_2$Na/HCl, 1 mM NaN$_3$, 90% H$_2$O/10% D$_2$O) with 40-fold perdeuterated DPC micelles were performed on all three bifunctional compound derivatives TY005, 027, and 025. At concentrations above the critical micelle point, DPC forms micelles with an aggregate number of 50 to 90, corresponding to one or two compound molecules per micelle.

Figure 38A:
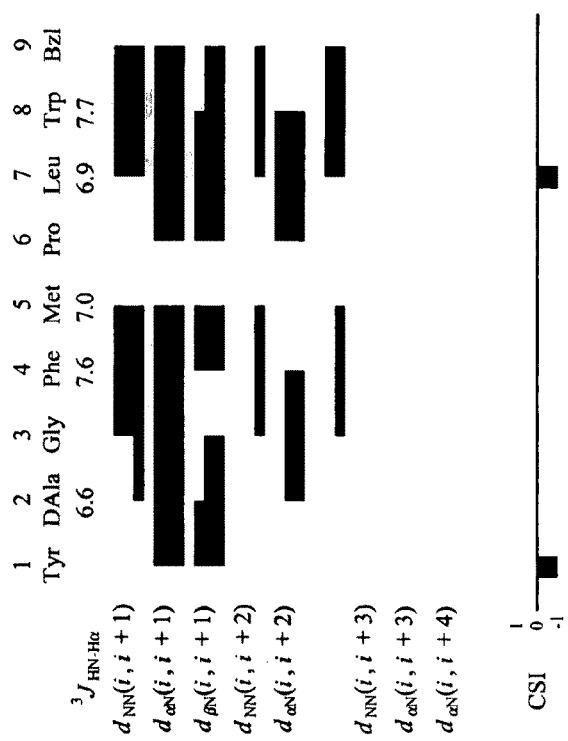
FIG. 38 A-D. Diagram of $H^N$-$H^\alpha$ coupling constants, NOE connectivities, and $H^\alpha$ chemical shift index (CSI) for (A) TY005, (B) TY027 and (C) TY025. The $H^\alpha$ CSI (36) was calculated using the random-coil values reported by Andersen et al. (37). The residual interresidue NOE distance restraints of TY005 (left), TY027 (middle) and TY025 (right) (D). Each column shows the sequential (i, i+1; open), medium-range (i, i+2-4; hatched) and long-range restraints (i, i+>4; filled), respectively. The residue Bzl or 9 stands for the respective C-terminal moieties.
Figure 38B:
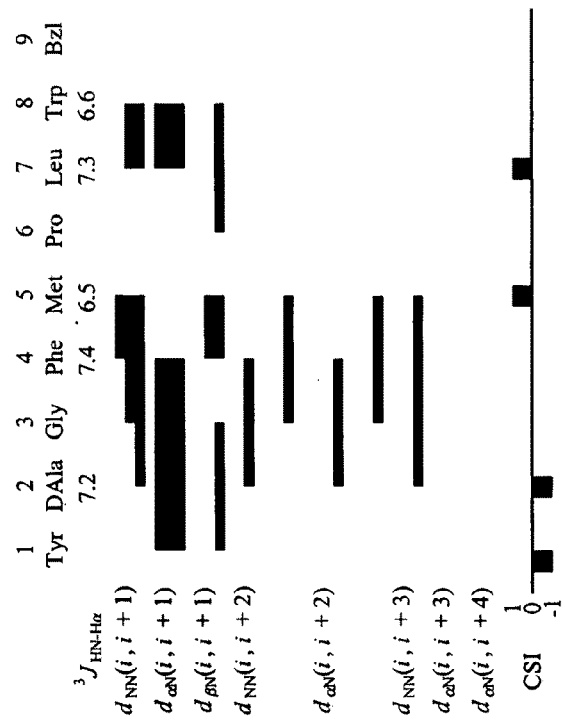
Figure 38C:
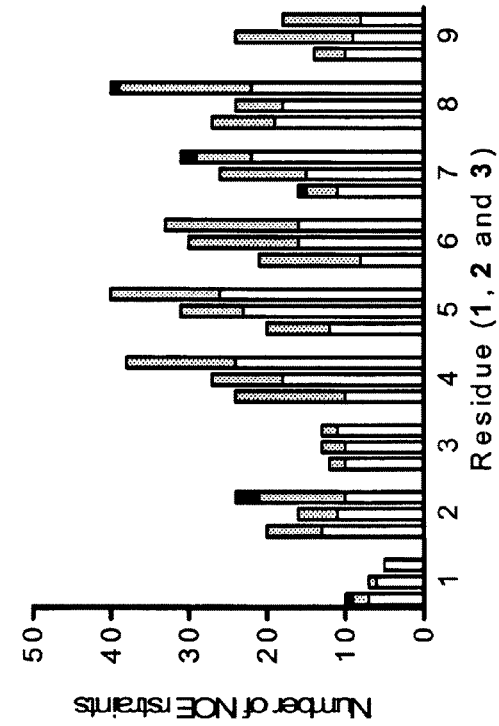

The interresidual NOE connectivities and the $^3J_{HN-H\alpha}$ coupling constants of all the compound derivatives are illustrated in FIG. 37 and FIGS. 42-45. The C-terminal benzyl moiety of TY027 and TY025 are represented as residue 9. The $^3J_{HN-H\alpha}$ coupling constants for all residues in all the three compound derivatives were within the range of 6-8 Hz except for Leu in TY025. This is most likely due to conformational averaging of the compounds in solution. The observed NOE patterns, including d$_{NN}$(i, i+1), d$_{\alpha N}$(i, i+1) and some medium-range (i, i+2 or 3) connectivities, suggest the possibility of β-turn structures around residues 1-4 in all three compound derivatives as well as around residues 5-8 in TY027. A few longer-range d$_{\alpha N}$(i, i+3) and d$_{\alpha N}$(i, i+4) connectivities found in TY025 indicate the existence of a helical structure in this molecule, consistent with its H$^\alpha$ CSI pattern (FIG. 38C). NMR structure of TY004, TY005, TY025, and TY027 is presented on FIG. 17.

2. Structural Calculations.

Figure 38D:
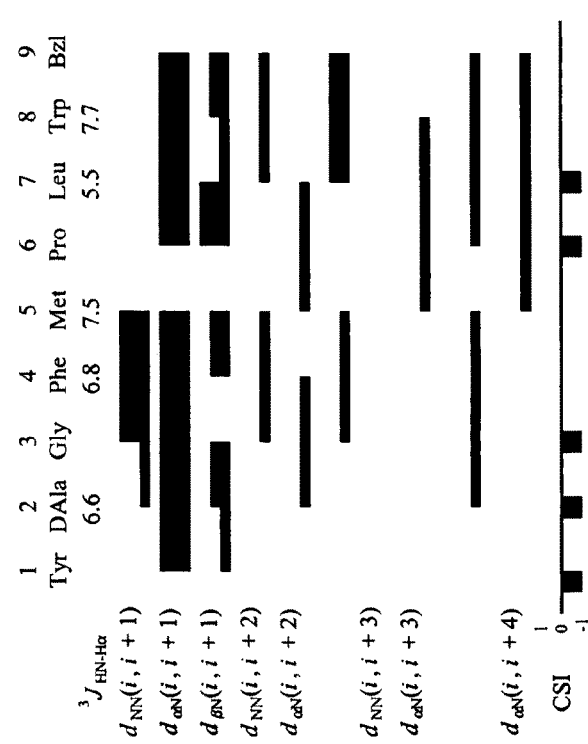

A total of 136, 155 and 184 non-redundant NOE restraints were used for TY005, TY027 and TY025, respectively, based on the NOESY cross-peak volumes including sequential (50, 63 and 72, respectively), medium-range (2-4 residues; 31, 36, and 46, respectively) and long-range (1, 0 and 3, respectively) restraints. The distribution of these restraints along the compound chain is shown in FIG. 38D. Only one dihedral angle restraint was used: the Leu φ angle in TY025. The total numbers of restraints were 136, 155 and 185, respectively (15.1, 17.2 and 20.4 per residue). The large numbers of NOEs per residue for non-cyclic compounds suggest that the compound derivatives exist in well-defined conformations in the DPC micelles. The 20 structures with the lowest total energies after rMD refinement were used to represent the structure of the compound derivatives in DPC micelles. Statistics for these 20 structures are shown in Table 10.

TABLE 10

Structural statistics.

| Compound | TY005 | | TY027 | | TY025 | |
|---|---|---|---|---|---|---|
| | final 20 structs | most stable structure | final 20 structs | most stable structure | final 20 structs | most stable structure |
| rmsd from NOE dist restraints (Å)[a] | 0.025 ± 0.004 | 0.028 | 0.027 ± 0.004 | 0.016 | 0.016 ± 0.001 | 0.016 |
| rmsd from backbone φ angle restraints (deg)[b] | —[c] | —[c] | —[c] | —[c] | 0.0 ± 0.0 | 0.0 |

TABLE 10-continued

Structural statistics.

| | | | | | | |
|---|---|---|---|---|---|---|
| NOE dist restraints violations | | | | | | |
| >0.01 Å | 13.9 ± 2.5 | 11 | 14.6 ± 1.5 | 14 | 14.2 ± 1.1 | 15 |
| >0.1 Å | 2.5 ± 1.4 | 3 | 3.9 ± 1.2 | 3 | 1.0 ± 0.0 | 1 |
| max dist violations (Å) | 0.17 ± 0.04 | 0.22 | 0.16 ± 0.02 | 0.13 | 0.11 ± 0.00 | 0.12 |
| dihedral backbone angle violations | | | | | | |
| >0.1° | —[c] | —[c] | —[c] | —[c] | 0 ± 0 | 0 |
| >1° | —[c] | —[c] | —[c] | —[c] | 0 ± 0 | 0 |
| max dihdral violations (deg) | —[c] | —[c] | —[c] | —[c] | 0 ± 0 | 0 |
| rms deviation from ideal geometry[d] | | | | | | |
| bond length (Å)[e] | 0.0061 ± 0.0004 | 0.0063 | 0.0052 ± 0.0002 | 0.0052 | 0.0035 ± 0.00004 | 0.0035 |
| bond valence angles (deg)[f] | 2.14 ± 0.11 | 2.16 | 1.78 ± 0.05 | 1.72 | 1.25 ± 0.003 | 1.25 |
| out-of-plane angles (deg)[g] | 3.57 ± 0.63 | 3.25 | 2.73 ± 0.40 | 2.90 | 1.54 ± 0.09 | 1.45 |
| AMBER energies (kcal mol$^{-1}$) | | | 9.08 | | | |
| restraint[h] | 2.48 ± 0.67 | 2.78 | 2.95 ± 0.58 | 2.41 | 1.13 ± 0.07 | 1.20 |
| bond stretching | 2.07 ± 0.22 | 2.20 | 1.42 ± 0.08 | 1.40 | 1.68 ± 0.02 | 1.70 |
| bond angles | 19.28 ± 1.84 | 19.49 | 12.8 ± 0.8 | 11.89 | 14.28 ± 0.22 | 14.00 |
| dihedral angles | 12.24 ± 1.9 | 9.54 | 9.57 ± 1.61 | 7.99 | 14.52 ± 0.38 | 14.53 |
| planarity | 1.63 ± 1.11 | 1.15 | 0.74 ± 0.33 | 0.61 | 0.19 ± 0.03 | 0.17 |
| van der Waals[i] | −11.65 ± 3.1 | −12.61 | −12.23 ± 1.4 | −13.80 | −17.4 ± 0.75 | −18.41 |
| electrostatic[j] | −9.6 ± 0.91 | −9.93 | −11.5 ± 0.68 | −11.84 | −9.59 ± 0.41 | −9.82 |
| Total | 13.25 ± 2.12 | 9.08 | −0.01 ± 2.25 | −4.44 | 3.14 ± 0.78 | 1.61 |

| | atomic rmsd (Å): final 19 structures v.s. most stable structure | | | | | |
|---|---|---|---|---|---|---|
| | 1 | | 2 | | 3 | |
| x | backbone atoms (N, C$^a$, C') | all non-hydrogen | backbone atoms (N, C$^a$, C') | all non-hydrogen | backbone atoms (N, C$^a$, C') | all non-hydrogen atoms |
| Calculated on whole molecule | 1.80 ± 0.47 | 2.72 ± 0.92 | 1.14 ± 0.43 | 2.09 ± 0.64 | 0.19 ± 0.20 | 0.84 ± 0.28 |
| Calculated only on 1-4 res. | 1.11 ± 0.54 | 2.49 ± 1.12 | 1.05 ± 0.63 | 2.16 ± 0.98 | 0.14 ± 0.30 | 0.32 ± 0.66 |
| Calculated only on 5-8 res. and C-terminus | 0.75 ± 0.26 | 1.82 ± 0.90 | 0.45 ± 0.38 | 1.02 ± 0.25 | 0.04 ± 0.01 | 0.76 ± 0.42 |

[a]The total number of NOE restraints were 136 for TY005, 155 for TY027 and 184 for TY025, respectively.
[b]Two backbone φ angle restraints were applied only on TY025.
[c]no restraints used.
[d]Derived from the rMD calculations using the AMBER force field in DISCOVER.
[e]The number of bond length was 160 for TY005, 161 for TY027 and 155 for TY025, respectively.
[f]The number of bond valence angles was 285 for TY005, 287 for TY027 and 275 for TY025, respectively.
[g]The number of out-of-plane angles was 36 for TY005, 36 for TY027 and 37 for TY025, respectively.
[h]Calculated with force constants of 25 kcal mol$^{-1}$ Å$^{-2}$ and 100 kcal mol$^{-1}$ rad$^{-2}$ for the NOE distance and dihedral angle restraints, respectively.
[i]Calculated with the Lennard-Jones potential using the AMBER force field and a 12 Å cutoff.
[j]Calculated with a distance-dependent dielectric constant (ε = 4r).

The average restraint violation energies were low (2.48, 2.95 and 1.13 kcal mol$^{-1}$ for TY005, TY027 and TY025, respectively), with average maximum NOE distance violations of 0.17, 0.11 and 0.11 Å with no dihedral angle violations. The 19 structures were aligned with the most stable structure using all backbone atoms (FIG. 39A), only the backbone atoms of residues 1-4 (FIG. 38B) or 5-8 (FIG. 38C). The backbone rmsd's of the 19 structures with respect to the most stable structure were 1.80, 1.14 and 0.19 Å for TY005, TY027 and TY025, respectively, for all residues. The decrease in rmsd going from a flexible ester (TY005) to a more rigid amide (TY027) linkage at the C-terminus was expected, but the much larger decrease (to 0.19 Å) resulting from removal of two trifluoromethyl groups of TY027 was surprising. The rmsd values are significantly decreased if alignment is carried out only on the backbone atoms of residues 5-8 (TY005: 0.75; TY027: 0.45; TY025: 0.04), indicating that the C-terminal half is much better defined by the NMR restraints than the N-terminal half (residues 1-4). This may be due to greater flexibility in the N-terminal portion. In fact, the aligned images in FIG. 39B clearly show the poorly-defined N-terminal halves as well as the well-defined C-terminal halves in the backbone structures of TY005 and TY027.

In Met-Enkephalin (Tyr$^1$-Gly$^2$-Gly$^3$-Phe$^4$-Met$^5$-OH) (SEQ ID NO: 5) and Leu-Enkephalin (Tyr$^1$-Gly$^2$-Gly$^3$-Phe$^4$-Leu$^5$-OH) (SEQ ID NO: 4), which form the basis for the design of the N-terminal portion of compound sequence of TY005, TY025, and TY027, β-turn structure was often found between Tyr$^1$ $_{and\ Phe}$$^4$ by several methods including X-ray crystallography and NMR spectroscopy in environments which mimic the membrane bilayer. In the case of compound derivatives TY005 and TY027, however, a distance of less than 7 Å between the C$_\alpha$ of D-Ala$^2$ and the C$_\alpha$ of Met$^5$ was observed in 15 of the best 20 structures for TY005, and in all 20 structures for TY027, implying the existence of an alternative β-turn (Table 10). All 35 structures were classified as Type IV ("distorted") β-turn by their backbone dihedral angles. This shifted β-turn between D-Ala$^2$ and Met$^5$ was more frequently found in TY005 and TY027 5 of 20 structures of TY005 and 3 of 20 structures of TY027. A second β-turn structure was found from Pro$^6$ to the C-terminal benzyl moiety (residue 9) in which the distance between the C$_\alpha$(Pro$^6$) and the benzylic carbon (CH$_2$) of the C-terminus was less than 7 Å in 17 and 19 out of the best 20 structures for TY005 and TY027, respectively (Table 11).

TABLE 11

| Number | Tyr$^1$-Phe$^4$ | DAla$^2$-Met$^5$ | Gly$^3$-Pro$^6$ | Met$^5$-Trp$^8$ | Pro$^6$-Bzl$^9$ |
|---|---|---|---|---|---|
| TY005 | 5 | 15 | 0 | 0 | 17 |
| TY027 | 3 | 20 | 0 | 0 | 19 |
| TY025[a] | 0 | 2 | 20 | 20 | 18 |

[a]Out of the best 20 calculated structures.
[b]Helical structure was found, in which no β-turn structures should not be defined according to the original definition. Bzl stands for the cross-peaks derived from the corresponding aromatic protons of benzyl moiety (residue 9).

For compound derivative TY027, 6 of 19 turns found in TY027 were classified as Type I β-turns, and a hydrogen bond between the H$^N$ of residue 9 and the carbonyl oxygen atom in Pro$^6$ was observed in 9 of the 19 (Table 12).

TABLE 12

Observed hydrogen bonds[a]

| Molecule | No.[b] | Donor | Acceptor | Distance (Å)[c] | Angle (deg)[d] |
|---|---|---|---|---|---|
| TY005 | 14 | Leu$^7$ H$^N$ | Met$^5$ O | 1.91 ± 0.07 | 141.1 ± 6.0 |
|  | 9 | Bzl$^9$ H$^{Ne}$ | Pro$^6$ O | 2.16 ± 0.11 | 158.5 ± 1.9 |
| TY027 | 7 | Gly$^3$ H$^N$ | Tyr$^1$ O | 2.05 ± 0.11 | 137.8 ± 8.1 |
|  | 5 | Trp$^8$ H$^N$ | Met$^5$ O | 2.04 ± 0.02 | 132.3 ± 1.1 |
| TY025 |  |  | No hydrogen bond observed |  |  |

[a]The hydrogen bonds which were observed in more than five structures were listed.
[b]The number of structures of the final 20 for which the listed hydrogen bond is observed.
[c]The distance is the mean proton-oxygen distance (±SD) in the structures for which a hydrogen bond is observed.
[d]The angle is the mean N—H----O angle (±SD) in the structures for which a hydrogen bond is observed.
[e]Amide proton of C-terminal benzyl moiety.

The C-terminal ester (TY005) showed only distorted β-turns in this region, with no hydrogen bonds, consistent with the larger backbone rmsd observed for C-terminal half (0.75 Å vs 0.45 Å for TY027). These implied secondary structure elements were consistent with the observed NOE connectivities.

FIGS. 40A and 40B depicts the corresponding Ramachandran plots for TY005 and TY027, respectively. Positive φ angles were observed for Gly$^3$ (10 structures in TY005 and 3 structures in TY027), Phe$^4$ (3 structures in TY005), Met$^5$ (13 structures in TY005 and 20 structures in TY027) and Leu$^7$ (1 structures in TY005 and 6 structures in TY027) in the seven L-amino acids, and some of D-Ala$^2$ (3 structures in TY005 and 3 structures in TY027) have negative φ angles. Among them, D-Ala$^2$, Gly$^3$, Phe$^4$ and Leu$^7$ were assigned to the (i+1) or (i+2) positions of the found β-turn structures. It should be noted that Met$^5$ which is located between two β-turns have positive φ angles.

Figure 39C:
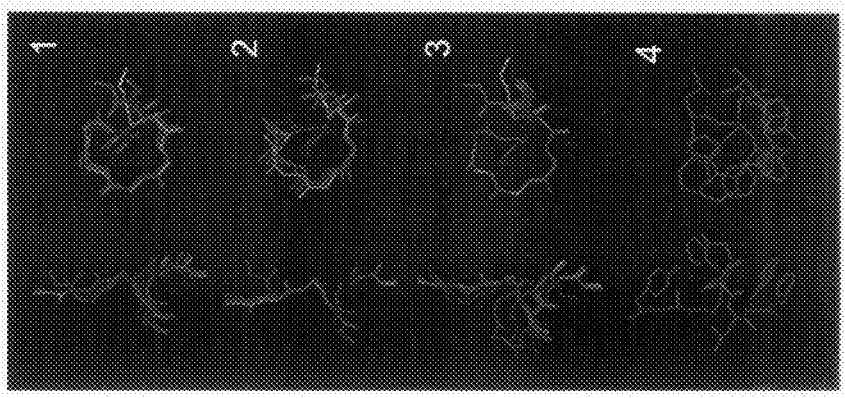
Figures 43D, 43E, 43F:
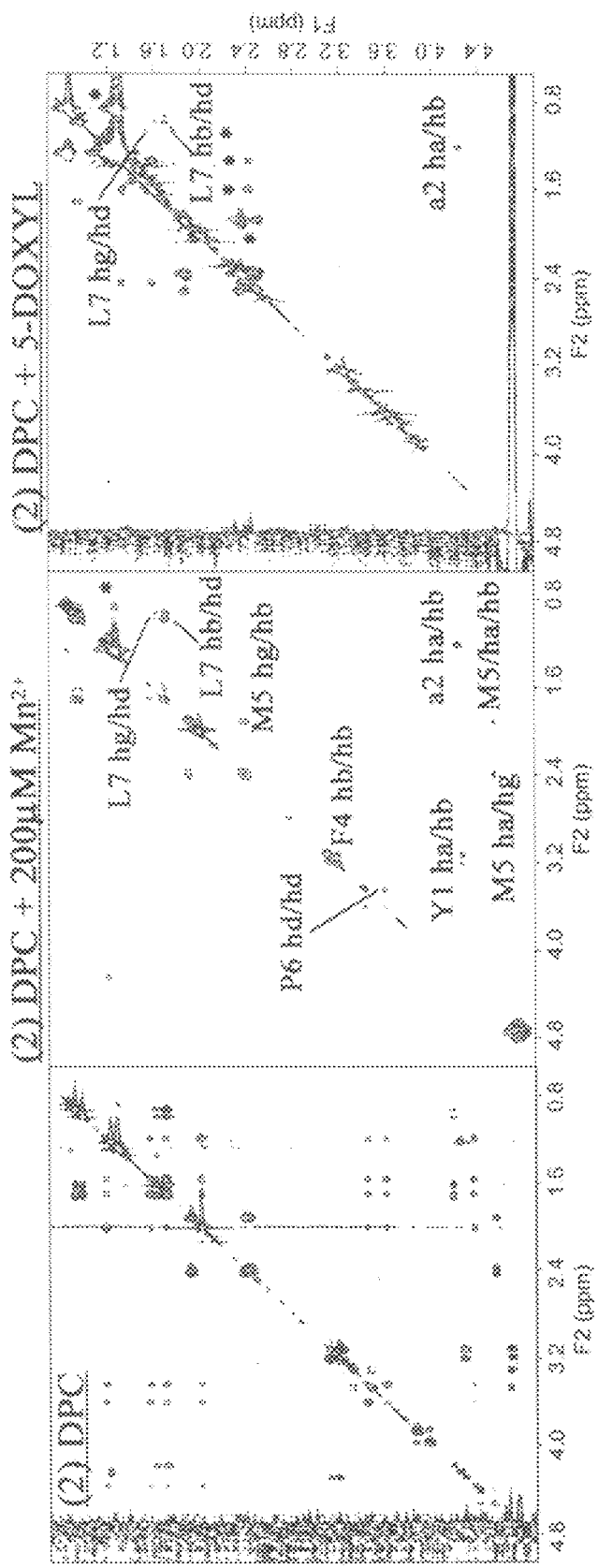
FIG. 43 A-I. Effect of Radicals on TOCSY Spectra. TY027 with DPC micelles (A, D, and G), with 200 μM Mn$^{2+}$ (B, E, and H) and 5-DOXYL stearic acid (C, F, and I). Preserved resonances (labeled) are in a phase not be missed by the phase-specific radical probe (Mn$^{2+}$ or DOXYL). X9 represents the cross-peaks derived from the corresponding aromatic protons of benzyl moiety. The resonances with asterisk (*) are DPC or 5-DOXYL derived ones. Spectra were compared from the same noise level.
Figures 44D, 44E, 44F:
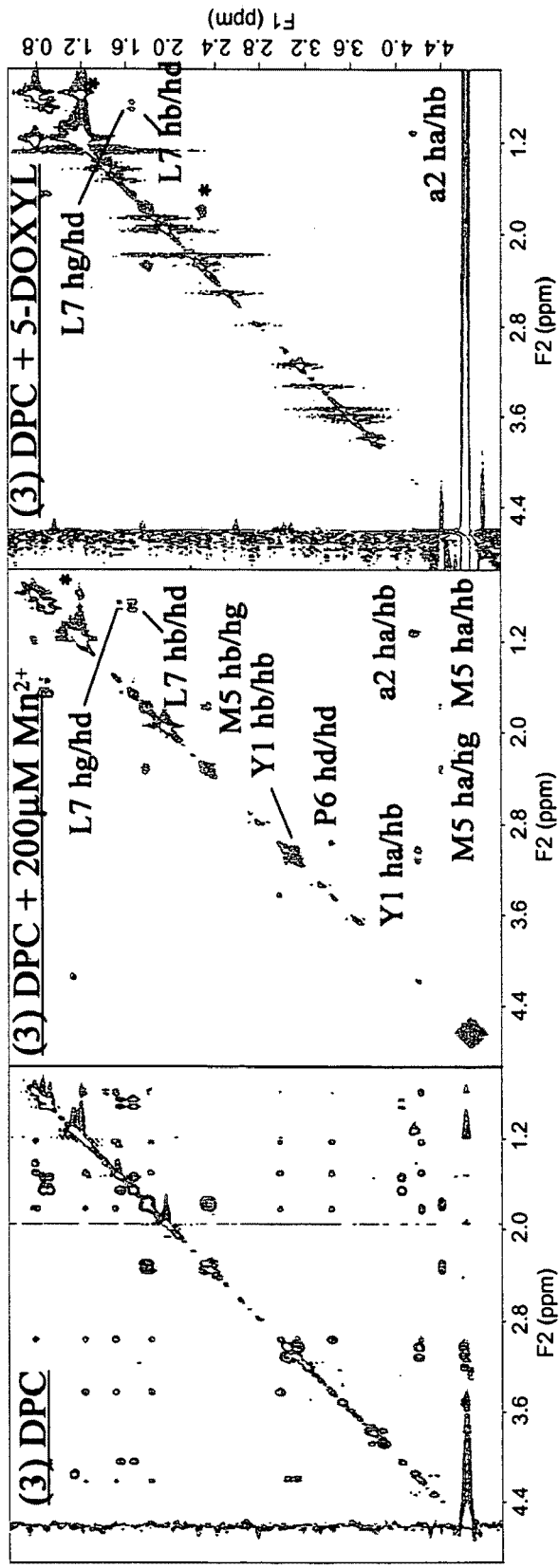
FIG. 44 A-I. Effect of Radicals on TOCSY Spectra. TY025 with DPC micelles(A, D, and G), with 200 μM Mn$^{2+}$ (B, E, and H) and 5-DOXYL stearic acid (C, F, and I). Preserved resonances (labeled) are in a phase not be affected by the phase-specific radical probe (Mn$^{2+}$ or DOXYL). X9 represents the cross-peaks derived from the corresponding aromatic protons of benzyl moiety. The resonances with asterisk (*) are DPC or 5-DOXYL derived ones. Spectra were compared from the same noise level.
Figure 45F:
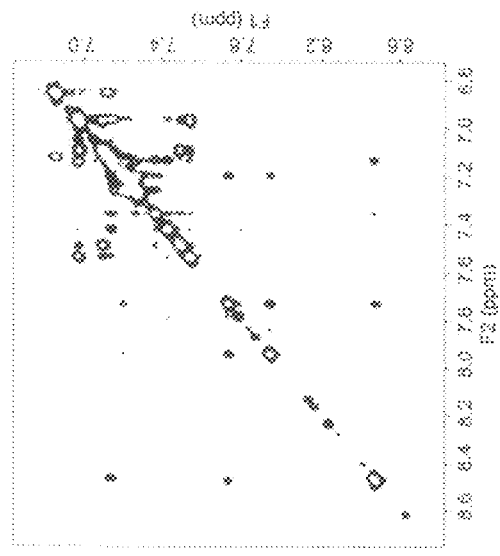
FIG. 45 A-F. Side-chain region (A, B, and C) and $H^N$-$H^N$ region (D, E, and F) of the NOESY spectrum of (A and D) TY005, (B and E) TY027 and (C and F) TY025 in DPC micelles.
Figure 45E:
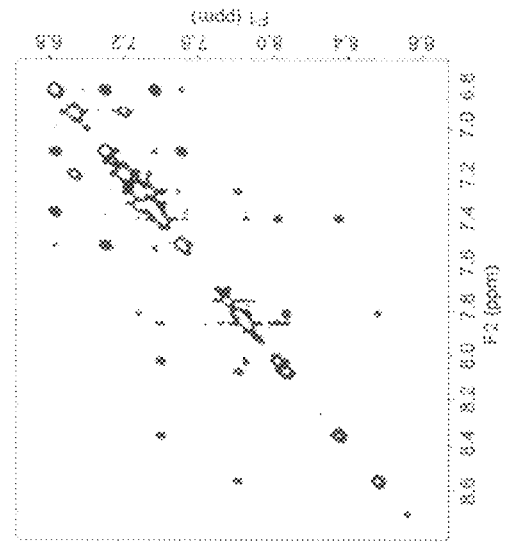
Figure 45D:
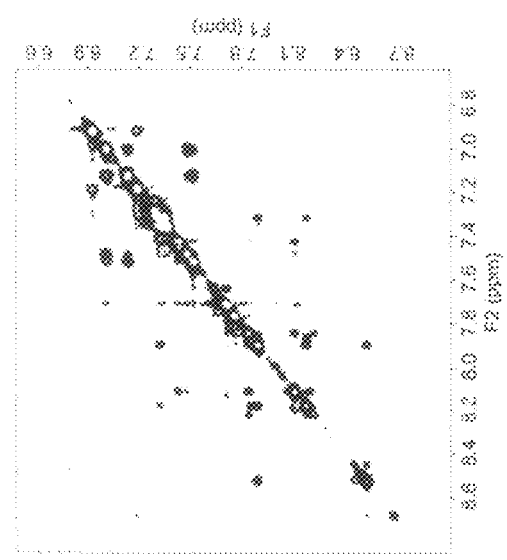

Comparing the tandem β-turn structures of TY005 and TY027, the compound with no trifluoromethyl groups in the C-terminus (TY025) showed different structural properties. First, the backbone of TY025 has a well-defined helical structure, consistent with the NOE connectivities and CSI values (FIG. 39). It is noteworthy that not only the C-terminal half of TY025, but also its N-terminus was found quite structured. This well-defined structure of TY025 was also confirmed by the Ramachandran plot and angular order parameters (FIG. 40). In the Ramachandran plot of TY025, only seven clear spots, corresponding to the respective residues 2-8, were found. Among them, only Gly$^3$ has positive (P angles in all of its 20 best structures. Both the φ and ψ angular order parameters of TY025 were close to 1 in all the residues, whereas TY005 and TY027 had smaller values in some residues.

It is important to note that structural modifications among TY005, TY027 and TY025 were made only in the C-terminal benzyl moiety. However, those rather small chemical modifications resulted in all the 3D and dynamic structural difference found in the NMR structures as well as in the activity differences for both opioid agonist and NK1 antagonist activities. Changing of structural rigidity related to C-terminal modifications s further illustrated on FIG. 18.

3. Fluorescence Study.

It is well known that the intrinsic fluorescence spectrum of tryptophan shifts to shorter wavelength ("blue shifted") as the polarity of the solvent surrounding the tryptophan residue decreases, and this blue shift is a good index to monitor the lipophilicity of the environment close to the tryptophan. The fluorescence of Trp$^8$ in TY005, TY027, and TY025 was measured with and without DPC micelles, in order to estimate the interaction between the compounds and membrane-like micelles. The fluorescence spectra in DPC micelles were compared to the spectra in the EtOH-buffer solution (EtOH: pH 7.4 HEPES buffer=1:1). The EtOH-buffer solution was chosen as the standard since the solubilities of the compound TY005, TY027, and TY025 in aqueous media were too low to run the experiment (Table 13).

TABLE 13

Solubility and lipophilicity of compound derivatives

|  | lipophilicity | | Solubility[c] |
|---|---|---|---|
| No | logD$_{7.4}$[a] | AlogP[b] | (μg/ml) |
| TY005 | >4.0 | 5.74 | <0.2 |
| TY027 | >4.0 | 5.45 | <0.2 |
| TY025 | 3.6 | 3.97 | 1.1 |

[a]Logarithm of octanol/saline distribution coefficient in 0.05 N HEPES buffer in 0.1 N NaCl solution.
[b]Calculated with ALOGPS 2.1 software. See ref. (Tetko, J. Comput. Aid. Mol. Des., 2005, 19, 453-63).
[c]solubility in 0.05 N HEPES buffer in 0.1 N NaCl solution.

The emission spectra were obtained by excitation at 290 nm to avoid the excitement of tyrosine residue. Obvious blue shifts of fluorescence spectra from the standard solution were observed in all of three compound derivatives (6 nm, TY005; 10 nm, TY027; 10 nm, TY025, respectively, FIG. 19). The results suggested that the Trp$^8$ at the C-terminal of the compounds were buried inside of the micelles, implying that the compounds have strong interactions with micelles at least in the C-terminus. Because poorly water-soluble compound TY005, TY027, and TY025 were easily dissolved at the millimolar concentration in the presence of micelles, strong interactions between the compound derivatives TY005, TY027, and TY025 and micelles were also suggested. Fluorescence blue shift of compounds in DCP micelle is illustrated on FIG. 19.

4. Paramagnetic Broadening Studies on $^1$H NMR.

To obtain further information about the location and orientation of the compound derivatives TY005, TY027, and TY025 in the DPC micelle, we used a nitroxyl spin-label, 5-doxylstearic acid, and Mn$^{2+}$ ions (MnCl$_2$) to induce selective broadening of NMR resonances close to the paramagnetic probes. The cross-peaks of protons exposed to an aqueous exterior are broadened or disappear due to the paramagnetic effect of Mn$^{2+}$, while cross-peaks of protons located inside the micelles and close to the phosphate groups of DPC are broadened by the free radical on the doxyl group, which is bound to carbon 5 of the stearic acid. The paramagnetic effects of these agents on the compound resonances were studied by comparing TOCSY spectra in the presence and absence of the paramagnetic agents, and all peaks were classified into three categories according to their sensitivities to the paramagnetic agents: missed by 5-DOXYL only (the proton is at or near the surface of micelles); missed by both $Mn^{2+}$ and 5-DOXYL (in the micelle, but not deeply buried) and preserved by either agent (deeply buried in the micelle) (FIG. 41-46). In fact, none of the $^1H$ resonances were missed by $Mn^{2+}$ only, indicating a strong association with the micelle for all three derivatives.

For all the compound derivatives TY005, TY027, and TY025, nearly all of the $H^N$ related cross-peaks were categorized as sensitive to both $Mn^{2+}$ and 5-DOXYL, implying that the compound backbones are located at or near the surface of micelles. On the other hand, most of the side-chain resonances were missed only by 5-DOXYL or were non-sensitive to either agent. Thus, generally, the backbones of TY005, TY027, and TY025 lie close to the surface with their side-chains buried in the micelle. However, there is one notable exception to this general observation: the $H^N$ resonances of $Met^5$ in TY005, TY027, and TY025 were affected only by 5-DOXYL, implying that the protons are not exposed to the surface of the micelles. Moreover, the side-chain cross-peaks of $Met^5$ in only TY005 were missed by either paramagnetic agent, indicating that $Met^5$ side-chains of TY005 were exposed to the surface of micelle, whereas those of TY027 and TY025 were sensitive only to 5-DOXYL, indicating a different orientation in the side-chain of $Met^5$ by the C-terminal linkage.

The sensitivity of side-chain protons to broadening by 5-DOXYL provides insight into their portioning in depth in the micelle. The cross-peaks of two different aromatic protons (para and ortho) in the C-terminal benzyl moiety were eliminated in TY005 and TY027 by 5-DOXYL, but the resonance of TY025 were preserved in spite of the hydrophobic trifluoromethyl group in TY005 and TY027. On the other hand, the cross-peaks of the aromatic protons of $Trp^8$ were unaffected in TY005, but were sensitive to 5-DOXYL for TY027 and TY025. Therefore, the C-terminal benzyl moiety (TY005 and TY027) and $Trp^8$ (TY027 and TY025) appear to locate close to the phosphate moiety of DPC micelles, but the $Trp^8$ of TY005 and the C-terminus of TY025 were rather deeply buried into the micelles. It is interesting that the structural modifications only at the C-terminus give rise to the different position of the compounds in amphipathic media, together with the different structural properties and variant biological activities at the membrane-bound GPCRs.

Example 11

Biological Activity

Example 11.1-11.6

Biological assays were carried out as in Examples 4.1-4.6.

Example 11.7

Octanol/saline distribution ($logD_{7.4}$) (Yamamoto, 2007, *J. Med. Chem.*, submitted). HEPES buffer (0.05 M HEPES buffer in 0.1 M NaCl, pH 7.4, 500 µL) was added to 2 mg of compound and mixed with 500 µL of 1-octanol. The sample was shaken at r.t. for 12 h to allow equilibrating. The sample was centrifuged at 6500 rpm in a VanGuard V6500 (GlaxoSmithKline, Research Triangle Park, N.C.) for 15 min. The layers were separated and each layer was centrifuged once again. The compound concentrations in the obtained layers were analyzed by HPLC (30-70% of acetonitrile containing 0.1% TFA within 20 min and up to 95% within additional 5 min, 1 mL/min, 230 nm, Vydac 218TP104 C-18 column). The logarithm of 1-octanol/saline distribution ($logD_{7.4}$) was calculated as the ratio of compound concentration in the 1-octanol and saline phases.

Discussion.

The rNK1 binding affinities were evaluated by competition analysis using [$^3H$]-Substance P label membranes from CHO cells that stably express the rNK1 receptors (Table 1). Compared to the subnanomolar-level affinities of C-terminal ester derivative TY005 ($K_i$=0.29 nM), the C-terminal amide derivative TY027 was 25 times less potent, but still could bind at nanomolar level for the rNK1 receptor ($K_i$=7.3 nM). The bind affinity at the rNK1 of TY025, which had no trifluoromethyl groups in the C-terminal benzyl moiety, was drastically decreased to a $K_i$=700 nM. However, in the functional assay using the guinea pig ileum (GPI) to examine their antagonist activities, the Ke value of TY025 (10 nM) was similar to that of TY27 (9.9 nM) and better than that of TY005 (25 nM) (Table 14).

TABLE 14

Opioid agonist functional activities in [$^{35}S$]GTPΓS binding assays

| | hDOR[a] | | | rMOR[a] | | |
|---|---|---|---|---|---|---|
| No | LogEC$_{50}$[b] | EC$_{50}$ (nM)[c] | Emax (%)[d] | LogEC$_{50}$[b] | EC$_{50}$ (nM)[c] | Emax (%)[d] |
| TY005 | −8.5 ± 0.21 | 2.9 | 48 | −7.5 ± 0.09 | 32 | 46 |
| TY027 | −8.1 ± 0.11 | 8.6 | 58 | −8.2 ± 0.17 | 7.0 | 55 |
| TY025 | −8.6 ± 0.13 | 2.6 | 52 | −7.7 ± 0.18 | 21 | 47 |
| Biphalin | −9.0 ± 0.17 | 1.1 | 83 | | | |
| DPDPE | −8.8 ± 0.25 | 1.6 | 69 | | | |
| DAMGO | | | | −7.4 ± 0.19 | 37 | 150 |

[a]Expressed from HN9.10 cell.
[b]Logarithmic values determined from the non-linear regression analysis of data collected from at least 2 dependent experiments performed in duplicate.
[c]Anti-logarithmic value of the respective EC50.
[d]Net total bound/basal binding × 100

This inconsistency can be explained with the known species difference between rat and guinea pig NK1 receptors (Datar, *Curr. Top Med. Chem.* 2004, 4, 75-103). It is well known that the human NK1 receptor has higher homology to the guinea pig NK1 receptor rather than the rat or mouse NK1, and some NK1 antagonists have a large species difference (Datar, *Curr. Top Med. Chem.* 2004, 4, 75-103; Lazaridis, *J. Phys. Chem. B* 2005, 109, 15098-15106). In fact, TY025 showed a 220 times better $K_i$ value at the hNK1 receptor (3.20 nM) compared to the value at the rNK1 receptor. A smaller species difference was found in TY005 whose $K_i$ value for hNK1 was 0.084 nM (3.4-fold species difference). Surprisingly, TY027, which is the C-terminal benzyl amide with two trifluoromethyl groups, showed the largest difference between the affinities at the rNK1 and at the hNK1 (1100-fold), and $K_i$ value for the hNK1 receptor was 6.5 pM. Therefore, substitution of the C-terminal ester for an amide gives rise to increased species difference at the human and rat NK1 receptors, and the existence of two trifluoromethyl groups at the C-terminus plays on important role in the affinities for both rNK1 and hNK1 receptors.

The opioid binding affinities of these compounds for the human δ opioid receptor (hDOR) or the rat μ opioid receptor (rMOR) were determined by radioligand competition assay using [$^3$H]-c[D-Pen$^2$,D-Pen$^5$]enkephalin (DPDPE) to label the δ opioid receptor and [$^3$H]-[D-Ala$^2$,NMePhe$^4$,Gly$^5$-ol] enkephalin (DAMGO) to label the μ opioid receptor in cell membrane preparations from transfected cells that stably express the respective receptor type (Table 15).

TY027 showed the potent activity for the MVD assay with the best o selectivity ($IC_{50}$=15 nM in MVD and 490 nM in GPI). The $IC_{50}$ value of TY025 in GPI assay ($IC_{50}$=61 nM) had large increase from those of TY005 and TY027 with the best $IC_{50}$ value in the MVD assay (4.8 nM). Therefore, TY025 was found to be a bifunctional compound derivative possessing potent agonist activities for both δ and μ opioid receptors together with a nanomolar level hNK1 antagonist activity, but its antagonist activity at the rNK1 receptor might be low. On the other hand, TY027 was characterized as a very potent hNK1 antagonist with potent and o selective opioid agonist activities, which also has nanomolar level affinity at the rNK1 receptor. Though both of TY027 and TY025 have different biological profiles, they are expected to be potent analgesics for pain control.

TABLE 15

Binding affinities of bifunctional compounds at δ/μ opioid receptors and NK1 receptors

| no | hDOR[a], [$^3$H]DPDPE[b] | | rMOR[a], [$^3$H]DAMGO[c] | | $K_i$(μ)/ $K_i$(δ) | hNK1[d], [$^3$H]Substance P[e] | | rNK1[d], [$^3$H]Substance P[f] | | $K_i$(hNK1)/ $K_i$(rN |
|---|---|---|---|---|---|---|---|---|---|---|
| | $LogIC_{50}$[g] | $K_i$ (nM) | $LogIC_{50}$[g] | $K_i$ (nM) | | $LogIC_{50}$[g] | $K_i$ (nM) | $LogIC_{50}$[g] | $K_i$ (nM) | |
| TY005 | −8.2 ± 0.06 | 2.8 | −7.1 ± 0.11 | 36 | 13 | −9.9 ± 0.25 | 0.084 | −9.0 ± 0.10 | 0.29 | 3.4 |
| TY027 | −8.8 ± 0.07 | 0.66 | −7.4 ± 0.05 | 16 | 24 | −10.9 ± 0.10 | 0.0065 | −7.6 ± 0.05 | 7.3 | 1100 |
| TY025 | −9.1 ± 0.09 | 0.44 | −8.4 ± 0.03 | 1.8 | 4.1 | −8.4 ± 0.42 | 3.20 | −5.6 ± 0.06 | 700 | 220 |
| Biphalin[h] | | 2.6 | | 1.4 | 0.54 | | | | | |
| L-732, 138 | | | | | | −8.8 +/− 0.02 | 0.73 | −6.4 ± 0.12 | 130 | 180 |

[a]Competition analyses were carried out using membrane preparations from transfected HN9.10 cells that constitutively expressed the δ and μ opioid receptors, respectively.
[b]$K_d$ = 0.45 ± 0.1 nM.
[c]$K_d$ = 0.50 ± 0.1 nM.
[d]Competition analyses were carried out using membrane preparations from transfected CHO cells that constitutively expressed rat or human NK1 receptors.
[e]$K_d$ = 0.16 ± 0.03 nM
[f]$K_d$ = 0.40 ± 0.17 nM
[g]Logarithmic values determined from the non-linear regression analysis of data collected from at least 2 independent experiments performed in duplicate.
[h]reference (Lipkowski, J. Bioorg. Med. Chem. Lett. 1999, 9(18), 2763-6).

TY027 has four-fold higher affinity at the DOR ($K_i$=0.66 nM) and two times more potent $K_i$ value at the MOR (16 nM) than those for TY005. The elimination of two trifluoromethyl groups led to further increased affinity at both the DOR ($K_i$=0.44 nM) and the MOR ($K_i$=1.8 nM) with 4.1-fold δ selectivity. It is interesting that the small modification at C-terminus, which is far from the opioid agonist pharmacophore, can influence the opioid activities so much. The binding affinity results correlated well with the ones from the GTPγS binding assay and the functional assays using GPI and MVD tissues (Table 13 and 16).

TABLE 16

Functional assay result for bifunctional compound ligands at opioid and Substance P receptors

| No | Opioid agonist | | Substance P GPI antagonist, Ke (nM)[b] |
|---|---|---|---|
| | MVD (δ), $IC_{50}$ (nM)[a] | GPI (μ), $IC_{50}$ (nM)[a] | |
| TY005 | 22 ± 1.2 | 360 ± 130 | 25 ± 8.8 |
| TY027 | 15 ± 2.0 | 490 ± 29 | 10 ± 2.1 |
| TY025 | 4.8 ± 0.35 | 61 ± 9.6 | 9.9 ± 2.8 |
| Biphalin | 2.7 ± 1.5 | 8.8 ± 0.3 | |
| L-732, 138 | | | 250 ± 87 |

[a]Concentration at 50% inhibition of muscle concentration at electrically stimulated isolated tissues.
[b]Inhibitory activity against the Substance P induced muscle contraction in the presence of 1 μM naloxone, Ke: concentration of antagonist needed to inhibit Substance P to half its activity.

It should be noted that the small chemical modification at the C-terminal lead to largely increased affinities for both the δ and μ opioid receptors as well as in the NK1 receptor. Since the C-terminus is away from the opioid agonist pharmacophore which is located in N-terminal half of the compound derivatives, the difference in the opioid agonist activities suggested the existence of a conformational change as well as the different membrane-compound interactions induced by the C-terminal modifications.

Example 12

Synthesis of Cyclic Compounds (FIGS. 4-5)

Example 12.1

Linear Compound Synthesis

The compound was synthesized manually by the $N^\alpha$-Fmoc solid-phase methodology using HCTU as the coupling reagents as previously reported. 2-Chlorotrityl resin (2.0 g, 1.56 mmol/g) was placed into a 50 mL polypropylene syringe with the frit on the bottom and swollen in DMF (20 mL) for 1 h. The resin was washed with DMF (3×15 mL) and then with DCM (3×15 mL). Fmoc-Trp(Boc)-OH (1.2 equiv) was dissolved in 30 mL of DCM, and then DIEA (5 equiv) was added. The reaction mixture was transferred into the syringe with the resin then shaken for 2 h. The resin was washed three times with DMF (15 mL) and three times with DCM (15 mL), and then with DMF (3×15 mL). The Fmoc protecting group was removed by 20% piperidine in DMF (20 mL, 1×2 min and 1×20 min). The deprotected resin was washed with DMF (3×15 mL), DCM (3×15 mL) and then with DMF (3×15 mL). The protected amino acid (3 equiv) and HCTU (2.9 equiv) were dissolved in 30 mL of DMF, then DIEA (6 equiv) was added. Fmoc-D-Cys(Trt)-OH, Fmoc-Cys(Trt)-OH, Fmoc-Pro-OH, Fmoc-Nle-OH, Fmoc-Phe-OH, Fmoc-Gly-OH and Boc-Tyr(tBu)-OH were used for respective coupling as protective amino acids. The coupling mixture was transferred into the syringe with the resin, and then shaken for 2 h. All the other amino acids were consecutively coupled using the procedure described above, using the TNBS test or chloranil test to check the extent of coupling. In case of a positive test result, the coupling was repeated until a negative test result was obtained. The resulting batch of the resin-bound protected compound was carefully washed with DMF (3×15 mL), DCM (3×15 mL), DMF (3×15 mL), and DCM (3×15 mL), and dried under reduced pressure. The compound was cleaved off the solid support with 1% v/v TFA in DCM (30 mL) for 30 min, and most of the organic solvent was removed under reduced pressure. The obtained protected compounds with free C-terminal were precipitated out by the addition of chilled petroleum ether (45 mL) to give a white precipitate. The suspensions were centrifuged for 20 min at 7000 rpm, and then the liquid was decanted off. The crude compounds were washed with petroleum ether (2×50 mL), and after the other centrifugation, the compounds were dried under vacuum (2 h) to obtain the title compound. The purity of the protected compounds with free C-terminal (>90%) were checked by analytical RP-HPLC using a Hewlett Packard 1100 system (230 nm) on a reverse phase column (Waters NOVA-Pak C-18 column, 3.9×150 mm, 5 μm, 60 Å). The compound was eluted with a linear gradient of aqueous $CH_3CN/0.1\%$ $CF_3CO_2H$ (10-90% in 40 minutes) at a flow rate of 1.0 mL/min. The crude compound was used for next reactions without further purification.

The protected compound with free C-terminal (300 mg, 0.173 mmol) and Cl-HOBt (33.4 mg, 0.208 mmol) were dissolved in DMF (3 mL). 3,5-bistrifluoromethylbenzyl amine (84.1 mg, 0.346 mmol) and EDC (39.7 mg, 0.208 mmol) were added to the solution at r.t and stirred until the starting material wasn't detected in TLC; then saturated aqueous sodium bicarbonate (100 mL) was added. The reaction mixture was extracted with ethyl acetate (100 mL) three times. The combined organic phases were washed with 5% aqueous citrate and saturated aqueous sodium chloride (100 mL each), then dried over sodium sulfate. The solvent was evaporated and the crude protected compound was precipitated in cold petroleum ether (45 mL). The product was twice dispersed in cold petroleum ether, centrifuged and decanted, then dried under reduced pressure. The obtained protected compound was treated with 82.5% v/v TFA, 5% water, 5% thioanisol, 2.5% 1,2-ethanedithiol, and 5% phenol (1.5 mL, 1 h). The crude compound was precipitated out by the addition of chilled diethyl ether (45 mL) to give a white precipitate. The resulting compound suspensions were centrifuged for 20 min at 7000 rpm, and the liquid was decanted. The crude compounds were washed with diethyl ether (2×45 mL), and after a final centrifugation, the compounds were dried under vacuum (2 h). The resulting white residues (225 mg, quantitative) were directly used for next cyclization.

Example 12.2

Oxidative Cyclization to Disulfides (FIG. 4-5)

A solution of $K_3Fe(CN)_6$ was prepared as follows: 1 mmol (330 mg) of $K_3Fe(CN)_6$ was dissolved in a mixture of water (100 mL) and $CH_3CN$ (100 mL), a saturated solution of ammonium acetate (20 mL) was added to it, and the pH was adjusted to 6.0 with glacial acetic acid. A solution of the linear compound (0.173 mmol) in the mixture of $CH_3CN$ (40 mL), DMSO (5 mL) and $H_2O$ (5 mL) was added to the above solution dropwise overnight with the help of a syringe pump. After the overnight reaction, glacial acetic acid was added to the reaction mixture to obtain pH 5.0, followed by 20 mL of Amberlite IRA-68 anion-exchange resin (pre-equilibrated with 1 M HCl and extensively washed with distilled water), and the suspension stirred for 30 min until the solution turned colorless and the resin turned yellow. The resin was suction-filtered and the filtrate rotoevaporated to remove most of the organic solvent. The remaining solution was concentrated on Sep-Pak C18 cartridge (10 g, Waters, Milford, Mass.), then eluted with $CH_3CN$. The obtained yellow solution was concentrated under reduced pressure for the final purification by preparative RP-HPLC, and then lyophilized.

Example 13

Characterization of Compounds

Example 13.1

Preparative RP-HPLC was performed on Waters Delta Prep 4000 with Waters XTerra C-18 column (19×250 mm, 10 μm, a linear gradient of 33-53% or 40-60% acedtonitrile/ 0.1% TFA at a flow rate of 15.0 mL/min). The purified compounds were characterized by HRMS, TLC, analytical HPLC and $^1$H-1D-NMR. Sequential assignment of proton resonances was achieved by 2D-TOCSY NMR experiments. High-resolution MS were taken in the positive ion mode using FAB methods at the University of Arizona Mass Spectrometry Facility. TLC was performed on aluminum sheets coated with a 0.2 mm layer of silica gel 60 $F_{254}$ Merck using the following solvent systems: (1) $CHCl_3$:MeOH:AcOH=90: 10:3; (2) EtOAc:n-BuOH:water:AcOH=5:3:1:1; and (3) n-BuOH:water:AcOH=4:1:1. TLC chromatograms were visualized by UV light and by ninhydrin spray followed by heating (hot plate). Analytical HPLC was performed on a Hewlett Packard 1100 or Hewlett Packard 1090m with Waters NOVA-Pak C-18 column (3.9×150 mm, 5 μm, 60 Å) or Vydac 218TP104 C-18 column (4.6×250 mm, 10 μm, 300 Å). $^1$H-1D-NMR spectra were obtained on Bruker DRX-500 or DRX-600 spectrometer. 2D-TOCSY NMR spectra were performed on a Bruker DRX-600 spectrometer equipped with a 5 mm Nalorac triple-resonance single-axis gradient probe. The NMR experiments were conducted in DMSO-$d_6$ solution at 298K. Spectra were referenced to residual solvent protons as 2.49 ppm. The processing of NMR data was performed with the XwinNmr software (Bruker BioSpin, Fremont, Calif.). In the TOCSY experiments, the TPPI mod with MLEV-17 Mixing Sequence were used with a mixing time of 62.2 ms, at a spin-lock field of 8.33 kHz. TOCSY spectra were acquired with 2 k complex pairs in $t_2$ and 750 FIDs using a 90'-shifted sine-squared window function in both dimensions.

Example 13.2

NMR Spectroscopy in DPC amphipathic media. All NMR spectra were recorded on a Bruker DRX600 600 MHz spectrometer with 5 mm Nalorac triple-resonance single-axis gradient probe. The compound concentration for the NMR experiments were 7.4, 8.0 and 7.8 mM for TY035, TY037 and TY038, respectively. The samples were prepared by dissolving the compound in 0.5 mL of 45 mM sodium acetate-$d_3$ buffer (pH 4.5) containing 40 equivalents of dodecylphosphocholine-$d_{38}$ and 1 mM sodium azide (90% $H_2O$/10% $D_2O$) followed by sonication for 5 min. Two-dimensional double quantum filtered correlation (DQF-COSY), nuclear Overhauser effect (NOESY), and total correlation spectra (TOCSY) were acquired using standard pulse sequences and processed using XwinNmr and Felix 2000 (Accelrys Inc, San Diego, Calif.). The mixing time for the NOESY spectra was 450 ms for all the cyclic compound derivatives. All 2D spectra were acquired in the TPPI mode with 2 k complex data points in $t_2$ and 750 real data points in $t_1$, and the spectral processing using shifted sine bell window functions in both dimensions. For suppressing the $H_2O$ signal, the 3-9-19 WATERGATE pulse sequence was used (Ananthan, J. Med. Chem. 2004, 47, 1400-1412). Experiments were conducted at 310 K, and referenced to the $H_2O$ shift (4.631 ppm). Coupling constants ($^3J_{HN-H\alpha}$) were measured from 2D DQF-COSY spectra by analysis of the fingerprint region. The matrix rows of each of the upper and lower halves of a cross-peak were summed to give an antiphase 1D spectrum, which was fitted using a 5-parameter Levenberg-Marquardt nonlinear least-squares protocol to a general antiphase doublet. The analysis yielded two independent determinations of the J coupling and line width for each cross-peak, one from the upper half and one from the lower half, and the one with better fitted curve was used for structure calculations. Cross-peak volumes for determination of distance restraints were measured using the Felix 2000 software. In the radical experiment using $Mn^{2+}$, a stock solution of 5 mM $MnCl_2$ was prepared and added to the sample to achieve a total concentration of 200 µM in $Mn^{2+}$.

Example 13.3

Conformational Structural Determination. The methods used for structure calculations have been described previously (Lee, J. Med. Chem. 2006, 49(5), 1773-1780; Agnes, J. Med. Chem. 2006, 49(10), 2868-2875). The volumes of the assigned cross-peaks in the 2D NOESY spectrum were converted into upper distance bounds of 3.0, 3.8, 4.8, or 5.8 Å. For overlapping cross-peaks, the distance categories was increased by one or two levels, depending on the qualitative estimate of the extent of overlap during the assignments. Pseudoatoms were created for nonstereospecifically assigned methylene protons with a correction of 1.0 Å applied to their upper bound distances. In addition to the distance constraints, φ dihedral angle constraints derived from $^3J_{HN-H\alpha}$ coupling constants were set to between -90 and -40° for $^3J_{HN-H\alpha}$<6 Hz and to between -150 and -90° for $^3J_{HN-H\alpha}$>8 Hz. Dihedral angles of 180°±5° for compound bonds (ω) were also used to maintain the planarity of these bonds.

Simulated annealing molecular dynamics analysis was done for all the compounds to obtain an ensemble of NMR structures using the NOE-derived distance constraints and dihedral angle (φ) constraints using the DGII program within the software package Insight II 2000 (Accelrys Inc., San Diego, Calif.). Solvent was not explicitly included in the calculations. All the embedded structures successfully passed the simulated annealing step and were minimized using the consistent valency force field (CVFF) (Accelrys Inc.). The 50 structures with the lowest penalty function were further refined by two rounds of restrained molecular dynamics (rMD) using the all-atom AMBER force field with additional parameters for fluorine atom (Ripley, Neuropharmacology, 2002, 43(8), 1258-68; Yamamoto, 2007, J. Med. Chem., in press; Yamamoto, 2007, J. Med. Chem., submitted; Yamamoto, 2007, J. Am. Chem. Soc., submitted) using the standalone DISCOVER ver. 2.98 program (Accelrys Inc.). A 12.0 Å cutoff for nonbonded interactions and a distance-dependent dielectric constant (4r) were used. All amide bonds were constrained to trans conformation by a 100 kcal $mol^{-1}$ $rad^{-2}$ energy penalty. The distance restraints and the constrained dihedral angles (φ) constraints were applied with a force constant of 25 kcal $mol^{-1}$ $Å^{-2}$ and 100 kcal $mol^{-1}$ $rad^{-2}$ were applied, respectively. After 100 steps of steepest descents minimization and 1000 steps of conjugate gradient minimization on the initial structures, an rMD equilibration at 500 K was performed for 1.5 ps, during which a scale factor of 0.1 was applied to the experimental restraint force constants. During the next 2 ps, full values of the experimental restraint force constants were applied. A further 1 ps rMD simulation was run at 500 K, and the system was then cooled to 0 K over 3 ps. After another 1 ps at 0 K, 100 cycles of steepest descents and 2000 steps of conjugate gradient minimization were performed. The final 20 structures with the lowest energies were used for the analysis. All calculations were performed on a Silicon Graphics Octane computer.

Discussion.

I. Secondary Structure Analysis Based on Assigned $^1H$ NMR Resonances.

Two-dimensional $^1H$ NMR studies including TOCSY, DQF-COSY and NOESY in pH 4.5 buffer (45 mM $CD_3CO_2Na$/HCl, 1 mM $NaN_3$, 90% $H_2O$/10% $D_2O$) with 40-fold perdeuterated DPC micelles were performed on the cyclic compound derivatives TY035, TY037, and TY038. The NMR structure of TY027 was already reported. DPC is the widely used lipid-like surfactant to determine the solution NMR structures of membrane-bound proteins and compounds, and form micelles above the critical micelle concentration. All $^1H$ chemical shift assignments of TY035, TY037, and TY038 in the aqueous media were found in the Supporting Information. As mentioned above, the $^1H$ NMR study of TY039 couldn't be executed because of its insolubility into the buffer with 40-fold DPC.

As can be seen in FIG. 31, the overall quality of the NOESY data is reasonably good, though the overlap of some resonances made the assignment of some NOE cross-peaks difficult. All the interresidue NOE connectivities and observed $^3J_{HN-H\alpha}$ coupling of the cyclic compound derivatives TY035, TY037, and TY038 were illustrated in FIG. 32. The C-terminal benzyl amide moiety were considered as the residue 9, and the connectivities of NOE were specified if they have cross-peaks related to their benzyl amide $H^N$ protons. In the case of the NOE patterns of linear compound derivative TY027, no (i, i+3) or (i, i+4) connectivities were found, whereas the cyclic compound TY035, TY037, and TY038 showed a numbers of these connectivities, implying their structures were better-defined with some secondary structure elements. According to the observed NOE connectivities of $d_{NN}$(i, i+1), $d_{\alpha N}$(i, i+1) and some medium-range (i, i+2-4) ones, the presence of some β-turn structures were expected in residues 1-4 (TY035 and TY037), 2-5 (TY035, TY037, and TY038), 5-8 (TY035, TY037, and TY038) and 6-9 (TY037 and TY038). Because of the longer range connectivities (i, i+3-4), it is also possible for TY027 and TY035 to have helical structures at their C-terminal halves.

2. Structural Calculations.

The structural calculations were performed based on NOE cross-peak volumes and $^3J_{HN-H\alpha}$ values using the previously described method (Agnes, J. Med. Chem. 2006, 49(10), 2868-2875; Schiller, Biochem. Biophys. Res. Commun., 1981, 101, 337-343). The 142, 224 and 174 non-redundant NOE restraints including intraresidue (52, 66 and 51), sequential (45, 74 and 57), medium-range (2-4 residues; 39, 80 and 62) and long-range (>4 residues; 6, 4 and 4) were used for TY035, TY037, and TY038, respectively. As for the $^3J_{HN-H\alpha}$ values, only the ones with more than 8 Hz or less than 6 Hz were used as the (P dihedral angle constraints. The numbers of applied dihedral angle constraints were 0, 1 and 2 for TY035, TY037, and TY038, and the total number of restraints were 142, 225 and 176, respectively (15.7, 24.9 and 19.3 per residue). In the spectra of TY035, TY037, and TY038, two isomers at Pro$^6$ were observed and their ratios were 4:1, 3:1 and 2.5:1 for TY035, TY037, and TY038, respectively. In the structural calculation, only the major isomer derived cross-peaks were considered, and all the D-Cys$^5$-Pro$^6$ or Nle$^5$-Pro$^6$ bonds were fixed as trans configuration, according to the observation of $^5H^\alpha$ to Pro$^6H^6$ sequential NOEs together with the absence of sequential $^5H^\alpha$-$^6H^\alpha$ NOEs. In the case of the linear compound derivative TY027 the cis isomer at Pro$^6$ was observed as the trace amount. Thus, the increased ratio of the minor cis isomers at Pro$^6$ by the cyclization might be one good reason of the decreased affinities at the opioid receptors as well as the NK1 receptors.

The analysis and statistics of the cyclic compound derivatives TY035, TY037, and TY038 were performed on the 20 structures with the lowest total energies after restrained molecular dynamics (rMD) refinement (Table 17).

TABLE 17

Structural statistics

| | Compound | | | |
|---|---|---|---|---|
| | TY027[a] | TY035 | TY037 | TY038 |
| | final 20 structs | final 20 structs | final 20 structs | final 20 structs |
| rms deviation from NOE dist restraints (Å)[b] | 0.027 ± 0.004 | 0.012 ± 0.002 | 0.022 ± 0.0006 | 0.030 ± 0.001 |
| rms deviation from backbone φ angle restraints (deg)[c] | —[d] | —[c] | 0.00 ± 0.00 | 0.037 ± 0.046 |
| NOE dist restraints violations | | | | |
| >0.01 Å | 14.6 ± 1.5 | 10.7 ± 1.8 | 22.4 ± 1.6 | 13.6 ± 1.2 |
| >0.1 Å | 3.9 ± 1.2 | 0.5 ± 0.6 | 3.8 ± 0.9 | 4.9 ± 0.9 |
| max dist violations (Å) | 0.16 ± 0.02 | 0.09 ± 0.02 | 0.13 ± 0.005 | 0.19 ± 0.02 |
| dihedral backbone angle violations | | | | |
| >0.1° | —[d] | —[c] | 0.00 ± 0.00 | 0.4 ± 0.5 |
| >1° | —[d] | —[c] | 0.00 ± 0.00 | 0 ± 0 |
| max dihdral violations (deg) | —[d] | —[c] | 0.00 ± 0.00 | 0.09 ± 0.15 |
| rms deviation from ideal geometry[e] | | | | |
| bond length (Å)[f] | 0.0052 ± 0.0002 | 0.0052 ± 0.0002 | 0.0060 ± 0.00003 | 0.0064 ± 0.00006 |
| bond valence angles (deg)[g] | 1.78 ± 0.05 | 1.55 ± 0.09 | 2.24 ± 0.03 | 2.25 ± 0.02 |
| out-of-plane angles (deg)[h] | 2.73 ± 0.40 | 1.99 ± 0.52 | 3.02 ± 0.08 | 2.54 ± 0.09 |
| AMBER energies (kcal mol$^{-1}$) | | 9.08 | | |
| restraint[i] | 2.95 ± 0.58 | 0.6 ± 1.2 | 3.0 ± 0.1 | 4.0 ± 0.7 |
| bond stretching | 1.42 ± 0.08 | 1.4 ± 0.1 | 1.8 ± 0.03 | 2.9 ± 0.04 |
| bond angles | 12.8 ± 0.8 | 9.5 ± 1.1 | 20.1 ± 0.6 | 19.9 ± 0.4 |
| dihedral angles | 9.57 ± 1.61 | 10.3 ± 0.9 | 17.1 ± 0.2 | 14.2 ± 0.4 |
| planarity | 0.74 ± 0.33 | 0.43 ± 0.2 | 1.2 ± 0.01 | 0.6 ± 0.05 |
| van der Waals[j] | −12.23 ± 1.4 | −20.3 ± 1.3 | −12.8 ± 1.0 | −3.4 ± 0.8 |
| electrostatic[k] | −11.5 ± 0.68 | −10.4 ± 1.4 | −10.2 ± 0.4 | −10.4 ± 0.7 |
| total | −0.01 ± 2.25 | −10.2 ± 0.2 | 16.4 ± 0.6 | 22.3 ± 0.3 |
| | 1[a] | 2 | 3 | 4 |
| Backbone atoms (N, C$^\alpha$, C') | | | | |
| Calculated on whole molecule | 1.14 ± 0.43 | 0.71 ± 0.15 | 0.18 ± 0.18 | 0.92 ± 0.33 |
| Calculated only on 1-4 res. | 1.05 ± 0.63 | 0.74 ± 0.28 | 0.21 ± 0.31 | 1.23 ± 0.44 |
| Calculated only on 5-8 res. | 0.45 ± 0.38 | 0.27 ± 0.27 | 0.01 ± 0.01 | 0.031 ± 0.01 |
| all non-hydrogen atoms | | | | |
| Calculated on whole molecule | 2.09 ± 0.64 | 1.22 ± 0.36 | 0.70 ± 0.20 | 1.36 ± 0.42 |
| Calculated only on 1-4 res. | 2.16 ± 0.98 | 1.10 ± 0.41 | 0.52 ± 0.46 | 1.52 ± 0.46 |

TABLE 17-continued

| Structural statistics | | | | |
|---|---|---|---|---|
| Calculated only on 5-8 res. and C-terminus | 1.02 ± 0.25 | 1.02 ± 0.41 | 0.02 ± 0.01 | 0.06 ± 0.02 |

[a]reference (Yamamoto, 2007, J. Am. Chem. Soc. submitted). NMR conformation-activity relationship and Locations in Micelle-bound States of C-Terminal Modified Bifunctional Compounds for δ/μ Opioid Receptor Agonists and Neurokinin 1 Receptor Antagonists. 2007, J. Am. Chem. Soc. submitted
[b]The total number of NOE restraints were 155 for TY027, 141 for TY035, 224 for TY037 and 174 for TY038, respectively.
[c]0, 0, 1 and 2 backbone φ angle restraints were applied TY027, TY035, TY07, and TY038, respectively.
[d]no restraints used.
[e]Derived from the rMD calculations using the AMBER force field in DISCOVER.
[f]The number of bond length was 161 for TY027 and 155 for TY35, TY37, and TY38.
[g]The number of bond valence angles were 287 for TY027 and 276 for TY035, TY037, and TY038.
[h]The number of out-of-plane angles were 36 for TY027, 36 for TY035, 37 for TY037 and 36 for TY038, respectively.
[i]Calculated with force constants of 25 kcal mol$^{-1}$ Å$^{-2}$ and 100 kcal mol$^{-1}$ rad$^{-2}$ for the NOE distance and dihedral angle restraints, respectively.
[j]Calculated with the Lennard-Jones potential using the AMBER force field and a 12 Å cutoff.
[k]Calculated with a distance-dependent dielectric constant ($\epsilon = 4$ r).

The number of total NOE restraints violations were 11.1, 26.1 and 18.5, and maximum NOE violations were 0.09, 0.13 and 0.19 for TY035, TY037, and TY038, respectively. The p dihedral angle violations were found only in TY037, but the extent was pretty small. For the restraints energies derived from the amber force field, 0.6, 3.0 and 4.0 kcal mol$^{-1}$ were found in the most stable 20 structures. The superimposed images of the best 20 structures were illustrated in FIG. 33. All the calculated structures of TY035, TY037, and TY038 were pretty well-defined, and their rmsd values for all the backbone atoms with respect to the most stable structures were 0.71, 0.18 and 0.92, respectively. The rmsd values were still 1.22, 0.70 and 1.36 when aligned with all the heavy atoms. Since these rmsd values were extensively decreased when the structures were aligned on only the residues 5-8, the conformations of the C-terminus in the DPC micelles were better defined than their N-terminal halves. These structured conformations of the cyclic compound derivatives TY035, TY037, and TY038 were also confirmed from the angular order parameters regarding to the backbone dihedral angles φ and ψ (FIGS. 34D and E). The order parameters looked increased as from the N- to the C-terminus, indicating that the backbones of polypeptide were more structured in the C-terminal halves.

Figure 33A:
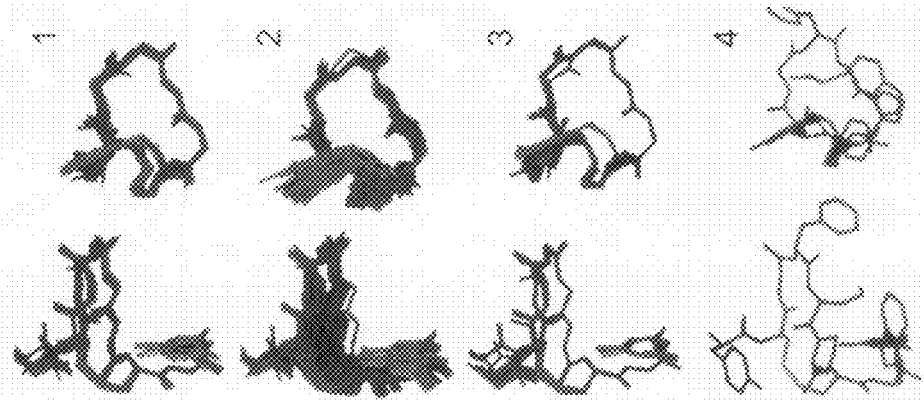
Figure 33B:
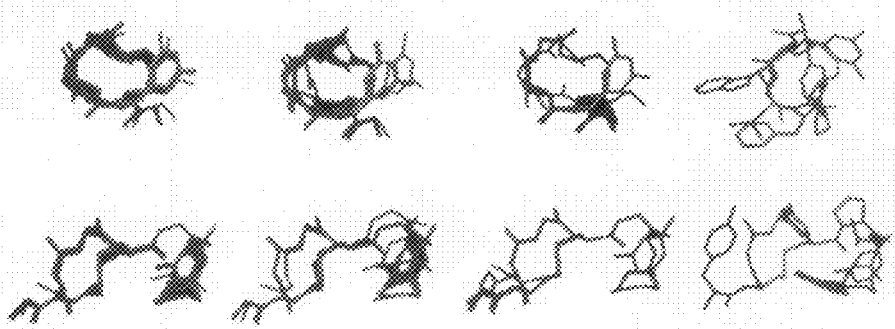
Figure 33C:
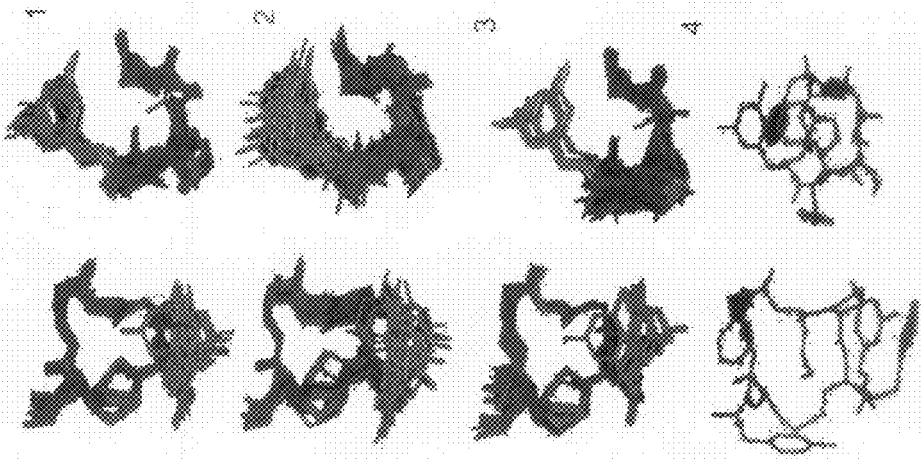
Figure 34E:
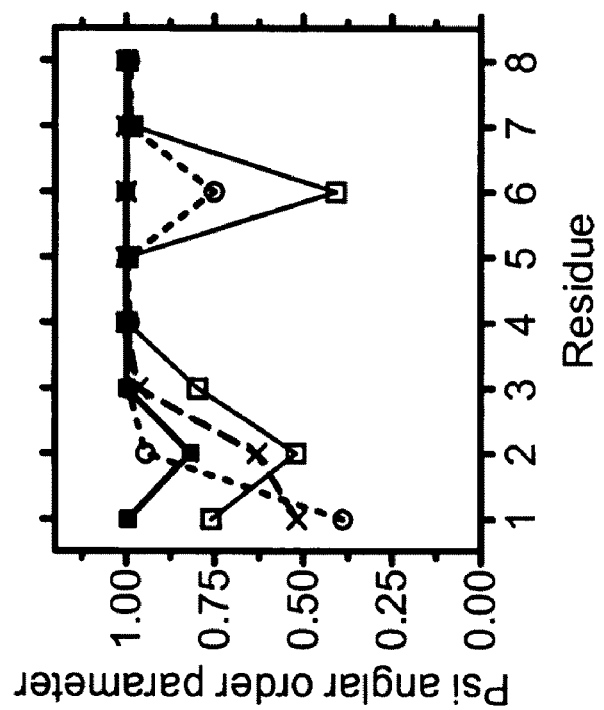
FIG. 34 A-E. The D-Cys (crosses) and Gly$^3$ (open circle) were indicated in the Ramachandran φ,ψ plots for (A) TY035, (B) TY037 and (C) TY038 for residues 2-7 of 20 final structures. Angular order parameters for φ (D) and ψ (E) angles calculated from the 20 final structures for TY027 (open square), TY035 (open circles), TY037 (filled squares) and TY038 (crosses). For calculating the ψ angles of Trp$^8$, the nitrogen atoms of C-terminal amide were used instead of N (i+3), respectively.
Figure 34D:
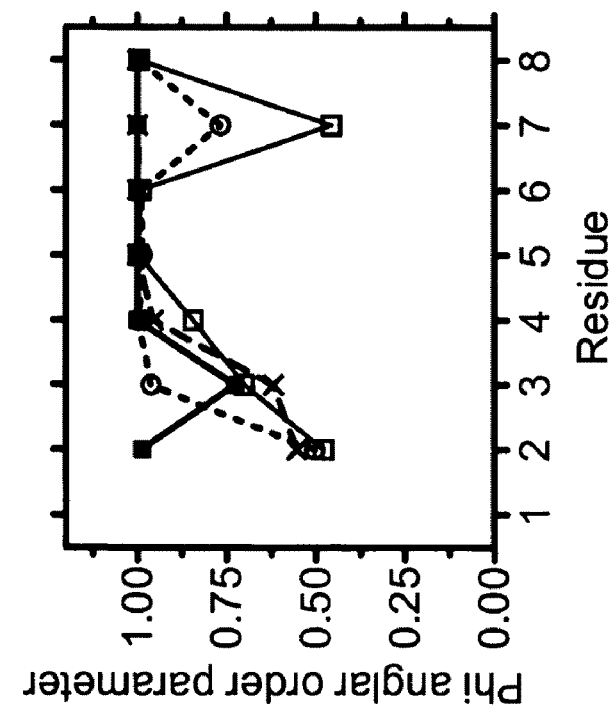

As expected from the NOE connectivities and $^3J_{HN-H\alpha}$ values, a number of β-turn structure elements were found in the cyclic compound derivatives TY035, TY037, and TY038 (FIG. 33). According to the original definition (Yamamoto, 2007, J. Med. Chem. submitted), the structure in which $C_\alpha$ of ith residue and $C_\alpha$ in the i+3 rd residues locate less than 7 Å are considered as β-turn. In the best 20 structure of [D-Cys$^2$, Cys$^7$]TY027 (TY35), the residues between $C_\alpha$ of D-Ala$^2$ and $C_\alpha$ of Nle$^5$ (20 structures out of the 20) as well as $C_\alpha$ of Nle$^5$ and $C_\alpha$ of Trp$^8$ (11 structures out of the 20) were found as the Type IV β-turns (Table 18).

TABLE 18

Number of structures with less than 7 Å distance between alpha carbons of i th and (i + 3) th residues.[a]

| | Residues | | | | |
|---|---|---|---|---|---|
| | Tyr$^1$–Phe$^4$ | DCys$^2$–Met$^5$ | Gly$^3$–Pro$^6$ | Met$^5$–Trp$^8$ | Pro$^6$–Bzl$^9$ |
| TY027 | 5 | 15[c] | 0 | 0 | 17 |
| TY035 | 11 | 20 | 20 | 11 | 0 |

TABLE 18-continued

Number of structures with less than 7 Å distance between alpha carbons of i th and (i + 3) th residues.[a]

| | Residues | | | | |
|---|---|---|---|---|---|
| | Tyr$^1$–Phe$^4$ | DCys$^2$–Met$^5$ | Gly$^3$–Pro$^6$ | Met$^5$–Trp$^8$ | Pro$^6$–Bzl$^9$ |
| TY037 | 0 | 20 | 0 | 20 | 20 |
| TY038 | 0 | 20 | 0 | 20 | 0 |

[a]Out of the best 20 calculated structures. Bzl stands for the cross-peaks derived from the corresponding aromatic protons of benzyl moiety (residue 9).
[b]reference (Yamamoto, 2007, J. Am. Chem. Soc. submitted)
[c]DAla$^2$ was introduced instead of DCys$^2$ These two β-turns were common elements for TY035, TY037, and TY038, and also found in both of T037 and TY038 (Table 17). However, the distance of $^1C_\alpha$-$^4C_\alpha$ (11 structures out of the 20, Type IV) and $^3C_\alpha$-$^6C_\alpha$ (all the 20 structures, Type VIII) in TY035 were also less than 7 Å. Both of these two β-turns were specific only for TY035, which alone has L-Cys in the sequence, implying that these two turns might affect on the decreased activities in the tissue assays. [D-Cys$^2$, D-Cys$^7$]TY027 (TY038) had only the two common β-turns in D-Ala$^2$-Nle$^5$ and Nle$^5$-Trp$^8$ for all the 20 best structures. Thus, the β-turn found in the Pro$^6$-C-terminal benzyl moiety (residue 9) of TY027 was eliminated by the disulfide ring introduction in residues 2-7. It is interesting to note that the elimination of the β-turn, which is located in the pharmacophore for NK1 antagonist, resulted in the better affinities at the NK1 receptors than those of the compound with the smaller rings (residues 2-5). However, the Type I β-turn at residues 6-9 was clearly found in all the 20 structures of [D-Cys$^2$, D-Cys$^5$]TY027 (TY037), which has the smallest atomic rmsd values. The secondary structure-related hydrogen bond was observed between the amide proton of C-terminus and carbonyl oxygen of Pro$^6$ in TY037 (Table 19), indicating the well-structured turn structure.

TABLE 19

| | Observed hydrogen bonds[a] | | | | |
|---|---|---|---|---|---|
| Molecule | No.[b] | Donor | Acceptor | Distance (Å)[c] | Angle (deg)[d] |
| TY035 | 16 | Tyr$^1$ OH | Trp$^8$ O | 1.94 ± 0.03 | 154.3 ± 10.3 |
| | 12 | Gly$^3$ H$^N$ | Met$^5$ O | 2.21 ± 0.12 | 152.6 ± 7.0 |

TABLE 19-continued

Observed hydrogen bonds[a]

| Molecule | No.[b] | Donor | Acceptor | Distance (Å)[c] | Angle (deg)[d] |
|---|---|---|---|---|---|
| TY037 | 6 | Tyr¹ OH | Phe⁴ O | 2.02 ± 0.00 | 155.8 ± 0.0 |
|  | 20 | Bzl⁹ H[Ne] | Leu⁷ O | 2.01 ± 0.00 | 152.0 ± 0.1 |
| TY038 | 15 | Gly³ H[N] | Bzl⁹ F[f] | 2.33 ± 0.04 | 155.2 ± 1.9 |

[a]The hydrogen bonds which were observed in more than five structures were listed.
[b]The number of structures of the final 20 for which the listed hydrogen bond is observed.
[c]The distance is the mean proton-acceptor atom distance (±SD) in the structures for which a hydrogen bond is observed.
[d]The angle is the mean angle (±SD) in the structures for which a hydrogen bond is observed.
[e]Amide proton of C-terminal benzyl moiety.
[f]Fluorine atom at C-terminal benzyl moiety.

It should be noted that the existence of relatively large numbers of β-turn elements for 8-amino-acids compounds implied their compact tandem-β-turns conformation as well as the zigzag backbones, which might contribute to their well-defined structures in the DPC micelles (FIG. 33).

The corresponding Ramachandran plots were depicted in FIG. 34. A number of the positive φ angles were found in Gly³ of TY035 (all the best 20 structures) and of TY037 (17 structures out of the 20), while only 5 in the best 20 structures of TY038 have Gly³ with positive φ angles, although all of the three cyclic compound derivatives TY035, TY037, and TY038 have β-turn structures in the same residues where Gly³ was at their (i+1)th position. In the case of the D-Cys² and Cys⁷ in TY035, small number of structures (6 out of the best 20) has negative φ angles in D-Cys², whereas Cys⁷ with positive φ angles were found in 19 structures out of the best 20, implying that the cyclization induced the distortion in Cys⁷ rather than in D-Cys². However, in TY037 and TY038, both of which have two D-Cys in their sequences, the negative φ angles were found only in D-Cys² (20 and 16 structures out of the best 20, respectively), but not in D-Cys⁵ (TY037) or D-Cys⁷ (TY038), indicating that the distortion was shifted into D-Cys² because of the inversion of chiralities at another cystein.

3. Paramagnetic Broadening Studies on ¹H NMR.

Figures 35A, 35B:
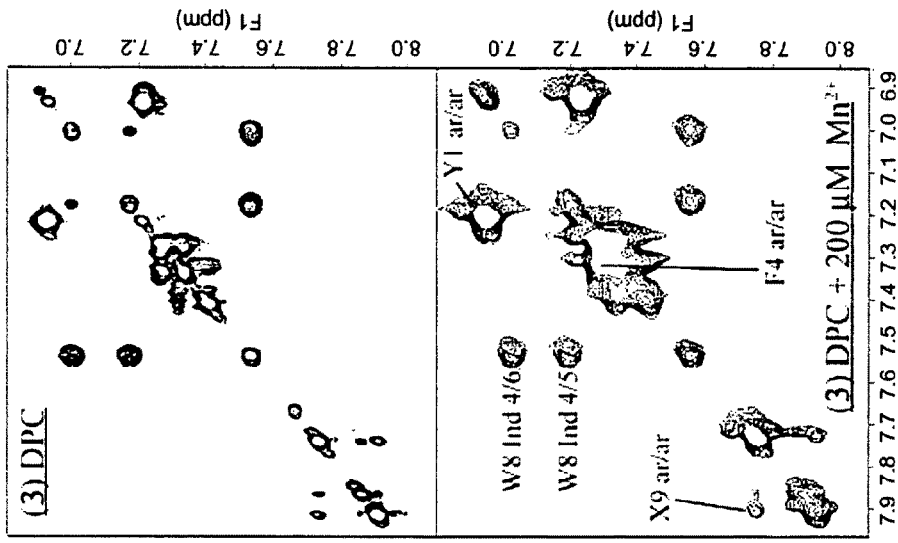
FIG. 35. Typical effect of radicals on TOCSY Spectra. TY037 with DPC micelles (A, C, and E) and with 200 μM $Mn^{2+}$ (B, D, and F), for $H^N$-$H^α$ region (A and B), aliphatic side-chain region (C and D) and aromatic region (E and F). Preserved resonances (labeled) are in a phase not be missed by the phase-specific radical probe ($Mn^{2+}$). Spectra were compared from the same noise level. X9represents the cross-peaks derived from the corresponding aromatic protons of benzyl moiety.
Figures 35C, 35D:
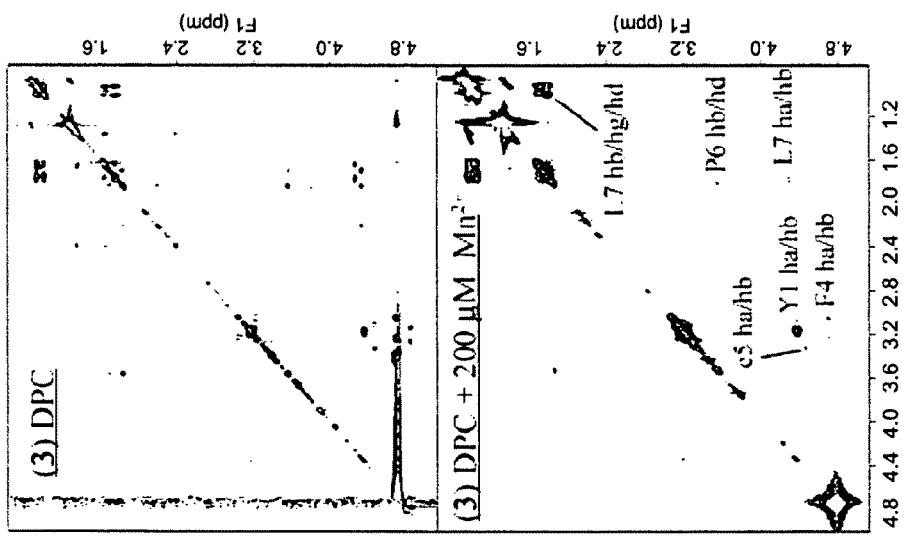
Figures 35E, 35F:
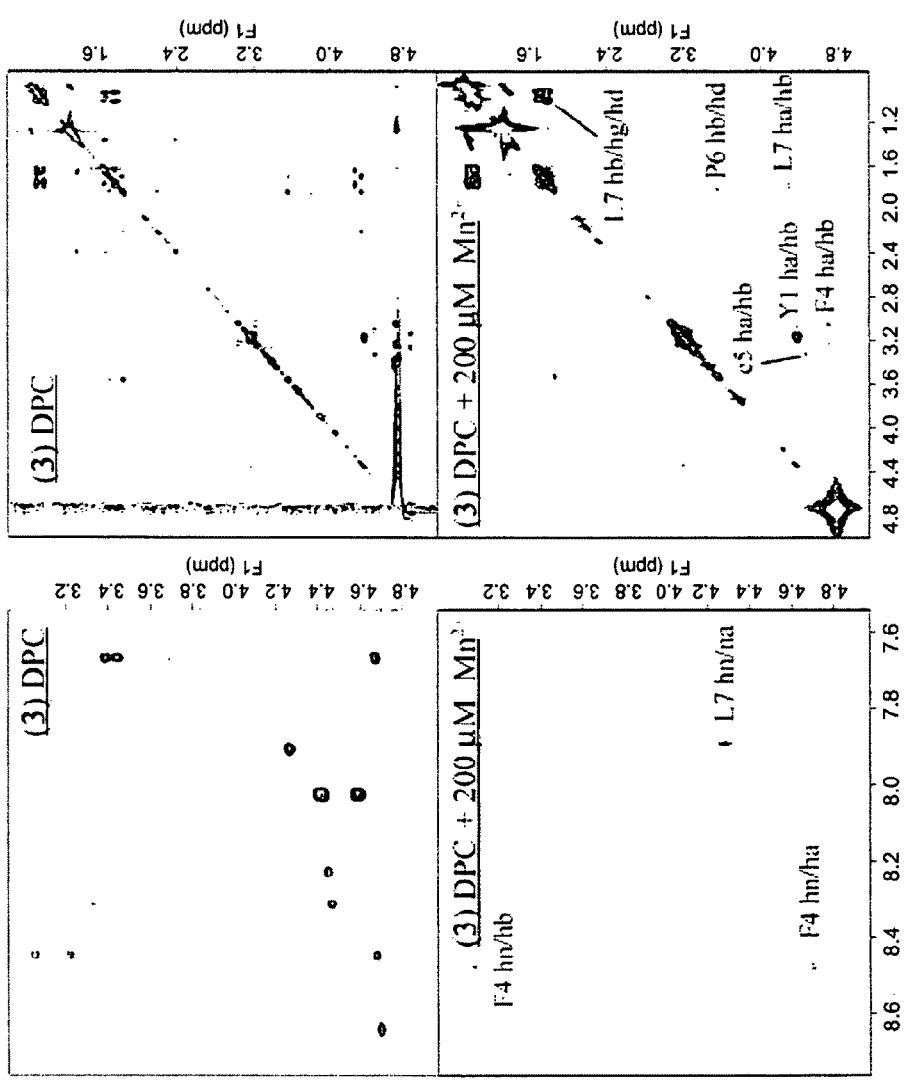

For the cyclic compound derivatives TY035, TY037, and TY038, $Mn^{2+}$ was used as a paramagnetic ion to determine their location and orientation in the micelles (FIG. 35 and Tables 5.1-5.7). $Mn^{2+}$ ions cause a reduction in the resonance intensities of the solvent-exposed protons, and the effects of the agent were observed as an ensemble of cross-peaks belonging to the same residue spin system in TOCSY spectra measured with a 62.2 ms mixing time. In TY037 and TY038, both of which have two D-Cys in their sequences, all the aromatic resonances were found preserved by the addition of $Mn^{2+}$, while most of the cross-peaks related to the indole ring of Trp⁸ and the phenyl ring of C-terminal benzyl moiety were missing in [D-Cys², Cys⁷]TY027 (TY035). The cross-peaks derived from the side chains of L or D-Cys, Nle⁵ and Leu⁷ were also unextinguished. Thus, it is obvious that the lipophilic side-chains of TY035, TY037, and TY038 interact with DPC micelles directly and being buried in them, but their orientations at C-terminus were different by the chirality of the induced cystein residues. On the other hand, all the backbone amide protons in TY035 and [D-Cys², D-Cys⁷]TY027 (TY038) were disappeared, implying their backbones were at the surface of micelles. However, in the case of TY037 whose disulfide bond formed at the residues 2-5, the H[N]-related signals of Phe⁴ and Leu⁷ were found after the $Mn^{2+}$ addition. Thus, the backbone of TY037 had different orientation from TY035 and TY038 in DPC micelles with the backbone atoms of Phe⁴ and Leu⁷ buried in the micelles.

Example 14

In Vitro Stability of compound derivatives in Rat Plasm (Yamamoto, 2007, *J. Am. Chem. Soc.* submitted). Stock solution of compounds (50 mg/mL in DMSO) were diluted 1000-fold into rat plasma (Lot 24927, Pel-Freez Biologicals, Rogers, Ak.) to result in an incubation concentration of 50 μg/mL. All samples were incubated at 37° C. for 6 h, and 200 μL of aliquots were withdrawn at 1 h, 2 h, 4 h and 6 h. The 300 μL of acetonitrile was added and the proteins were removed by centrifugation, then the supernatant was analyzed for the amount of remaining parent compound by HPLC (Hewlett Packard 1090m with Vydac 218TP104 C-18 column; 4.6× 250 mm, 10 μm, 300 Å). The samples were run in triplicate.

Discussion.

Figure 36:
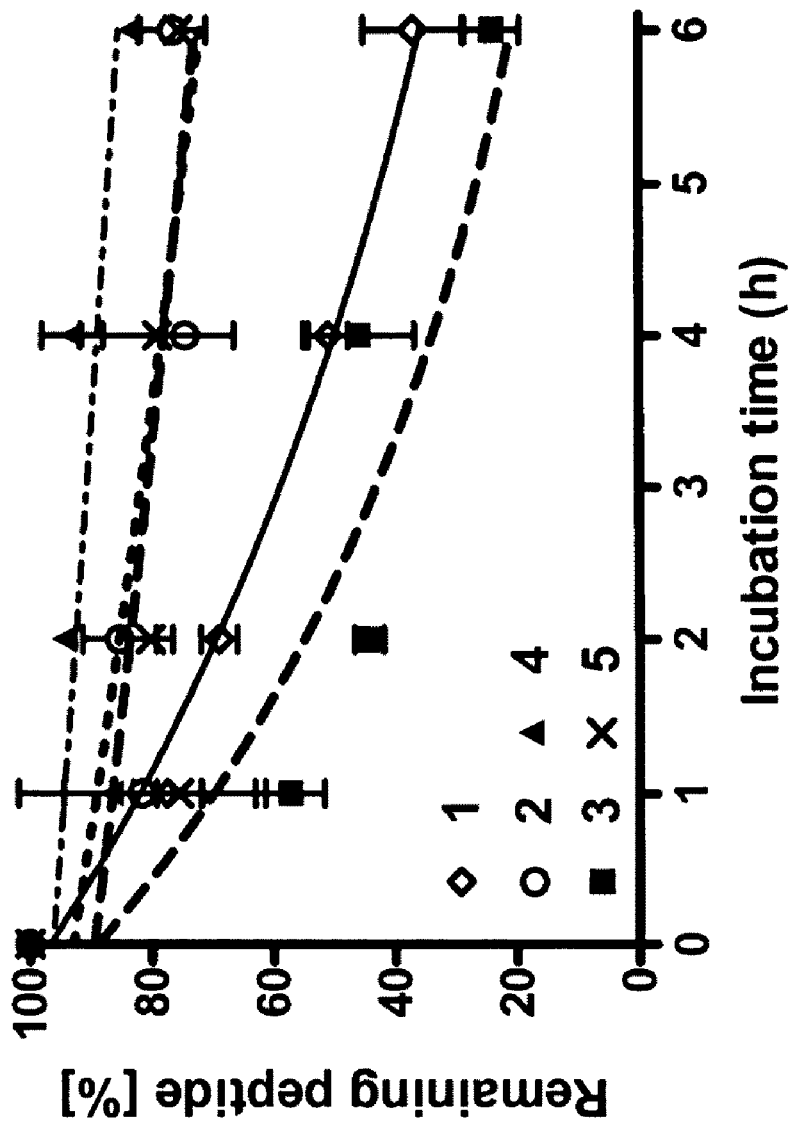
FIG. 36. Comparison of the in vitro stability of compound derivatives for TY027 (crossings), TY035 (open circle), TY037 (filled square), TY038 (filled triangle) and TY039 (open diamond) incubated in rat plasma at 37° C. Calculated half lives of compound derivatives ($T_{1/2}$) were 4.8 h for TY027 and 3.7 h for TY037, and >6 h for TY035, TY038 and TY039, respectively.

The cyclized compound derivatives TY035, TY037, TY038, and TY039 as well as the linear compound derivative TY027 were tested on their metabolical stability for the effect of the disulfide bond cyclization (FIG. 1). The compound derivatives were incubated in rat plasma at 37° C., and aliquots were withdrawn at various time points and analyzed by HPLC to determine the concentration of remaining compound derivatives. The linear compound TY027 had good stability with the half life ($T_{1/2}$) of 4.8 h, presumably because of the unnatural C-terminus and D-Ala² introduction. DCDCE like cyclic compound [D-Cys², D-Cys⁵]TY027 (TY037) showed slightly less stability, though it had the disulfide ring in the structure ($T_{1/2}$=3.7 h). However, the stability of TY035, TY038, and T039 were found to be improved from TY027, and their half lives were more than 6 h. Thus, basically, the introduction of disulfide bond is significantly effective for the prevention of metabolical degradation, and the substitution and chirality at the fifth residue of the compound derivatives might be crucial for the recognition by splitting enzymes. According to the result, it is interesting to clarify their three-dimensional structures for their conformation activity relationship as well as the key structure of splitting enzymatic recognition. Concentration of TY compounds in rat plasma after incubation at 37° C. is illustrated in FIGS. 16 and 36.

Example 15

Structure Activity Relationships

Example 15.1-15.6

Biological Activity

The biological activity was determined as in Examples 4.1-4.6.

Discussion.

The binding affinities at human NK1 receptor (hNK1) was evaluated as previously reported, by competition analysis using [³H]-Substance P as a radioligand on the cells which stably express the hNK1 receptors. Since the species difference between rat and human in NK1 receptor was generally known for many small molecule NK1 antagonists, the binding assay at rat NK1 (rNK1) receptor was also tested (Table 20).

TABLE 20

Binding affinities of bifunctional compound derivatives at δ/μ opioid receptors and NK1 receptors

| No | hDOR[a], [³H]DPDPE[b] LogIC$_{50}$[g] | K$_i$ (nM) | rMOR[a], [³H]DAMGO[c] LogIC$_{50}$[g] | K$^i$ (nM) | K$_i$(μ)/ K$_i$(δ) | hNK1[d], [³H] Substance P[e] LogIC$_{50}$[g] | K$_i$ (nM) | rNK1[d], [³H]Substance P[f] LogIC$_{50}$[g] | K$_i$ (nM) | K$_i$(hNK1)/ K$_i$(rNK1) |
|---|---|---|---|---|---|---|---|---|---|---|
| TY027 | −8.8 ± 0.07 | 0.66 | −7.4 ± 0.05 | 16 | 24 | −10.9 ± 0.10 | 0.0065 | −7.6 ± 0.03 | 7.3 | 1100 |
| TY035 | −8.6 ± 0.15 | 1.3 | −6.8 ± 0.09 | 79 | 61 | −9.7 ± 0.03 | 0.10 | −7.0 ± 0.09 | 30 | 30 |
| TY037 | −7.8 ± 0.11 | 7.8 | −6.9 ± 0.03 | 52 | 6.7 | −9.0 ± 0.02 | 0.52 | −6.9 ± 0.08 | 45 | 88 |
| TY038 | −6.9 ± 0.14 | 56 | −8.8 ± 0.40 | 160 | 2.9 | −9.3 ± 0.02 | 0.25 | −7.7 ± 0.09 | 7.1 | 28 |
| TY039 | −7.6 ± 0.16 | 11 | −6.4 ± 0.10 | 200 | 18 | −8.1 ± 0.04 | 3.7 | −5.8 ± 0.09 | 560 | 150 |
| Biphalin[h] | | 2.6 | | 1.4 | 0.54 | | | | | |
| L-732, 138 | | | | | | −8.8 +/− 0.02 | 0.73 | −6.4 ± 0.03 | 134 | 180 |

[a]Competition analyses were carried out using membrane preparations from transfected HN9.10 cells that constitutively expressed the δ and μ opioid receptors, respectively.
[b]K$_d$ = 0.45 ± 0.1 nM.
[c]K$_d$ = 0.50 ± 0.1 nM.
[d]Competition analyses were carried out using membrane preparations from transfected CHO cells that constitutively expressed rat or human NK1 receptors.
[e]K$_d$ = 0.16 ± 0.03 nM
[f]K$_d$ = 0.40 ± 0.17 nM
[g]Logarithmic values determined from the non-linear regression analysis of data collected from at least three independent experiments.
[h]reference (Thornton, Biochemistry, 1994, 33, 3532-3539).

The functional activities of the compound derivatives for substance P antagonist were determined by tissue bioassays using the guinea pig ileum (GPI) in the presence of naloxone (Table 21).

TABLE 21

Opioid agonist functional activities in [³⁵S]GTPγS binding assays

| No | hDOR[a] LogEC$_{50}$[b] | EC$_{50}$ (nM)[c] | Emax (%)[d] | rMOR[a] LogEC$_{50}$[b] | EC$_{50}$ (nM)[c] | Emax (%)[d] |
|---|---|---|---|---|---|---|
| TY027 | −8.1 ± 0.11 | 8.6 | 58 | −8.2 ± 0.17 | 7.0 | 55 |
| TY035 | −10.8 ± 0.51 | 0.020 | 11 | −7.4 ± 0.25 | 36 | 41 |
| TY037 | −7.9 ± 0.08 | 14 | 22 | −7.3 ± 0.59 | 53 | 12 |
| TY038 | −7.3 ± 0.12 | 51 | 87 | −7.7 ± 0.33 | 22 | 12 |
| TY039 | −9.0 ± 0.29 | 0.90 | 37 | −6.9 ± 0.51 | 118 | 17 |
| Biphalin | −9.0 ± 0.17 | 1.1 | 83 | | | |
| DPDPE | −8.8 ± 0.25 | 1.6 | 69 | | | |
| DAMGO | | | | −7.4 ± 0.19 | 37 | 150 |

[a]Expressed from HN9.10 cell.
[b]Logarithmic values determined from the non-linear regression analysis of data collected from at least three independent experiments.
[c]Anti-logarithmic value of the respective EC$_{50}$.
[d]Net total bound/basal binding × 100

At the hNK1 receptor, the binding affinities for the compound with the disulfide ring at residues 2-7 (K$_i$=0.10 for TY035 and 0.25 nM for TY038) were higher than those with the corresponding analogues with the ring at residues 2-5 (K$_i$=0.52 nM for TY37 and 3.7 nM for TY039). It is interesting that the disulfide rings of TY035 and TY038 exist close to Trp[8], which is the "message" residue for NK1 antagonist activity, their affinities at the hNK1 were more potent than those of TY037 and TY039 whose ring were apart from the NK1 pharmacophore. Among the synthesized cyclic compound derivatives TY035, TY037, TY038, and TY039 [D-Cys², Cys⁷]TY027 (TY035) showed the best affinity at hNK1 receptor with the potent subnanomolar K$_i$ value, although which was decreased from that of the linear compound TY027. In the case of the affinities for the rNK1 receptors, the derivatives with a ring at residues 2-7 also showed better affinities than those with the larger ring (residues 2-7), but all of their affinities were 28 to 150-fold lower than those at the hNK1 receptor. In the rNK1 assay result, L-Cys substitution was more preferable than D-Cys regardless of the ring size, and [D-Cys², D-Cys⁷]TY027 (TY38) showed the best (K$_i$=7.1 nM) and equipotent affinity to that of linear compound TY027. The activities using GPI showed different trend from these of radioligand binding assay on the cell membranes. First, TY035 and TY037 showed better activities (Ke=2.2 and 4.7 nM, respectively) than that of TY027, and the activity of TY038 (Ke=12 nM) can be considered as equipotent to TY027 whose K$_i$ values for hNK1 receptor were 15, 80 and 38 times better than those of TY035, TY037, and TY038, respectively. Among the tested cyclized compound derivatives, only TY039 showed particularly low affinities and activity at NK1 receptors. Interestingly, TY039 had characteristic physicochemical properties, difficult to solve into organic solvents and extraordinarily slow washout from the tested GPI tissues. Moreover, TY039 couldn't be dissolved in an aqueous media even with 40-fold amount of lipid-like surfactant, dodecylphosphocholine (DPC). From these observations, remarkably poor interaction property of TY039 with lipidic media was expected, and it might result in rather low affinities at the membrane-bind GPCR and functional activity in the tissue assay.

The binding affinities of the synthesized bifunctional compound derivatives for human δ-opioid receptors (hDOR) and rat μ-opioid receptors (rMOR) were evaluated using [$^3$H]-c[D-Pen$^2$, D-Pen$^5$]-enkephalin ([$^3$H]DPDPE) and [$^3$H]-[D-Ala$^2$, NMePhe$^4$, Gly$^5$-ol]-enkephalin ([$^3$H]DAMGO) as their corresponding radioligands, with the cells that stably express these receptors (Table 19). For the functional characterization of the compound derivatives at the opioid receptors, [$^{35}$S]GTPγS binding assay was used to examine their δ and μ opioid agonist efficacy (Table 20).

The tissue level functional assays were also performed to evaluate their opioid agonist activities in the GPI (δ) and Mouse Vas Deferens (MVD) (μ) (Table 22).

TABLE 22

Functional assay result for bifunctional compound derivative ligands at opioid and Substance P receptors

| No | Opioid agonist MVD (δ), IC$_{50}$ (nM)$^a$ | Opioid agonist GPI (μ), IC$_{50}$ (nM)$^a$ | Substance P GPI antagonist, Ke (nM)$^b$ |
|---|---|---|---|
| TY027 | 15 ± 2.0 | 490 ± 29 | 10 ± 2.1 |
| TY035 | 85 ± 18 | 1000 ± 200 | 2.2 ± 0.6 |
| TY037 | 8.3 ± 1.8 | 280 ± 39 | 4.7 ± 0.6 |
| TY038 | 19 ± 3.2 | 3% inh. at 1 uM$^d$ | 12 ± 1.4 |
| TY039$^c$ | 73 ± 4.2 | 10% inh. at 1 uM$^d$ | 430 ± 160 |
| Biphalin | 2.7 ± 1.5 | 8.8 ± 0.3 | |
| L-732, 138 | | | 250 ± 87 |

$^a$Concentration at 50% inhibition of muscle concentration at electrically stimulated isolated tissues.
$^b$Inhibitory activity against the Substance P induced muscle contraction in the presence of 1 μM naloxone, Ke: concentration of antagonist needed to inhibit Substance P to half its activity.
$^c$Unusually slow washout from tissue was observed.
$^d$No antagonist activity was observed at the tested concentration.

Contrary to the reported result of [D-Cys$^2$, D-Cys$^5$]enkephaliamide (DCDCE-NH$_2$) and [D-Cys$^2$, Cys$^5$]enkephaliamide (DCLCE-NH$_2$), both of which had slight t selectivity over δ receptor (Porreca, *J. Pharmacol. Exp. Ther.*, 1987, 241, 393-400; Porreca, *J. Pharmacol. Exp. Ther.*, 1984, 230, 341-348); Audigier, *Eur. J. Pharmacol.* 1980, 63, 35-46), the synthesized cyclic compound derivatives showed the TY035, TY037, TY038, and TY039 δ opioid selectivity, but the ratios were 3 to 60-fold and not so large as DPDPE and its analogues. The K$_i$ values for opioid receptors showed no relationships with the ring size as like seen in the results at NK1 receptors. Among the cyclized compounds TY035, TY037, TY038, and TY039, [D-Cys$^2$, Cys$^7$]TY027 (TY035) had the best affinity for the δ opioid receptor with moderate affinity at the μ opioid receptor (K$_i$=1.3 and 79 nM, respectively). While, [D-Cys$^2$, D-Cys$^5$]TY027 (TY037) was the best affinity for μ opioid receptor (K$_i$=52 nM) whose affinity at the δ opioid receptor was at the second best (K$_i$=7.8 nM). The affinities of [D-Cys$^2$, D-Cys$^7$]TY027 (TY038) for the δ and μ opioid receptors showed relatively lower than those of TY035 and TY037 (K$_i$=56 and 160 nM, respectively). TY039 also showed lower opioid affinities (K$_i$=11 and 200 nM, respectively). However, these radioligand binding assay results were not generally comparable with the result in the [$^{35}$S]GTPγS binding assay, mostly because of their low stimulation efficacy at both the δ and t opioid receptors (Table 20). Among them, only TY038 showed 87% stimulation at the δ opioid receptor, but the rest of the stimulations were less than 40%. Especially, the stimulation of TY035 at the δ opioid receptor and of TY037, TY038 and TY039 at the μ opioid receptor were observed to be pretty low as less than 20%. Because of these low partial agonist activities, TY038 and TY039 showed nearly no agonist effect as well as no antagonist activities in the functional assay using GPI at the concentration of 1 μM. Since they showed potent antagonist activities against substance P stimulation in the GPI tissue, and their metabolical stabilities were confirmed in rat plasma as described below (FIGS. 16 and 36), the observed "no effect" of TY038 and TY039 at the μ opioid receptor didn't come from their metabolical degradation, but simply from the weak stimulation at the corresponding receptor. Interestingly, the affinity of TY037 at the δ and μ opioid receptors were 12 and 3-fold lower than those of linear compound TY027, but their functional activities in the MVD and GPI assays (IC$_{50}$=8.3 and 280 nM, respectively) were higher than those of TY027. Similarly, the IC$_{50}$ value of TY038 in the MVD assay was 19 nM, which is nearly equivalent to that of TY027, though the affinity of TY038 at the δ opioid receptor was 85 times lower than that of TY027. TY039 also showed the extraordinarily slow washout from the MVD tissues as like seen in the GPI assay, and its IC$_{50}$ value in the MVD assay was 73 nM. Thus, it should be noted that the introduction of only D-Cys at residue 5 or 7 increased the functional activities in the assays based on the tissues. Consequently, TY038 was found as the selective δ opioid stimulator with the potent substance P antagonist activities in the tissues. NMR structure of TY037, TY035, and TY038 is presented on FIGS. 23 and 27. NMR structure of TY027 using paramagnetic agents is presented on FIG. 26.

Example 15.7

Biological Activity of Cyclic Compounds with Disulfide Bond using Pen

The biological activity was determined as in Examples 4.1-4.6.

TABLE 23

Biological activity of compounds

| | Affinity | | | | GTP binding hDOR | | GTP binding rMOR | |
|---|---|---|---|---|---|---|---|---|
| ID | hDOR (Ki; nM) | rMOR (Ki; nM) | hNK1 (Ki; nM) | rNK1 (Ki; nM) | EC$_{50}$ (nM) | Emax (%) | EC$_{50}$ (nM) | Emax (%) |
| TY047 | 152 | 1970 | 59 | 162.69 | N.T. | N.T. | 2910 | 15 |
| TY048 | N.T. | N.T. | 1.9 | 25.99 | N.T. | N.T. | N.T. | N.T. |
| TY046 | 1.7 | 2330 | 0.0053 | 10.33 | 17.3 | 15 | 28.8 | 14 |
| TY049 | N.T. | N.T. | 0.18 | 4.54 | N.T. | N.T. | N.T. | N.T. |

Concentration of cyclic compounds in rat plasma after incubation at 37° C. is illustrated in FIG. 47.

Example 16

Example 16.1

Synthesis of Glycosylated Compounds

Synthesis of glycosylated compounds was performed as shown on FIG. 6. Example 16.2. Biological activity. The biological activity was determined as in Examples 4.1-4.6.

TABLE 24

Biological activity of glycosylated compounds.

| | Affinity | | | | GTP binding | | | | MVD Opioid ($\delta$) | GPI/LMMP Opioid ($\mu$) | SP |
| --- | --- | --- | --- | --- | --- | --- | --- | --- | --- | --- | --- |
| | | | | | hDOR | | rMOR | | | | |
| ID | hDOR (Ki; nM) | rMOR (Ki; nM) | hNK1 (Ki; nM) | rNK1 (Ki; nM) | $EC_{50}$ (nM) | Emax (%) | $EC_{50}$ (nM) | Emax (%) | Agonist ($IC_{50}$; nM) | Agonist $IC_{50}$; nM) | Antagonist (Ke; nM) |
| TY045 | 1.0 | 32.0 | 0.0028 | 6.8 | 5.0 | 125 | 18.4 | 67 | 13.6 | 463 | 40.8 |
| TY042 | 58.5 | 256 | 0.00027 | 1.5 | 51.9 | 47 | 176 | 28 | 109 | 1891 | 2.83 |
| TY044 | 36.3 | 3370 | 1.3 | 23 | 50.9 | 162 | 380 | 85 | 18.0 | 249 | 18.4 |
| TY041 | 3.7 | 8.0 | 0.00077 | 14 | 7.9 | 62 | 18.0 | 42 | 12.7 | 517 | 1.80 |

TABLE 25

Biological activity of glycosylated compounds.

| | Affinity | | | | GTP binding | | | | MVD Opioid ($\delta$) | GPI/LMMP Opioid ($\mu$) | SP |
| --- | --- | --- | --- | --- | --- | --- | --- | --- | --- | --- | --- |
| | | | | | hDOR | | rMOR | | | | |
| ID | hDOR (Ki; nM) | rMOR (Ki; nM) | hNK1 (Ki; nM) | rNK1 (Ki; nM) | $EC_{50}$ (nM) | Emax (%) | $EC_{50}$ (nM) | Emax (%) | Agonist ($IC_{50}$; nM) | Agonist $IC_{50}$; nM) | Antagonist (Ke; nM) |
| TY041 | 3.7 | 8.0 | 0.00077 | 14 | 7.9 | 62 | 18.0 | 42 | 12.7 | 517 | 1.80 |
| TY055 | N.T. | 30 | 0.052 | 34 | N.T. | N.T. | N.T. | N.T. | N.T. | N.T. | N.T. |
| TY056 | N.T. | 1.9 | 0.0017 | 10 | N.T. | N.T. | 44.9 | 66 | N.T. | N.T. | N.T. |

Figure 48:
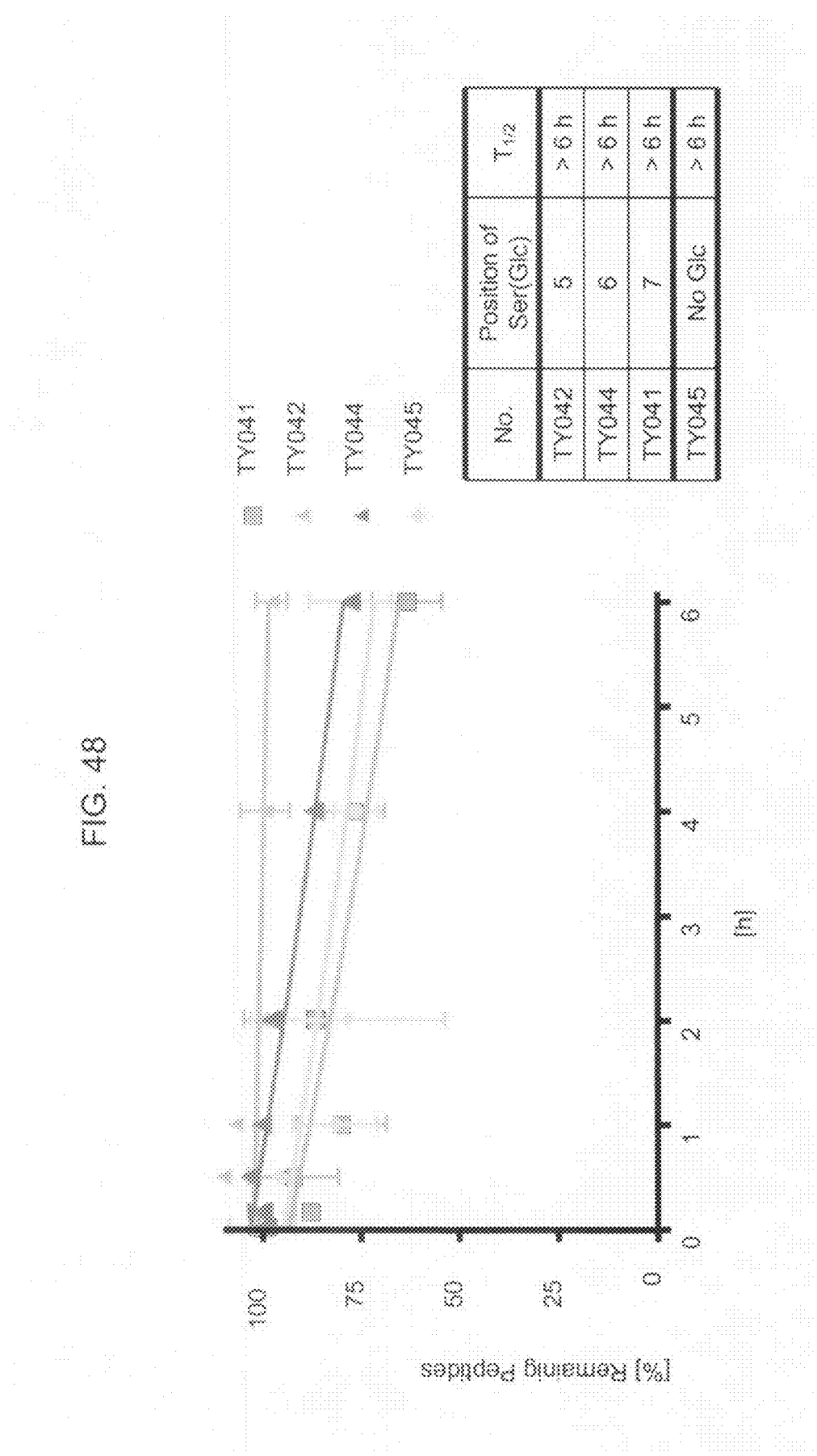
FIG. 48. Concentration of glycosylated compounds TY041, TY042, TY044, and TY045 in rat plasma after incubation at 37° C.

Concentration of glycosylated compounds in rat plasma after incubation at 37° C. is illustrated in FIG. 48-49.

Example 16.2

Solubility and Lipophilicity of Glycosylated Compounds

TABLE 26

| No. | Glycosylation | Solubility (µg/ml) | logD7.4 | AlogP |
| --- | --- | --- | --- | --- |
| TY045 | — | <1.0 | >3.0 | 5.64 |
| TY042 | Ser5(Glc) | 1.4 | 2.3 | 3.17 |
| TY044 | Ser6(Glc) | <1.0 | >2.7 | 3.50 |
| TY041 | Ser7(Glc) | <1.0 | >2.7 | 3.29 |
| TY055 | Leu7-Ser8(Glc) | N.T. | N.T. | 3.63 |
| TY056 | Ser7(Glc) | N.T. | N.T. | 3.48 |

Example 16.3

NMR structure of the glycosylated compounds in DCP micelle (FIGS. 23 and 28) was obtained as described in Example 13. NMR, CD, and fluorescent data were obtained as described in Example 13 (FIGS. 24-25 and 29).

Example 17

Optimization of a Linker Amino Acid of Linear Compounds

H-Tyr-DAla-Gly-Phe-Xxx-Pro-Leu-Trp-O-3,5-Bzl(CF3)2

TABLE 27

Biological activity of compounds.

| | | Affinity | | | GTP binding | | | |
| | | | | | hDOR | | rMOR | |
| ID | Xxx | hDOR (Ki; nM) | rMOR (Ki; nM) | rNK1 (IC$_{50}$; nM) | EC$_{50}$ (nM) | Emax (%) | EC$_{50}$ (nM) | Emax (%) |
|---|---|---|---|---|---|---|---|---|
| TY001 | — | 50.4 | 180 | 21.7 | 35.0 | 16.0 | 143 | 26.4 |
| TY003 | Phe | 14.6 | 28.3 | 19.3 | 20.8 | 39.0 | 58.7 | 36.3 |
| TY007 | DPhe | 110 | 410 | 66.7 | 16.7 | 22.9 | 345 | 23.6 |
| TY006 | Gly | 36.1 | 27.0 | 15.6 | 50.2 | 33.6 | 41.7 | 35.9 |
| TY004 | Leu | 5.0 | 23.3 | 20.9 | 9.6 | 42.5 | 39.8 | 44.5 |
| TY005 | Met | 2.8 | 36.3 | 6.4 | 2.9 | 47.6 | 31.6 | 45.6 |
| TY018 | Nle | 1.8 | 9.8 | 14.8 | 4.0 | 131 | 27.6 | 121 |
| TY023 | Met(O) | 5.1 | 5.5 | 54.5 | 1.8 | 52.8 | 33.8 | 55.2 |
| TY019 | N-Me-Nle | 77.1 | 137 | 135 | 364 | 283 | 150 | 114 |

TABLE 28

Biological activity of compounds.

| | | MVD | GPI/LMMP | | |
| | | Opioid (d) | Opioid(m) | SP | |
| ID | Xxx | Agonist (IC50; nM) | Agonist (IC50; nM) | Agonist (IC50; nM) | Antagonist (Ke; nM) |
|---|---|---|---|---|---|
| TY001 | — | 399.0 | 518.7 | None | 3.6 |
| TY003 | Phe | 905.3 | 7% inh. at 1 mM | None | 14.4 |
| TY007 | DPhe | 412.1 | 9% inh. at 1 mM | None | 69.6 |
| TY006 | Gly | 171.6 | 383.7 | None | 5.4 |
| TY004 | Leu | 101.2 | 340.7 | None | 19.4 |
| TY005 | Met | 22.3 | 358.8 | None | 24.7 |
| TY018 | Nle | 16.8 | 372.0 | None | 7.9 |
| TY023 | Met(O) | 33.0 | 154.0 | N.T. | 7.8 |
| TY019 | N-Me-Nle | 187.9 | 12% inh. at 1 mM | 2% inh. at 1 mM | 4.6 |

Example 18

Introduction of Dmt into the Compounds Instead of Tyr

Example 18.1

Biological Activity of Compounds

TABLE 29

H-Xxx-DAla-Gly-Phe-Met-Pro-Leu-Trp-R

| | | | Affinity | | | |
| ID | Xxx | R | hDOR (Ki; nM) | rMOR (Ki; nM) | hNK1 (Ki; nM) | rNK1 (Ki; nM) |
|---|---|---|---|---|---|---|
| TY005 | Tyr | O-3,5-Bn(CF3)2 | 2.8 | 36.3 | 0.082 | 0.20 |
| TY027 | Tyr | NH-3,5-Bn(CF3)2 | 0.66 | 15.7 | 0.0064 | 7.27 |
| TY025 | Tyr | NH-Bn | 0.44 | 1.80 | 3.1 | 695.7 |
| TY033 | Dmt | O-3,5-Bn(CF3)2 | 0.22 | 1.2 | 1.2 | 0.96 |
| TY032 | Dmt | NH-3,5-Bn(CF3)2 | 0.12 | 2.0 | 0.0079 | 2.30 |
| TY034 | Dmt | NH-Bn | 0.10 | 0.14 | 2.4 | 317.0 |

TABLE 30

H-Xxx-DAla-Gly-Phe-Met-Pro-Leu-Trp-R

| | | | MVD | GPI/LMMP | | |
|---|---|---|---|---|---|---|
| | | | Opioid (d) | Opioid(m) | Substance P | |
| ID | Xxx | R | Agonist (IC50; nM) | Agonist (IC50; nM) | Agonist (IC50; nM) | Antagonist (Ke; nM) |
| TY005 | Tyr | O-3,5-Bn(CF3)2 | 22.3 | 358.8 | None | 24.7 |
| TY027 | Tyr | NH-3,5-Bn(CF3)2 | 14.5 | 487.9 | None | 10.0 |
| TY025 | Tyr | NH-Bn | 4.8 | 61.1 | None | 9.9 |
| TY033 | Dmt | O-3,5-Bn(CF3)2 | 1.3 | 100.5 | None | 24.5 |
| TY032 | Dmt | NH-3,5-Bn(CF3)2 | 1.8 | 18.6 | None | 7.5 |
| TY034 | Dmt | NH-Bn | 6.9 | 11.4 | None | 36.9 |

TABLE 31

H-Dmt-DAla-Gly-Phe-Xxx-Pro-Leu-Trp-R

| | | | Affinity | | | |
|---|---|---|---|---|---|---|
| ID | Xxx | R | hDOR (Ki; nM) | rMOR (Ki; nM) | hNK1 (Ki; nM) | rNK1 (Ki; nM) |
| TY032 | Met | NH-3,5-Bn(CF3)2 | 0.12 | 2.0 | 0.0079 | 2.30 |
| TY050 | Nle | NH-3,5-Bn(CF3)2 | N.T. | N.T. | 0.075 | 13.0 |
| TY052 | Nle | NMe-3,5-Bn(CF3)2 | 0.46 | 1.77 | 0.21 | 11.1 |
| TY053 | Nle | NH-3-Bn(CF3) | N.T. | 0.74 | 1.04 | 138 |
| TY054 | Nle | NH-3,5-Bn(OMe)2 | 0.15 | 0.34 | 0.95 | 318 |

Example 18.2

Figure 21A:
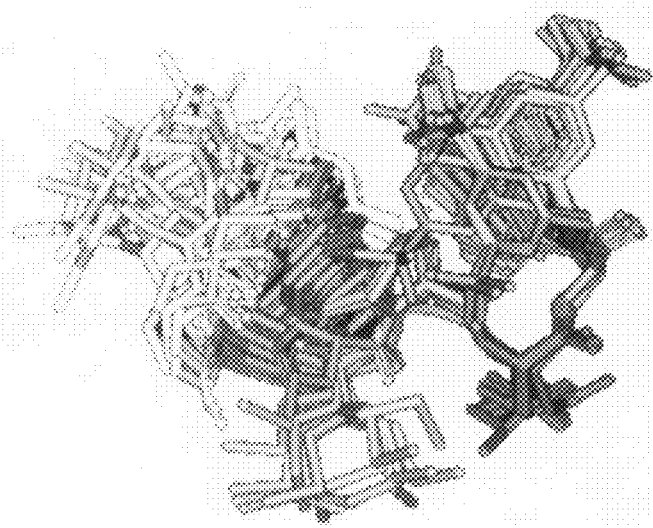
FIG. 21 A, B. NMR structure of TY032 (A) and TY037 (B).
Figure 21B:
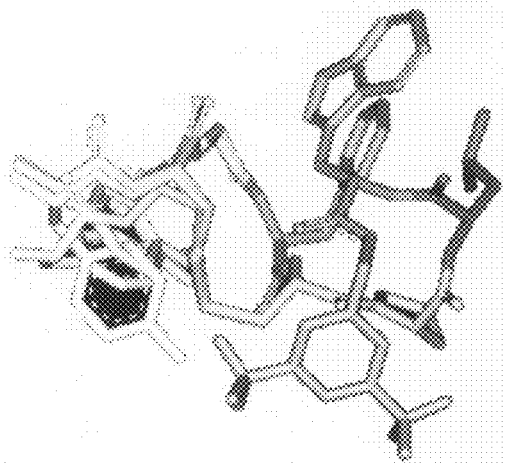
Figure 22B:
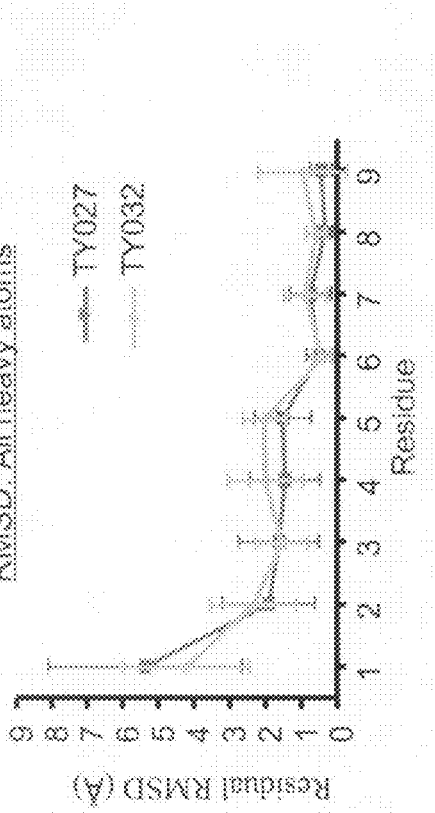
FIG. 22 A-D. Comparison of structural rigidity of TY027 and TY032 (A-B) and CD spectra (D).
Figure 22A:
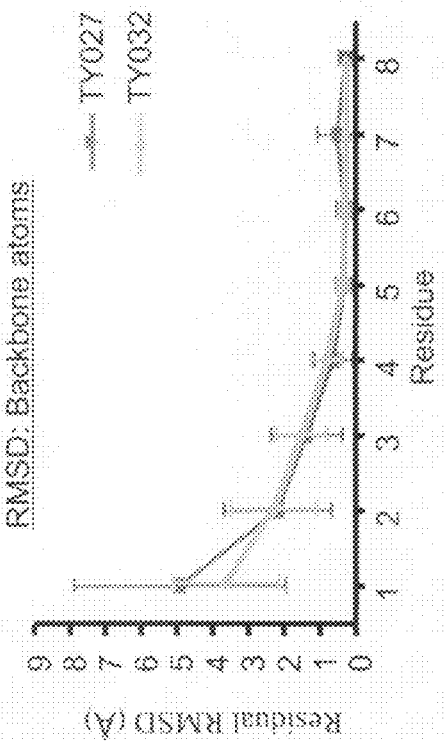
Figure 22C:
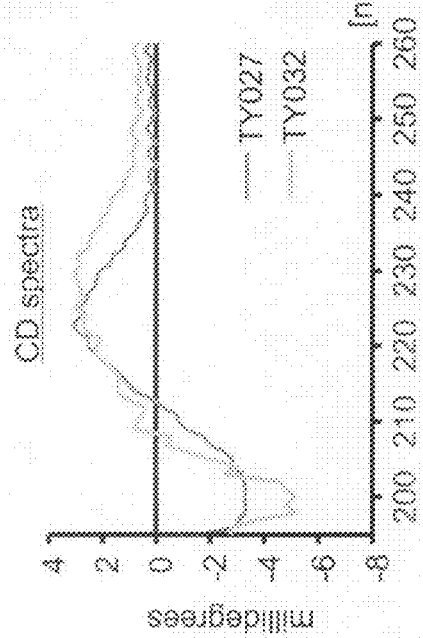
Figure 22D:
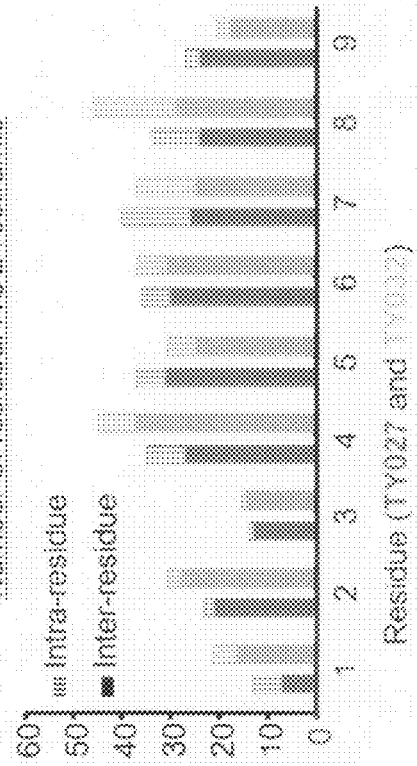
Figure 23C:
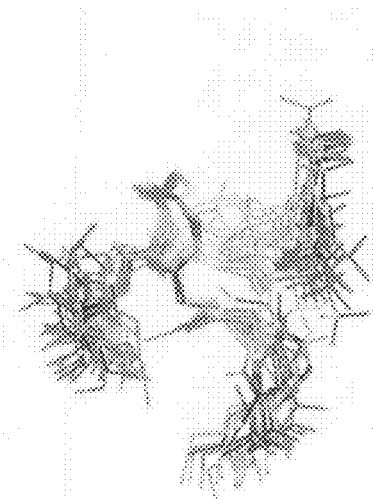
FIG. 23 A-C. NMR structure of TY041 (C), TY042 (A), and TY044 (B) in DPC micelle.
Figure 23B:
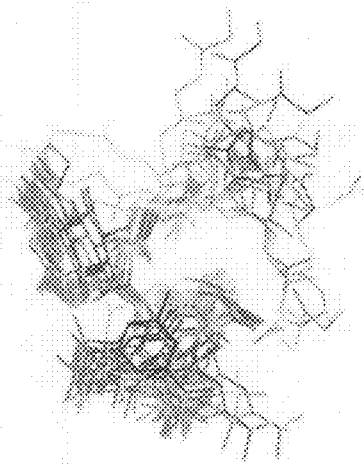
Figure 23A:
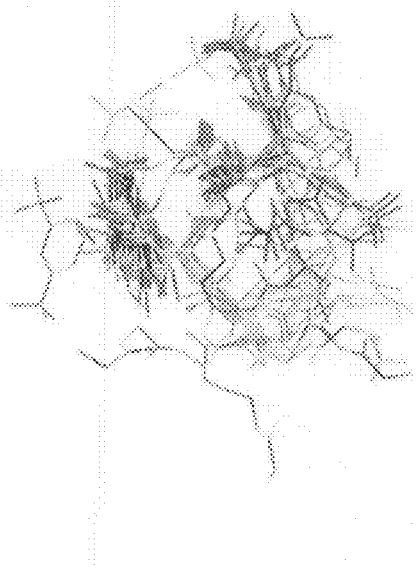
Figure 24A:
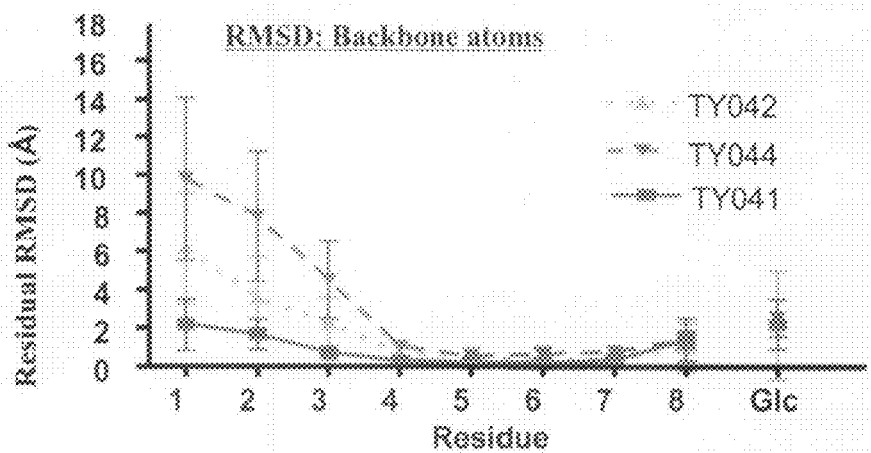
FIG. 24 A-D. Comparison of structural rigidity of TY041, TY042, and TY044 (A-B) and CD spectra (D).
Figure 24B:
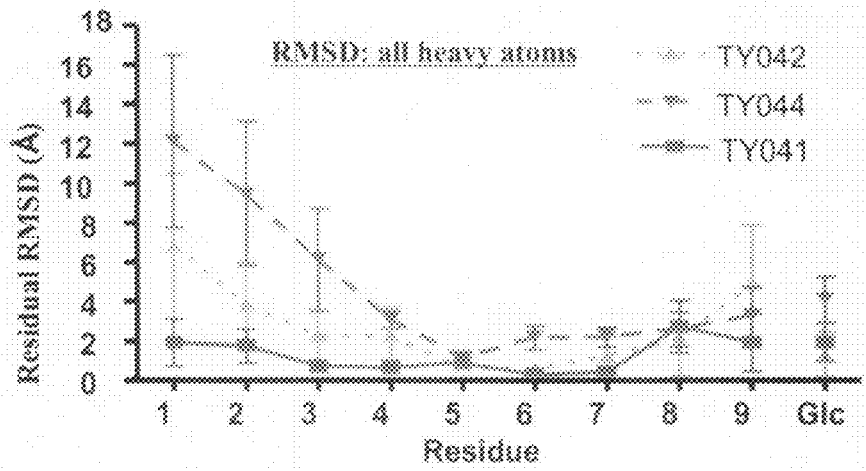
Figure 24C:
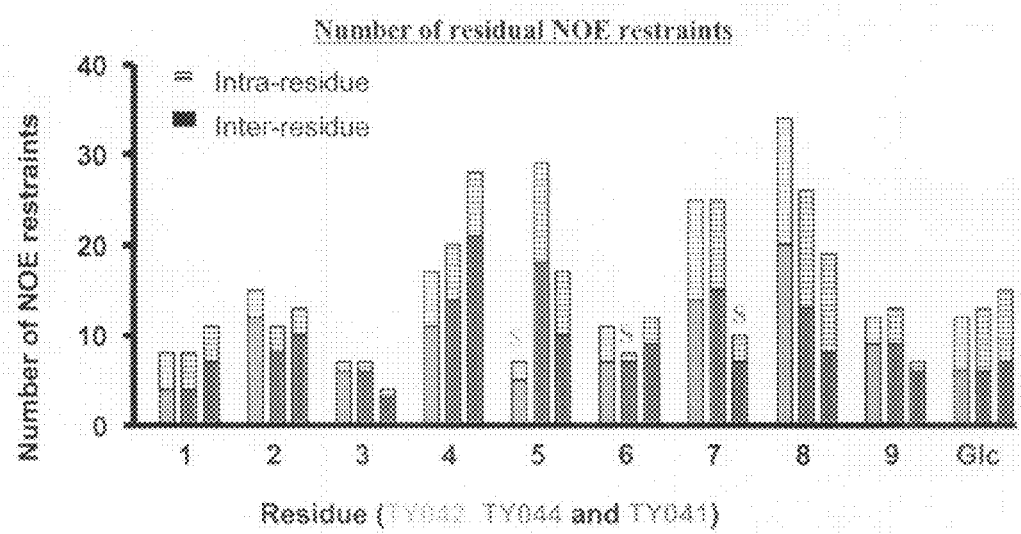
Figure 24D:
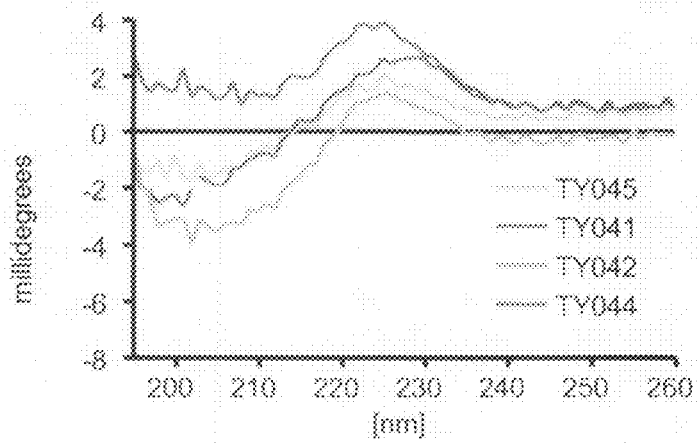

NMR Structure of TY032 and Rigidity Data are Presented on FIGS. 21-22

Example 19

Brain Distribution of TY Compounds In Situ Perfusion Model

Figure 20:
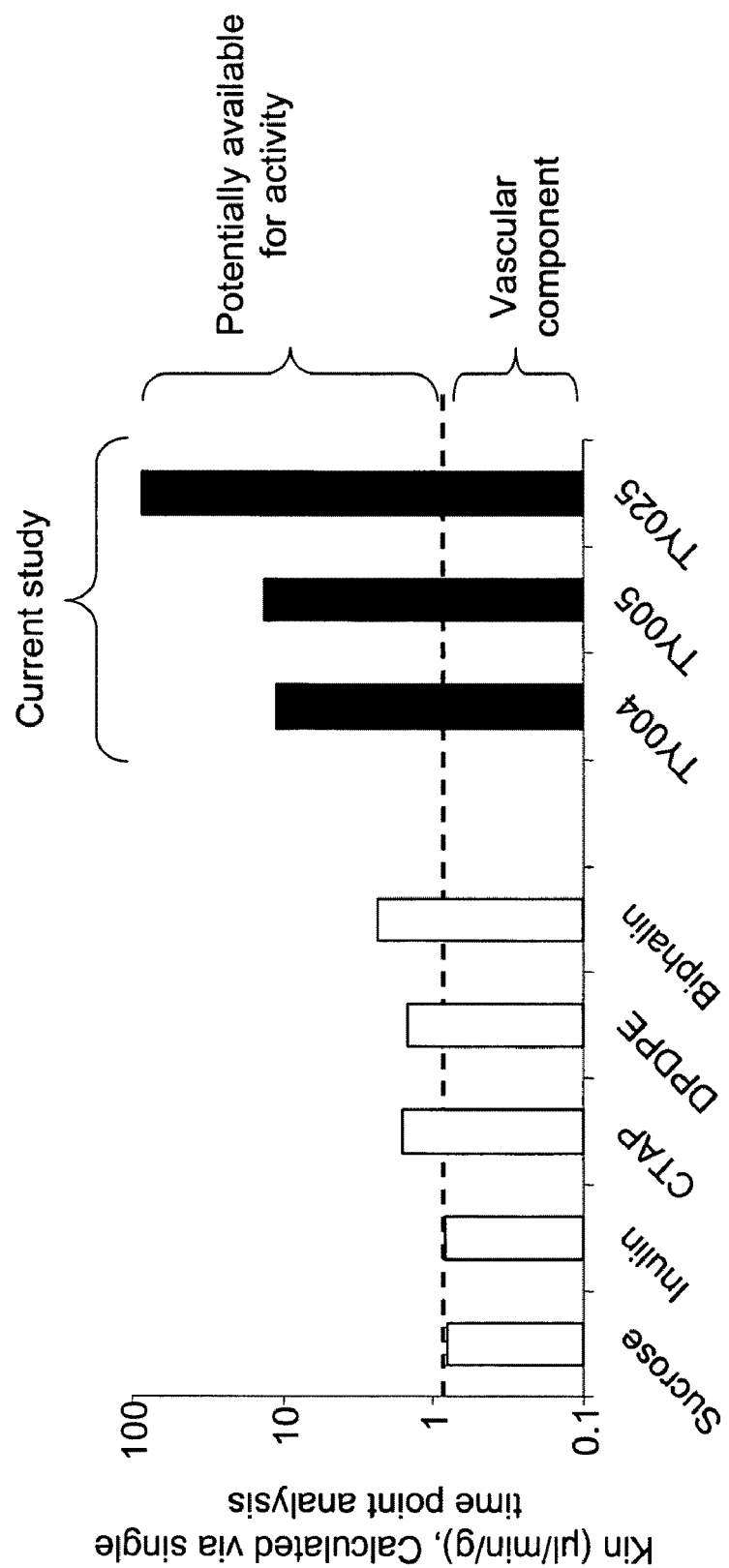
FIG. 20. Brain distribution using in situ perfusion technique for TY004, TY005 and TY025.

TY004, TY005, and TY025 penetrate blood brain barrier as presented at FIG. 20.

Example 20

Synthesis and Biological Activity of NP Compounds

Example 20.1

Synthesis of the Compounds is Illustrated at FIG. 30

Example 20.2

Binding Assay Data for NP Compounds. The biological activity was determined as shown in Examples 4.1-4.6.

TABLE 32

Optimization of a linker - biological activity of the NP compounds. Tyr-DAla-Gly-Phe-Linker-Trp-O-Bzl(CF3)2

| | | Affinity (Ki, nM) | | | | GTP | | | |
|---|---|---|---|---|---|---|---|---|---|
| | | | | | | hDOR EC50 | | rMOR EC50 | |
| Compound | Linker | hDOR | rMOR | rNK1 | hNK1 | EMax | | EMax | |
| NP30 | Gly | 4.7 | 0.29 | 4.2 | 0.0057 | 27.0 | 87 | 10.0 | 36 |
| NP31 | Ala | 1.2 | 3.6 | 8.6 | nd | 3.3 | 91 | 11.0 | 50 |
| NP32 | β-Ala | 58 | 11.2 | 1.6 | nd | 160.0 | 87 | 59 | 70 |
| NP33 | α-Abu | 1.6 | 11.4 | 1.2 | 0.12 | 2.9 | 43 | 8.6 | 32 |
| NP34 | γ-Abu | 25.4 | 2.2 | 7.4 | 0.001 | 16.5 | 40 | 17.4 | 27 |
| NP37 | Leu | 2.9 | 23.3 | 0.29 | 0.090 | 4.8 | 60 | 14.0 | 54 |
| NP38 | Met | 0.60 | 3.3 | 0.089 | 0.009 | 1.1 | 36 | 0.80 | 51 |
| NP39 | Pro | 5.7 | 14.8 | 1.6 | 0.10 | 75.5 | 56 | 36.6 | 47 |
| NP40 | D-Ala | 3.9 | 2.8 | 2.4 | 0.011 | 71.3 | 89 | 93.1 | 19 |
| NP41 | Aib | 24.2 | 13.3 | 3.4 | 0.008 | 37.7 | 65 | 105 | 36 |

TABLE 33

Binding assay.

| Cpds | Compound sequence | Ki (nM) hDOR | Ki (nM) rMOR | Ki (nM) rNK1 | Ki (nM) hNK1 | GTP EC50 (nM) hDOR | GTP EC50 (nM) rMOR |
|---|---|---|---|---|---|---|---|
| NP36 | Tyr-D-Ala-Gly-Phe-Trp-O-3',5'(CF3)2-Bzl | 34.8 | 36.7 | 0.15 | 0.0005 | 151 | 101 |
| NP42 | Tyr-Gly-Trp-O-3',5'(CF3)2-Bzl | nd | nd | 0.36 | 0.003 | nd | nd |
| NP43 | Tyr-D-Ala-Trp-O-3',5'(CF3)2-Bzl | 100 | 178 | 2.94 | 0.004 | 90.9 | 168 |
| NP44 | Tyr-D-Ala-Gly-Trp-O-3',5'(CF3)2-Bzl | 306 | 48.5 | 3.4 | 0.03 | 280 | 22.9 |
| NP48 | DMT-D-Ala-Trp-O-3',5'(CF3)2-Bzl | 0.8 | 0.3 | 0.28 | 0.016 | 11.5 | 1.6 |
| NP52 | Tyr-D-Ala-Gly-pClPhe-O-3',5'(CF3)2-Bzl | 42.5 | 15.7 | 136.6 | 8.04 | 29.0 | 43.1 |
| NP62 | Tyr-D-Ala-Gly-pFPhe-O-3',5'(CF3)2-Bzl | nd | 3.2 | nd | 0.20 | nd | nd |

TABLE 34

Binding assay.
Trp-DAla-Gly-X-Gly-Trp-O-Bzl(CF3)2

| Cpds | X | KI (nM) hDOR | KI (nM) rMOR | KI (nM) rNK1 | KI (nM) hNK1 | GTP EC50 (nM) hDOR | GTP EC50 (nM) rMOR |
|---|---|---|---|---|---|---|---|
| NP45 | pFPhe | 4.5 | 0.05 | 0.042 | 0.004 | 3.4 | 5.5 |
| NP46 | pClPhe | 11.2 | 0.20 | 4.85 | 0.47 | 25.1 | 16.2 |
| NP47 | pBrPhe | nd | nd | nd | 0.57 | nd | nd |

TABLE 35

Functional assay - linker variations.
Tyr-DAla-Gly-Phe-Linker-Trp-O-Bzl(OF3)2

| Compound | Linker | MVD δ-agonist IC50 (nM) | GPI/LMMP μ-agonist IC50 (nM) | GPI/LMMP SP agonist IC50 (nM) | GPI/LMMP SP antagonist Ke (nM) |
|---|---|---|---|---|---|
| NP30 | Gly | 20.9 | 25.7 | — | 58.9 |
| NP31 | Ala | 6.4 | 401 | — | 18.6 |
| NP32 | β-Ala | 12.6 | 434.9 | — | 250 |
| NP33 | α-Abu | 12.4 | 600 | — | 5.6 |
| NP34 | γ-Abu | 67.9 | 200 | — | 0.96 |
| NP37 | Leu | 25.7 | 45..4 | — | nd |
| NP38 | Met | 9.07 | 393.4 | — | 2.0 |
| NP39 | Pro | 84.6 | 258.7 | — | 1.8 |
| NP40 | D-Ala | 58.0 | 528.2 | — | 608 |
| NP41 | Aib | 36.2 | nd | — | nd |

TABLE 36

Functional assay.

| Cpds | Compound sequence | MVD δ-agonist IC50 (nM) | GPI μ-agonist IC50 (nM) | GPI SP-antagonist Ke (nM) |
|---|---|---|---|---|
| NP36 | Tyr-D-Ala-Gly-Phe-Trp-O-3',5'(CF3)2-Bzl | 43.14 | 522.8 | 38 |
| NP42 | Tyr-Gly-Trp-O-3',5'(CF3)2-Bzl | 7.5% at 1 μM | 2.6% at 1 μM | None @ 1 μM |
| NP43 | Tyr-D-Ala-Trp-O-3',5'(CF3)2-Bzl | 5.5% at 1 μM | 3.3% at 1 μM | 49.4 |
| NP44 | Tyr-D-Ala-Gly-Trp-O-3',5'(CF3)2-Bzl | 302.7 | 844.4 | 5 |
| NP48 | DMT-D-Ala-Trp-O-3',5'(CF3)2-Bzl | 408 | 20.4% at 1 μM | nd |
| NP62 | Tyr-D-Ala-Gly-pFPhe-O-3',5'(CF3)2-Bzl | 183.6 | 207.6 | 51.8 |

TABLE 37

Functional assay.
Tyr-DAla-Gly-Phe-Linker-Trp-O-Bzl(CF3)2

| Cpds | Linker | MVD δ-agonist IC50 (nM) | GPI μ-agonist IC50 (nM) | SP-antagonist Ke (nM) |
|---|---|---|---|---|
| NP45 | pFPhe | 9.5 | 60.01 | 10.3 |
| NP46 | pClPhe | 33.1 | 123.6 | 30.0 |
| NP47 | pBrPhe | nd | nd | nd |

TABLE 38

ALogP values of selected ligands.

| Cpd | Mol Wt. | ALogP |
|---|---|---|
| NP30 | 925.8 | 4.38 |
| NP38 | 1000.2 | 5.04 |
| NP45 | 943.8 | 4.42 |
| NP48 | 692.6 | 4.65 |
| NP62 | 700.6 | 3.80 |

TABLE 39

Summary of the compounds: an amino acid sequence and biological activity.

| ID | Compound | Affinity hDOR (Ki; nM) | rMOR (Ki; nM) | hNK1 (Ki; nM) | rNK1 (Ki; nM) | GTP binding hDOR (nM, %) EC$_{50}$ | Emax |
|---|---|---|---|---|---|---|---|
| TY001 | TyrDAlaGlyPheProLeuTrpOBn(CF3)2 | 50.4 +/− 0.8 | 180 | 0.0023 | 1.56 | 35.0 +/− 34.5 | 16.0 +/− 0.7 |
| TY003 | TyrDAlaGlyPhePheProLeuTrpOBn(CF3)2 | 14.6 +/− 10.7 | 28.3 +/− 4.9 | 0.021 | 0.88 | 20.8 +/− 1.2 | 39.0 +/− 4.3 |
| TY004 | TyrDAlaGlyPheLeuProLeuTrpOBn(CF3)2 | 5.0 +/− 1.5 | 23.3 +/− 5.0 | 0.016 | 0.80 | 9.6 +/− 6.8 | 42.5 +/− 1.8 |
| TY005 | TyrDAlaGlyPheMetProLeuTrpOBn(CF3)2 | 2.8 +/− 1.1 | 36.3 +/− 11.3 | 0.082 | 0.29 | 2.9 +/− 1.1 | 47.6 +/− 4.5 |
| TY006 | TyrDAlaGlyPheGlyProLeuTrpOBn(CF3)2 | 36.1 +/− 3.9 | 27.0 +/− 0.1 | 0.016 | 1.00 | 50.2 +/− 18.1 | 33.6 +/− 3.9 |
| TY007 | TyrDAlaGlyPheDPheProLeuTrpOBn(CF3)2 | 110 +/− 25.1 | 410 +/− 16.3 | 1.3 | 3.00 | 16.7 | 22.9 |
| TY008 | TyrDAlaGlyPheProLeuTrpNHBn | 10.3 +/− 4.5 | 0.6 +/− 0.1 | 14 | 803.24 | 17 | 56 |
| TY010 | TyrDAlaGlyPheProLeuTrpNMeBn | 77.1 +/− 16.7 | 46.2 +/− 56.5 | 100.1 | 266.59 | 152 | 70 |
| TY011 | TyrDAlaGlyPheProLeuTrpOBn | 31.3 +/− 0.2 | 28.5 +/− 5.4 | 2 | 658.94 | 84.5 | 140 |
| TY012 | TyrDAlaGlyPheProLeuTrpNHBn(CF3)2 | 71.70 | 9.5 +/− 25.2 | 0.61 | 32.57 | 80 | 162 |
| TY013 | TyrDAlaGlyPheProLeuTrpNMeBn(CF3)2 | 31.2 +/− 0.8 | 6.8 +/− 5.0 | 1.4 | 6.05 | 121 | 136 |
| TY014 | TyrDAlaGlyPhePheProLeuTrpOBn | 11.5 | 36.3 | 0.265 | 124.31 | 25.6 | 137 |
| TY015 | TyrDAlaGlyPhePheProLeuTrpNHBn(CF3)2 | 12.5 | 53.7 | 0.192 | 0.98 | 81.4 | 142 |
| TY017 | TyrDAlaGlyPhePheProLeuTrpNMeBn(CF3)2 | 26.5 | 74.7 | 0.213 | 0.57 | 122 | 125 |
| TY018 | TyrDAlaGlyPheNleProLeuTrpOBn(CF3)2 | 1.8 | 9.8 | 0.14 | 0.60 | 4.0 | 131 |
| TY019 | TyrDAlaGlyPheNle(NMe)ProLeuTrpOBn(CF3)2 | 77.1 | 137 | 0.82 | 0.71 | 364 | 283 |
| TY020 | TyrDAlaGlyPheMetAlaLeuTrpOBn(CF3)2 | 24.8 | 151 | 0.034 | 1.11 | 2.5 | 26.4 |
| TY021 | TyrDAlaGlyPheMetCLeuLeuTrpOBn(CF3)2 | 5.0 | 112 | 0.066 | 7.75 | 0.26 | 41.1 |
| TY022 | TyrDAlaGlyPheMetAibLeuTrpOBn(CF3)2 | 3.1 | 62.6 | 0.118 | 9.78 | 5.5 | 28 |
| TY023 | TyrDAlaGlyPheMet(O)ProLeuTrpOBn(CF3)2 | 5.08 | 5.50 | 0.00015 | 0.20 | 1.8 | 52.8 |
| TY024 | TyrDAlaGlyPheMetDProLeuTrpOBn(CF3)2 | 13.2 | 76.8 | 0.877 | 3.57 | 190 | 21 |
| TY025 | TyrDAlaGlyPheMetProLeuTrpNHBn | 0.44 | 1.80 | 3.13 | 695.68 | 2.6 | 51.7 |
| TY026 | TyrDAlaGlyPheMetProLeuTrpNMeBn | 0.32 | 2.08 | 0.001 | 44.51 | 8.9 | 93 |
| TY027 | TyrDAlaGlyPheMetProLeuTrpNHBn(CF3)2 | 0.66 | 15.7 | 0.0064 | 7.27 | 8.6 | 58 |
| TY028 | TyrDAlaGlyPheMetProLeuTrpNMeBn(CF3)2 | 2.15 | 23.8 | 0.111 | 2.01 | 12.9 | 59 |
| TY029 | TyrDAlaGlyPheMetProLeuTrpOBn | 1.3 | 16.0 | 2.187 | 20.27 | 3.4 | 98 |
| TY030 | TyrDAlaGlyPheMetProLeuTrpOBn(OMe)2 | 0.93 | 6.87 | 0.668 | 9.53 | 0.8 | 61 |

TABLE 39-continued

Summary of the compounds: an amino acid sequence and biological activity.

| ID | Sequence | | | | | | |
|---|---|---|---|---|---|---|---|
| TY031 | TyrDCysGlyPheMetProLeuTrpOBn(CF3)2 | 55.4 | 172 | 0.847 | 7.06 | 4.6 | 18 |
| TY032 | DmtDAlaGlyPheMetProLeuTrpNHBn(CF3)2 | 0.12 | 2.0 | 0.008 | 2.30 | 1.2 | 24 |
| TY033 | DmtDAlaGlyPheMetProLeuTrpOBn(CF3)2 | 0.22 | 1.2 | 1.204 | 0.96 | 0.73 | 200 |
| TY034 | DmtDAlaGlyPheMetProLeuTrpNHBn | 0.1 | 0.14 | 2.391 | 317.03 | 0.3 | 21 |
| TY035 | Tyr[DCysGlyPheNleProCys]TrpNHBn(CF3)2 | 1.29 | 79.2 | 0.091 | 29.99 | 0.02 | 11 |
| TY036 | MetProLeuTrpOBn(CF3)2 (SEQ ID NO: 6) | 1280 | 4550 | 0.000 | 0.99 | | |
| TY037 | Tyr[DCysGlyPheDCys]ProLeuTrpNHBn(CF3)2 | 7.8 | 51.5 | 0.49 | 45.48 | 98.2 | 26 |
| TY038 | Tyr[DCysGlyPheNleProDCys]TrpNHBn(CF3)2 | 55.5 | 156 | 0.24 | 7.11 | 14 | 87 |
| TY039 | Tyr[DCysGlyPheCys]ProLeuTrpNHBn(CF3)2 | 10.7 | 201 | 3.5 | 556 | 50.9 | 37 |
| TY040 | TyrDAlaGlyPheMetNH2 | 0.66 | 0.5 | 145 | 1096 | 0.9 | 7 |
| TY041 | TyrDAlaGlyPheNleProSer(OGlu)TrpNHBn(CF3)2 | 3.7 | 8.0 | 0.00077 | 13.61 | 7.9 | 62 |
| TY042 | TyrDAlaGlyPheSer(OGlu)ProLeuTrpNHBn(CF3)2 | 58.5 | 256 | 0.00027 | 1.45 | 51.9 | 47 |
| TY043 | TyrDAlaGlyPheMetProLeuTrpOH | 1.1 | 14.2 | 3212 | 9854 | 0.51 | 62 |
| TY044 | TyrDAlaGlyPheNleSer(OGlu)LeuTrpNHBn(CF3)2 | 36.3 | 3370 | 1.3 | 23.46 | 50.9 | 162 |
| TY045 | TyrDAlaGlyPheNleProLeuTrpNHBn(CF3)2 | 1.0 | 32 | 0.0028 | 6.81 | 5 | 125 |
| TY046 | Tyr[DPenGlyPhePen]ProLeuTrpNHBn(CF3)2 | 1.7 | 2330 | 0.0053 | 10.33 | 17.2 | 15 |
| TY047 | Tyr[DPenGlyPheNleProPen]TrpNHBn(CF3)2 | 152 | 1970 | 59 | 162.69 | | |
| TY048 | Tyr[DPenGlyPheNleProDPen]TrpNHBn(CF3)2 | | 998 | 1.9 | 25.99 | | |
| TY049 | Tyr[DPenGlyPheDPen]ProLeuTrpNHBn(CF3)2 | | 2050 | 0.18 | 4.54 | | |
| TY050 | DmtDAlaGlyPheNleProLeuTrpNHBn(CF3)2 | 11.4 | 1.23 | 0.075 | 13.02 | | |
| TY051 | MetProLeuTrpNHBn(CF3)2 | | 866 | 0.922 | 62.01 | | |
| TY052 | DmtDAlaGlyPheNleProLeuTrpNMeBn(CF3)2 | 0.46 | 1.77 | 0.21 | 11.10 | | |
| TY053 | DmtDAlaGlyPheNleProLeuTrpNHBn-3-(CF3) | 4.1 | 0.74 | 1.042 | 137.85 | | |
| TY054 | DmtDAlaGlyPheNleProLeuTrpNHBn-2,4-(OMe)2 | 0.15 | 0.34 | 0.952 | 318.47 | | |
| TY055 | TyrDAlaGlyPheNleProLeuSer(OGlu)TrpNHBn(CF3)2 | | 30 | 0.052 | 33.93 | | |
| TY056 | DmtDAlaGlyPheNleProSer(OGlu)TrpNHBn(CF3)2 | | 1.9 | 0.0017 | 10.07 | | |

| | GTP binding | | MVD opioid(delta) | | GPI/LMMP opioid(mu) | | SP | |
|---|---|---|---|---|---|---|---|---|
| | rMOR(nM, %) | | agonist | | agonist | | Agonist | antagonist |
| ID | $EC_{50}$ | Emax | ($IC_{50}$; nM) | Antagonist | ($IC_{50}$; nM) | Antagonist | ($IC_{50}$; nM) | (Ke; nM) |
| TY001 | 143 +/− 31.5 | 26.4 +/− 5.0 | 399.0 +/− 23.4 | | 518.7 +/− 40.0 | | none | 3.64 +/− 1.08 |
| TY003 | 58.7 +/− 57.1 | 36.3 +/− 6.2 | 905.3 +/− 186.2 | | 6.6% @ 1 uM | none | none | 14.40 +/− 4.87 |
| TY004 | 39.8 +/− 20.4 | 44.5 +/− 1.5 | 101.2 +/− 25.3 | | 340.7 +/− 71.2 | | none | 19.43 +/− 4.96 |
| TY005 | 31.6 +/− 3.4 | 45.6 +/− 1.9 | 22.34 +/− 1.22 | | 358.8 +/− 126.7 | | none | 24.69 +/− 8.79 |
| TY006 | 41.7 +/− 31.7 | 35.9 +/− 5.6 | 171.6 +/− 25.5 | | 383.7 +/− 28.2 | | none | 5.40 +/− 1.40 |
| TY007 | 345 | 23.6 | 412.1 +/− 106.1 | | 9.20% | | none | 69.6 +/− 7.1 |
| TY008 | 0.7 | 104 | 49.74 +/− 10.36 | | 13.04 +/− 3.27 | | none | 26.1 +/− 3.90 |
| TY010 | 20.2 | 120 | 40.96 +/− 8.60 | | 9.045 +/− 0.452 | | none at 100 nM | 59.2 +/− 17.9 |
| TY011 | 36.2 | 66.1 | 39.48 +/− 4.41 | | 74.34 +/− 25.07 | | none at 100 nM | 156 +/− 17 |
| TY012 | 57.3 | 61.4 | 45.19 +/− 6.30 | | 350.5 +/− 91.1 | | none at 100 nM | 8.48 +/− 2.10 |

TABLE 39-continued

Summary of the compounds: an amino acid sequence and biological activity.

| | | | | | | | |
|---|---|---|---|---|---|---|---|
| TY013 | 72 | 68.2 | 153.6 +/− 25.6 | 51.99 +/− 9.44 | | none at 100 nM | 6.93 +/− 1.13 |
| TY014 | 76 | 72.3 | | | | | |
| TY015 | 176 | 64.4 | | | | | |
| TY017 | 349 | 62.4 | | | | | |
| TY018 | 27.6 | 121 | 16.82 +/− 2.35 | 372.0 +/− 65.0 | | none | 7.93 +/− 1.92 |
| TY019 | 150 | 114 | 187.9 +/− 21.1 | 11.90% | | 1.6%@ 1 uM | 4.60 +/− 1.20 |
| TY020 | 71.6 | 51.4 | | | | | |
| TY021 | 53.8 | 51.4 | | | | | |
| TY022 | 100 | 32 | | | | | |
| TY023 | 33.8 | 52.2 | 33.03 +/− 7.03 | 153.9 +/− 50.6 | | | 7.8 +/− 4.0 |
| TY024 | 123 | 28 | | | | | |
| TY025 | 20.7 | 46.8 | 4.758 +/− 0.353 | 61.07 +/− 9.61 | | none | 9.9 +/− 2.8 |
| TY026 | 19.0 | 118 | 7.889 +/− 2.546 | 86.69 +/− 13.95 | | none | 10.85 +/− 0.44 |
| TY027 | 7.0 | 55 | 14.50 +/− 1.99 | 487.9 +/− 29.0 | | | 10.0 +/− 2.1 |
| TY028 | 5.7 | 52 | 11.24 +/− 0.77 | 970.9 +/− 137.2 | | none at 100 nM | 4.6 +/− 0.8 |
| TY029 | 1.3 | 133 | 7.625 +/− 1.102 | 22.23 +/− 5.20 | | none at 10 nM | 5.1 +/− 4.8 |
| TY030 | 0.9 | 59 | 11.98 +/− 1.58 | 30.99 +/− 7.08 | | none at 30 nM | 4.1 +/− 0.5 |
| TY031 | 108 | 68 | 235.1 +/− 29.2 | | | | |
| TY032 | 62 | 74 | 1.823 +/− 0.552 | 18.59 +/− 4.54 | | none at 100 nM | 7.5 +/− 0.5 |
| TY033 | 0.87 | 59 | 1.273 +/− 0.267 | 100.5 +/− 71.2 | | none at 1 uM | 24.5 +/− 9.3 |
| TY034 | 0.4 | 58 | 6.847 +/− 2.417 | 11.39 +/− 0.67 | | none at 100 nM | 36.9 +/− 3.3 |
| TY035 | 36 | 39 | 84.70 +/− 18.10 | 1007 +/− 205 | | none at 30 nM | 2.2 +/− 0.6 |
| TY036 | | | | | | | |
| TY037 | 52.9 | 8 | 8.279 +/− 1.810 | 283.7 +/− 38.7 | | none at 10 nM | 4.7 +/− 0.6 |
| TY038 | 21.7 | 11 | 18.90 +/− 3.17 | 3% at 1 uM | none | none at 100 nM | 12.0 +/− 1.4 |
| TY039 | 118 | 20 | 73.07 nM +/− 4.24 unusually slow washout from tissue | 10.1% at 1 uM | none | none at 1 uM | 433.6 +/− 161.8 |
| TY040 | 6.3 | 14 | | | | | |
| TY041 | 18 | 42 | 12.70 +/− 5.77 | 517.1 +/− 55.9 | | none at 100 nM | 1.8 +/− 0.3 |
| TY042 | 176 | 28 | 108.9 +/− 20.86 | 1891 +/− 469 | | none at 10 nM | 2.83 +/− 0.73 |
| TY043 | 4.6 | 36 | 8.175 +/− 1.723 | 272.3 +/− 99.9 | | none at 1 uM | no shift |
| TY044 | 380 | 85 | 17.99 +/− 4.89 | 248.6 +/− 47.5 kappa sensitive | | none at 30 nM | 18.4 +/− 6.0 |
| TY045 | 18.4 | 67 | 13.58 +/− 1.56 | 462.8 +/− 158.4 | | none at 100 nM | 40.8 +/− 32.8 |
| TY046 | 28.8 | 14 | | | | | |
| TY047 | 2910 | 15 | | | | | |
| TY048 | 135 | 29 | | | | | |
| TY049 | 134 | 25 | | | | | |
| TY050 | 0.57 | 45 | | | | | |
| TY051 | no response | | | | | | |
| TY052 | 8 | 29 | | | | | |
| TY053 | 0.83 | 20 | | | | | |

TABLE 39-continued

| Summary of the compounds: an amino acid sequence and biological activity. | | | | | | |
|---|---|---|---|---|---|---|
| TY054 | 0.72 | 57 | | | | |
| TY055 | | | 17.36 +/− 4.34 | 669.7 +/− 133.7 | none at 30 nM | 8.4 +/− 1.0 |
| TY056 | 44.9 | 66 | 3.623 +/− 1.063 | 24.93 +/− 5.23 | none at 30 nM | 1.2 + 1.0 |

Obviously, numerous modifications and variations of the present invention are possible in light of the above teachings. It is therefore to be understood that within the scope of the appended claims, the invention may be practiced otherwise than as specifically described herein.

We claim:

1. A chimeric compound of formula (1) comprising an agonist opioid receptor binding moiety at its N-terminus and an antagonist neurokinin-1 (NK1) receptor binding moiety at its C-terminus, X1-X2-X3-X4-X5-X6-X7-X8-Trp-R1-R2 (SEQ ID NO: 7)   formula (1)

wherein:
X1 is absent or is Tyr or substituted Tyr;
X2 is absent or is Gly or D-amino acid;
X3 is absent or is Gly;
X4 is Phe or substituted Phe;
X5 is Phe, Leu, Met, Gly, DPhe, Nle, Nle(R3), DCys, Cys, Ser(O—R4), substituted Cys, or substituted DCys;
X6 is absent or is Pro, Ala, DLeu, DPro, Ser(O—R4) or Aib;
X7 is absent or is Leu, Cys, DCys, Ser(O—R4), Pen, DPen, Ala, DAla, beta Ala, alpha Abu, gamma Abu, Ava, or Aib;
X8 is absent or is Ser(O—R4);
R1 is O, NH, or N—R5;
R2 is benzyl (Bzl) or substituted benzyl;
R3 is alkyl or a substituted alkyl;
R4 is sugar;
R5 is alkyl or substituted alkyl, or salts thereof,
wherein the chimeric compound is optionally a cyclic compound,
wherein the C-terminus moiety optionally comprises an antagonist of substance P, with the proviso that the chimeric compound is not Tyr-DAla-Gly-Phe-Gly-Trp-O-Bzl(CF$_3$)$_2$ and Tyr-DAla-Gly-Phe-Ala-Trp-O-Bzl(CF$_3$)$_2$, wherein the compound induces analgesia.

2. A chimeric compound of formula (2) comprising an agonist opioid receptor binding moiety at its N-terminus and an antagonist neurokinin-1 (NK1) receptor binding moiety at its C-terminus, X1-X2-X3-X4-X5-X6-X7-X8-Trp-R1-R2 (SEQ ID NO: 8)  formula (2)

wherein:
X1 is absent or is Tyr or Dmt(2',6'-dimethyl-L-tyrosine);
X2 is absent or is Gly, DAla, DCyc, or DPhe;
X3 is absent or is Gly;
X4 is Phe, pClPhe, pFPhe, pBrPhe, or DPhe;
X5 is Phe, Leu, Met, Gly, DPhe, Nle, Nle(NMe), DCys, Cys, Ser(OGlc), Pen, or DPen;
X6 is absent or is Pro, Ala, DLeu, DPro, Ser(OGlc) or Aib;
X7 is absent or is Leu, Cys, DCys, Ser(OGlc), Pen, DPen, Ala, DAla, beta Ala, alpha Abu, gamma Abu, Ava, or Aib;
X8 is absent or is Ser(OGlc);
R1 is O, NH, or NMe; and
R2 is Bzl; 3',5'-Bzl(CF3)2; Bzl-3'-(CF3); 3',5'-Bzl(OMe)2; Bzl-2',4'-(OMe)2, or salts thereof, with the proviso that the chimeric compound is not Tyr-DAla-Gly-Phe-Gly-Trp-O-Bzl(CF$_3$)$_2$ and Tyr-DAla-Gly-Phe-Ala-Trp-O-Bzl(CF$_3$)$_2$, wherein the compound induces analgesia.

3. The compound of claim 1, wherein X1 is Tyr.

4. The compound of claim 1, wherein X1 is Dmt (2',6'-dimethyl-L-tyrosine).

5. The compound of claim 1, wherein X1 is Tyr; X2 is DAla; X3 is Gly; X4 is Phe; X5 is Phe, DPhe, Gly, Leu, Met, Met(O), Nle, or N-Me-Nle; X6 is Pro; X7 is Leu, and X8 is absent.

6. The compound of claim 1, wherein X1 is Tyr; X2 is DAla; X3 is Gly; X4 is Phe; X6 is Pro; X7 is Leu; and X8 is absent.

7. The compound of claim 1, wherein X1 is Tyr; X2 is DCys or DPen; X3 is Gly; X4 is Phe; X5 is Nle, Cys, DCys, Pen, or DPen; X6 is Pro; and X7 is Cys, DCys, Leu, Pen, or DPen, wherein if X2 is DCys, then X5 is Nle, Cys, or DCys, and X7 is Cys, DCys, or Leu;

and if X2 is DPen, then X5 is Nle, Pen, or DPen, and X7 is Pen, DPen, or Leu.

8. The compound of claim 1, wherein X1 is Tyr or Dmt, X2 is DAla, X3 is Gly, X4 is Phe, X5 is Ser(OGlc) or Nle, X6 is Pro or Ser(OGlc), and X7 is Leu or Ser(OGlc).

9. The compound of claim 1, wherein X1 is Tyr or Dmt, X2 is DAla, X3 is Gly, X4 is Phe, X5 is Met or Nle, X6 is Pro, X7 is Leu, and X8 is absent.

10. The compound of claim 1, wherein the compound is a cyclic compound comprising a disulfide bond between at least two Cys and/or DCys.

11. The compound of claim 1, wherein the compound is a cyclic compound comprising a disulfide bond between at least two Pen and/or DPen.

12. The compound of claim 1, further comprising glycosylation.

13. The compound of claim 1, wherein the opioid receptor is δ and/or μ opioid receptor.

14. The compound of claim 1, wherein the δ opioid receptor is human-opioid receptor (hDOR).

15. The compound of claim 1, wherein the μ opioid receptor is rat-opioid receptor (rMOR).

16. The compound of claim 1, wherein the NK1 receptor is a rat NK1 receptor.

17. The compound of claim 1, wherein the NK1 receptor is a human NK1 receptor.

18. The compound of claim 1, wherein the C-terminus moiety comprises an antagonist of substance P.

19. The compound of claim 1, wherein the compound shows substantially no agonistic activity against substance P stimulation.

20. The compound of claim 1, wherein the peptide has higher potency at the δ opioid receptor than at the μ opioid receptor.

21. The compound of claim 1, wherein the peptide has higher potency at the μ opioid receptor than at the δ opioid receptor.

22. The compound of claim 1, wherein the compound has antinociceptive activity in an acute pain state.

23. The compound of claim 1, wherein analgesic efficacies of the compound comprise anti-nociceptive, anti-hyperalgesic, and anti-allodynic effects.

24. The compound of claim 1, wherein the compound is selected from the group consisting of TY001-TY035 (TyrDAlaGlyPheProLeuTrpOBn(CF$_3$)$_2$-Tyr[DCysGlyPheNleProCys]TrpNHBn(CF$_3$)$_2$), TY037-TY039 (Tyr[DCysGlyPheDCys]ProLeuTrpNHBn(CF$_3$)$_2$-Tyr[DCysGlyPheCys]ProLeuTrpNHBn(CF$_3$)$_2$), TY041-TY042 (TyrDAlaGlyPheNleProSer(OGlu)TrpNHBn(CF$_3$)$_2$-TyrDAlaGlyPheSer(OGlu)ProLeuTrpNHBn(CF$_3$)$_2$), TY044-TY050 (TyrDAlaGlyPheNleSer(OGlu)LeuTrpNHBn(CF$_3$)$_2$-DmtDAlaGlyPheNleProLeuTrpNHBn(CF$_3$)$_2$), TY052-TY-56 (DmtDAlaGlyPheNleProLeuTrpNMeBn(CF$_3$)$_2$-TyrDAlaGlyPheNleProLeuSer(OGlu)TrpNHBn(CF$_3$)$_2$), NP32-34 (TyrDAlaGlyPheβAlaTrp-O-Bzl(CF3)2-TyrDAlaGlyPheγAbuTrp-O-Bzl(CF$_3$)$_2$), and NP62 (TyrDAlaGlypFPhe-O-3',5'(CF$_3$)$_2$-Bzl).

25. A composition comprising the compound of claim 1 and a pharmaceutically acceptable carrier.

26. The composition of claim 25, wherein the composition shows substantially no agonistic activity against substance P stimulation.

27. The composition of claim 25, wherein the composition has higher potency at the δ opioid receptor that at the μ opioid receptor.

28. The composition of claim 25, wherein the composition has higher potency at the μ opioid receptor that at the δ opioid receptor.

29. The composition of claim 25, wherein the composition has antinociceptive activity in an acute pain state.

30. The composition of claim 25, wherein analgesic efficacies of the composition comprise anti-nociceptive, anti-hyperalgesic, and anti-allodynic effects.

31. The composition of claim 25, wherein the composition comprises the compound selected from the group consisting of TY001-TY035 (TyrDAlaGlyPheProLeuTrpOBn(CF$_3$)$_2$-Tyr[DCysGlyPheNleProCys]TrpNHBn(CF$_3$)$_2$), TY037-TY039 (Tyr[DCysGlyPheDCys]ProLeuTrpNHBn(CF$_3$)$_2$-Tyr[DCysGlyPheCys]ProLeuTrpNHBn(CF$_3$)$_2$), TY041-TY042 (TyrDAlaGlyPheNleProSer(OGlu)TrpNHBn(CF$_3$)$_2$-TyrDAlaGlyPheSer(OGlu)ProLeuTrpNHBn(CF$_3$)$_2$), TY044-TY050 (TyrDAlaGlyPheNleSer(OGlu)LeuTrpNHBn(CF$_3$)$_2$-DmtDAlaGlyPheNleProLeuTrpNHBn(CF$_3$)$_2$), TY052-TY-56 (DmtDAlaGlyPheNleProLeuTrpNMeBn(CF$_3$)$_2$-TyrDAlaGlyPheNleProLeuSer(OGlu)TrpNHBn(CF$_3$)$_2$), NP32-34 (TyrDAlaGlyPheβAlaTrp-O-Bzl(CF3)2-

TyrDAlaGlyPheγAbuTrp-O-Bzl(CF$_3$)$_2$), and NP62 (TyrDAlaGlypFPhe-O-3',5'(CF$_3$)$_2$-Bzl).

32. A method of treating pain comprising administering to a subject in need thereof an effective amount of at least one compound of claim 1.

33. The method of treating pain according to claim 32, wherein pain is an acute pain.

34. The method of treating pain according to claim 32, wherein pain is a chronic pain.

35. The method of treating pain according to claim 32, wherein the compound is selected from the group consisting of TY001-TY035 (TyrDAlaGlyPheProLeuTrpOBn(CF$_3$)$_2$-Tyr[DCysGlyPheNleProCys]TrpNHBn(CF$_3$)$_2$), TY037-TY039 (Tyr[DCysGlyPheDCys]ProLeuTrpNHBn(CF$_3$)$_2$-Tyr[DCysGlyPheCys]ProLeuTrpNHBn(CF$_3$)$_2$), TY041-TY042 (TyrDAlaGlyPheNleProSer(OGlu)TrpNHBn(CF$_3$)$_2$-TyrDAlaGlyPheSer(OGlu)ProLeuTrpNHBn(CF$_3$)$_2$), TY044-TY050 (TyrDAlaGlyPheNleSer(OGlu)LeuTrpNHBn(CF$_3$)$_2$-DmtDAlaGlyPheNleProLeuTrpNHBn(CF$_3$)$_2$), TY052-TY-56 (DmtDAlaGlyPheNleProLeuTrpNMeBn (CF$_3$)$_2$-TyrDAlaGlyPheNleProLeuSer(OGlu)TrpNHBn (CF$_3$)$_2$), NP32-34 (TyrDAlaGlyPheβAlaTrp-O-Bzl(CF3)2-TyrDAlaGlyPheγAbuTrp-O-Bzl(CF$_3$)$_2$), and NP62 (TyrDAlaGlypFPhe-O-3',5'(CF$_3$)$_2$-Bzl).

36. The method of treating pain according to claim 32, wherein the compound possesses analgesic efficacy.

37. A method of making the chimeric compound of claim 1 comprising the steps:
  a. introducing Fmoc-Trp(Boc)-OH on a resin;
  b. removing an N-Fmoc protecting group;
  c. conducting a step-wise chain elongation, wherein the following amino acids are coupled using in situ activating reagents to obtain a protected intermediate having Boc-Tyr(tBu) or Boc-Dmt on its N-terminus and -Trp (Boc)-O— attached to the resin on its C-terminus;
  d. treating the protected intermediate with a cleavage reagent to free the protected intermediate from the resin;
  e. conducting esterification or amidation of the protected intermediate peptide;
  f. conducting a cleavage of the protected intermediate; and removing the protecting groups, thereby obtaining the chimeric compound.

38. The method of claim 37, wherein the resin is a 2-chlorotrityl resin or other resins suitable for a solid phase synthesis.

39. The method according to claim 37, wherein esterification is performed using cesium carbonate to form a cesium salt of the protected intermediate, wherein the cesium salt is further reacted with benzyl bromide or 3', 5'-bis(trifluoromethyl)-benzyl bromide.

40. The method according to claim 37, wherein amidation is performed using EDC/Cl-HOBt coupling chemistry and benzyl amine, 3', 5'-bis(trifluoromethyl)-benzyl amine, or N-methyl-3', 5'-bis-(trifluoromethyl-benzyl) amine.

41. The method according to claim 37, wherein cyclization of the synthesized compound is further conducted.

42. A method of making the glycosylated compound of claim 1, comprising the steps:
  a. conducting glycosylation of Fmoc-Ser-OBzl to obtain Fmoc-Ser(Glc(OAc)$_4$)—OBzl;
  b. deprotecting benzyl group to afford Fmoc-Ser(Glc(OAc)$_4$)—OH;
  c. introducing 3', 5'-bis(trifluoromethyl)-benzyl amine on FMPB (4-(4-Formyl-3-methoxyphenoxy)butyryl) AM resin;
  d. conducting a step-wise chain elongation, wherein the following amino acids are coupled using in situ activating reagents to obtain a protected intermediate having Boc-Tyr(tBu) or Boc-Dmt on its N-terminus and -Trp(Boc)-N-3', 5'-bis(trifluoromethyl)-benzyl attached to the resin on its C-terminus;
  e. treating the protected intermediate to deprotect the protective groups on a sugar; and
  f. treating the intermediate to free the chimeric compound.

43. A method of synthesis of the chimeric compound of claim 1 comprising the steps:
  a. coupling reaction of Boc-Pro-Leu-OH and tryptophan 3,5-(bistrifluoromethyl)benzyl ester hydrochloride;
  b. deprotecting of Boc group;
  c. conducting a stepwise chain elongation using PyBOP/HOBt chemistry, wherein the following amino acids are coupled using activating reagents;
  d. conducting coupling of the compound of step (c) with Boc-Tyr-DAla-Gly-OH; and
  e. conducting a cleavage of the protected intermediate and removing the protecting group.

* * * * *